United States Patent
Li et al.

(10) Patent No.: US 10,865,393 B2
(45) Date of Patent: *Dec. 15, 2020

(54) ENGINEERED GLUCOSYLTRANSFERASES

(71) Applicant: DUPONT INDUSTRIAL BIOSCIENCES USA, LLC, Wilmington, DE (US)

(72) Inventors: Yougen Li, Pennington, NJ (US); Ellen D. Semke, Newark, DE (US); Qiong Cheng, Wilmington, DE (US); Jian Ping Lai, Wallingford, PA (US)

(73) Assignee: DUPONT INDUSTRIAL BIOSCIENCES USA, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 16/127,293

(22) Filed: Sep. 11, 2018

(65) Prior Publication Data

US 2019/0078063 A1 Mar. 14, 2019

Related U.S. Application Data

(60) Provisional application No. 62/557,840, filed on Sep. 13, 2017.

(51) Int. Cl.
  C12N 9/10 (2006.01)
  C12P 19/04 (2006.01)
  C12P 19/18 (2006.01)
  C08B 37/00 (2006.01)
  G16B 25/00 (2019.01)

(52) U.S. Cl.
  CPC ........ *C12N 9/1048* (2013.01); *C08B 37/0009* (2013.01); *C12N 9/1051* (2013.01); *C12P 19/04* (2013.01); *C12P 19/18* (2013.01); *C12Y 204/01005* (2013.01); *C12Y 204/01* (2013.01); *G16B 25/00* (2019.02)

(58) Field of Classification Search
  None
  See application file for complete search history.

(56) References Cited

U.S. PATENT DOCUMENTS

| | | | |
|---|---|---|---|
| 5,952,205 A | 9/1999 | Catani et al. | |
| 6,207,149 B1 | 3/2001 | Fuglsang et al. | |
| 6,242,225 B1 | 6/2001 | Catani et al. | |
| 6,660,502 B2 | 12/2003 | Catani et al. | |
| 7,000,000 B1 | 2/2006 | O'Brien | |
| 7,524,645 B2 | 4/2009 | Monsan et al. | |
| 8,269,064 B2 | 9/2012 | Kok-Jacon et al. | |
| 8,859,848 B2 | 10/2014 | Jugde et al. | |
| 8,871,474 B2 | 10/2014 | Payne et al. | |
| 9,228,177 B2 | 1/2016 | Payne et al. | |
| 9,260,701 B2 | 2/2016 | Payne et al. | |
| 9,260,702 B2 | 2/2016 | Payne et al. | |
| 9,284,539 B2 | 3/2016 | Payne et al. | |
| 9,284,540 B2 | 3/2016 | Payne et al. | |
| 9,296,996 B2 | 3/2016 | Payne et al. | |
| 9,296,997 B2 | 3/2016 | Payne et al. | |
| 9,399,765 B2 | 7/2016 | Monsan et al. | |
| 9,968,910 B2 | 5/2018 | Behabtu et al. | |
| 10,301,604 B2 | 5/2019 | Li et al. | |
| 10,308,968 B2 | 6/2019 | Payne et al. | |
| 2002/0155568 A1 | 10/2002 | Van Geel-Schutten et al. | |
| 2006/0057704 A1 | 3/2006 | Schlothauer et al. | |
| 2006/0127328 A1 | 6/2006 | Monsan et al. | |
| 2010/0192985 A1* | 8/2010 | Aehle .................... | C11D 3/386 |
| | | | 134/26 |
| 2011/0144317 A1 | 6/2011 | Mulard et al. | |
| 2013/0036968 A1 | 2/2013 | Suzuki et al. | |
| 2013/0096502 A1 | 4/2013 | Kawamoto et al. | |
| 2013/0096511 A1 | 4/2013 | MacArthur | |
| 2013/0244287 A1 | 9/2013 | O'Brien et al. | |
| 2013/0244288 A1 | 9/2013 | O'Brien et al. | |
| 2014/0087431 A1 | 3/2014 | Payne et al. | |
| 2015/0218532 A1 | 8/2015 | Cote et al. | |
| 2015/0232785 A1 | 8/2015 | Paullin et al. | |
| 2015/0232819 A1 | 8/2015 | Paullin et al. | |
| 2017/0002335 A1 | 1/2017 | Payne et al. | |
| 2017/0002336 A1 | 1/2017 | Payne et al. | |
| 2017/0166938 A1 | 6/2017 | Nagy et al. | |
| 2017/0218093 A1 | 8/2017 | Cheng et al. | |
| 2018/0072998 A1* | 3/2018 | Li ........................ | C12N 9/1051 |
| 2018/0340199 A1 | 11/2018 | Nagy et al. | |
| 2019/0078062 A1 | 3/2019 | Li et al. | |

FOREIGN PATENT DOCUMENTS

| | | |
|---|---|---|
| JP | 2000175694 A | 6/2000 |
| WO | 2013036918 A2 | 3/2013 |
| WO | 2015183714 A1 | 12/2015 |
| WO | 2015183721 A1 | 12/2015 |

(Continued)

OTHER PUBLICATIONS

UniProt Database Accession No. T0TT57, Sep. 2016, 2 pages (Year: 2016).*
Database UniProt—EBI Accession No. A0A1G6C1V1, Dextransucrase, Apr. 12, 2017.
Database UniProt—EBI Accession No. A0A135YLE3, SubName: Full=KxYKxGKxW signal domain protein, Jun. 8, 2016.
International Search Report and Written Opinion, PCT/US2018/050354, dated Nov. 16, 2018.
Simpson et al., Four Glucosyltransferases, GTFJ, GTFK, GTFL and GTFM, From *Streptococcus Salivarius* ATCC 25975, Microbiology, vol. 141 (1995), pp. 1451-1460.
Leemhuis et al., Glucansucrases: Three-Dimensional Structures, Reactions, Mechanism, α-Glucan Analysis and Their Implications in Biotechnology and Food Applications, Journal of Biotechnology, vol. 163 (2013), pp. 250-272.

(Continued)

*Primary Examiner* — David Steadman

(57) ABSTRACT

Disclosed herein are glucosyltransferases with modified amino acid sequences. Such engineered enzymes exhibit improved alpha-glucan product yields and/or lower leucrose yields, for example. Further disclosed are reactions and methods in which engineered glucosyltransferases are used to produce alpha-glucan.

23 Claims, No Drawings
Specification includes a Sequence Listing.

(56) References Cited

FOREIGN PATENT DOCUMENTS

| | | |
|---|---|---|
| WO | 2015183722 A1 | 12/2015 |
| WO | 2015183724 A1 | 12/2015 |
| WO | 2015183726 A1 | 12/2015 |
| WO | 2015183729 A1 | 12/2015 |
| WO | 2018/052942 A1 | 3/2018 |

OTHER PUBLICATIONS

Monchois et al., Glucansucrases: Mechanism of Action and Structure-Function Relationships, FEMS Microbiology Reviews, vol. 23 (1999), pp. 131-151.
Monchois et al., Isolation of an Active Catalytic Core of *Streptococcus Downei* MFE28 GTF-I Glucosyltransferase, Journal of Bacteriology, vol. 181, No. 7 (1999), pp. 2290-2292.
Rogers, Chapter 5: The Molecular Biology of Cariogenic Bacteria, From Molecular Biology, Horizon Scientific Press, Roy RB Russell (2008), pp. 120-122.
Konishi et al., Structure and Enzymatic Properties of Genetically Truncated Forms of the Water-Insoluble Glucan-Synthesizing Glucosyltransferase From *Streptococcus Sobrinus*, J. Biochem., vol. 126 (1999), pp. 287-295.
Tsumuraya et al., Structure of the Water-Insoluble α-D-Glucan of *Streptococcus Salivarius* HHT, Carbohydrate Research, vol. 74 (1979), pp. 217-225.
Weaver et al., Weighted Intrinsic Viscosity Relationships for Polysaccharide Mixtures in Dilute Aqueous Solutions, Journal of Applied Polymer Science, vol. 35 (1988), pp. 1631-1637.
Yakushiji et al., Inter-Serotype Comparison of Polysaccharides Produced by Extracellular Enzymes From *Streptococcus Mutans*, Carbohydrate Research, vol. 127 (1984), pp. 253-266.
Yoshimi et al., Functional Analysis of the α-1,3-Glucan Synthase Genes AGSA and AGSB in Aspergillus Nidulans: AGSB Is the Major α-1,3-Glucan Synthase in This Fungus, Plos One, vol. 8, Issue 1 (2013), pp. 1-16.
Cote and Skory, Effects of mutations at threonine-654 on the insoluble glucan synthesized by Leuconostoc mesenteroides NRRL B-1118 glucansucrase, Appl. Microbiol. Biotechnol., vol. 98, (2014), pp. 6651-6658.
Chia et al., Functional Analyses of a Conserved Region in Glucosyltransferases of *Streptococcus mutans*, Infection and Immunity, vol. 66, No. 10, pp. 4797-4803 (1998).
Meng et al., Characterization of the glucansucrase GTF180 W1065 mutant enzymes producing polysaccharides and oligosaccharides with altered linkage composition, Food Chem., vol. 217, pp. 81-90 (2017).
Meng et al., Characterization of the Functional Roles of Amino Acid Residues in Acceptor-binding Subsite +1 in the Active Site of the Glucansucrase GTF180 from Lactobacillus reuteri 180*, J. Bio. Chem., vol. 290, No. 50, pp. 30131-30141 (2015).
Monchois et al., Mutagenesis of Asp-569 of Glucosyltransferase I Glucansucrase Modulates Glucan and Oligosaccharide Synthesis, Appl. Env. Micro., vol. 66, No. 5, pp. 1923-1927 (2000).
Monchois et al., Characterization of Leuconostoc mesenteroides NRRL B-512F dextransucrase (DSRS) and Identification of amino-acid residues playing a key role in enzyme activity, Appl. Micro. Bio. vol. 48, pp. 465-472 (1997).
Van Hijum et al., Structure-Function Relationships of Glucansucrase and Fructansucrase Enzymes from Lactic Acid Bacteria, Micro. Mol. Bio. Rev., vol. 70, No. 1, pp. 157-176 (2006).
Meng et al., Structure-function relationships of family GH70 glucansucrase and 4,6-x-glucanotransferase enzymes, and their evo-lutionary relationships with family GH13 enzymes, Cell. Mol. Life Sci., vol. 73, pp. 2681-2706 (2016).
Shimamura et al., Identification of Amino Acid Residues in Streptococcus mutans Glucosyltransferases Influencing the Structure of the Glucan Product, Journal of Bacteriology, vol. 176, pp. 4845-4850 (1994.
Cote et al., Some Structural Features of an Insoluble -D-Glucan From a Mutant Strain of Leuconostoc Mesenteroides NRRL B-1355, Journal of Industrial Microbiology & Biotechnology, vol. 23 (1999), pp. 656-660.
Meng et al., Residue Leu 940 Has a Crucial Role in the Linkage and Reaction Specificity of the Glucansucrase GTF180 of the Probiotic Bacterium Lactobacillus Reuteri 180, Journal of Biological Chemistry, vol. 289, No. 47 (2014), pp. 32773-32782.
Castillo et al., Synthesis of Levan in Water-Miscible Organic Solvents, Journal of Biotechnology, vol. 114 (2004), pp. 209-217.
Aman et al., Influence of Temperature, Metal Ions and Organic Solvents on Extracellular Glucansucrase Activity of Leuconostoc Mesenteroidses AA1, J. Chem. Soc., vol. 30, No. 6 (2008), pp. 849-853.
Girard et al., Activity and Stability of Dextransucrase From Leuconostoc Mesenteroides NRRL B-512F in the Presence of Organic Solvents, Enzyme and Microbial Technology, vol. 24 (1999), pp. 425-432.
Chambert et al, Study of the Effect of Organic Solvents on the Synthesis of Levan and the Hydrolysis of Sucrose by Bacillus Subtilis Levansucrase, Carbohydrate Research, vol. 191 (1989), pp. 117-123.
Kralj et al., Rational Transformation of Lactobacillus Reuteri 121 Reuteransucrase Into a Dextrasucrase, Biochemistry, vol. 44 (2005), pp. 9206-9216.
Ozimek et al, Single Amino Acid Residue Changes in Subsite—1 of Inulosucrase From Lactobacillus Reuteri 121 Strongly Influence the Size of Products Synthesized, FEBS Journal, vol. 273 (2006), pp. 4104-4113.
Kralj et al., Biochemical and Molecular Characterization of Lactobacillus Reuteri 121 Reuteransucrase, Microbiology, vol. 150 (2004), pp. 2099-2112.
Van Der Veen et al., Hydrophobic Amino Acid Residues in the Acceptor Binding Site Are Main Determinants for Reaction Mechanism and Specificity of Cyclodextrin-Glycosyltransferase, the Journal of Biological Chemistry, vol. 276, No. 48 (2001), pp. 4457-44562.
Kralj et al., Role of Asparagine 1134 in Glucosidic Bond and Transglycosylation Specificity of Reuteransucrase From Lactobacillus Reuteri 121, FEBS Journal, vol. 273 (2006), pp. 3735-3742.
Kang et al., Bioengineering of Leuconostoc Mesenteroides Glucansucrases That Gives Selected Bond Formation for Glucan Synthesis and/or Acceptor-Product Synthesis, Journal of Agricultural and Food Chemistry, vol. 59 (2011), pp. 4148-4155.
Irague et al., Combinatorial Engineering of Dextransucrase Specificity, Plos One, vol. 8, No. 10 (2013), pp. 1-14.
Vujicic-Zagar et al., Crystal Structure of 117 KDA Glucansucrase Fragment Provides Insight Into Evolution and Product Specificity of GH70 Enzymes, PNAS, vol. 107, No. 50 (2010), pp. 21406-21411.
Jan Leeuwen et al., Structural Characterization of Bioengineered α-D-Glucans Produced by Mutant Glucansucrase GTF180 Enzymes of Lactobacillus Reuteri Strain 180, Biomacromolecules, vol. 10 (2009), pp. 580-588.
Jan Leeuwen et al., Structural of Bioengineered α-D-Glucan Produced by a Triple Mutant of the Glucansucrase GTF180 Enzyme From Lactobacillus Reuteri Strain 180: Generation of (α1->4) Linkages in a Native (1->3)(1->6)-α-D-Glucan, Biomacromolecules, vol. 9 (2008), pp. 2251-2258.

* cited by examiner

ENGINEERED GLUCOSYLTRANSFERASES

This application claims the benefit of U.S. Provisional Application No. 62/557,840 (filed Sep. 13, 2017), which is incorporated herein by reference in its entirety.

FIELD

The present disclosure is in the field of enzyme catalysis. For example, the disclosure pertains to glucosyltransferase enzymes with modified amino acid sequences. Such modified enzymes have improved product yield properties, for example.

REFERENCE TO SEQUENCE LISTING SUBMITTED ELECTRONICALLY

The official copy of the sequence listing is submitted electronically via EFS-Web as an ASCII formatted sequence listing with a file named 20180911_CL6613USNP_SequenceListing_ST25 created on Sep. 11, 2018, and having a size of about 406 kilobytes and is filed concurrently with the specification. The sequence listing contained in this ASCII-formatted document is part of the specification and is herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., Microbiology 141:1451-1460, 1995). Also for example, U.S. Pat. No. 7,000,000 disclosed the preparation of a spun fiber from enzymatically produced alpha-1,3-glucan. Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages.

While these and other advances have been made in producing glucan polymers using glucosyltransferase enzymes, less attention appears to have been drawn to improving the glucan yields of such enzymes. Addressing this technological gap, disclosed herein are glucosyltransferases engineered to have modified amino acid sequences endowing these enzymes with enhanced glucan production properties.

SUMMARY

In one embodiment, the present disclosure concerns a non-native glucosyltransferase comprising at least two amino acid substitutions at positions corresponding with amino acid residues Gln-588, Phe-607, or Arg-741 of SEQ ID NO:62, wherein the non-native glucosyltransferase synthesizes alpha-glucan comprising 1,3-linkages, and wherein the non-native glucosyltransferase has: (i) an alpha-glucan yield that is higher than the alpha-glucan yield of a second glucosyltransferase that only differs from the non-native glucosyltransferase at the substitution positions, and/or (ii) a leucrose yield that is lower than the leucrose yield of the second glucosyltransferase.

In another embodiment, the present disclosure concerns a polynucleotide comprising a nucleotide sequence encoding a non-native glucosyltransferase as presently disclosed, optionally wherein one or more regulatory sequences are operably linked to the nucleotide sequence, and preferably wherein the one or more regulatory sequences include a promoter sequence.

In another embodiment, the present disclosure concerns a reaction composition comprising water, sucrose, and a non-native glucosyltransferase as presently disclosed.

In another embodiment, the present disclosure concerns a method of producing alpha-glucan comprising: (a) contacting at least water, sucrose, and a non-native glucosyltransferase enzyme as presently disclosed, whereby alpha-glucan is produced; and b) optionally, isolating the alpha-glucan produced in step (a).

In another embodiment, the present disclosure concerns a method of preparing a polynucleotide sequence encoding a non-native glucosyltransferase, the method comprising: (a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes alpha-glucan comprising 1,3-linkages; and (b) modifying the polynucleotide sequence identified in step (a) to substitute at least two amino acids of the parent glucosyltransferase at positions corresponding with amino acid residues Gln-588, Phe-607 or Arg-741 of SEQ ID NO:62, thereby providing a polynucleotide sequence encoding a non-native glucosyltransferase that has: (i) an alpha-glucan yield that is higher than the alpha-glucan yield of the parent glucosyltransferase, and/or (ii) a leucrose yield that is lower than the leucrose yield of the parent glucosyltransferase.

BRIEF DESCRIPTION OF THE SEQUENCES

TABLE 1

Summary of Nucleic Acid and Protein SEQ ID Numbers[b]

| Description | Nucleic acid SEQ ID NO. | Protein SEQ ID NO. |
|---|---|---|
| GTF 0874, *Streptococcus sobrinus*. The first 156 amino acids of the protein are deleted compared to GENBANK Identification No. 450874; a start methionine is included. | 1[a] | 2 (1435 aa) |
| GTF 6855, *Streptococcus salivarius* SK126. The first 178 amino acids of the protein are deleted compared to GENBANK Identification No. 228476855 (Acc. No. ZP_04061500.1); a start methionine is included. | 3[a] | 4 (1341 aa) |
| GTF 2379, *Streptococcus salivarius*. The first 203 amino | 5[a] | 6 |

TABLE 1-continued

Summary of Nucleic Acid and Protein SEQ ID Numbers[b]

| Description | Nucleic acid SEQ ID NO. | Protein SEQ ID NO. |
|---|---|---|
| acids of the protein are deleted compared to GENBANK Identification No. 662379; a start methionine is included. | | (1247 aa) |
| GTF 7527 or GTFJ, *Streptococcus salivarius*. The first 42 amino acids of the protein are deleted compared to GENBANK Identification No. 47527; a start methionine is included. | 7[a] | 8 (1477 aa) |
| GTF 1724, *Streptococcus downei*. The first 162 amino acids of the protein are deleted compared to GENBANK Identification No. 121724; a start methionine is included. | 9[a] | 10 (1436 aa) |
| GTF 0544, *Streptococcus mutans*. The first 164 amino acids of the protein are deleted compared to GENBANK Identification No. 290580544; a start methionine is included. | 11[a] | 12 (1313 aa) |
| GTF 5926, *Streptococcus dentirousetti*. The first 144 amino acids of the protein are deleted compared to GENBANK Identification No. 167735926; a start methionine is included. | 13[a] | 14 (1323 aa) |
| GTF 4297, *Streptococcus oralis*. The first 228 amino acids of the protein are deleted compared to GENBANK Identification No. 7684297; a start methionine is included. | 15[a] | 16 (1348 aa) |
| GTF 5618, *Streptococcus sanguinis*. The first 223 amino acids of the protein are deleted compared to GENBANK Identification No. 328945618; a start methionine is included. | 17[a] | 18 (1348 aa) |
| GTF 2765, unknown *Streptococcus* sp. C150. The first 193 amino acids of the protein are deleted compared to GENBANK Identification No. 322372765; a start methionine is included. | 19[a] | 20 (1340 aa) |
| GTF 0427, *Streptococcus sobrinus*. The first 156 amino acids of the protein are deleted compared to GENBANK Identification No. 940427; a start methionine is included. | 25[a] | 26 (1435 aa) |
| GTF 2919, *Streptococcus salivarius* PS4. The first 92 amino acids of the protein are deleted compared to GENBANK Identification No. 383282919; a start methionine is included. | 27[a] | 28 (1340 aa) |
| GTF 2678, *Streptococcus salivarius* K12. The first 188 amino acids of the protein are deleted compared to GENBANK Identification No. 400182678; a start methionine is included. | 29[a] | 30 (1341 aa) |
| GTF 3929, *Streptococcus salivarius* JIM8777. The first 178 amino acids of the protein are deleted compared to GENBANK Identification No. 387783929; a start methionine is included. | 33[a] | 34 (1341 aa) |
| GTF 3298, *Streptococcus* sp. C150. The first 209 amino acids of the protein are deleted compared to GENBANK Identification No. 322373298; a start methionine is included. | | 59 (1242 aa) |
| Wild type GTFJ, *Streptococcus salivarius*. GENBANK Identification No. 47527. | | 60 (1518 aa) |
| Wild type GTF corresponding to GTF 2678, *Streptococcus salivarius* K12. | | 61 (1528 aa) |
| Wild type GTF corresponding to GTF 6855, *Streptococcus salivarius* SK126. | | 62 (1518 aa) |
| Wild type GTF corresponding to GTF 2919, *Streptococcus salivarius* PS4. | | 63 (1431 aa) |
| Wild type GTF corresponding to GTF 2765, unknown *Streptococcus* sp. C150. | | 64 (1532 aa) |
| Shorter version of GTF 7527, *Streptococcus salivarius*, (also referred to as "7527-NT" herein. The first 178 amino acids of the protein are deleted compared to GENBANK Identification No. 47527; a start methionine is included. | | 65 (1341 aa) |
| Terminator sequence added to pHY300PLK to derive the pHYT vector. | 67 | |
| Aclglu1 alpha-glucosidase. | | 68 (971 aa) |
| Nfiglu1 alpha-glucosidase. | | 69 (969 aa) |
| Ncrglu1 alpha-glucosidase. | | 70 (1022 aa) |
| TauSec098_b alpha-glucosidase. | | 71 (1012 aa) |
| TauSec098_c alpha-glucosidase. | | 72 (984 aa) |
| TauSec098_d alpha-glucosidase. | | 73 (984 aa) |
| TauSec099 alpha-glucosidase. | | 74 (973 aa) |
| BloGlu1 alpha-glucosidase. | | 75 (604 aa) |
| BloGlu2 alpha-glucosidase. | | 76 (604 aa) |

TABLE 1-continued

Summary of Nucleic Acid and Protein SEQ ID Numbers[b]

| Description | Nucleic acid SEQ ID NO. | Protein SEQ ID NO. |
|---|---|---|
| BloGlu3 alpha-glucosidase. | | 77 (604 aa) |
| BpsGlu1 alpha-glucosidase. | | 78 (585 aa) |
| BthGlu1 alpha-glucosidase. | | 79 (601 aa) |
| BbrGlu2 alpha-glucosidase. | | 80 (662 aa) |
| BbrGlu5 alpha-glucosidase. | | 81 (606 aa) |

[a]This DNA coding sequence is codon-optimized for expression in E. coli and is merely disclosed as an example of a suitable coding sequence.
[b]SEQ ID NOs: 21-24, 31, 32, 35-58 and 66 are intentionally not included in this table and merely serve as placeholders.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The terms "alpha-glucan", "alpha-glucan polymer" and the like are used interchangeably herein. An alpha-glucan is a polymer comprising glucose monomeric units linked together by alpha-glycosidic linkages. In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of alpha-glucan polymers herein include alpha-1,3-glucan.

The terms "poly alpha-1,3-glucan", "alpha-1,3-glucan", "alpha-1,3-glucan polymer" and the like are used interchangeably herein. Alpha-1,3-glucan is a polymer comprising glucose monomeric units linked together by glycosidic linkages, typically wherein at least about 50% of the glycosidic linkages are alpha-1,3. Alpha-1,3-glucan in certain embodiments comprises at least 90% or 95% alpha-1,3 glycosidic linkages. Most or all of the other linkages in alpha-1,3-glucan herein typically are alpha-1,6, though some linkages may also be alpha-1,2 and/or alpha-1,4.

The terms "glycosidic linkage", "glycosidic bond", "linkage" and the like are used interchangeably herein and refer to the covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. The term "alpha-1,6-glycosidic linkage" as used herein refers to the covalent bond that joins alpha-D-glucose molecules to each other through carbons 1 and 6 on adjacent alpha-D-glucose rings. The glycosidic linkages of a glucan polymer herein can also be referred to as "glucosidic linkages". Herein, "alpha-D-glucose" will be referred to as "glucose".

The glycosidic linkage profile of an alpha-glucan herein can be determined using any method known in the art. For example, a linkage profile can be determined using methods using nuclear magnetic resonance (NMR) spectroscopy (e.g., $^{13}$C NMR or $^{1}$H NMR). These and other methods that can be used are disclosed in, for example, Food Carbohydrates: Chemistry, Physical Properties, and Applications (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as $DP_w$ (weight average degree of polymerization) or $DP_n$ (number average degree of polymerization). The molecular weight of smaller alpha-glucan polymers such as oligosaccharides typically can be provided as "DP" (degree of polymerization), which simply refers to the number of glucoses comprised within the alpha-glucan. Various means are known in the art for calculating these various molecular weight measurements such as with high-pressure liquid chromatography (HPLC), size exclusion chromatography (SEC), or gel permeation chromatography (GPC).

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The terms "leucrose" and "D-glucopyranosyl-alpha(1-5)-D-fructopyranose" are used interchangeably herein and refer to a disaccharide containing an alpha-1,5 glucosyl-fructose linkage.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (by-products) of a GTF reaction can include glucose, various soluble gluco-oligosaccharides, and leucrose. Wild type forms of glucosyltransferase enzymes generally contain (in the N-terminal to C-terminal direction) a signal peptide (which is typically removed by cleavage processes), a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., Nucleic Acids Res. 37:D233-238, 2009).

The term "glucosyltransferase catalytic domain" herein refers to the domain of a glucosyltransferase enzyme that provides alpha-glucan-synthesizing activity to a glucosyltransferase enzyme. A glucosyltransferase catalytic domain typically does not require the presence of any other domains to have this activity.

The terms "enzymatic reaction", "glucosyltransferase reaction", "glucan synthesis reaction", "reaction composition", "reaction formulation" and the like are used interchangeably herein and generally refer to a reaction that initially comprises water, sucrose, at least one active glucosyltransferase enzyme, and optionally other components. Components that can be further present in a glucosyltransferase reaction typically after it has commenced include fructose, glucose, leucrose, soluble gluco-oligosaccharides (e.g., DP2-DP7) (such may be considered as products or by-products, depending on the glucosyltransferase used), and/or insoluble alpha-glucan product(s) of DP8 or higher (e.g., DP100 and higher). It would be understood that certain glucan products, such as alpha-1,3-glucan with a degree of polymerization (DP) of at least 8 or 9, are water-insoluble and thus not dissolved in a glucan synthesis reaction, but rather may be present out of solution (e.g., by virtue of having precipitated from the reaction). It is in a glucan synthesis reaction where the step of contacting water, sucrose and a glucosyltransferase enzyme is performed. The term "under suitable reaction conditions" as used herein refers to reaction conditions that support conversion of sucrose to alpha-glucan product(s) via glucosyltransferase enzyme activity.

The "yield" of an alpha-glucan product in a glucosyltransferase reaction in some aspects herein represents the molar yield based on the converted sucrose. The molar yield of an alpha-glucan product can be calculated based on the moles of the alpha-glucan product divided by the moles of the sucrose converted. Moles of converted sucrose can be calculated as follows: (mass of initial sucrose−mass of final sucrose)/molecular weight of sucrose [342 g/mol]. This molar yield calculation can be considered as a measure of selectivity of the reaction toward the alpha-glucan. In some aspects, the "yield" of an alpha-glucan product in a glucosyltransferase reaction can be based on the glucosyl component of the reaction. Such a yield (yield based on glucosyl) can be measured using the following formula:

Alpha-Glucan Yield=((IS/2−(FS/2+LE/2+GL+SO))/(IS/2−FS/2))×100%.

The fructose balance of a glucosyltransferase reaction can be measured to ensure that HPLC data, if applicable, are not out of range (90-110% is considered acceptable). Fructose balance can be measured using the following formula:

Fructose Balance=((180/342×(FS+LE)+FR)/(180/342×IS))×100%.

In the above two formulae, IS is [Initial Sucrose], FS is [Final Sucrose], LE is [Leucrose], GL is [Glucose], SO is [Soluble Oligomers] (gluco-oligosaccharides), and FR is [Fructose]; the concentrations of each foregoing substrate/product provided in double brackets are in units of grams/L and as measured by HPLC, for example.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "aqueous conditions", "aqueous reaction conditions", "aqueous setting", "aqueous system" and the like are used interchangeably herein. Aqueous conditions herein refer to a solution or mixture in which the solvent is at least about 60 wt % water, for example. A glucosyltransferase reaction herein is performed under aqueous conditions.

The terms "soluble", "aqueous-soluble", "water-soluble" and the like as used herein characterize a glucan that has the capability of dissolving in water and/or an aqueous solution herein. Examples of soluble glucans herein are certain oligosaccharides, such as alpha-1,3-glucan with a DP less than 8. In contrast, a glucan that is "insoluble", "aqueous-insoluble", "water-insoluble" (and like terms) does not dissolve (or does not appreciably dissolve) in water and/or an aqueous solution herein. Optionally, the conditions for determining solubility include a water/solution temperature range of about 1 to 85° C. (e.g., 20-25° C.) and/or a pH range of about 4-9 (e.g., 6-8).

The terms "polynucleotide", "polynucleotide sequence", "nucleic acid molecule" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene can refer to a gene that is introduced into the host organism by gene transfer. Foreign/heterologous genes can comprise native genes inserted into a non-native organism, native genes introduced into a new location within the native host, or chimeric genes. Polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

As used herein, the term "polypeptide" is defined as a chain of amino acid residues, usually having a defined sequence. As used herein the term polypeptide is interchangeable with the terms "peptides" and "proteins". Typical amino acids contained in polypeptides herein include (respective three- and one-letter codes shown parenthetically): alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), valine (Val, V).

The term "heterologous" means not naturally found in the location of interest. For example, a heterologous gene can be one that is not naturally found in a host organism, but that is introduced into the host organism by gene transfer. As another example, a nucleic acid molecule that is present in a chimeric gene can be characterized as being heterologous, as such a nucleic acid molecule is not naturally associated with the other segments of the chimeric gene (e.g., a promoter can be heterologous to a coding sequence).

A "non-native" amino acid sequence or polynucleotide sequence comprised in a cell or organism herein does not occur in a native (natural) counterpart of such cell or organism. Such an amino acid sequence or polynucleotide sequence can also be referred to as being heterologous to the cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". A promoter may alternatively be inducible. One or more promoters herein may be heterologous to a coding region herein.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator", "terminator" and the like as used herein refer to DNA sequences located downstream of a coding sequence. This includes polyadenylation recognition sequences and other sequences encoding regulatory signals capable of affecting mRNA processing or gene expression.

As used herein, a first nucleic acid sequence is "hybridizable" to a second nucleic acid sequence when a single-stranded form of the first nucleic acid sequence can anneal to the second nucleic acid sequence under suitable annealing conditions (e.g., temperature, solution ionic strength). Hybridization and washing conditions are well known and exemplified in Sambrook J, Fritsch E F and Maniatis T, *Molecular Cloning: A Laboratory Manual*, 2nd ed., Cold Spring Harbor Laboratory: Cold Spring Harbor, N.Y. (1989), which is incorporated herein by reference, particularly Chapter 11 and Table 11.1.

The term "DNA manipulation technique" refers to any technique in which the sequence of a DNA polynucleotide sequence is modified. Although the DNA polynucleotide sequence being modified can be used as a substrate itself for modification, it does not have to be physically in hand for certain techniques (e.g., a sequence stored in a computer can be used as the basis for the manipulation technique). A DNA manipulation technique can be used to delete and/or mutate one or more DNA sequences in a longer sequence. Examples of a DNA manipulation technique include recombinant DNA techniques (restriction and ligation, molecular cloning), polymerase chain reaction (PCR), and synthetic DNA methods (e.g., oligonucleotide synthesis and ligation). Regarding synthetic DNA techniques, a DNA manipulation technique can entail observing a DNA polynucleotide in silico, determining desired modifications (e.g., one or more deletions) of the DNA polynucleotide, and synthesizing a DNA polynucleotide that contains the desired modifications.

The term "in silico" herein means in or on an information storage and/or processing device such as a computer; done or produced using computer software or simulation, i.e., virtual reality.

The terms "upstream" and "downstream" as used herein with respect to polynucleotides refer to "5' of" and "3' of", respectively.

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be up-regulated or down-regulated in certain embodiments.

The term "operably linked" as used herein refers to the association of two or more nucleic acid sequences such that the function of one is affected by the other. For example, a promoter is operably linked with a coding sequence when it is capable of affecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) (Griffin, A. M., and Griffin, H. G., Eds.) Humana: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, Wis.), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.,* 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, *CABIOS.* 5:151-153 (1989); Higgins, D. G. et al., *Comput. Appl. Biosci.* 8:189-191(1992); Thompson, J. D. et al, *Nucleic Acids Research,* 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergent Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The terms "aligns with", "corresponds with", and the like can be used interchangeably herein. Some embodiments herein relate to a glucosyltransferase comprising at least one amino acid substitution at a position corresponding with at least one particular amino acid residue of SEQ ID NO:62. An amino acid position of a glucosyltransferase or subsequence thereof (e.g., catalytic domain or catalytic domain plus glucan-binding domains) (can refer to such an amino acid position or sequence as a "query" position or sequence) can be characterized to correspond with a particular amino acid residue of SEQ ID NO:62 (can refer to such an amino acid position or sequence as a "subject" position or sequence) if (1) the query sequence can be aligned with the subject sequence (e.g., where an alignment indicates that the query sequence and the subject sequence [or a subsequence of the subject sequence] are at least about 30%, 40%, 50%, 60%, 70%, 80%, or 90% identical), and (2) if the query amino acid position directly aligns with (directly lines up against) the subject amino acid position in the alignment of (1). In general, one can align a query amino acid sequence with a subject sequence (SEQ ID NO:62 or a subsequence of SEQ ID NO:62) using any alignment algorithm, tool and/or software described disclosed herein (e.g., BLASTP, ClustalW, ClustalV, Clustal-Omega, EMBOSS) to determine percent identity. Just for further example, one can align a query sequence with a subject sequence herein using the Needleman-Wunsch algorithm (Needleman and Wunsch, *J. Mol. Biol.* 48:443-453, 1970) as implemented in the Needle program of the European Molecular Biology Open Software Suite (EMBOSS [e.g., version 5.0.0 or later], Rice et al., *Trends Genet.* 16:276-277, 2000). The parameters of such an EMBOSS alignment can comprise, for example: gap open penalty of 10, gap extension penalty of 0.5, EBLOSUM62 (EMBOSS version of BLOSUM62) substitution matrix.

The numbering of particular amino acid residues of SEQ ID NO:62 herein (e.g., Leu-373, Leu-428, Ala-472, Ala-510, Leu-513, Met-529, Gln-588, Phe-607, Asn-613, Gln-616, Ser-631, Gly-633, Phe-634, Ser-710, Thr-635, Arg-722, Arg-741, Thr-877, Asp-948, Phe-951, Gln-957, Val-1188, Met-1253) is with respect to the full-length amino acid sequence of SEQ ID NO:62. The first amino acid (i.e., position 1, Met-1) of SEQ ID NO:62 is at the start of the signal peptide. Unless otherwise disclosed, substitutions herein are with respect to the full-length amino acid sequence of SEQ ID NO:62.

A "non-native glucosyltransferase" herein ("mutant", "variant", "modified" and like terms can likewise be used to describe such a glucosyltransferase) has at least one amino acid substitution at a position corresponding with a particular amino acid residue of SEQ ID NO:62. Such at least one amino acid substitution typically is in place of the amino acid residue(s) that normally (natively) occurs at the same position in the native counterpart (parent) of the non-native glucosyltransferase (i.e., although SEQ ID NO:62 is used as a reference for position, an amino acid substitution herein is with respect to the native counterpart of a non-native glucosyltransferase) (considered another way, when aligning the sequence of a non-native glucosyltransferase with SEQ ID NO:62, determining whether a substitution exists at a particular position does not depend in-and-of-itself on the respective amino acid residue in SEQ ID NO:62, but rather depends on what amino acid exists at the subject position within the native counterpart of the non-native glucosyltransferase). The amino acid normally occurring at the relevant site in the native counterpart glucosyltransferase often (but not always) is the same as (or conserved with) the particular amino acid residue of SEQ ID NO:62 for which the alignment is made. A non-native glucosyltransferase optionally can have other amino acid changes (mutations, deletions, and/or insertions) relative to its native counterpart sequence.

It may be instructive to illustrate a substitution/alignment herein. SEQ ID NO:12 (GTF 0544) is a truncated form of a *Streptococcus sobrinus* glucosyltransferase. It is noted that Leu-193 of SEQ ID NO:12 corresponds with Leu-373 of SEQ ID NO:62 (alignment not shown). If SEQ ID NO:12 is mutated at position 193 to substitute the Leu residue with a different residue (e.g., Gln), then it can be stated that the position 193-mutated version of SEQ ID NO:12 represents a non-native glucosyltransferase having an amino acid substitution at a position corresponding with Leu-373 of SEQ ID NO:62, for example.

The term "isolated" means a substance (or process) in a form or environment that does not occur in nature. Non-limiting examples of isolated substances include (1) any non-naturally occurring substance (e.g., a non-native glucosyltransferase herein), (2) any substance including, but not limited to, any host cell, enzyme, variant, nucleic acid, protein, peptide, cofactor, or carbohydrate/saccharide that is at least partially removed from one or more or all of the naturally occurring constituents with which it is associated in nature; (3) any substance modified by the hand of man relative to that substance found in nature (e.g., a non-native glucosyltransferase herein); or (4) any substance modified by increasing the amount of the substance relative to other components with which it is naturally associated. It is believed that the embodiments (e.g., enzymes and reaction compositions) disclosed herein are synthetic/man-made, and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

While advances have been made in producing glucan polymers using glucosyltransferase enzymes, less attention appears to have been drawn to improving the glucan yields of such enzymes. Addressing this technological gap, disclosed herein are glucosyltransferases engineered to have modified amino acid sequences endowing these enzymes with enhanced glucan production properties.

Certain embodiments of the present disclosure concern a non-native glucosyltransferase comprising at least two or three amino acid substitutions at positions corresponding with amino acid residues Gln-588, Phe-607, and/or Arg-741 of SEQ ID NO:62, wherein the non-native glucosyltransferase synthesizes alpha-glucan comprising 1,3-linkages, and wherein the non-native glucosyltransferase has:

(i) an alpha-glucan yield that is higher than the alpha-glucan yield of a second glucosyltransferase that only differs from the non-native glucosyltransferase at the substitution position(s), and/or (ii) a leucrose yield that is lower than the leucrose yield of the second glucosyltransferase.

Thus, in general, mutant glucosyltransferase enzymes are disclosed herein that can synthesize higher amounts of alpha-glucan, and/or lower yields of leucrose, which is a by-product often considered undesirable when the main goal is alpha-glucan synthesis.

A non-native glucosyltransferase herein synthesizes alpha-glucan comprising 1,3-linkages. In some aspects, at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% of the glycosidic linkages of such an alpha-glucan can be alpha-1,3 linkages. The linkage profile of an alpha-glucan can optionally be characterized as having a range between any two of these values. The other linkages in any of these aspects having 30%-99% alpha-1,3 linkages can be alpha-1,6, and/or not include any alpha-1,4 or alpha-1,2 linkages, for example.

Alpha-glucan in some aspects can have, for example, less than 10%, 9%, 8%, 7%, 6%, 5%, 4%, 3%, 2%, 1%, or 0.5% of alpha-1,2 or alpha-1,4 glycosidic linkages. In another embodiment, an alpha-glucan only has alpha-1,3 and optionally alpha-1,6 linkages (i.e., no alpha-1,2 or alpha-1,4 linkages).

Alpha-glucan in some aspects can be linear/unbranched (no branch points). Alternatively, there can be branches in an alpha-glucan herein. For example, an alpha-glucan can have less than about 10%, 9%, 8%, 7%, 6%, 5%, 4%, 3%, 2%, or 1% branch points as a percent of the linkages in the polymer.

In certain aspects, an alpha-glucan can have a molecular weight in $DP_w$ or $DP_n$ of at least about 100. For example, the $DP_w$ or $DP_n$ can be about, or at least about, 100, 150, 200, 250, 300, 350, 400, 450, 500, 550, 600, 650, 700, 750, 800, 850, 900, 950, 1000, 1100, or 1200. The molecular weight of an alpha-glucan can optionally be expressed as a range between any two of these values (e.g., 100-1200, 400-1200, 700-1200, 100-1000, 400-1000, 700-1000).

An alpha-glucan produced by a non-native glucosyltransferase herein typically is water-insoluble. Alpha-1,3-glucan is generally insoluble at a $DP_w$ of 8 or 9 and above in neutral (e.g., pH 6-8) aqueous conditions.

Any of the foregoing linkage profiles and/or molecular weight profiles, for example, can be combined herein to appropriately characterize an alpha-glucan product of a non-native glucosyltransferase of the present disclosure. In some aspects, the linkage and/or molecular weight profile of an alpha-glucan product can be as disclosed in any of the following publications, all of which are incorporated herein by reference: U.S. Pat. Nos. 7,000,000 and 8,871,474, U.S. Patent Appl. Publ. No. 2015/0232819.

A non-native glucosyltransferase, for example, can comprise the amino acid sequence of any glucosyltransferase disclosed in the following publications that is capable of producing alpha-glucan as presently disclosed, but with the exception that the non-native glucosyltransferase comprises at least two of, or all three of, amino acid substitutions at positions corresponding with amino acid residues Gln-588, Phe-607, and/or Arg-741 of SEQ ID NO:62: U.S. Pat. Nos. 7,000,000 and 8,871,474; and U.S. Patent Appl. Publ. Nos. 2015/0232819 and 2017/0002335, all of which are incorporated herein by reference. In some aspects, such a non-native glucosyltransferase (i) comprises the foregoing substitutions, and (ii) comprises an amino acid sequence that is at least about 90%, 91%, 92%, 93%, 94%, 95%, 96%, 97%, 98%, 99%, or 99.5% identical to the amino acid sequence of the respective counterpart/parent glucosyltransferase not having the foregoing substitutions.

In some aspects, a non-native glucosyltransferase (i) comprises at least two of, or all three of, amino acid substitutions at positions corresponding with amino acid residues Gln-588, Phe-607, and/or Arg-741 of SEQ ID NO:62, and (ii) comprises or consists of an amino acid sequence that is at least about 90%, 91%, 92%, 93%, 94%, 95%, 96%, 97%, 98%, 99%, or 99.5% identical to SEQ ID NO:2, 4, 6, 8, 10, 12, 14, 16, 18, 20, 26, 28, 30, 34, or 59. Certain information regarding alpha-glucan products of glucosyltransferases with most of these amino acid sequences is provided in Table 2.

TABLE 2

GTF Enzymes and Related Alpha-Glucan Products[a]

| GTF ID | SEQ ID NO. | Reducing Sugars | Insoluble Product | % alpha-1,3 | % alpha-1,6 | $DP_n$ |
|---|---|---|---|---|---|---|
| 0874 | 2 | yes | yes | 100 | 0 | 60 |
| 6855 | 4 | yes | yes | 100 | 0 | 440 |
| 2379 | 6 | yes | yes | 37 | 63 | 310 |
| 7527 | 8 | yes | yes | 100 | 0 | 440 |
| 1724 | 10 | yes | yes | 100 | 0 | 250 |
| 0544 | 12 | yes | yes | 62 | 36 | 980 |
| 5926 | 14 | yes | yes | 100 | 0 | 260 |
| 4297 | 16 | yes | yes | 31 | 67 | 800 |
| 5618 | 18 | yes | yes | 34 | 66 | 1020 |
| 2765 | 20 | yes | yes | 100 | 0 | 280 |
| 0427 | 26 | yes | yes | 100 | 0 | 120 |
| 2919 | 28 | yes | yes | 100 | 0 | 250 |
| 2678 | 30 | yes | yes | 100 | 0 | 390 |
| 3929 | 34 | yes | yes | 100 | 0 | 280 |

[a]GTF reactions and product analyses were performed as follows. Reactions were prepared comprising sucrose (50 g/L), potassium phosphate buffer (pH 6.5, 20 mM) and a GTF enzyme (2.5% bacterial cell extract by volume; extracts prepared according to U.S. application Pub. No. 2017/0002335, in a manner similar to procedure disclosed in U.S. Pat. No. 8,871,474). After 24-30 hours at 22-25° C., insoluble product was harvested by centrifugation, washed three times with water, washed once with ethanol, and dried at 50° C. for 24-30 hours. Approximate linkages and $DP_n$ are shown for each insoluble product. Linkages and $DP_n$ were determined by $^{13}C$ NMR and SEC, respectively.

In some aspects, a non-native glucosyltransferase (i) comprises at least two of, or all three of, amino acid substitutions at positions corresponding with amino acid residues Gln-588, Phe-607 and/or Arg-741 of SEQ ID NO:62, and (ii) comprises or consists of a glucosyltransferase catalytic domain that is at least about 90%, 91%, 92%, 93%, 94%, 95%, 96%, 97%, 98%, 99%, or 99.5% identical to amino acid residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20. Such a non-native glucosyltransferase, for instance, is believed to be able to produce alpha-glucan that is water-insoluble and comprise at least about 50% (e.g., 90% or 95%) alpha-1,3 linkages, and optionally further have a $DP_w$ of at least 100. It is noted that a glucosyltransferase with amino acid positions 54-957 of SEQ ID NO:65 can produce alpha-1,3-glucan with 100% alpha-1,3 linkages and a $DP_w$ of at least 400 (data not shown, refer to Table 6 of U.S. Pat. Appl. Publ. No. 2017/0002335, which is incorporated herein by reference), for example. It is further noted that SEQ ID NOs:65 (GTF 7527), 30 (GTF 2678), 4 (GTF 6855), 28 (GTF 2919), and 20 (GTF 2765) each represent a glucosyltransferase that, compared to its respective wild type counterpart, lacks the signal peptide domain and all or a substantial portion of the variable domain. Thus, each of these glucosyltransferase enzymes has a catalytic domain followed by a glucan-binding domain. The approximate location of catalytic domain sequences in these enzymes is as follows: 7527 (residues 54-957 of SEQ ID NO:65), 2678 (residues 55-960 of SEQ ID NO:30), 6855 (residues 55-960 of SEQ ID NO:4), 2919 (residues 55-960 of SEQ ID NO:28), 2765 (residues 55-960 of SEQ ID NO:20). The amino acid sequences of the catalytic domains (approx.) of GTFs 2678, 6855, 2919 and 2765 have about 94.9%, 99.0%, 95.5% and 96.4% identity, respectively, with the approximate catalytic domain sequence of GTF 7527 (i.e., amino acids 54-957 of SEQ ID NO:65). Each of these particular glucosyltransferases (GTFs 2678, 6855, 2919 and 2765) can produce alpha-1,3-glucan with 100% alpha-1,3 linkages and a $DP_w$ of at least 400 (data not shown, refer to Table 4 of U.S. Pat. Appl. Publ. No. 2017/0002335). Based on this activity, and the relatedness (high percent identity) of the foregoing catalytic domains, it is contemplated that a non-native glucosyltransferase herein having one of the foregoing catalytic domains further with an amino acid substitution combination as presently disclosed can produce alpha-glucan comprising at least about 50% (e.g., 90% or 95%) alpha-1,3 linkages and a $DP_w$ of at least 100.

In some aspects, a non-native glucosyltransferase (i) comprises at least two of, or all three of, amino acid substitutions at positions corresponding with amino acid residues Gln-588, Phe-607 and/or Arg-741 of SEQ ID NO:62, and (ii) comprises or consists of an amino acid sequence that is at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:62 or a subsequence thereof such as SEQ ID NO:4 (without start methionine thereof) or positions 55-960 of SEQ ID NO:4 (approximate catalytic domain).

Although it is believed that a non-native glucosyltransferase in certain aspects need only have a catalytic domain, the non-native glucosyltransferase can be comprised within a larger amino acid sequence. For example, a catalytic domain may be linked at its C-terminus to a glucan-binding domain, and/or linked at its N-terminus to a variable domain and/or signal peptide.

Although amino acid substitutions in a non-native glucosyltransferase are generally disclosed herein with respect to the corresponding positions in SEQ ID NO:62, such substitutions can alternatively be stated simply with respect to its position number in the sequence of the non-native glucosyltransferase itself, as convenience may dictate.

Still further examples of non-native glucosyltransferases can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example. A non-native glucosyltransferase herein typically lacks an N-terminal signal peptide; such an enzyme can optionally be characterized as being mature if its signal peptide was removed during a secretion process.

A non-native glucosyltransferase herein can be derived from any microbial source, for example, such as bacteria. Examples of bacterial glucosyltransferases are those derived from a *Streptococcus* species, *Leuconostoc* species, or *Lactobacillus* species. Examples of *Streptococcus* species include *S. salivarius*, *S. sobrinus*, *S. dentirousetti*, *S. downei*, *S. mutans*, *S. oralis*, *S. gallolyticus* and *S. sanguinis*. Examples of *Leuconostoc* species include *L. mesenteroides*, *L. amelibiosum*, *L. argentinum*, *L. carnosum*, *L. citreum*, *L. cremoris*, *L. dextranicum* and *L. fructosum*. Examples of *Lactobacillus* species include *L. acidophilus*, *L. delbrueckii*, *L. helveticus*, *L. salivarius*, *L. casei*, *L. curvatus*, *L. plantarum*, *L. sakei*, *L. brevis*, *L. buchneri*, *L. fermentum* and *L. reuteri*.

A non-native glucosyltransferase herein can be prepared by fermentation of an appropriately engineered microbial strain, for example. Recombinant enzyme production by fermentation is well known in the art using microbial species such as *E. coli*, *Bacillus* strains (e.g., *B. subtilis*), *Ralstonia eutropha*, *Pseudomonas fluorescens*, *Saccharomyces cerevisiae*, *Pichia pastoris*, *Hansenula polymorpha*, and species of *Aspergillus* (e.g., *A. awamori*) and *Trichoderma* (e.g., *T. reesei*) (e.g., see Adrio and Demain, *Biomolecules* 4:117-139, 2014, which is incorporated herein by reference). A nucleotide sequence encoding a non-native glucosyltransferase amino acid sequence is typically linked to a heterologous promoter sequence to create an expression cassette for the enzyme, and/or is codon-optimized accordingly. Such an expression cassette may be incorporated in a suitable plasmid or integrated into the microbial host chromosome, using methods well known in the art. The expression cassette may include a transcriptional terminator nucleotide sequence following the amino acid coding sequence. The expression cassette may also include, between the promoter sequence and glucosyltransferase amino acid coding sequence, a nucleotide sequence encoding a signal peptide (e.g., heterologous signal peptide) that is designed for direct secretion of the glucosyltransferase enzyme. At the end of fermentation, cells may be ruptured accordingly (generally when a signal peptide for secretion is not employed) and the glucosyltransferase enzyme can be isolated using methods such as precipitation, filtration, and/or concentration. Alternatively, a lysate or extract comprising a glucosyltransferase can be used without further isolation. If the glucosyltransferase was secreted (i.e., it is present in the fermentation broth), it can optionally be used as isolated from, or as comprised in, the fermentation broth. The activity of a glucosyltransferase enzyme can be confirmed by biochemical assay, such as measuring its conversion of sucrose to glucan polymer.

A non-native glucosyltransferase herein can comprise amino acid substitutions at positions corresponding with at least two of, or all three of, amino acid residues Gln-588, Phe-607 and/or Arg-741 of SEQ ID NO:62. In some aspects, the amino acid substitution at a position corresponding with amino acid Gln-588 of SEQ ID NO:62 can be with a Leu, Ala, or Val residue. In some aspects, the amino acid substitution at a position corresponding with amino acid Phe-607 of SEQ ID NO:62 can be with a Trp, Tyr, or Asn residue. In some aspects, the amino acid substitution at a position corresponding with amino acid Arg-741 of SEQ ID NO:62 can be with a Ser or Thr residue. Examples of a non-native glucosyltransferase herein comprise at least: (A) Gln-588-Ala, Phe-607-Tyr and Arg-741-Ser substitutions; (B) Gln-588-Leu, Phe-607-Trp and Arg-741-Ser substitutions; or (C) Gln-588-Leu, Phe-607-Tyr and Arg-741-Thr substitutions. In some aspects, a non-native glucosyltransferase herein can comprise amino acid substitutions at positions corresponding with amino acid residues (i) Gln-588 and Phe-607, (ii) Gln-588 and Arg-741, or (iii) Phe-607 and Arg-741 of SEQ ID NO:62.

A non-native glucosyltransferase herein can comprise, in addition to the foregoing two or three amino acid substitutions, one, two, three, four, five, six, seven, eight, nine, or more of the disclosed amino acid substitutions, for instance. For example, a non-native glucosyltransferase can further comprise at least one amino acid substitution at a position corresponding with amino acid residue Ala-510 and/or Asp-948 of SEQ ID NO:62. In some aspects, the amino acid substitution at a position corresponding with amino acid Ala-510 of SEQ ID NO:62 can be with an Asp, Glu, Ile, or Val residue. In some aspects, the amino acid substitution at a position corresponding with amino acid Asp-948 of SEQ ID NO:62 can be with a Gly, Val, or Ala residue. Examples of a non-native glucosyltransferase herein comprise at least: (D) Ala-510-Glu and Asp-948-Val substitutions; (E) an Asp-948-Ala substitution; or (F) Ala-510-Asp and Asp-948-Gly substitutions, (in addition to any of the foregoing substitution combinations of A, B, or C, for example).

In another example, a non-native glucosyltransferase can further comprise at least one amino acid substitution at a position corresponding with amino acid residue Ser-631, Ser-710, Arg-722, and/or Thr-877 of SEQ ID NO:62. In some aspects, the amino acid substitution at a position corresponding with amino acid Ser-631 of SEQ ID NO:62 can be with a Thr, Asp, Glu, or Arg residue. In some aspects, the amino acid substitution at a position corresponding with amino acid Ser-710 of SEQ ID NO:62 can be with a Gly, Ala, or Val residue. In some aspects, the amino acid substitution at a position corresponding with amino acid Arg-722 of SEQ ID NO:62 can be with a His or Lys residue. In some aspects, the amino acid substitution at a position corresponding with amino acid Thr-877 of SEQ ID NO:62 can be with a Lys, His, or Arg residue. Examples of a non-native glucosyltransferase herein comprise at least: (G) Ser-631-Thr, Ser-710-Gly, Arg-722-His and Thr-877-Lys substitutions; (H) Ser-710-Ala, Arg-722-Lys and Thr-877-Lys substitutions; or (I) Ser-631-Ser, Ser-710-Gly, and Thr-877-Arg substitutions, (in addition to any of the foregoing substitution combinations of [i] A, B, or C; or [ii] A, B, or C with D, E, or F).

In another example, a non-native glucosyltransferase can further comprise at least one amino acid substitution at a position corresponding with amino acid residue Val-1188, Met-1253, and/or Gln-957 of SEQ ID NO:62. In some aspects, the amino acid substitution at a position corresponding with amino acid Val-1188 of SEQ ID NO:62 can be with a Glu or Asp residue. In some aspects, the amino acid substitution at a position corresponding with amino acid Met-1253 of SEQ ID NO:62 can be with an Ile, Leu, Ala, or Val residue. In some aspects, the amino acid substitution at a position corresponding with amino acid Gln-957 of SEQ ID NO:62 can be with a Pro residue. Examples of a non-native glucosyltransferase herein comprise at least: (J) a Val-1188-Asp substitution; (K) a Met-1253-Ile substitution; (L) Val-1188-Glu and Met-1253-Ile substitutions; (M) Val-1188-Glu, Met-1253-Ile and Gln-957-Pro substitutions; or (N) a Val-1188-Glu substitution (in addition to any of the foregoing substitution combinations of [i] A, B, or C; [ii] A, B, or C with D, E, or F; [iii] A, B, or C with G, H, or I; [iv] A, B, or C with one of D, E, or F, and one of G, H, or I).

Other suitable substitutions that can be in addition to those listed above, for example, include those as listed in Table 3 in Example 1 (below) that are associated with (i) a decrease in leucrose production by at least about 5%, 10%, 15%, 20%, 25%, 30%, 35%, 40%, 45%, 50%, 55%, 60%, 65%, 70%, 75%, 80%, 85%, 90%, or 95%, and/or (ii) an increase in glucan yield by at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, or 150%. In some aspects, suitable additional substitutions include those as listed in Table 3 in Example 1 (below) that are associated with a decrease in glucose production by at least about 5%, 10%, 15%, 20%, 25%, 30%, 35%, 40%, 45%, 50%, 55%, 60%, 65%, 70%, 75%, or 80%. In some aspects, suitable additional substitutions include those as listed in Table 3 in Example 1 (below) that are associated with a decrease in gluco-oligosaccharide (oligomer) production by at least about 5%, 10%, 15%, 20%, 25%, 30%, 35%, 40%, 45%, 50%, 55%, 60%, or 65%. The foregoing substitutions as listed in Table 3 are as they correspond with the listed residue position number in SEQ ID NO:62. In some aspects, one or more substitutions are conserved or non-conserved substitutions; such conservation (or not) can be, for instance, with respect to the amino acid that occurs in the native glucosyltransferase from which the non-native glucosyltransferase is derived.

Simply for illustration purposes, a non-native glucosyltransferase herein can comprise a combination of amino acid substitutions at positions as follows (i-xix), where each substitution position corresponds with the respective amino acid position number of SEQ ID NO:62:

(i) A510, Q588, F607, R741, D948, R722, T877, M1253 and K1277;
(ii) A510, Q588, F607, R741, D948, R722, T877, V1188, M1253 and Q957;
(iii) A510, Q588, F607, R741, D948, T877, V1188, M1253 and Q957;
(iv) A510, Q588, F607, R741, D948 and M1253;
(v) A510, Q588, F607, R741 and D948;
(vi) Q588, F607, R741 and D948;
(vii) A510, Q588, F607, R741, D948, N628, T635, T877, M1253, F929 and R1172;
(viii) A510, Q588, F607, R741, D948, S631, S710, R722, T877, V1188 and M1253;
(ix) A510, Q588, F607, R741, D948, S631, S710, R722, T877 and V1188;
(x) A510, Q588, F607, R741, D948, S631, S710, T877, V1188 and M1253;
(xi) A510, Q588, F607, R741 and D948;
(xii) A510, Q588, F607, R741, D948 and V1188;
(xiii) A510, Q588, F607, R741, D948, S631, S710 and V1188;
(xiv) A510, Q588, F607, R741, D948, S710, R722, T877 and M1253;
(xv) A510, Q588, F607, R741, D948, S631, R722, T877, V1188 and M1253;
(xvi) A510, Q588, F607, R741, D948, S631, T877, V1188 and M1253;
(xvii) A510, Q588, F607, R741, D948, S631 and V1188;
(xviii) A510, Q588, F607, R741, D948, S631, R722, T877, V1188 and M1253; or
(xix) A510, Q588, F607, R741, D948, V1188 and M1253, Some particular examples of embodiments i-xix are disclosed in Example 4 below (Table 7). Thus, a non-native glucosyltransferase in some aspects can comprise one of the following combinations of substitutions (xx-xxxviii), where each substitution corresponds with the respective amino acid residue of SEQ ID NO:62:

(xx) A510D/Q588L/F607Y/R741S/D948G/R722H/T877K/M1253I/K1277N,
(xxi) A510D/Q588L/F607Y/R741S/D948G/R722H/T877K/V1188E/M1253I/Q957P,
(xxii) A510D/Q588L/F607Y/R741S/D948G/T877K/V1188E/M1253I/Q957P,
(xxiii) A510D/Q588L/F607Y/R741S/D948G/M1253I,
(xxiv) A510D/Q588L/F607W/R741S/D948G,
(xxv) Q588L/F607Y/R741S/D948G,
(xxvi) A510D/Q588L/F607Y/R741S/D948G/N628D/T635A/T877K/M1253I/F929L/R11720,
(xxvii) A510D/Q588L/F607W/R741S/D948G/S631T/S710G/R722H/T877K/V1188E/M1253I,
(xxviii) A510D/Q588L/F607W/R741S/D948G/S631T/S710G/R722H/T877K/V1188E,
(xxix) A510D/Q588L/F607W/R741S/D948G/S631T/S710G/T877KA/1188E/M1253I,
(xxx) A510D/Q588L/F607Y/R741S/D948G,
(xxxi) A510D/Q588L/F607Y/R741S/D948GA/1188E,
(xxxii) A510D/Q588L/F607W/R741S/D948G/S631T/S710G/V1188E,
(xxxiii) A510D/Q588L/F607W/R741S/D948G/S710G/R722H/T877K/M1253I,
(xxxiv) A510D/Q588L/F607Y/R741S/D948G/S631T/R722H/T877K/V1188E/M1253I,
(xxxv) A510D/Q588L/F607W/R741S/D948G/S631T/T877K/V1188E/M1253I,
(xxxvi) A510D/Q588L/F607W/R741S/D948G/S631T/V1188E,
(xxxvii) A510D/Q588L/F607Y/R741S/D948G/S631T/R722H/T877K/V1188E/M1253I, or
(xxxviii) A510D/Q588L/F607W/R741S/D948G/V1188E/M1253I.

A non-native glucosyltransferase with a combination of amino acid substitutions herein can be based on any of a variety of glucosyltransferase amino acid sequences as presently disclosed, for example. Simply for illustration purposes, examples of such a non-native glucosyltransferase include those with a combination of amino acid substitutions as described herein (e.g., any of embodiments i-xxxviii above) and comprising or consisting of an amino acid sequence that is at least about 90%, 91%, 92%, 93%, 94%, 95%, 96%, 97%, 98%, 99%, or 99.5% identical to SEQ ID NO:65 (optionally without the start methionine of SEQ ID NO:65) or residues 54-957 of SEQ ID NO:65, SEQ ID NO:30 (optionally without the start methionine of SEQ ID NO:30) or residues 55-960 of SEQ ID NO:30, SEQ ID NO:4 (optionally without the start methionine of SEQ ID NO:4) or residues 55-960 of SEQ ID NO:4, SEQ ID NO:28 (optionally without the start methionine of SEQ ID NO:28) or residues 55-960 of SEQ ID NO:28, or SEQ ID NO:20 (optionally without the start methionine of SEQ ID NO:20) or residues 55-960 of SEQ ID NO:20.

A non-native glucosyltransferase herein can have (i) an alpha-glucan yield that is higher than the alpha-glucan yield of a second glucosyltransferase (or, simply, "another" glucosyltransferase) (e.g., parent glucosyltransferase) that only differs from the non-native glucosyltransferase at the substitution positions, and/or (ii) a leucrose yield that is lower than the leucrose yield of the second glucosyltransferase. A second glucosyltransferase herein, for example, can be comprised of all of, or mostly, native amino acid sequence. Thus, while a second glucosyltransferase herein can be a native glucosyltransferase in some aspects, it can be a prior-modified glucosyltransferase in other aspects (e.g., a glucosyltransferase with one or more other amino acid substitutions differing from the substitution[s] of the present disclosure). In some embodiments, a second glucosyltransferase to which a non-native glucosyltransferase is compared has native amino acid residues at the substitution positions. Determining whether an amino acid residue is native can be done by comparing the second glucosyltransferase amino acid sequence to the native/wild type glucosyltransferase amino acid sequence from which the second glucosyltransferase is derived. Optionally, a non-native glucosyltransferase in some embodiments can be characterized as having higher selectivity toward alpha-glucan synthesis (as compared to by-product synthesis).

In some aspects, a non-native glucosyltransferase herein can have an alpha-glucan yield that is at least about 5%, 10%, 20%, 40%, 60%, 80%, 100%, 120%, 140%, 160%, 180%, 200%, 220%, 240%, 260%, 280%, 300%, 320%, 340%, 360%, or 380% higher than the alpha-glucan yield of a second glucosyltransferase as presently disclosed. In some additional or alternative embodiments, a non-native glucosyltransferase can have a decrease in leucrose yield by at least about 5%, 10%, 15%, 20%, 25%, 30%, 35%, 40%, 45%, 50%, 55%, 60%, 65%, 70%, 75%, 80%, 85%, 90%, or 95% compared to the leucrose yield of a second glucosyltransferase. These determinations (alpha-glucan and/or leucrose yield) can be made with respect to any glucan synthesis reaction/process as disclosed herein (e.g., taking into account initial sucrose conc., temperature, pH, and/or reaction time), and using any suitable measurement technique (e.g., HPLC or NIR spectroscopy). Typically, a comparison between non-native and second glucosyltransferases herein can be made under identical or similar reaction conditions. The yield of a glucosyltransferase reaction in some aspects can be measured based on the glucosyl component of the reaction.

In some embodiments, a non-native glucosyltransferase can exhibit a decrease in the yield of soluble gluco-oligosaccharides by at least about 5%, 10%, 15%, 20%, 25%, 30%, 35%, 40%, 45%, 50%, 55%, 60%, 65%, 70%, or 75% compared to the soluble gluco-oligosaccharide yield of a second glucosyltransferase. A soluble gluco-oligosaccharide in some aspects can be DP2-7 or DP2-8, and have any linkage profile disclosed herein. In some aspects, the DP is or up to 10, 15, 20, or 25, but with a linkage profile allowing solubility (e.g., not over 90% or 95% alpha-1,3).

In some embodiments, a non-native glucosyltransferase can exhibit a decrease in the yield of glucose by at least about 5%, 10%, 15%, 20%, 25%, 30%, 35%, 40%, 45%, 50%, 55%, 60%, 65%, 70%, 75%, or 80% compared to the glucose yield of a second glucosyltransferase.

Some embodiments disclosed herein concern a polynucleotide comprising a nucleotide sequence that encodes a non-native glucosyltransferase as presently disclosed. Optionally, one or more regulatory sequences are operably linked to the nucleotide sequence, and preferably a promoter sequence is included as a regulatory sequence.

A polynucleotide comprising a nucleotide sequence encoding a non-native glucosyltransferase herein can be a vector or construct useful for transferring a nucleotide sequence into a cell, for example. Examples of a suitable vector/construct can be selected from a plasmid, yeast artificial chromosome (YAC), cosmid, phagemid, bacterial artificial chromosome (BAC), virus, or linear DNA (e.g., linear PCR product). A polynucleotide sequence in some aspects can be capable of existing transiently (i.e., not integrated into the genome) or stably (i.e., integrated into the genome) in a cell. A polynucleotide sequence in some aspects can comprise, or lack, one or more suitable marker sequences (e.g., selection or phenotype marker).

A polynucleotide sequence in certain embodiments can comprise one or more regulatory sequences operably linked to the nucleotide sequence encoding a non-native glucosyltransferase. For example, a nucleotide sequence encoding a non-native glucosyltransferase may be in operable linkage with a promoter sequence (e.g., a heterologous promoter). A promoter sequence can be suitable for expression in a cell (e.g., bacterial cell such as *E. coli* or *Bacillus*; eukaryotic cell such as a fungus, yeast, insect, or mammalian cell) or in an in vitro protein expression system, for example. Examples of other suitable regulatory sequences include transcription terminator sequences.

Some aspects herein are drawn to a cell comprising a polynucleotide sequence as presently disclosed; such a cell can be any type disclosed herein (e.g., bacterial cell such as *E. coli* or *Bacillus*; eukaryotic cell such as a fungus, yeast, insect, or mammalian cell). A cell can optionally express a non-native glucosyltransferase encoded by the polynucleotide sequence. In some aspects, the polynucleotide sequence exists transiently (i.e., not integrated into the genome) or stably (i.e., integrated into the genome) in the cell.

Some embodiments disclosed herein concern reaction compositions comprising water, sucrose, and one or more non-native glucosyltransferases herein. Such a reaction composition produces, at least, alpha-glucan comprising 1,3-linkages as disclosed.

The temperature of a reaction composition herein can be controlled, if desired, and can be about 5-50° C., 20-40° C., 30-40° C., 20-30° C., 20-25° C., 20° C., 25° C., 30° C., 35° C., or 40° C., for example.

The initial concentration of sucrose in a reaction composition herein can be about 20-400 g/L, 75-175 g/L, or 50-150 g/L, for example. In some aspects, the initial sucrose concentration is at least about 50, 75, 100, 150 or 200 g/L, or is about 50-600 g/L, 100-500 g/L, 50-100 g/L, 100-200 g/L, 150-450 g/L, 200-450 g/L, or 250-600 g/L. "Initial concentration of sucrose" refers to the sucrose concentration in a reaction composition just after all the reaction components have been added/combined (e.g., at least water, sucrose, non-native glucosyltransferase enzyme).

The pH of a reaction composition in certain embodiments can be about 4.0-9.0, 4.0-8.5, 4.0-8.0, 5.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. The buffer concentration in a reaction composition herein can be about 0.1-300 mM, 0.1-100 mM, 10-100 mM, 10 mM, 20 mM, or 50 mM, for example.

A reaction composition can be contained within any vessel (e.g., an inert vessel/container) suitable for applying one or more of the reaction conditions disclosed herein. An inert vessel in some aspects can be of stainless steel, plastic, or glass (or comprise two or more of these components) and be of a size suitable to contain a particular reaction. For example, the volume/capacity of an inert vessel (and/or the volume of a reaction composition herein), can be about, or at least about, 1, 10, 50, 100, 500, 1000, 2500, 5000, 10000, 12500, 15000, or 20000 liters. An inert vessel can optionally be equipped with a stirring device.

A reaction composition herein can contain one, two, or more glucosyltransferase enzymes, for example, just as long that at least one of the enzymes is a non-native glucosyltransferase as presently disclosed. In some embodiments, only one or two glucosyltransferase enzymes is/are comprised in a reaction composition. A glucosyltransferase reaction herein can be, and typically is, cell-free (e.g., no whole cells present).

Any of the features disclosed herein (e.g., above and in the below Examples) regarding a reaction composition can characterize appropriate aspects of a glucan production method herein, and vice versa.

The present disclosure also concerns a method for producing alpha-glucan, the method comprising: (a) contacting at least water, sucrose, and at least one non-native glucosyltransferase as disclosed herein that produces an alpha-glucan, whereby alpha-glucan is produced; and b) optionally, isolating the alpha-glucan produced in step (a). Conducting such a method, which can optionally be characterized as a glucan synthesis method, is typically also performed when conducting a reaction composition herein.

A glucan synthesis method as presently disclosed comprises contacting at least water, sucrose, and a non-native glucosyltransferase herein that produces an alpha-glucan. These and optionally other reagents can be added altogether or in any order as discussed below. This step can optionally be characterized as providing a reaction composition comprising water, sucrose and a non-native glucosyltransferase enzyme that synthesizes alpha-glucan. The contacting step herein can be performed in any number of ways. For example, the desired amount of sucrose can first be dissolved in water (optionally, other components may also be added at this stage of preparation, such as buffer components), followed by addition of glucosyltransferase enzyme. The solution may be kept still, or agitated via stirring or orbital shaking, for example. A glucan synthesis method can be performed by batch, fed-batch, continuous mode, or by any variation of these modes.

Completion of a reaction in certain embodiments can be determined visually (e.g., no more accumulation of insoluble glucan), and/or by measuring the amount of sucrose left in the solution (residual sucrose), where a percent sucrose consumption of at least about 90%, 95%, or 99% can indicate reaction completion. A reaction of the disclosed process can be conducted for about 1 hour to about 2, 4, 6, 8, 10, 12, 14, 16, 18, 20, 22, 24, 36, 48, 60, 72, 96, 120, 144, or 168 hours, for example.

The yield of an alpha-glucan produced in some aspects of a glucan synthesis method herein can be at least about 40%, 45%, 50%, 55%, 60%, 65%, 70%, 75%, 80%, 85%, 90%, 91%, 92%, 93%, 94%, 95%, or 96%. Yield in some aspects can be measured based on the glucosyl component of the reaction. In some additional or alternative embodiments, the yield of leucrose can be less than about 18%, 17%, 16%, 15%, 14%, 13%, 12%, 11%, 10%, 9%, 8%, 7%, 6%, 5%, 4%, 3%, 2%, or 1%. Such a yield in alpha-glucan and/or leucrose in some aspects is achieved in a reaction conducted for about 16-24 hours (e.g., ~20 hours), and/or is as measured using HPLC or NIR spectroscopy.

Insoluble alpha-glucan produced in a method herein can optionally be isolated. In certain embodiments, isolating insoluble alpha-glucan can include at least conducting a step of centrifugation and/or filtration. Isolation can optionally further comprise washing alpha-glucan one, two, or more times with water or other aqueous liquid, and/or drying the alpha-glucan product.

An isolated alpha-glucan product herein, as provided in a dry form, can comprise no more than 2.0, 1.5, 1.0, 0.5, 0.25, 0.10, 0.05, or 0.01 wt % water, for example. In some aspects, an alpha-glucan product is provided in an amount of at least 1 gram (e.g., at least about 2.5, 5, 10, 25, 50, 100, 250, 500, 750, 1000, 2500, 5000, 7500, 10000, 25000, 50000, or 100000 g); such an amount can be a dry amount, for example.

A glucan synthesis method in some aspects can further comprise contacting a soluble fraction of the glucosyltransferase reaction, and/or the glucosyltransferase reaction itself, with an alpha-glucosidase enzyme to hydrolyze at least one glycosidic linkage of one or more oligosaccharides present in the soluble fraction and/or glucosyltransferase reaction, thereby increasing the monosaccharide content in the soluble fraction. A soluble fraction herein can be contacted with an alpha-glucosidase after its separation from an insoluble fraction comprising alpha-1,3-glucan, or before its separation (e.g., while it is being formed in the reaction, and/or after completion of the reaction) (i.e., in contacting step [a] and/or after separation step [b]). A soluble fraction can be a filtrate or supernatant, for example, of a glucosyltransferase reaction, and is typically obtained following the completion of insoluble alpha-1,3-glucan synthesis. Examples of suitable alpha-glucosidases herein include those comprising an amino acid sequence that (i) is 100% identical to, or at least about 90%, 91%, 92%, 93%, 94%, 95%, 96%, 97%, 98%, or 99% A identical to, any of SEQ ID NOs:68-81, and (ii) has hydrolytic activity toward alpha-1,5 glucosyl-fructose linkages, alpha-1,3 glucosyl-glucose linkages, and/or alpha-1,6 glucosyl-glucose linkages in saccharides.

Any of the disclosed conditions for synthesizing an alpha-glucan, such as the foregoing or those described in the below Examples, can be applied to practicing a reaction composition as presently disclosed (and vice versa), and/or used to characterize features/activity of a non-native glucosyltransferase, accordingly.

The present disclosure also concerns a method of preparing a polynucleotide sequence encoding a non-native glucosyltransferase herein. This method comprises:

(a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes alpha-glucan comprising 1,3-linkages; and (b) modifying the polynucleotide sequence identified in step (a) to substitute at least two or three amino acids of the parent glucosyltransferase at positions corresponding with amino acid residues Gln-588, Phe-607 and/or Arg-741 of SEQ ID NO:62, thereby providing a polynucleotide sequence encoding a non-native glucosyltransferase that has:

(i) an alpha-glucan yield that is higher than the alpha-glucan yield of the parent glucosyltransferase, and/or
(ii) a leucrose yield that is lower than the leucrose yield of the parent glucosyltransferase.

Such a method can optionally further comprise using a polynucleotide prepared in this manner in a method of expressing the non-native glucosyltransferase encoded by the polynucleotide. Such an expression method can follow any heterologous protein expression method as known in the art, for example. The present method of preparing a polynucleotide can optionally alternatively be characterized as a method of increasing the product yield of a glucosyltransferase.

Identification step (a) herein can, in some instances, comprise identifying an amino acid sequence of a parent glucosyltransferase enzyme. A polynucleotide sequence could be determined from this amino acid sequence according to the genetic code (codons), such as the genetic code used in the species from which the parent glucosyltransferase was identified.

Identifying a polynucleotide encoding a parent glucosyltransferase herein can be performed (a) in silico, (b) with a method comprising a nucleic acid hybridization step, (c) with a method comprising a protein sequencing step, and/or (d) with a method comprising a protein binding step, for example.

Regarding in silico detection, the amino acid sequences of candidate parent glucosyltransferase enzymes (and/or nucleotide sequences encoding such glucosyltransferase enzymes) stored in a computer or database (e.g., public databases such as GENBANK, EMBL, REFSEQ, GENEPEPT, SWISS-PROT, PIR, PDB) can be reviewed in silico to identify a glucosyltransferase enzyme comprising an amino acid sequence with a percent sequence identity as described above for a parent glucosyltransferase. Such review could comprise using any means known in the art such as through use of an alignment algorithm or software as described above (e.g., BLASTN, BLASTP, ClustalW, ClustalV, Clustal-Omega, EMBOSS).

Identifying a parent glucosyltransferase as disclosed above can optionally be performed via a method comprising a nucleic acid hybridization step. Such a method can comprise using DNA hybridization (e.g., Southern blot, dot blot), RNA hybridization (e.g., northern blot), or any other method that has a nucleic acid hybridization step (e.g., DNA sequencing, PCR, RT-PCR, all of which may comprise hybridization of an oligonucleotide), for example. A polynucleotide sequence encoding SEQ ID NO:4 or a subsequence thereof (e.g., positions 55-960 of SEQ ID NO:4) can be used as a probe, for example, in such a hybridization. Conditions and parameters for carrying out hybridization methods in general are well known and disclosed, for example, in Sambrook J, Fritsch E F and Maniatis T, *Molecular Cloning: A Laboratory Manual*, Cold Spring Harbor Laboratory: Cold Spring Harbor, N.Y. (1989); Silhavy T J, Bennan M L and Enquist L W, *Experiments with Gene Fusions*, Cold Spring Harbor Laboratory: Cold Spring Harbor, N.Y. (1984); Ausubel F M et al., *Current Protocols in Molecular Biology*, published by Greene Publishing Assoc. and Wiley-Interscience, Hoboken, N.J. (1987); and Innis M A, Gelfand D H, Sninsky J J and White T J (Editors), *PCR Protocols: A Guide to Methods and Applications*, Academic Press, Inc., San Diego, Calif. (1990).

Identifying a parent glucosyltransferase as disclosed above can optionally be performed via a method comprising a protein sequencing step. Such a protein sequencing step can comprise one or more procedures such as N-terminal amino acid analysis, C-terminal amino acid analysis, Edman degradation, or mass spectrometry, for example.

Identifying a parent glucosyltransferase as disclosed above can optionally be performed via a method comprising a protein binding step. Such a protein binding step can be performed using an antibody that binds to a motif or epitope within SEQ ID NO:4 (e.g., within positions 55-960 of SEQ ID NO:4), for example.

A polynucleotide identified in step (a) (i.e., before its modification in step [b]) can, in some aspects, encode a glucosyltransferase comprising an amino acid sequence that is identical to, or at least 90%, 91%, 92%, 93%, 94%, 95%, 96%, 97%, 98%, or 99% identical to, the amino acid sequence of any glucosyltransferase disclosed in Table 1. An alpha-glucan as produced by such a glucosyltransferase can be as disclosed herein, for example.

A method of preparing a polynucleotide sequence encoding a non-native glucosyltransferase herein comprises step (b) of modifying the polynucleotide sequence (encoding a parent glucosyltransferase) identified in step (a). Such modification substitutes at least two or three amino acids of the parent glucosyltransferase at positions corresponding with amino acid residues Gln-588, Phe-607 and/or Arg-741 of SEQ ID NO:62. The non-native glucosyltransferase (encoded by the modified polynucleotide sequence) resulting from such substitutions can be optionally characterized as a "child glucosyltransferase" herein.

A parent glucosyltransferase enzyme herein can comprise an amino acid sequence that is at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:4 (optionally without start methionine thereof) or positions 55-960 of SEQ ID NO:4 (approximate catalytic domain), for example. It is noted simply for reference purposes that SEQ ID NO:4 without its start methionine is a subsequence of SEQ ID NO:62.

A suitable modification of a polynucleotide in step (b) can be made following any DNA manipulation technique known in the art. Modifying step (b) can optionally be performed in silico, followed by synthesis of the polynucleotide sequence encoding a non-native glucosyltransferase. For example, a polynucleotide sequence identified in step (a) can be manipulated in silico using a suitable sequence manipulation program/software (e.g., VECTOR NTI, Life Technologies, Carlsbad, Calif.; DNAStrider; DNASTAR, Madison, Wis.). Following such virtual manipulation, the modified polynucleotide sequence can be artificially synthesized by any suitable technique (e.g., annealing-based connection of oligonucleotides, or any technique disclosed in Hughes et al., *Methods Enzymol.* 498:277-309, which is incorporated herein by reference). It should be appreciated that the foregoing methodology is not believed to necessarily rely on having a pre-existing polynucleotide (encoding a parent glucosyltransferase) in hand.

Modifying step (b) can optionally be performed using a physical copy of a polynucleotide sequence identified in step (a) encoding a parent glucosyltransferase. As an example, such a polynucleotide can serve as a template for amplification using primers designed in a manner such that the amplified product encodes a non-native glucosyltransferase herein (e.g., refer to Innis et al., ibid.).

The amino acid substitutions in this method can be any of those combinations of substitutions as disclosed herein.

Essentially any non-native glucosyltransferase as presently disclosed can be encoded by a polynucleotide as prepared by this method, for instance, and consequently can have the higher alpha-glucan yield and/or lower leucrose yield profiles disclosed herein.

Non-limiting examples of compositions and methods disclosed herein include:

1. A non-native glucosyltransferase comprising at least two or three amino acid substitutions at positions corresponding with amino acid residues Gln-588, Phe-607, and/or Arg-741 of SEQ ID NO:62, wherein the non-native glucosyltransferase synthesizes alpha-glucan comprising 1,3-linkages, and wherein the non-native glucosyltransferase has: (i) an alpha-glucan yield that is higher than the alpha-glucan yield of a second glucosyltransferase that only differs from the non-native glucosyltransferase at the substitution positions, and/or (ii) a leucrose yield that is lower than the leucrose yield of the second glucosyltransferase.

2. The non-native glucosyltransferase of embodiment 1, wherein the glucosyltransferase comprises amino acid substitutions at positions corresponding with amino acid residues Gln-588, Phe-607 and Arg-741 of SEQ ID NO:62.

3. The non-native glucosyltransferase of embodiment 1 or 2, wherein: (i) the amino acid substitution at the position corresponding with amino acid residue Gln-588 is with a Leu, Ala, or Val residue; (ii) the amino acid substitution at the position corresponding with amino acid residue Phe-607 is with a Trp, Tyr, or Asn residue; and/or (iii) the amino acid substitution at the position corresponding with amino acid residue Arg-741 is with a Ser or Thr residue.

4. The non-native glucosyltransferase of embodiment 1, 2, or 3, wherein the glucosyltransferase further comprises at least one amino acid substitution at a position corresponding with amino acid residue Ala-510 and/or Asp-948 of SEQ ID NO:62; optionally wherein: (i) the amino acid substitution at the position corresponding with amino acid residue Ala-510 is with an Asp, Glu, Ile, or Val residue; and/or (ii) the amino acid substitution at the position corresponding with amino acid residue Asp-948 is with a Gly, Val, or Ala residue.

5. The non-native glucosyltransferase of embodiment 1, 2, 3, or 4, wherein the glucosyltransferase further comprises at least one amino acid substitution at a position corresponding with amino acid residue Ser-631, Ser-710, Arg-722, and/or Thr-877 of SEQ ID NO:62; optionally wherein: (i) the amino acid substitution at the position corresponding with amino acid residue Ser-631 is with a Thr, Asp, Glu, or Arg residue; (ii) the amino acid substitution at the position corresponding with amino acid residue Ser-710 is with a Gly, Ala, or Val residue; (iii) the amino acid substitution at the position corresponding with amino acid residue Arg-722 is with a His or Lys residue; and/or (iv) the amino acid substitution at the position corresponding with amino acid residue Thr-877 is with a Lys, His, or Arg residue.

6. The non-native glucosyltransferase of embodiment 1, 2, 3, 4, or 5, wherein the glucosyltransferase further comprises at least one amino acid substitution at a position corresponding with amino acid residue Val-1188, Met-1253, and/or Gln-957 of SEQ ID NO:62; optionally wherein: (i) the amino acid substitution at the position corresponding with amino acid residue Val-1188 is with a Glu or Asp residue; (ii) the amino acid substitution at the position corresponding with amino acid residue Met-1253 is with an Ile, Leu, Ala, or Val residue; and/or (iii) the amino acid substitution at the position corresponding with amino acid residue Gln-957 is with a Pro residue.

7. The non-native glucosyltransferase of embodiment 1, 2, 3, 4, 5, or 6, wherein the alpha-glucan produced by the non-native glucosyltransferase is insoluble and comprises at least about 50% alpha-1,3 linkages, and optionally wherein it has a weight average degree of polymerization ($DP_w$) of at least 100.

8. The non-native glucosyltransferase of embodiment 7, comprising a catalytic domain that is at least about 90% identical to residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20.

9. The non-native glucosyltransferase of embodiment 7 or 8, comprising an amino acid sequence that is at least about 90% identical to SEQ ID NO:4, SEQ ID NO:65, SEQ ID NO:30, SEQ ID NO:28, or SEQ ID NO:20.

10. The non-native glucosyltransferase of embodiment 1, 2, 3, 4, 5, 6, 7, 8, or 9, wherein the non-native glucosyltransferase synthesizes insoluble alpha-1,3-glucan having at least about 90% (or at least 95%) alpha-1,3-linkages.

11. The non-native glucosyltransferase of embodiment 1, 2, 3, 4, 5, 6, 7, 8, 9, or 10, wherein the alpha-glucan yield is at least about 10% higher than the alpha-glucan yield of the second glucosyltransferase.

12. A polynucleotide comprising a nucleotide sequence encoding a non-native glucosyltransferase according to any one of embodiments 1-11, optionally wherein one or more regulatory sequences are operably linked to the nucleotide sequence, and preferably wherein the one or more regulatory sequences include a promoter sequence.

13. A reaction composition comprising water, sucrose, and a non-native glucosyltransferase according to any one of embodiments 1-11.

14. A method of producing alpha-glucan comprising: (a) contacting at least water, sucrose, and a non-native glucosyltransferase enzyme according to any one of embodiments 1-11, whereby alpha-glucan is produced; and (b) optionally, isolating the alpha-glucan produced in step (a).

15. A method of preparing a polynucleotide sequence encoding a non-native glucosyltransferase (e.g., of any one of embodiments 1-11), the method comprising: (a) identifying a polynucleotide sequence encoding a parent glucosyltransferase that (i) comprises an amino acid sequence that is at least about 40% identical to SEQ ID NO:4 or positions 55-960 of SEQ ID NO:4, and (ii) synthesizes alpha-glucan comprising 1,3-linkages; and (b) modifying the polynucleotide sequence identified in step (a) to substitute at least two or three amino acids of the parent glucosyltransferase at positions corresponding with amino acid residues Gln-588, Phe-607, and/or Arg-741 of SEQ ID NO:62, thereby providing a polynucleotide sequence encoding a non-native glucosyltransferase that has: (i) an alpha-glucan yield that is higher than the alpha-glucan yield of the parent glucosyltransferase, and/or (ii) a leucrose yield that is lower than the leucrose yield of the parent glucosyltransferase.

16. The method of embodiment 15, wherein the identifying step is performed: (a) in silico, (b) with a method comprising a nucleic acid hybridization step, (c) with a method comprising a protein sequencing step, and/or (d) with a method comprising a protein binding step; and/or wherein the modifying step is performed: (e) in silico, followed by synthesis of the polynucleotide sequence encoding the non-native glucosyltransferase enzyme, or (f) using a physical copy of the polynucleotide sequence encoding the parent glucosyltransferase.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Analysis of Amino Acid Sites Affecting Glucosyltransferase Selectivity Toward Alpha-Glucan Synthesis This Example describes screening for glucosyltransferase variants with improved selectivity toward alpha-glucan synthesis from sucrose. Another aim of this screening was to identify glucosyltransferase variants that exhibit reduced synthesis of by-products such as leucrose and gluco-oligosaccharides. Variants having either or both of these yield properties were identified.

The amino acid sequence of the glucosyltransferase used to prepare amino acid substitutions in this Example was SEQ ID NO:4 (GTF 6855), which essentially is an N-terminally truncated (signal peptide and variable region removed) version of the full-length wild type glucosyltransferase (represented by SEQ ID NO:62) from *Streptococcus salivarius* SK126 (see Table 1). Substitutions made in SEQ ID NO:4 can be characterized as substituting for native amino acid residues, as each amino acid residue/position of SEQ ID NO:4 (apart from the Met-1 residue of SEQ ID NO:4) corresponds accordingly with an amino acid residue/position within SEQ ID NO:62. In reactions comprising at least sucrose and water, the glucosyltransferase of SEQ ID NO:4 typically produces alpha-glucan having about 100% alpha-1,3 linkages and a $DP_w$ of 400 or greater (e.g., refer to U.S. Pat. Nos. 8,871,474 and 9,169,506, and U.S. Pat. Appl. Publ. No. 2017/0002336, which are incorporated herein by reference). This alpha-glucan product, which is insoluble, can be isolated following enzymatic synthesis via filtration, for example.

To summarize this Example, GTF 6855 variants (each with a single amino acid substitution) from site evaluation libraries (SEL) were each bacterially expressed, purified, and normalized to a concentration of 100 ppm. Each enzyme preparation was then screened (in triplicate) using sucrose as substrate in alpha-1,3 glucan synthesis reactions. In addition to determining the amount of alpha-1,3 glucan polymer produced in each reaction, the soluble sugar products (fructose, glucose, leucrose, gluco-oligosaccharides) and residual sucrose of each reaction were analyzed by HPLC after about a 20-hour incubation.

Plasmids for individually expressing various single amino acid-substituted variants of GTF 6855 (SEQ ID NO:4) in a *Bacillus subtilis* host were prepared. Such plasmids were prepared as follows. A DNA expression cassette having (operably linked in 5'-to-3' order) the *B. subtilis* aprE promoter, a codon-optimized sequence encoding SEQ ID NO:4 (GTF 6855), and a BPN' terminator was synthesized. This expression cassette was cloned into the pHYT replicating shuttle vector (forming pHYT-GTF6855) and transformed into *B. subtilis* CBS12-1. The pHYT vector was derived from pHY300PLK (Takara) by adding a terminator sequence (SEQ ID NO:67) after the tetracycline resistance gene using the BstEII and EcoRI sites. The HindIII site in pHY300PLK had been removed by cloning a linker sequence (not shown) into the BamHI and HindIII sites. The pHYT-GTF6855 plasmid was amplified and used for generating SELs. The resulting plasmids encoding single-amino acid substituted GTFs were sequenced to verify each substitution.

To produce GTF 6855 (SEQ ID NO:4) and single amino acid-substituted variants thereof, *B. subtilis* individually transformed with pHYT-GTF6855 or mutated versions thereof were cultivated in Tryptone Soya Broth (Oxoid Ltd., UK) and Grant's II medium. Heart infusion agar plates (Difco Laboratories, MI) were used to select transformants. Plasmid integrity was maintained by the addition of 25 μg/mL tetracycline. Each GTF targeted for expression was detected in the growth medium after incubation for about 6 hours at 37° C. After centrifugation and filtration, culture supernatants with expressed GTF were obtained. GTF enzyme present in the supernatant was purified to apparent homogeneity by affinity chromatography using washed (2×MILLIQ 1×25 mM $NaH_2PO_4$ pH 5.7 with intermediate centrifugation steps 100× g) SUPERDEX 200 resin (GE Healthcare). Each GTF was eluted with a 15% solution of Dextran T1 (Pharmacosmos) in 25 mM $NaH_2PO_4$ pH 5.7 by centrifugation 100× g. Each purified GTF was dialyzed against 25 mM $NaH_2PO_4$ pH 5.7 buffer (at least 100×) using a Harvard Apparatus 96-well DISPODIALYZER (10000-Dalton MWCO).

After dialysis, GTF enzyme concentration was determined by OD280 using purified GTF 6855 as a standard. Normalization of each purified GTF to 100 ppm was achieved by diluting appropriately with 25 mM $NaH_2PO_4$ pH 5.7. Protein concentration for each sample was confirmed using an AGILENT 1200 (Agilent Technologies) HPLC equipped with an AGILENT BIO SEC3 guard-column column (3 μm 100 Å (4.6×50 mm). Five (5) μL of sample was injected onto the column for each determination. Compounds were eluted with isocratic flow of 25 mM $KH_2PO_4$ pH 6.8+0.1 M NaCl for 1.3 min at 0.5 mL/min flow rate.

Each GTF (GTF 6855 and each variant thereof) was entered into a reaction with sucrose to determine yield and selectivity. Each reaction was performed as follows: 37.5 μL of 100 ppm enzyme sample (ppm based on a BSA calibration curve) was added to 262.5 μL of 86 g/L sucrose (75 g/L final) in 20 mM $Na_2HPO_4/NaH_2PO_4$ pH 5.7 and incubated overnight (about 20 hours) at 30° C. After this incubation, each reaction was quenched by incubation for 1 hour at 80° C. A 200-4 aliquot of each quenched reaction was filtered in vacuo via a 0.45-μm filter plate (Millipore 0.45-μm Hydrophilic) and each filtrate was diluted 5× (10 μL sample+40 μL 20 mM $Na_2HPO_4/NaH_2PO_4$) in preparation for HPLC sugar analysis.

Sucrose, glucose, fructose, leucrose and relative oligosaccharide concentrations in each diluted filtrate were determined using an AGILENT 1200 (Agilent Technologies) HPLC equipped with a 150×7.80 mm PHENOMENEX REZEX RNM carbohydrate $Na^+$ 8% column PHENOMENX KRUDKATCHER 0.5-μm guard column. The column was operated at 80° C. with an isocratic flow-rate of 0.9 m L/min with 10 mM $Na_2HPO_4/NaH_2PO_4$ pH 6.7 (5 min per sample). Five μL of diluted sample was injected. Appropriate sucrose, glucose, fructose, and leucrose calibration curves were used to determine sugar concentrations. A mixture of purified gluco-oligosaccharides was used to determine oligomer concentration.

The profiles of reactions (~20 hours) as measured via the above methodology are provided in Table 3.

TABLE 3

Product Profiles of GTF 6855 (SEQ ID NO: 4) and
Single Amino Acid-Substituted Variants thereof

| GTF | Sucrose (g/L)[d] | Leucrose (g/L)[d] | Glucose (g/L)[d] | Fructose (g/L)[d] | Oligomers (g/L)[d,e] | Alpha-1,3 Glucan[f] Yield[i] | Fructose Balance |
|---|---|---|---|---|---|---|---|
| Plate 1[a] | | | | | | | |
| 6855[b] | 1.6 | 21.1 | 6.3 | 28.9 | 9.1 | 31% | 97% |
| 6855[b] | 1.6 | 21.3 | 6.3 | 29.1 | 10.5 | 27% | 98% |
| 6855[b] | 1.6 | 21.2 | 6.3 | 29.3 | 10.0 | 29% | 98% |
| 6855[b] | 1.6 | 21.1 | 6.3 | 28.9 | 10.8 | 27% | 97% |
| V186A[c] | 1.6 | 21.3 | 6.4 | 28.8 | 10.7 | 27% | 97% |
| V186M | 1.6 | 21.4 | 6.4 | 28.7 | 10.6 | 27% | 97% |
| E194C | 1.6 | 21.2 | 6.3 | 29.0 | 9.4 | 30% | 98% |
| L434N | 1.9 | 22.7 | 7.1 | 28.4 | 12.7 | 18% | 99% |
| A472C | 31.0 | 2.6 | 2.5 | 23.8 | 4.6 | 38% | 99% |
| A472S | 5.3 | 2.8 | 13.9 | 36.5 | 9.1 | 31% | 97% |
| A510E | 8.5 | 5.4 | 5.5 | 34.5 | 5.6 | 53% | 100% |
| A510E | 1.9 | 6.5 | 5.6 | 36.7 | 6.1 | 58% | 98% |
| A510I | 4.3 | 6.8 | 5.4 | 35.2 | 5.4 | 57% | 98% |
| A510V | 1.7 | 9.5 | 6.4 | 35.6 | 6.8 | 51% | 99% |
| L513Y | 1.4 | 10.3 | 4.2 | 35.3 | 7.2 | 54% | 99% |
| M529L | 1.9 | 10.4 | 4.2 | 35.2 | 10.9 | 44% | 99% |
| K578M | 1.6 | 21.0 | 6.4 | 28.8 | 10.8 | 27% | 97% |
| Y605W | 6.1 | 8.0 | 2.6 | 33.3 | 5.4 | 59% | 97% |
| F607N | 8.4 | 11.4 | 4.1 | 30.5 | 7.1 | 45% | 98% |
| F607W | 9.1 | 4.6 | 3.8 | 33.9 | 8.6 | 49% | 98% |
| N613I | 4.5 | 7.7 | 6.4 | 35.8 | 14.8 | 29% | 101% |
| N613M | 2.7 | 11.0 | 5.3 | 34.6 | 12.1 | 37% | 100% |
| N613T | 1.7 | 10.3 | 4.6 | 35.0 | 7.1 | 53% | 98% |
| N613V | 2.8 | 0.0 | 6.3 | 37.3 | 12.1 | 48% | 92% |
| Q616E | 3.9 | 2.4 | 5.8 | 37.3 | 8.8 | 53% | 97% |
| K625A | 1.5 | 21.2 | 6.3 | 29.4 | 9.9 | 29% | 99% |
| K625M | 1.5 | 21.3 | 6.3 | 29.3 | 10.6 | 27% | 99% |
| S631T | 5.4 | 11.4 | 4.6 | 32.0 | 7.6 | 46% | 97% |
| T635H | 4.1 | 11.0 | 5.0 | 32.7 | 8.2 | 46% | 97% |
| T635W | 13.1 | 8.5 | 4.5 | 29.6 | 7.0 | 42% | 98% |
| I636H | 7.0 | 11.7 | 5.0 | 31.1 | 8.1 | 42% | 98% |
| D947G | 2.4 | 19.1 | 6.1 | 29.8 | 9.9 | 31% | 98% |
| F951Y | 4.0 | 1.5 | 9.9 | 38.0 | 15.4 | 28% | 97% |
| E849M | 1.4 | 20.7 | 6.2 | 29.5 | 10.4 | 29% | 98% |
| Q1007A | 1.4 | 19.4 | 6.2 | 30.2 | 10.1 | 31% | 98% |
| D1003G | 13.8 | 10.7 | 4.6 | 28.3 | 5.4 | 42% | 98% |
| A1022M | 1.7 | 20.6 | 6.2 | 29.3 | 12.2 | 24% | 98% |
| D1028L | 1.6 | 22.1 | 6.6 | 28.9 | 11.6 | 23% | 99% |
| D1028Q | 1.6 | 21.7 | 6.5 | 29.4 | 10.9 | 26% | 99% |
| A1057H | 1.5 | 21.4 | 6.4 | 29.2 | 10.6 | 27% | 98% |
| N1096A | 1.6 | 22.4 | 6.6 | 28.6 | 10.7 | 25% | 98% |
| E1132A | 1.5 | 21.4 | 6.4 | 29.2 | 10.6 | 27% | 98% |
| E1132H | 1.5 | 21.3 | 6.4 | 29.2 | 10.5 | 27% | 98% |
| E1132K | 1.5 | 21.4 | 6.4 | 29.2 | 10.4 | 27% | 98% |
| E1132R | 1.5 | 21.6 | 6.4 | 29.1 | 10.8 | 26% | 99% |
| L1212N | 1.5 | 20.9 | 6.3 | 29.5 | 10.4 | 28% | 98% |
| T1431M | 1.5 | 21.4 | 6.3 | 29.4 | 10.5 | 27% | 99% |
| A1442R | 1.5 | 21.3 | 6.4 | 29.1 | 10.6 | 27% | 98% |
| Dead[g] | 79.4 | 0.0 | 0.0 | 0.0 | 0.0 | 0% | 100% |
| Blank[h] | 79.7 | 0.0 | 0.1 | 0.0 | 0.0 | 0% | 100% |
| Blank[h] | 80.1 | 0.0 | 0.0 | 0.0 | 0.0 | 0% | 100% |
| Plate 2[a] | | | | | | | |
| 6855[b] | 1.4 | 20.1 | 6.4 | 28.2 | 10.0 | 29% | 99% |
| 6855[b] | 1.4 | 20.1 | 6.4 | 28.2 | 10.1 | 28% | 99% |
| 6855[b] | 1.4 | 20.0 | 6.3 | 28.3 | 10.3 | 28% | 99% |
| 6855[b] | 1.5 | 20.2 | 6.3 | 28.2 | 10.0 | 29% | 100% |
| Y219C[c] | 1.5 | 20.6 | 6.5 | 27.7 | 10.7 | 25% | 99% |
| E243H | 1.4 | 20.3 | 6.3 | 28.2 | 10.1 | 28% | 100% |
| L373A | 2.4 | 11.3 | 11.2 | 27.4 | 21.6 | −7% | 87% |
| L373Q | 4.0 | 7.5 | 10.7 | 28.4 | 21.5 | −2% | 87% |
| L373V | 2.5 | 11.6 | 11.5 | 27.5 | 21.8 | −9% | 88% |
| A377I | 2.9 | 15.5 | 6.6 | 29.3 | 11.3 | 29% | 98% |
| D425Q | 1.8 | 15.3 | 5.3 | 30.3 | 9.6 | 39% | 99% |
| L428V | 5.3 | 10.5 | 6.2 | 30.8 | 8.2 | 42% | 98% |
| N475F | 6.1 | 26.8 | 20.5 | 24.9 | 7.2 | −16% | 106% |
| N475W | 1.5 | 61.8 | 7.5 | 9.1 | 1.9 | −8% | 106% |
| L513F | 1.0 | 10.9 | 4.6 | 33.3 | 7.1 | 55% | 99% |
| L513W | 1.3 | 11.5 | 4.9 | 32.4 | 8.9 | 48% | 98% |
| M529N | 3.5 | 11.6 | 4.8 | 31.6 | 7.6 | 49% | 99% |
| I608Y | 2.4 | 15.7 | 5.7 | 29.9 | 9.8 | 35% | 99% |

TABLE 3-continued

Product Profiles of GTF 6855 (SEQ ID NO: 4) and
Single Amino Acid-Substituted Variants thereof

| GTF | Sucrose (g/L)[d] | Leucrose (g/L)[d] | Glucose (g/L)[d] | Fructose (g/L)[d] | Oligomers (g/L)[d,e] | Alpha-1,3 Glucan[f] Yield[i] | Fructose Balance |
|---|---|---|---|---|---|---|---|
| N613G | 2.2 | 10.5 | 5.0 | 33.5 | 10.6 | 43% | 101% |
| N613L | 2.9 | 13.3 | 5.0 | 32.1 | 11.7 | 35% | 102% |
| D617E | 8.4 | 10.2 | 6.9 | 29.8 | 9.0 | 34% | 99% |
| E621T | 1.5 | 18.6 | 6.0 | 29.1 | 10.4 | 30% | 100% |
| I623H | 69.8 | 0.2 | 1.4 | 3.3 | 0.0 | 4% | 101% |
| I627W | 7.7 | 12.2 | 5.2 | 28.9 | 7.9 | 40% | 99% |
| S631D | 9.8 | 12.3 | 5.7 | 27.5 | 8.0 | 35% | 98% |
| S631E | 10.1 | 12.6 | 5.6 | 27.3 | 8.0 | 35% | 99% |
| S631R | 6.7 | 12.3 | 5.4 | 28.7 | 8.1 | 40% | 97% |
| G633W | 7.0 | 7.2 | 5.5 | 31.9 | 8.5 | 46% | 99% |
| F634A | 7.4 | 8.4 | 5.7 | 30.8 | 8.2 | 43% | 98% |
| T635E | 1.6 | 17.2 | 6.0 | 29.9 | 9.5 | 35% | 100% |
| T635I | 1.5 | 17.4 | 6.2 | 30.5 | 10.1 | 32% | 102% |
| T635Y | 13.8 | 8.0 | 4.6 | 28.0 | 6.7 | 43% | 99% |
| A510E | 2.5 | 5.9 | 5.5 | 34.8 | 4.3 | 66% | 99% |
| N904E | 5.7 | 6.9 | 12.6 | 32.5 | 13.5 | 15% | 98% |
| K930G | 1.4 | 19.8 | 6.2 | 28.4 | 10.0 | 30% | 99% |
| K930V | 1.4 | 19.6 | 6.3 | 28.6 | 10.0 | 30% | 100% |
| D947F | 1.4 | 20.3 | 6.2 | 27.8 | 9.9 | 29% | 99% |
| D947I | 1.4 | 19.9 | 6.3 | 28.6 | 10.7 | 27% | 100% |
| D947K | 1.4 | 19.9 | 6.2 | 28.6 | 9.7 | 30% | 100% |
| D947N | 1.4 | 20.5 | 6.3 | 27.9 | 10.0 | 28% | 99% |
| D947Q | 1.4 | 19.5 | 6.2 | 28.4 | 9.6 | 31% | 99% |
| D947S | 1.3 | 18.9 | 6.1 | 28.8 | 9.4 | 33% | 99% |
| D947V | 1.4 | 19.8 | 6.2 | 28.3 | 9.7 | 30% | 99% |
| D947Y | 1.4 | 20.7 | 6.3 | 28.1 | 10.0 | 28% | 100% |
| Q1007S | 1.3 | 18.3 | 6.1 | 29.1 | 9.6 | 33% | 99% |
| D1003N | 3.6 | 13.1 | 5.7 | 30.5 | 9.8 | 38% | 99% |
| I1026H | 1.4 | 19.4 | 6.2 | 28.7 | 9.7 | 31% | 100% |
| D1028A | 1.5 | 20.1 | 6.5 | 28.4 | 10.8 | 26% | 100% |
| D1028M | 1.5 | 20.4 | 6.6 | 28.1 | 11.1 | 24% | 100% |
| V1037A | 1.5 | 20.2 | 6.4 | 28.4 | 10.3 | 28% | 100% |
| K1041A | 4.3 | 19.6 | 6.5 | 27.0 | 10.7 | 23% | 99% |
| K1041M | 1.5 | 20.5 | 6.4 | 28.0 | 10.5 | 26% | 100% |
| D1080M | 1.4 | 20.0 | 6.4 | 28.3 | 10.1 | 29% | 99% |
| F1244P | 1.4 | 19.6 | 6.3 | 28.6 | 9.9 | 30% | 100% |
| F1244Q | 1.4 | 19.7 | 6.4 | 28.6 | 9.9 | 30% | 100% |
| T1431Q | 1.4 | 20.0 | 6.2 | 28.5 | 8.9 | 33% | 100% |
| G1484P | 1.5 | 20.1 | 6.3 | 28.5 | 9.2 | 31% | 100% |
| W1437N | 1.4 | 19.5 | 6.0 | 28.9 | 8.4 | 35% | 100% |
| Dead[g] | 75.5 | 0.0 | 0.0 | 0.0 | 0.0 | 0% | 100% |
| Blank[h] | 75.5 | 0.0 | 0.0 | 0.0 | 0.0 | 0% | 100% |
| Blank[h] | 76.0 | 0.0 | 0.0 | 0.0 | 0.5 | -2% | 100% |

[a]Glucan synthesis reactions were run in microtiter plate format (two plates).
[b]GTF 6855, SEQ ID NO: 4. Reactions with this GTF were run in quadruplicate per plate.
[c]Each listed GTF with a substitution is a version of GTF 6855 comprising a substitution at a respective position, where the position number is in correspondence with the residue numbering of SEQ ID NO: 62. The wild type residue is listed first (before residue position number) and the substituting residue is listed second (after the residue position number) (this "wild type residue-position number-variant residue" annotation format applies throughout the present disclosure).
[d]Sucrose, leucrose, glucose, fructose and oligomers were measured as present in filtrate prepared post reaction.
[e]"Oligomers", gluco-oligosaccharides (believed to all or mostly be of DP ≤ 7 or 8).
[f]Insoluble alpha-1,3 glucan product.
[g]GTF with destroyed activity was entered into the reaction.
[h]No GTF was added to the reaction.
[i]Alpha-glucan yield based on glucosyl.

Based on the data in Table 3, it is apparent that certain single amino acid substitutions in GTF 6855 (SEQ ID NO:4) can increase this enzyme's yield of alpha-1,3-glucan and/or decrease its leucrose yield in glucan synthesis reactions, for example.

Example 2

Analysis of the Effects of Single Amino Acid Substitutions on Other Glucosyltransferases This Example describes the effects of certain single amino acid substitutions on the activities of glucosyltransferases other than GTF 6855 (SEQ ID NO:4). In general, it appears that substitutions corresponding to (or similar to) those observed in Example 1 having a significant effect on alpha-glucan and/or leucrose yields may be useful for imparting similar effects to different glucosyltransferases.

Phe-607-Tyr

Example 1 demonstrated, for example, that substitutions in GTF 6855 (SEQ ID NO:4) at the position corresponding to position 607 of SEQ ID NO:62 affected enzyme activity (Table 3). In particular, substitutions of the Phe residue with an Asn or Trp residue both had significant effects on alpha-1,3 glucan yield (increased) and leucrose yield (decreased) compared to the respective yields of the non-substituted enzyme.

To test whether a similar substitution could similarly affect yields in a different GTF, a substitution was made at a position in GTF 7527 (GTFJ, SEQ ID NO:65) corresponding to position 607 of SEQ ID NO:62, exchanging a Phe for a Tyr residue. GTF 7527 (SEQ ID NO:65) essentially is an N-terminally truncated (signal peptide and variable region removed) version of the full-length wild type glucosyltransferase (represented by SEQ ID NO:60) from *Streptococcus salivarius* (see Table 1). Substitutions made in SEQ ID NO:65 can be characterized as substituting for native amino acid residues, as each amino acid residue/position of SEQ ID NO:65 (apart from the Met-1 residue of SEQ ID NO:65) corresponds accordingly with an amino acid residue/position within SEQ ID NO:60. In reactions comprising at least sucrose and water, the glucosyltransferase of SEQ ID NO:65 typically produces alpha-glucan having about 100% alpha-1,3 linkages and a $DP_w$ of 400 or greater (e.g., refer to U.S. Pat. Nos. 8,871,474 and 9,169,506, and U.S. Pat. Appl. Publ. No. 2017/0002336, which are incorporated herein by reference). Glucan synthesis reactions were prepared as follows using GTF 7527 (SEQ ID NO:65) or a version thereof comprising a Phe-to-Tyr substitution at the position corresponding to position 607 of SEQ ID NO:62: vessel, 250-mL indented shake flask agitated at 100 rpm; initial pH, 5.5; reaction volume, 50 mL; sucrose, 100.1 g/L; GTF, 100 U/L; $KH_2PO_4$, 25 mM; temperature, 25° C.; time, 20 hours. The profiles of each reaction (as measured via methodology similar to that disclosed in Example 1), which were run in duplicate, are provided in Table 4.

TABLE 4

Product Profiles of GTF 7527 (SEQ ID NO: 65) and a Single Amino Acid-Substituted Variant thereof

| GTF | Sucrose Conv. | Yield Alpha-Glucan[d] based on Glucosyl | Leucrose Yield | Glucose Yield | Oligomer[c] Yield | Fructose balance |
|---|---|---|---|---|---|---|
| 7527[a] | 99.7% | 29.24% | 42% | 4.20% | 28% | 105.62% |
| 7527 | 99.8% | 22.21% | 43% | 6.26% | 29% | 109.02% |
| F607Y[b] | 99.8% | 64.92% | 16% | 3.33% | 15% | 102.73% |
| F607Y | 99.8% | 62.97% | 17% | 3.35% | 17% | 109.17% |

[a]GTF 7527, SEQ ID NO: 65.
[b]F607Y, version of GTF 7527 (SEQ ID NO: 65) comprising a Phe-to-Tyr substitution at the position corresponding to position 607 of SEQ ID NO: 62.
[c]"Oligomer", gluco-oligosaccharides (believed to all or mostly be of DP ≤ 7 or 8).
[d]"Alpha-Glucan", insoluble alpha-1,3 glucan.

Based on the data in Table 4, it is apparent that the F607Y substitution in GTF 7527 (SEQ ID NO:65) can increase this enzyme's yield of alpha-1,3-glucan and/or decrease its leucrose yield in glucan synthesis reactions, for example.

Ala-510-Glu, Ala-510-Val, or Ala-510-Cys

Example 1 demonstrated, for example, that substitutions in GTF 6855 (SEQ ID NO:4) at the position corresponding to position 510 of SEQ ID NO:62 affected enzyme activity (Table 3). In particular, substitutions of the Ala residue with a Glu, Ile, or Val residue all had significant effects on alpha-1,3 glucan yield (increased) and leucrose yield (decreased) compared to the respective yields of the non-substituted enzyme.

To test whether these or similar substitutions could similarly affect yields in different GTFs, substitutions were made at positions in GTFs 2919 (SEQ ID NO:28), 0427 (SEQ ID NO:26), 5926 (SEQ ID NO:14), 0847 (SEQ ID NO:2), 0544 (SEQ ID NO:12), 2379 (SEQ ID NO:6), 5618 (SEQ ID NO:18), 4297 (SEQ ID NO:16), 1366 (SEQ ID NO:24), and 6907 (SEQ ID NO:36) corresponding to position 510 of SEQ ID NO:62, exchanging an Ala for a Glu, Val, or Cys residue. Each of these GTFs essentially is an N-terminally truncated (signal peptide and variable region removed) version of a full-length wild type glucosyltransferase (e.g., refer to respective GENBANK annotation information, such as that listed in Table 1). Substitutions made in each of SEQ ID NOs:28, 26, 14, 2, 12, 6, 18, 16, 24 and 36 can be characterized as substituting for native amino acid residues, as each amino acid residue/position of these sequences (apart from the Met-1 residues of each) corresponds accordingly with an amino acid residue/position within each respective full-length wild type glucosyltransferase counterpart. Table 2 lists the alpha-glucan typically produced by each of SEQ ID NOs:28, 26, 14, 2, 12, 6, 18, 16, 24 and 36 in reactions comprising at least sucrose and water.

Preparation of GTF 2919 (SEQ ID NO:28), 0427 (SEQ ID NO:26), 5926 (SEQ ID NO:14), 0847 (SEQ ID NO:2), 0544 (SEQ ID NO:12), 2379 (SEQ ID NO:6), 5618 (SEQ ID NO:18), 4297 (SEQ ID NO:16), 1366 (SEQ ID NO:24), or 6907 (SEQ ID NO:36), or versions thereof comprising a substitution at the position corresponding to position 510 of SEQ ID NO:62 was performed as follows. Codon-optimized (for *E. coli*) sequences encoding each of these GTFs were individually cloned into a suitable plasmid for bacterial expression. Each construct was then transformed into *E. coli* BL21-AI (Invitrogen, Carlsbad, Calif.). Transformed strains were grown in 10 mL auto-induction medium (10 g/L Tryptone, 5 g/L Yeast Extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose, 0.05% arabinose) containing 100 mg/L ampicillin at 37° C. for 20 hours under 200 rpm agitation. The cells were harvested by centrifugation at 8000 rpm at 4° C. and resuspended in 1 mL of 20 mM sodium phosphate buffer pH 6.0 with CelLytic™ Express (Sigma, St. Louise, Mo.) according to the manufacturer's instructions. In addition, resuspended cells were subjected to no less than one freeze-thaw cycle to ensure cell lysis. Lysed cells were centrifuged for 10 minutes at 12,000 g at room temperature. Each resulting supernatant was analyzed by SDS-PAGE to confirm expression of the particular GTF enzyme being expressed. Each supernatant was kept on ice at 4° C. until enzyme activity could be determined (within 1 hour), and/or stored at −20° C.

Glucan synthesis reactions were prepared, and the products thereof analyzed, largely according to the disclosure of U.S. Pat. Appl. Publ. No. 2014/0087431, which is incorporated herein by reference. Each reaction was run for 24-30 hours. The profiles of each reaction are provided in Table 5.

TABLE 5

Product Profiles of Various GTFs and Single Amino Acid-Substituted Variants thereof

| GTF | Sucrose Conv. | Yield Alpha-Glucan based on Glucosyl | Leucrose Yield | Glucose Yield | Oligomer Yield | Fructose balance |
|---|---|---|---|---|---|---|
| 2919[a] | 92% | 20% | 28% | 15% | 37% | 90% |
| A510E[b] | 98% | 40% | 13% | 15% | 31% | 93% |
| A510V[b] | 97% | 45% | 15% | 15% | 26% | 84% |
| A510C[b] | 95% | 35% | 19% | 15% | 32% | 87% |
| 0427[a] | 96% | 15% | 33% | 11% | 41% | 97% |
| A510E[b] | 96% | 1.0% | 40% | 16% | 43% | 104% |
| A510V[b] | poor conversion | | | | | |
| A510C[b] | 96% | 9% | 30% | 12% | 50% | 97% |

TABLE 5-continued

Product Profiles of Various GTFs and Single Amino Acid-Substituted Variants thereof

| GTF | Sucrose Conv. | Yield Alpha-Glucan based on Glucosyl | Leucrose Yield | Glucose Yield | Oligomer Yield | Fructose balance |
|---|---|---|---|---|---|---|
| 5926[a] | 97% | 12% | 37% | 11% | 41% | 93% |
| A510E[b] | 96% | 12% | 40% | 14% | 34% | 94% |
| A510V[b] | 97% | 25% | 31% | 14% | 31% | 81% |
| A510C[b] | 97% | −1% | 35% | 14% | 52% | 97% |
| 0847[a] | 97% | 18% | 33% | 11% | 38% | 92% |
| A510E[b] | 98% | 11% | 35% | 14% | 40% | 95% |
| A510V[b] | 80% | 32% | 21% | 16% | 31% | 80% |
| A510C[b] | 97% | 10% | 33% | 13% | 44% | 97% |
| 0544[a] | 99% | 37% | 22% | 8% | 33% | 86% |
| A510E[b] | 93% | 46% | 21% | 8% | 25% | 85% |
| A510V[b] | | | poor conversion | | | |
| A510C[b] | 92% | 39% | 16% | 9% | 37% | 90% |
| 2379[a] | 95% | 4% | 30% | 18% | 48% | 92% |
| A510E[b] | 97% | −2% | 23% | 23% | 56% | 93% |
| A510V[b] | 94% | 5% | 20% | 23% | 52% | 82% |
| A510C[b] | 93% | −10% | 37% | 21% | 53% | 101% |
| 5618[a] | 99% | 80% | 10% | 5% | 5% | 89% |
| A510E[b] | 94% | 82% | 5% | 4% | 9% | 93% |
| A510V[b] | 99% | 83% | 7% | 5% | 5% | 78% |
| A510C[b] | 98% | 83% | 9% | 4% | 4% | 96% |
| 4297[a] | 97% | 78% | 12% | 6% | 4% | 86% |
| A510E[b] | 99% | 84% | 7% | 4% | 5% | 83% |
| A510V[b] | 99% | 78% | 8% | 8% | 6% | 77% |
| A510C[b] | 80% | 71% | 8% | 9% | 7% | 84% |
| 1366[a] | 97% | 12% | 39% | 7% | 43% | 91% |
| A510E[b] | 99% | 9% | 39% | 16% | 36% | 89% |
| A510V[b] | 78% | 17% | 28% | 16% | 39% | 80% |
| A510C[b] | 97% | 1% | 39% | 12% | 48% | 96% |
| 6907[a] | 85% | 7% | 42% | 17% | 34% | 91% |
| A510E[b] | 89% | 14% | 35% | 25% | 26% | 94% |
| A510V[b] | | | poor conversion | | | |
| A510C[b] | | | poor conversion | | | |

[a]GTF 2919 (SEQ ID NO: 28), 0427 (SEQ ID NO: 26), 5926 (SEQ ID NO: 14), 0847 (SEQ ID NO: 2), 0544 (SEQ ID NO: 12), 2379 (SEQ ID NO: 6), 5618 (SEQ ID NO: 18), 4297 (SEQ ID NO: 16), 1366 (SEQ ID NO: 24), or 6907 (SEQ ID NO: 36).
[b]A510E/V/C, version of listed GTF (footnote [a]) comprising a substitution with Glu, Val, or Cys at the position corresponding to position 510 of SEQ ID NO: 62.
[c]"Oligomer", gluco-oligosaccharides.

Based on the data in Table 5, it is apparent that some substitutions in various GTFs at the position corresponding to position 510 of SEQ ID NO:62 can increase a GTF's yield of alpha glucan and/or decrease its leucrose yield in glucan synthesis reactions, for example.

Example 3

Analysis of the Effects of Two or More Amino Acid Substitutions on Glucosyltransferase Selectivity Toward Alpha-Glucan Synthesis This Example describes the effects of introducing multiple amino acid substitutions to a glucosyltransferase and determining their effect on enzyme selectivity toward alpha-glucan synthesis.

Briefly, certain amino acid substitutions were made to SEQ ID NO:4 (GTF 6855, see Table 1 and Example 1 for description of this glucosyltransferase). These substitutions are listed in Table 6 below. Each variant enzyme was entered into a glucan synthesis reaction with parameters that were the same as, or similar to, the following: vessel, 250-mL indented shake flask agitated at 120 rpm; initial pH, 5.7; reaction volume, 50 mL; sucrose, 75 g/L; GTF, 1.5 mL lysate of E. coli cells heterologously expressing enzyme; $KH_2PO_4$, 20 mM; temperature, 30° C.; time, about 20-24 hours. The alpha-1,3 glucan yield of each reaction (as measured via methodology similar to that disclosed in Example 1) is provided in Table 6.

TABLE 6

Alpha-1,3 Glucan Yields of GTF 6855 (SEQ ID NO: 4) Variants with Multiple Amino Acid Substitutions

| GTF[a] | Alpha-1,3 Glucan[b] Yield[c] |
|---|---|
| A510D/F607Y/R741S | 72.6% |
| A510D/F607Y/N743S | 79.2% |
| A510D/F607Y/D948G | 88.2% |
| A510D/R741S/D948G | 74.5% |
| A510D/F607Y/R741S/D948G | 82.8% |
| A510E/F607Y/R741S/R1172C | 78.2% |
| A510D/F607Y/D820G/D948G | 87.8% |
| A510D/F607Y/D948G/R1172C | 88.6% |
| A510D/F607Y/N743S/D948G/R1172C | 89.4% |
| A510D/F607Y/R741S/L784Q/F929L/R1172C | 79.3% |

[a]Each listed GTF is a version of GTF 6855 (SEQ ID NO: 4) comprising substitutions at respective positions, where each position number is in correspondence with the residue numbering of SEQ ID NO: 62.
[b]Insoluble alpha-1,3 glucan product.
[c]Alpha-1,3-glucan yield based on glucosyl.

Based on the data in Table 6, it is apparent that introduction of multiple amino acid substitutions to GTF 6855 (SEQ ID NO:4) can increase this enzyme's yield of alpha-1,3-glucan; for example, compare these yields to those of GTF 6855 (SEQ ID NO:4) without substitutions shown in Table 3. Each of the variant GTF enzymes listed in Table 6 also exhibited significant reductions in yields of leucrose, glucose and gluco-oligomers (data not shown).

It is apparent, for example, that a GTF with multiple substitutions such as at positions corresponding to positions 510 and/or 607 of SEQ ID NO:62 can increase a GTF's yield of alpha glucan.

Example 4

Analysis of the Effects of Additional Amino Acid Substitution Combinations on Glucosyltransferase Selectivity Toward Alpha-Glucan Synthesis This Example describes the effects of introducing multiple amino acid substitutions to a glucosyltransferase and determining their effect on enzyme selectivity toward alpha-glucan synthesis. While this analysis supplements the analysis disclosed above in Example 3, it is interesting to note that several of the additional amino acid substitution combinations provide modified glucosyltransferases with even higher alpha-1,3-glucan yields.

Briefly, certain combinations of amino acid substitutions were made to SEQ ID NO:4 (GTF 6855, see Table 1 and Example 1 for description of this glucosyltransferase) by site-directed mutagenesis of appropriate DNA templates contained in a plasmid. The plasmid sequences encoding each modified glucosyltransferase were individually sequenced to confirm the intended codon changes. Each combination of substitutions is listed in Table 7 below.

Expression plasmids encoding the modified glucosyltransferases were individually used to transform a B. subtilis strain containing nine protease deletions (amyE::xylRPxylAcomK-ermC, degUHy32, oppA, ΔspoIIE3501, ΔaprE, ΔnprE, Δepr, ΔispA, Δbpr, Δvpr, ΔwprA, Δmpr-ybfJ, ΔnprB). Transformed cells were spread onto LB plates supplemented with 5 μg/mL chloramphenicol. Colonies growing on these plates were streaked several times onto LB plates with 25 µg/mL chloramphenicol. Each resulting *Bacillus* strain for expressing a particular variant glucosyltransferase was then grown for 6-8 hours in LB medium containing 25 µg/mL chloramphenicol, and then subcultured into Grants II medium at 30° C. for 2-3 days. The cultures were spun at 15000 g for 30 minutes at 4° C., and the supernatants were filtered through 0.22-µm filters. The filtered supernatants, each of which contained an expressed secreted variant glucosyltransferase, were aliquoted and frozen at −80° C., and later used (below) for analyzing alpha-1,3-glucan synthesis activity.

The same amount of each variant enzyme, activity-wise, was entered into a glucan synthesis reaction with parameters that were the same as, or similar to, the following: vessel, 500-mL jacketed reactor with Teflon®-pitched blade turbine (45-degree angle) on a glass stir rod and agitated at 50-200 rpm; initial pH, 5.5; reaction volume, 500 mL; sucrose, 108 g/L; $KH_2PO_4$, 1 mM; temperature, 39° C.; time, about 18-24 hours; filtrate from a previous alpha-1,3-glucan synthesis reaction, 50 vol %. The alpha-1,3 glucan yield of each reaction (as measured via methodology similar to that disclosed in Example 1) is provided in Table 7.

TABLE 7

Alpha-1,3 Glucan Yields of GTF 6855 (SEQ ID NO: 4) Variants with Multiple Amino Acid Substitutions

| GTF[a] | | | | | | | | | | | | | Alpha-1,3-Glucan[b] Yield[c] |
|---|---|---|---|---|---|---|---|---|---|---|---|---|---|
| A510D | Q588L | F607Y | R741S | D948G |  |  | R722H | T877K |  | M1253I | K1277N |  | 88% |
| A510D | Q588L | F607Y | R741S | D948G |  |  | R722H | T877K | V1188E | M1253I | Q957P |  | 92% |
| A510D | Q588L | F607Y | R741S | D948G |  |  |  | T877K | V1188E | M1253I | Q957P |  | 91% |
| A510D | Q588L | F607Y | R741S | D948G |  |  |  |  |  | M1253I |  |  | 89% |
| A510D | Q588L | F607W | R741S | D948G |  |  |  |  |  |  |  |  | 91% |
|  | Q588L | F607Y | R741S | D948G |  |  |  |  |  |  |  |  | 91% |
| A510D | Q588L | F607Y | R741S | D948G | N628D | T635A |  | T877K |  | M1253I | F929L | R1172C | 92% |
| A510D | Q588L | F607W | R741S | D948G | S631T | S710G | R722H | T877K | V1188E | M1253I |  |  | 94% |
| A510D | Q588L | F607W | R741S | D948G | S631T | S710G | R722H | T877K | V1188E |  |  |  | 93% |
| A510D | Q588L | F607W | R741S | D948G | S631T | S710G |  | T877K | V1188E | M1253I |  |  | 96% |
| A510D | Q588L | F607Y | R741S | D948G |  |  |  |  |  |  |  |  | 89% |
| A510D | Q588L | F607Y | R741S | D948G |  |  |  |  | V1188E |  |  |  | 88% |
| A510D | Q588L | F607W | R741S | D948G | S631T | S710G |  |  | V1188E |  |  |  | 96% |
| A510D | Q588L | F607W | R741S | D948G |  | S710G | R722H | T877K |  | M1253I |  |  | 96% |
| A510D | Q588L | F607Y | R741S | D948G | S631T |  | R722H | T877K | V1188E | M1253I |  |  | 96% |
| A510D | Q588L | F607W | R741S | D948G | S631T |  |  | T877K | V1188E | M1253I |  |  | 94% |
| A510D | Q588L | F607W | R741S | D948G | S631T |  |  |  | V1188E |  |  |  | 98% |
| A510D | Q588L | F607Y | R741S | D948G | S631T |  | R722H | T877K | V1188E | M1253I |  |  | 95% |
| A510D | Q588L | F607W | R741S | D948G |  |  |  |  | V1188E | M1253I |  |  | 93% |

[a]Each listed GTF is a version of GTF 6855 (SEQ ID NO: 4) comprising substitutions at respective positions, where each position number is in correspondence with the residue numbering of SEQ ID NO: 62.
[b]Insoluble alpha-1,3 glucan product.
[c]Alpha-1,3-glucan yield based on glucosyl.

Based on the data in Table 7, it is further apparent that introduction of multiple amino acid substitutions to GTF 6855 (SEQ ID NO:4) can increase this enzyme's yield of alpha-1,3-glucan; for example, compare these yields to those of GTF 6855 (SEQ ID NO:4) without substitutions shown in Table 3. Each of the variant GTF enzymes listed in Table 7 also exhibited significant reductions in yields of leucrose, glucose and gluco-oligomers (data not shown).

It is apparent, for example, that a GTF with multiple substitutions, including those at positions corresponding to positions 588, 607 and 741 of SEQ ID NO:62, can increase a GTF's yield of alpha glucan.

What is claimed is:

1. A non-native glucosyltransferase comprising at least two amino acid substitutions at positions corresponding with amino acid residues Gln-588, Phe-607, or Arg-741 of SEQ ID NO:62, wherein the non-native glucosyltransferase synthesizes insoluble alpha-glucan comprising 1,3-linkages, and wherein the non-native glucosyltransferase has:

(i) an insoluble alpha-glucan yield that is higher than the insoluble alpha-glucan yield of a second glucosyltransferase that only differs from the non-native glucosyltransferase at the substitution positions, and/or (ii) a leucrose yield that is lower than the leucrose yield of the second glucosyltransferase;

wherein the non-native glucosyltransferase comprises an amino acid sequence that has at least 90% sequence identity to the amino acid sequence of residues 55-960 of SEQ ID NO:4 or the amino acid sequence of residues 54-957 of SEQ ID NO:65.

2. The non-native glucosyltransferase of claim 1, wherein the glucosyltransferase comprises amino acid substitutions at positions corresponding with amino acid residues Gln-588, Phe-607 and Arg-741 of SEQ ID NO:62.

3. The non-native glucosyltransferase of claim 1, wherein:
   (i) the amino acid substitution at the position corresponding with amino acid residue Gln-588 is with a Leu, Ala, or Val residue;
   (ii) the amino acid substitution at the position corresponding with amino acid residue Phe-607 is with a Trp, Tyr, or Asn residue; and/or
   (iii) the amino acid substitution at the position corresponding with amino acid residue Arg-741 is with a Ser or Thr residue.

4. The non-native glucosyltransferase of claim 1, wherein the glucosyltransferase further comprises at least one amino acid substitution at a position corresponding with amino acid residue Ala-510 and/or Asp-948 of SEQ ID NO:62.

5. The non-native glucosyltransferase of claim 1, wherein the glucosyltransferase further comprises at least one amino acid substitution at a position corresponding with amino acid residue Ser-631, Ser-710, Arg-722, and/or Thr-877 of SEQ ID NO:62.

6. The non-native glucosyltransferase of claim 1, wherein the glucosyltransferase further comprises at least one amino acid substitution at a position corresponding with amino acid residue Val-1188, Met-1253, and/or Gln-957 of SEQ ID NO:62.

7. The non-native glucosyltransferase of claim 1, wherein the insoluble alpha-glucan comprises at least 50% alpha-1,3 linkages.

8. The non-native glucosyltransferase of claim 1, comprising an amino acid sequence that has at least 92% sequence identity to the amino acid sequence of residues 55-960 of SEQ ID NO:4 or the amino acid sequence of residues 54-957 of SEQ ID NO:65.

9. The non-native glucosyltransferase of claim 1, comprising an amino acid sequence that has at least 90% sequence identity to the amino acid sequence of SEQ ID NO:4 or the amino acid sequence of SEQ ID NO:65.

10. The non-native glucosyltransferase of claim 7, wherein the insoluble alpha-glucan comprises at least 90% alpha-1,3 linkages.

11. The non-native glucosyltransferase of claim 1, wherein the insoluble alpha-glucan yield is at least 10% higher than the insoluble alpha-glucan yield of the second glucosyltransferase.

12. A reaction composition comprising water, sucrose, and the non-native glucosyltransferase of claim 1.

13. A method of producing insoluble alpha-glucan comprising:
   contacting at least water, sucrose, and the non-native glucosyltransferase of claim 1, whereby insoluble alpha-glucan is produced.

14. The method of claim 13, wherein the method further comprises isolating the insoluble alpha-glucan.

15. The non-native glucosyltransferase of claim 4, wherein:
   (i) the amino acid substitution at the position corresponding with amino acid residue Ala-510 is with an Asp, Glu, Ile, or Val residue; and/or
   (ii) the amino acid substitution at the position corresponding with amino acid residue Asp-948 is with a Gly, Val, or Ala residue.

16. The non-native glucosyltransferase of claim 5, wherein:
   (i) the amino acid substitution at the position corresponding with amino acid residue Ser-631 is with a Thr, Asp, Glu, or Arg residue;
   (ii) the amino acid substitution at the position corresponding with amino acid residue Ser-710 is with a Gly, Ala, or Val residue;
   (iii) the amino acid substitution at the position corresponding with amino acid residue Arg-722 is with a His or Lys residue; and/or
   (iv) the amino acid substitution at the position corresponding with amino acid residue Thr-877 is with a Lys, His, or Arg residue.

17. The non-native glucosyltransferase of claim 6, wherein:
   (i) the amino acid substitution at the position corresponding with amino acid residue Val-1188 is with a Glu or Asp residue;
   (ii) the amino acid substitution at the position corresponding with amino acid residue Met-1253 is with an Ile, Leu, Ala, or Val residue; and/or
   (iii) the amino acid substitution at the position corresponding with amino acid residue Gln-957 is with a Pro residue.

18. The non-native glucosyltransferase of claim 8, comprising an amino acid sequence that has at least 95% sequence identity to the amino acid sequence of residues 55-960 of SEQ ID NO:4 or the amino acid sequence of residues 54-957 of SEQ ID NO:65.

19. The non-native glucosyltransferase of claim 18, comprising an amino acid sequence that has at least 97% sequence identity to the amino acid sequence of residues 55-960 of SEQ ID NO:4 or the amino acid sequence of residues 54-957 of SEQ ID NO:65.

20. The non-native glucosyltransferase of claim 9, comprising an amino acid sequence that has at least 92% sequence identity to the amino acid sequence of SEQ ID NO:4 or the amino acid sequence of SEQ ID NO:65.

21. The non-native glucosyltransferase of claim 20, comprising an amino acid sequence that has at least 95% sequence identity to the amino acid sequence of SEQ ID NO:4 or the amino acid sequence of SEQ ID NO:65.

22. The non-native glucosyltransferase of claim 20, comprising an amino acid sequence that has at least 97% sequence identity to the amino acid sequence of SEQ ID NO:4 or the amino acid sequence of SEQ ID NO:65.

23. The non-native glucosyltransferase of claim 7, wherein the insoluble alpha-glucan has a weight average degree of polymerization ($DP_w$) of at least 100.

* * * * *

SEQUENCE LISTING

<160> NUMBER OF SEQ ID NOS: 81

<210> SEQ ID NO 1
<211> LENGTH: 4308
<212> TYPE: DNA
<213> ORGANISM: Streptococcus sobrinus

<400> SEQUENCE: 1
atggttgacg gcaaatacta ctattatgat caggacggta acgtaaagaa gaatttcgcg     60
gtgagcgttg gtgacaaaat ctactacttc gatgaaactg gtgcatataa ggataccagc    120
aaagtggacg ccgacaagag cagcagcgcg gttagccaaa acgcgaccat ctttgcggcg    180

```
aataaccgtg cgtacagcac ctctgcaaag aattttgaag cggtggataa ctacctgacc    240
gcagacagct ggtatcgtcc gaaatccatc ctgaaggacg gcaaaacctg gaccgagagc    300
ggtaaggatg atttccgtcc actgctgatg gcatggtggc ctgacaccga aactaagcgc    360
aactacgtga actatatgaa taaagtggtc ggtattgaca agacgtacac tgcggaaacg    420
tcgcaagcgg atttgaccgc agcggcggag ctggttcaag cgcgtatcga gcagaagatt    480
accagcgaaa acaacaccaa atggctgcgc gaagcaatct ccgcgttcgt taagacgcag    540
cctcagtgga acggcgagtc cgaaaagccg tatgacgatc acttgcagaa cggtgcgctg    600
ctgtttgata accaaaccga cctgacgcca gacacccaaa gcaattaccg tttgctgaac    660
cgtaccccga ccaatcagac tggtagcctg gatagccgtt ttacgtataa tccgaatgac    720
ccgttgggcg gctacgattt cttgctggcg aacgacgttg acaatagcaa tccggtcgtc    780
caggctgaac agttgaactg gctgcattat ctgctgaact ttggctctat ttacgctaac    840
gatgccgacg ccaattttga cagcattcgc gttgatgccg tcgataatgt cgatgctgat    900
ctgctgcaaa tcagcagcga ttacctgaaa gcagcgtatg gcatcgacaa gaataacaag    960
aatgcgaaca accatgttag catcgtcgaa gcgtggagcg acaatgatac cccgtatttg   1020
cacgacgatg gcgataatct gatgaacatg gacaacaaat ttcgcctgtc catgctgtgg   1080
agcctggcaa agccgctgga caaacgtagc ggtttgaacc cgctgattca aatagcctg    1140
gtggaccgcg aggtggacga tcgtgaagtg gaaaccgtgc cgtcctacag ctttgctcgt   1200
gcacatgata gcgaggtgca ggacatcatc cgtgacatta tcaaggctga gattaaccca   1260
aatagctttg gttatagctt cactcaagaa gagatcgagc aagcctttaa gatttacaac   1320
gaggatttga agaaaacgga caagaaatac acccactaca atgtgccgct gagctacacc   1380
ctgctgctga ccaacaaggg cagcatcccg cgtgtgtact atggtgatat gttcaccgat   1440
gatggccaat acatggcaaa caagaccgtc aactacgacg caatcgagag cctgctgaaa   1500
gcccgtatga aatatgtcag cggtggccaa gcaatgcaga actatcaaat tggtaatggc   1560
gagattttga ccagcgtgcg ctatggtaaa ggtgccctga gcagagcga taagggtgac    1620
gcgacgacgc gcactagcgg tgttggcgtg gttatgggta atcagccgaa cttctccctg   1680
gacggtaaag ttgtggccct gaatatgggt gcggcccatg cgaatcaaga ataccgtgca   1740
ctgatggtca gcactaaaga cggtgtggca acttacgcaa ccgatgctga cgcatccaaa   1800
gcgggcctgg tcaagcgtac cgacgagaac ggctacctgt acttcctgaa tgatgatctg   1860
aagggcgtcg cgaaccctca ggtttccggc ttcttgcaag tgtgggttcc agttggtgcc   1920
gccgatgacc aggacattcg cgtcgccgcc agcgacacgg cgagcacgga tggtaaaagc   1980
ctgcatcaag atgcggcgat ggacagccgc gtcatgtttg agggtttcag caattttcaa   2040
tccttcgcga ccaaagaaga agaatacacg aatgttgtta tcgcgaacaa tgtcgataag   2100
ttcgttagct ggggtatcac cgattttgaa atggctccgc agtatgttag cagcaccgac   2160
ggtcagttct tggacagcgt catccagaat ggctatgcgt ttactgatcg ctatgatctg   2220
ggtatgtcca aggcgaacaa gtatggcacg gcagaccaac tggttaaggc aatcaaagcc   2280
ctgcacgcta aaggcctgaa agttatggcg gactgggtcc ggatcaaat gtacacccttt   2340
ccaaaacagg aagttgtgac cgttacccgc accgacaaat tcggtaaacc gatcgccggc   2400
tctcaaatca atcacagctt gtatgtgacc gacaccaaat ccagcggcga cgactaccaa   2460
gcgaagtacg gcggtgcctt cctggatgaa ctgaaagaaa agtacccgga actgttcacg   2520
```

-continued

```
aaaaagcaaa ttagcacggg ccaagcgatt gatccgagcg tgaaaatcaa gcagtggagc    2580
gcaaaatact tcaatggttc gaatatcctg ggtcgcggtg cggactatgt gctgagcgac    2640
caggtcagca ataagtattt caacgtggcg agcgacacct tgttcctgcc gtccagcctg    2700
ctgggcaagg tcgtggagag cggcattcgt tacgacggca agggttacat ctacaacagc    2760
tccgcgaccg gcgatcaggt caaagcgtct ttcattacgg aagccggtaa cctgtattac    2820
ttcggcaaag acggttacat ggttactggt gcccagacga ttaatggcgc caactacttc    2880
ttcctggaaa acggtacggc actgcgtaat acgatttaca ccgatgctca aggtaatagc    2940
cactattacg cgaatgatgg caaacgctat gaaaatggct atcaacagtt cggtaacgat    3000
tggcgctact ttaaagatgg taacatggca gtcggcctga ccacggttga tgcaacgtg     3060 caatactttg acaaagacgg cgtccaggca aggataaga ttatcgtcac ccgtgatggc      3120
aaggtccgtt acttcgatca gcacaacggt aacgcggcga ccaacacgtt cattgctgat    3180
aaaactggcc attggtatta cctgggtaaa gatggcgtcg cggtgactgg cgcccagacc    3240
gtcggcaaac aaaaactgta cttcgaggcc aacggtcaac aagttaaagg tgactttgtt    3300
acgtccgatg agggcaaact gtatttctat gacgttgatt ctggtgacat gtggacggac    3360
accttcatcg aggataaggc gggcaactgg ttctatttgg gcaaggatgg tgcggcagtt    3420
acgggtgccc aaacgattcg cggtcagaag ctgtacttca aggccaatgg tcaacaggtc    3480
aagggtgaca ttgttaaggg caccgacggt aaaatccgct actatgatgc aaaatccggt    3540
gaacaggtgt tcaacaaaac ggtgaaagct gcggatggca aaacgtatgt tatcggtaat    3600
gatggtgtcg cggtggaccc tagcgtggtt aaaggtcaaa cctttaagga cgcttcgggc    3660
gctctgcgtt tctacaactt gaagggtcaa ctggtcactg cagcggctg gtatgaaacc      3720 gcgaaccatg actgggttta cattcagtcc ggcaaggcac tgaccggcga acagaccatt    3780
aacggtcaac acctgtattt caaagaagat ggtcaccaag tcaagggtca gttggtcacg    3840
ggcaccgatg taaagtgcg ttactatgac gccaacagcg gtgaccaagc attcaacaag     3900
agcgtcactg tgaatggtaa aacctattac tttggcaacg atggtacggc gcagactgct    3960
ggcaacccga agggtcagac gttcaaggat ggctccgaca tccgttttta ctctatggaa    4020
ggccaactgg tgaccggctc gggttggtac gagaacgcgc aaggccagtg gctgtatgtg    4080
aaaaacggta aggtgctgac tggtctgcaa accgttggca gccagcgtgt ttacttcgac    4140
gagaatggta ttcaggccaa gggcaaagca gtgcgtacca gcgatggcaa aattcgttat    4200
ttcgacgaaa acagcggcag catgatcacg aatcaatgga gttcgtcta tggtcagtat     4260 tactactttg gtaacgacgg tgcacgtatt taccgtggtt ggaactaa                 4308
```

<210> SEQ ID NO 2
<211> LENGTH: 1435
<212> TYPE: PRT
<213> ORGANISM: Streptococcus sobrinus

<400> SEQUENCE: 2

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
    50                  55                  60
```

```
Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
            115                 120                 125

Val Val Gly Ile Asp Lys Thr Tyr Thr Ala Glu Thr Ser Gln Ala Asp
            130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
            195                 200                 205

Thr Pro Asp Thr Gln Ser Asn Tyr Arg Leu Leu Asn Arg Thr Pro Thr
210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Asn Asp Ala Asp Ala Asn Phe Asp Ser
            275                 280                 285

Ile Arg Val Asp Ala Val Asp Asn Val Asp Ala Asp Leu Leu Gln Ile
            290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
            370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Glu Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
            450                 455                 460

Asn Lys Gly Ser Ile Pro Arg Val Tyr Tyr Gly Asp Met Phe Thr Asp
465                 470                 475                 480
```

```
Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765

Met Ala Asp Trp Val Pro Asp Gln Met Tyr Thr Phe Pro Lys Gln Glu
    770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
```

```
                900              905               910
Gly Lys Gly Tyr Ile Tyr Asn Ser Ser Ala Thr Gly Asp Gln Val Lys
            915              920              925

Ala Ser Phe Ile Thr Glu Ala Gly Asn Leu Tyr Tyr Phe Gly Lys Asp
        930              935              940

Gly Tyr Met Val Thr Gly Ala Gln Thr Ile Asn Gly Ala Asn Tyr Phe
945              950              955              960

Phe Leu Glu Asn Gly Thr Ala Leu Arg Asn Thr Ile Tyr Thr Asp Ala
            965              970              975

Gln Gly Asn Ser His Tyr Tyr Ala Asn Asp Gly Lys Arg Tyr Glu Asn
            980              985              990

Gly Tyr Gln Gln Phe Gly Asn Asp Trp Arg Tyr Phe Lys Asp Gly Asn
            995             1000             1005

Met Ala Val Gly Leu Thr Thr Val Asp Gly Asn Val Gln Tyr Phe
       1010             1015             1020

Asp Lys Asp Gly Val Gln Ala Lys Asp Lys Ile Ile Val Thr Arg
       1025             1030             1035

Asp Gly Lys Val Arg Tyr Phe Asp Gln His Asn Gly Asn Ala Ala
       1040             1045             1050

Thr Asn Thr Phe Ile Ala Asp Lys Thr Gly His Trp Tyr Tyr Leu
       1055             1060             1065

Gly Lys Asp Gly Val Ala Val Thr Gly Ala Gln Thr Val Gly Lys
       1070             1075             1080

Gln Lys Leu Tyr Phe Glu Ala Asn Gly Gln Gln Val Lys Gly Asp
       1085             1090             1095

Phe Val Thr Ser Asp Glu Gly Lys Leu Tyr Phe Tyr Asp Val Asp
       1100             1105             1110

Ser Gly Asp Met Trp Thr Asp Thr Phe Ile Glu Asp Lys Ala Gly
       1115             1120             1125

Asn Trp Phe Tyr Leu Gly Lys Asp Gly Ala Ala Val Thr Gly Ala
       1130             1135             1140

Gln Thr Ile Arg Gly Gln Lys Leu Tyr Phe Lys Ala Asn Gly Gln
       1145             1150             1155

Gln Val Lys Gly Asp Ile Val Lys Gly Thr Asp Gly Lys Ile Arg
       1160             1165             1170

Tyr Tyr Asp Ala Lys Ser Gly Glu Gln Val Phe Asn Lys Thr Val
       1175             1180             1185

Lys Ala Ala Asp Gly Lys Thr Tyr Val Ile Gly Asn Asp Gly Val
       1190             1195             1200

Ala Val Asp Pro Ser Val Val Lys Gly Gln Thr Phe Lys Asp Ala
       1205             1210             1215

Ser Gly Ala Leu Arg Phe Tyr Asn Leu Lys Gly Gln Leu Val Thr
       1220             1225             1230

Gly Ser Gly Trp Tyr Glu Thr Ala Asn His Asp Trp Val Tyr Ile
       1235             1240             1245

Gln Ser Gly Lys Ala Leu Thr Gly Glu Gln Thr Ile Asn Gly Gln
       1250             1255             1260

His Leu Tyr Phe Lys Glu Asp Gly His Gln Val Lys Gly Gln Leu
       1265             1270             1275

Val Thr Gly Thr Asp Gly Lys Val Arg Tyr Tyr Asp Ala Asn Ser
       1280             1285             1290

Gly Asp Gln Ala Phe Asn Lys Ser Val Thr Val Asn Gly Lys Thr
       1295             1300             1305
```

| | | | | | | | | | | |
|---|---|---|---|---|---|---|---|---|---|---|
| Tyr | Tyr | Phe | Gly | Asn | Asp | Gly | Thr | Ala | Gln | Thr | Ala | Gly | Asn | Pro |
| 1310 | | | | | 1315 | | | | | 1320 | | | | |

Lys Gly Gln Thr Phe Lys Asp Gly Ser Asp Ile Arg Phe Tyr Ser
    1325                1330                1335

Met Glu Gly Gln Leu Val Thr Gly Ser Gly Trp Tyr Glu Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Tyr Phe Gly Asn Asp Gly Ala
    1415                1420                1425

Arg Ile Tyr Arg Gly Trp Asn
    1430                1435

<210> SEQ ID NO 3
<211> LENGTH: 4026
<212> TYPE: DNA
<213> ORGANISM: Streptococcus salivarius SK126

<400> SEQUENCE: 3

```
atgatcgacg gcaaatacta ttatgttaat gaggacggta gccacaaaga aaactttgcg      60
attacggtta atggtcaact gctgtatttc ggtaaggacg gcgcactgac ctctagcagc     120
acttacagct ttccccagg tacgacgaac atcgtggatg gcttttctat caacaaccgc     180
gcgtatgact ccagcgaagc gtcctttgaa ctgattgatg gctacttgac tgccgactcc     240
tggtatcgtc cggcttccat catcaaggac ggtgtcacgt ggcaggccag caccgcagag     300
gactttcgcc gctgctgat ggcgtggtgg ccaaacgtgg atacccaggt gaactatctg     360
aactacatgt ctaaagtgtt taacctggac gcaaagtata gcagcaccga taacaagag     420
actctgaagg ttgcagctaa ggatattcag attaagatcg agcagaaaat tcaggcggag     480
aaaagcaccc aatggctgcg cgaaacgatc agcgcttttg tgaaaaccca accacagtgg     540
aacaaagaga ctgagaatta ctcgaaaggt ggtggtgagg atcatctgca aggcggtgca     600
ctgctgtacg tgaatgatag ccgtaccccg tgggcaaata gcgattatcg ccgcctgaac     660
cgcaccgcta ccaatcaaac gggtacgatt gacaagtcca ttctggacga gcagagcgac     720
ccaaatcaca tgggcggttt cgacttcctg ctggcgaatg atgttgacct gtccaacccg     780
gttgtgcagg cagagcagct gaaccagatt cactacttga tgaattgggg ctctatcgtg     840
atgggtgaca agacgcaaa ctttgatggt atccgtgtcg atgcagttga caacgtcgat     900
gccgacatgc tgcaactgta taccaactac ttccgtgaat actacggtgt taacaaaagc     960
gaagcgaacg cactggcgca cattagcgtt ttggaagcgt ggagcttgaa tgataatcac    1020
tacaacgaca aaaccgatgg tgcagcattg gcgatggaga ataagcagcg tctggcgctg    1080
ctgtttagcc tggctaaacc gattaaagag cgcaccccgg cagtgagccc gctgtataac    1140
aacaccttca atacgaccca acgcgatgag aaaaccgact ggatcaataa agacggttct    1200
aaggcctata acgaggatgg tactgtgaag cagagccacca ttggtaagta caatgaaaaa    1260
tatggtgatg catcgggcaa ttatgtgttc atccgtgccc atgataacaa tgtccaagac    1320
```

```
atcattgcgg agatcattaa gaaagaaatc aacccgaaaa gcgatggttt caccatcact   1380
gacgccgaaa tgaaacaagc gttcgagatt tacaataagg acatgctgag cagcgacaag   1440
aagtacaccc tgaataacat cccggcagct tatgccgtga tgttgcagaa catggaaacg   1500
attacccgtg tctattatgg tgacctgtac accgacgacg ccactacat ggaaaccaag    1560 tccccgtatt acgacaccat cgttaacctg atgaaaagcc gtatcaagta cgtcagcggt   1620
ggccaggccc aacgtagcta ctggctgccg accgacggca gatgggacaa tagcgacgtt   1680
gagctgtatc gcaccaacga agtgtatacc agcgtccgtt acggtaaaga cattatgacc   1740
gcgaacgata ccgagggtag caagtacagc cgcaccagcg gccaggtcac cctggttgca   1800
aacaacccga agctgaccct ggaccagagc gcgaagctga atgtggaaat gggtaagatt   1860
cacgcgaatc agaaataccg tgccctgatt gtgggcacgg ctgacggtat caagaatttc   1920
accagcgacg cagatgctat cgcggcaggc tacgtgaaag aaaccgactc caatggcgtt   1980 ctgactttg gcgctaatga catcaaaggt tatgaaacct tcgacatgtc cggctttgtt     2040
gctgtttggg tgccggtcgg cgcgagcgat gatcaggaca ttcgtgtcgc tcctagcact   2100
gaggccaaga aagagggtga attgaccctg aaagcgaccg aagcatacga ttcccagctg   2160
atctatgaag gttttagcaa ttttcaaacc atcccggatg gtagcgaccc gagcgtgtac   2220
accaatcgca agatcgcaga gaacgtggac ctgttcaagt cctggggtgt tacctcgttt   2280
gaaatggcac cgcagttcgt ttccgcagat gatggcactt ttctggactc tgtgatccaa   2340
aacggctatg cgtttgccga tcgttacgat ttggcgatga gcaagaacaa caaatacggc   2400
agcaaagagg acttgcgtga cgcgctgaaa gccctgcata agcaggcat ccaggcgatt    2460 gcagactggg tcccggacca gatttatcag ttgccgggca aagaagtggt cacggcgact   2520
cgcaccgacg gcgcaggccg taaaatcgcg gacgcgatca ttgatcatag cctgtacgtt   2580
gcgaacacta gagcagcgg caaagattac caggcgaagt acggtggtga gttcttggcg    2640
gagctgaagg ccaagtaccc ggagatgttc aaagtgaaca tgatttctac cggcaaaccg   2700
attgatgaca gcgtcaaact gaaacagtgg aaagcagaat actttaacgg caccaacgtc   2760
ttggagcgcg gtgtgggtta tgtcctgagc gatgaagcca cgggtaaata ctttaccgtc   2820
acgaaggatg gcaacttcat tccgttgcag ctgacgggta tgagaaagt cgtgaccggc    2880 tttagcaatg atggcaaagg tatcacctac ttcggtacga gcggcactca agcgaaatct   2940
gcgttcgtta cgttcaatgg taatacttac tattttgacg ctcgtggtca catggttacg   3000
aacggcgagt attcgccgaa cggtaaggat gtttaccgtt tcctgccgaa tggtattatg   3060
ctgtctaacg cttttacgt tgatgcaaat ggtaacacgt acctgtacaa cagcaagggc    3120
caaatgtaca aaggcggtta caccaaattt gacgttaccg aaacggacaa agatggtaag   3180
gaaagcaagg tggtgaagtt tcgttacttt acgaacgaag gtgtcatggc aaaaggcgtt   3240
accgtgattg acggcttcac gcaatacttt ggtgaagatg gtttccaagc gaaagacaag   3300
ctggtcacgt tcaagggcaa gacgtactac ttcgatgcac acaccggcaa tgcgatcaag   3360
gacacctggc gtaatatcaa tggcaagtgg tatcatttcg acgcgaacgg cgttgcagcg   3420
accggcgctc aggtcatcaa tggccaaaaa ctgtatttca acgaggacgg cagccaagtg   3480
aaaggcggtg ttgtcaaaaa cgcggacggt acgtattcta aatacaaaga gggttctggt   3540
gaactggtta ccaacgagtt cttcacgacg gatggcaatg tttggtacta cgcaggcgcg   3600
aatggcaaga ccgttacggg tgcccaggtg attaacggcc aacacctgta cttcaatgcg   3660
```

-continued

```
gacggttcgc aagtgaaggg cggtgtggtc aagaacgcgg atggcaccta tagcaaatat    3720
gatgcgtcta ccggcgaacg cctgaccaat gagtttttca ccacgggtga taacaactgg    3780
tactacattg gcgcaaacgg caagagcgtg acgggcgagg tcaagatcgg tgacgatacc    3840
tatttctttg ccaaagatgg caagcaagtt aagggtcaaa ctgtcagcgc gggtaacggt    3900
cgtattagct actactatgg tgatagcggt aagcgtgcgg tgagcacttg gatcgaaatc    3960
caaccgggtg tttatgtcta cttcgacaag aacggcattg cctatccgcc tcgtgtgctg    4020
aattaa                                                                4026
```

<210> SEQ ID NO 4
<211> LENGTH: 1341
<212> TYPE: PRT
<213> ORGANISM: Streptococcus salivarius SK126

<400> SEQUENCE: 4

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300
```

```
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
                340                 345                 350
Glu Asn Lys Gln Arg Leu Ala Leu Leu Phe Ser Leu Ala Lys Pro Ile
                355                 360                 365
Lys Glu Arg Thr Pro Ala Val Ser Pro Leu Tyr Asn Asn Thr Phe Asn
            370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                405                 410                 415
Tyr Asn Glu Lys Tyr Gly Asp Ala Ser Gly Asn Tyr Val Phe Ile Arg
                420                 425                 430
Ala His Asp Asn Asn Val Gln Asp Ile Ile Ala Glu Ile Ile Lys Lys
            435                 440                 445
Glu Ile Asn Pro Lys Ser Asp Gly Phe Thr Ile Thr Asp Ala Glu Met
450                 455                 460
Lys Gln Ala Phe Glu Ile Tyr Asn Lys Asp Met Leu Ser Ser Asp Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
            500                 505                 510
Asp Gly His Tyr Met Glu Thr Lys Ser Pro Tyr Tyr Asp Thr Ile Val
            515                 520                 525
Asn Leu Met Lys Ser Arg Ile Lys Tyr Val Ser Gly Gly Gln Ala Gln
530                 535                 540
Arg Ser Tyr Trp Leu Pro Thr Asp Gly Lys Met Asp Asn Ser Asp Val
545                 550                 555                 560
Glu Leu Tyr Arg Thr Asn Glu Val Tyr Thr Ser Val Arg Tyr Gly Lys
                565                 570                 575
Asp Ile Met Thr Ala Asn Asp Thr Glu Gly Ser Lys Tyr Ser Arg Thr
            580                 585                 590
Ser Gly Gln Val Thr Leu Val Ala Asn Asn Pro Lys Leu Thr Leu Asp
                595                 600                 605
Gln Ser Ala Lys Leu Asn Val Glu Met Gly Lys Ile His Ala Asn Gln
            610                 615                 620
Lys Tyr Arg Ala Leu Ile Val Gly Thr Ala Asp Gly Ile Lys Asn Phe
625                 630                 635                 640
Thr Ser Asp Ala Asp Ala Ile Ala Ala Gly Tyr Val Lys Glu Thr Asp
                645                 650                 655
Ser Asn Gly Val Leu Thr Phe Gly Ala Asn Asp Ile Lys Gly Tyr Glu
                660                 665                 670
Thr Phe Asp Met Ser Gly Phe Val Ala Val Trp Val Pro Val Gly Ala
            675                 680                 685
Ser Asp Asp Gln Asp Ile Arg Val Ala Pro Ser Thr Glu Ala Lys Lys
            690                 695                 700
Glu Gly Glu Leu Thr Leu Lys Ala Thr Glu Ala Tyr Asp Ser Gln Leu
705                 710                 715                 720
Ile Tyr Glu Gly Phe Ser Asn Phe Gln Thr Ile Pro Asp Gly Ser Asp
```

```
                     725                 730                 735
         Pro Ser Val Tyr Thr Asn Arg Lys Ile Ala Glu Asn Val Asp Leu Phe
                 740                 745                 750

Lys Ser Trp Gly Val Thr Ser Phe Glu Met Ala Pro Gln Phe Val Ser
                 755                 760                 765

Ala Asp Asp Gly Thr Phe Leu Asp Ser Val Ile Gln Asn Gly Tyr Ala
                 770                 775                 780

Phe Ala Asp Arg Tyr Asp Leu Ala Met Ser Lys Asn Asn Lys Tyr Gly
         785                 790                 795                 800

Ser Lys Glu Asp Leu Arg Asp Ala Leu Lys Ala Leu His Lys Ala Gly
                         805                 810                 815

Ile Gln Ala Ile Ala Asp Trp Val Pro Asp Gln Ile Tyr Gln Leu Pro
                         820                 825                 830

Gly Lys Glu Val Val Thr Ala Thr Arg Thr Asp Gly Ala Gly Arg Lys
                         835                 840                 845

Ile Ala Asp Ala Ile Ile Asp His Ser Leu Tyr Val Ala Asn Thr Lys
                         850                 855                 860

Ser Ser Gly Lys Asp Tyr Gln Ala Lys Tyr Gly Gly Glu Phe Leu Ala
         865                 870                 875                 880

Glu Leu Lys Ala Lys Tyr Pro Glu Met Phe Lys Val Asn Met Ile Ser
                         885                 890                 895

Thr Gly Lys Pro Ile Asp Asp Ser Val Lys Leu Lys Gln Trp Lys Ala
                         900                 905                 910

Glu Tyr Phe Asn Gly Thr Asn Val Leu Glu Arg Gly Val Gly Tyr Val
                         915                 920                 925

Leu Ser Asp Glu Ala Thr Gly Lys Tyr Phe Thr Val Thr Lys Asp Gly
                         930                 935                 940

Asn Phe Ile Pro Leu Gln Leu Thr Gly Asn Glu Lys Val Val Thr Gly
         945                 950                 955                 960

Phe Ser Asn Asp Gly Lys Gly Ile Thr Tyr Phe Gly Thr Ser Gly Thr
                         965                 970                 975

Gln Ala Lys Ser Ala Phe Val Thr Phe Asn Gly Asn Thr Tyr Tyr Phe
                         980                 985                 990

Asp Ala Arg Gly His Met Val Thr Asn Gly Glu Tyr Ser Pro Asn Gly
                         995                 1000                1005

Lys Asp Val Tyr Arg Phe Leu Pro Asn Gly Ile Met Leu Ser Asn
                 1010                1015                1020

Ala Phe Tyr Val Asp Ala Asn Gly Asn Thr Tyr Leu Tyr Asn Ser
                 1025                1030                1035

Lys Gly Gln Met Tyr Lys Gly Gly Tyr Thr Lys Phe Asp Val Thr
                 1040                1045                1050

Glu Thr Asp Lys Asp Gly Lys Glu Ser Lys Val Val Lys Phe Arg
                 1055                1060                1065

Tyr Phe Thr Asn Glu Gly Val Met Ala Lys Gly Val Thr Val Ile
                 1070                1075                1080

Asp Gly Phe Thr Gln Tyr Phe Gly Glu Asp Gly Phe Gln Ala Lys
                 1085                1090                1095

Asp Lys Leu Val Thr Phe Lys Gly Lys Thr Tyr Tyr Phe Asp Ala
                 1100                1105                1110

His Thr Gly Asn Ala Ile Lys Asp Thr Trp Arg Asn Ile Asn Gly
                 1115                1120                1125

Lys Trp Tyr His Phe Asp Ala Asn Gly Val Ala Ala Thr Gly Ala
                 1130                1135                1140
```

```
Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ser Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
    1265                1270                1275

Asp Thr Tyr Phe Phe Ala Lys Asp Gly Lys Gln Val Lys Gly Gln
    1280                1285                1290

Thr Val Ser Ala Gly Asn Gly Arg Ile Ser Tyr Tyr Gly Asp
    1295                1300                1305

Ser Gly Lys Arg Ala Val Ser Thr Trp Ile Glu Ile Gln Pro Gly
    1310                1315                1320

Val Tyr Val Tyr Phe Asp Lys Asn Gly Ile Ala Tyr Pro Pro Arg
    1325                1330                1335

Val Leu Asn
    1340

<210> SEQ ID NO 5
<211> LENGTH: 3744
<212> TYPE: DNA
<213> ORGANISM: Streptococcus salivarius

<400> SEQUENCE: 5
atgccaagcc acattaagac catcaacggc aaacaatact acgtggagga tgacggtacg      60
attcgcaaga attcgtcct ggagcgtatc ggtggcagcc aatactttaa tgcagaaacc      120
ggtgaactgt ctaatcagaa agagtatcgt ttcgacaaaa atggtggtac tggtagcagc     180
gcggacagca cgaacaccaa cgtgactgtg aacggtgaca aaaacgcatt ttacggtacc     240
acggacaaag acattgagct ggtcgacggc tatttcaccg cgaacacctg gtatcgcccg     300
aaagaaatcc tgaaagacgg caaagaatgg accgccagca cggagaacga taaacgcccg     360
ctgctgaccg tctggtggcc tagcaaagca atccaggcgt cttatctgaa ctacatgaaa     420
gagcaaggcc tgggtaccaa ccaaacgtac acgagcttct ccagccaaac ccaaatggat     480
caagcagccc tggaagtgca aaagcgtatt gaagagcgca tcgcacgcga gggcaatacc     540
gactggctgc gcacgaccat caagaacttc gtgaaaaccc aaccgggttg aacagcacc     600
tctgaaaatc tggacaataa tgatcatctg caaggtggcg ccctgctgta caataacgac     660
tcccgcacga gccacgcgaa cagcgactat cgcctgctga atcgtacgcc gaccagccag     720
accggcaaac acaatccgaa atacaccaaa gataccagca atggtggttt cgaatttctg     780
ctggcgaacg acatcgataa ctctaatccg gcggttcaag cagagcaact gaactggctg     840
```

```
cattacatta tgaacatcgg taccatcacg ggcggttctg aggatgaaaa cttcgacggc    900
gttcgtgttg acgctgtgga taatgtgaat gcggatctgc tgcaaatcgc gagcgactat    960
ttcaaagcaa aatacggtgc tgatcaaagc caagatcagg cgatcaaaca cttgagcatc   1020
ctggaagcgt ggtcccataa cgacgcctac tataacgaag ataccaaagg cgcgcagttg   1080
ccgatggatg atccgatgca cctggctctg gtctactcgc tgctgcgtcc gatcggcaat   1140
cgcagcggtg tggaaccgct gatttccaac agcctgaatg accgtagcga gtccggtaag   1200
aacagcaaac gtatggcgaa ctacgcgttc gtacgcgcgc atgatagcga ggtgcaatcg   1260
attattggcc agatcatcaa aaacgagatc aatccgcaaa gcaccggtaa tacgttcacc   1320
ctggatgaga tgaagaaagc gtttgagatt tacaacaagg atatgcgtag cgcgaataag   1380
cagtatacgc agtacaacat cccgagcgcg tatgcgttga tgctgaccca caaggatacc   1440
gttccgcgtg tgtattacgg tgatatgtat acggacgacg tcagtacat ggcgcaaaag   1500 agcccatact atgatgcgat cgaaacgctg ctgaaaggtc gcatccgcta tgccgcaggt   1560
ggtcaggaca tgaaggtcaa ctatattggt tacggtaaca ctaacggctg ggatgctgcg   1620
ggcgtgctga ccagcgtacg ttatggcacg ggcgcaaata cgccagcga tacgggtacc   1680 gccgaaacgc gtaatcaagg tatggcagtg attgttagca accaaccggc gctgcgtctg   1740
actagcaatt tgaccattaa catgggtgcc gcacaccgta atcaggctta ccgtccgctg   1800
ctgctgacga ccaacgatgg cgtcgcgacc tatttgaacg atagcgatgc gaatggtatc   1860
gttaagtaca ccgacggtaa tggtaatctg accttctccg caaacgagat tcgtggcatc   1920
cgtaacccgc aagttgatgg ctatctggcc gtctgggttc cggtaggtgc gtcggagaat   1980
caggatgttc gtgtggcgcc gagcaaagag aagaacagct ccggtctggt ttacgagagc   2040
aatgctgccc tggatagcca agttatctac gaaggcttca gcaacttcca ggacttcgtt   2100
cagaatccga gccagtatac caacaaaaag attgcagaga atgcaaattt gttcaaatcc   2160 tgggtatta ccagctttga atttgcgccg cagtacgtga gctcggatga tggtagcttc   2220
ctggacagcg ttattcagaa cggttatgcg tttacggacc gctacgacat tggtatgagc   2280
aaagacaaca aatatggttc gctggcggat ttgaaggcag cactgaagag cttgcatgcc   2340
gttggtatta gcgcaatcgc ggattgggtt cctgatcaga tctacaatct gccaggcgac   2400
gaggtcgtca ccgcaacccg cgttaacaac tacggcgaaa ccaaagatgg tgcaatcatt   2460
gatcactctt tgtacgcggc caaaacccgt acttttggta acgactacca gggtaagtat   2520
ggtggtgcgt tcctggacga gctgaaacgt ctgtatccgc agatctttga ccgcgttcag   2580
atttctaccg gtaagcgcat gaccacggac gagaagatca cccaatggtc tgcaaagtat   2640
atgaacggta cgaacatctt ggaccgtggc tctgaatacg ttttgaagaa tggtctgaat   2700
ggttactatg gcaccaatgg tggcaaagtt tcgctgccga agttgtggg tagcaatcaa   2760 agcacgaatg cgacaatca aaacggcgac ggtagcggca gtttgaaaa gcgtctgttc   2820 agcgtgcgtt accgttataa caatggccag tacgcgaaaa atgcctttat caaagataac   2880
gacggcaatg tttactattt cgacaatagc ggtcgtatgg ctgtcggtga aaaacgatt   2940 gacggcaagc agtacttctt cctggctaat ggcgttcagc tgcgtgacgg ctaccgtcaa   3000
aatcgtcgcg gtcaggtgtt ttactacgac cagaatggtg tgctgaacgc aaacggtaaa   3060
caagacccga agcctgacaa caataacaat gcgagcggcc gtaatcaatt cgtccagatc   3120
ggtaacaacg tgtgggcgta ttatgatggc aatggtaaac gtgtcaccgg tcaccagaac   3180
atcaacggtc aggagttgtt tttcgataac aacggtgtcc aggttaaggg tcgtacggtg   3240
```

-continued

```
aatgagaacg gtgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tggcaacctg cgctattacg acgttaacag cggtgagctg    3480
taccgtaatc gtttccacga aatcgacggc agctggtatt actttgatgg taacggtaat    3540
gcggtgaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag gttggtgggt ttactttgac    3720
ggtgaaggtc gtggtcagat ctaa                                            3744
```

<210> SEQ ID NO 6
<211> LENGTH: 1247
<212> TYPE: PRT
<213> ORGANISM: Streptococcus salivarius

<400> SEQUENCE: 6

```
Met Pro Ser His Ile Lys Thr Ile Asn Gly Lys Gln Tyr Tyr Val Glu
  1               5                  10                  15

Asp Asp Gly Thr Ile Arg Lys Asn Tyr Val Leu Glu Arg Ile Gly Gly
                 20                  25                  30

Ser Gln Tyr Phe Asn Ala Glu Thr Gly Glu Leu Ser Asn Gln Lys Glu
             35                  40                  45

Tyr Arg Phe Asp Lys Asn Gly Gly Thr Gly Ser Ser Ala Asp Ser Thr
         50                  55                  60

Asn Thr Asn Val Thr Val Asn Gly Asp Lys Asn Ala Phe Tyr Gly Thr
 65                  70                  75                  80

Thr Asp Lys Asp Ile Glu Leu Val Asp Gly Tyr Phe Thr Ala Asn Thr
                 85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
        115                 120                 125

Lys Ala Ile Gln Ala Ser Tyr Leu Asn Tyr Met Lys Glu Gln Gly Leu
    130                 135                 140

Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Glu Arg Ile Ala Arg
                165                 170                 175

Glu Gly Asn Thr Asp Trp Leu Arg Thr Thr Ile Lys Asn Phe Val Lys
            180                 185                 190

Thr Gln Pro Gly Trp Asn Ser Thr Ser Glu Asn Leu Asp Asn Asn Asp
        195                 200                 205

His Leu Gln Gly Gly Ala Leu Leu Tyr Asn Asn Asp Ser Arg Thr Ser
    210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
                245                 250                 255

Phe Glu Phe Leu Leu Ala Asn Asp Ile Asp Asn Ser Asn Pro Ala Val
            260                 265                 270

Gln Ala Glu Gln Leu Asn Trp Leu His Tyr Ile Met Asn Ile Gly Thr
```

```
            275                 280                 285
Ile Thr Gly Gly Ser Glu Asp Glu Asn Phe Asp Gly Val Arg Val Asp
290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
            340                 345                 350

Glu Asp Thr Lys Gly Ala Gln Leu Pro Met Asp Asp Pro Met His Leu
        355                 360                 365

Ala Leu Val Tyr Ser Leu Leu Arg Pro Ile Gly Asn Arg Ser Gly Val
370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Gly Gln Ile Ile Lys Asn Glu Ile Asn Pro
            420                 425                 430

Gln Ser Thr Gly Asn Thr Phe Thr Leu Asp Glu Met Lys Lys Ala Phe
        435                 440                 445

Glu Ile Tyr Asn Lys Asp Met Arg Ser Ala Asn Lys Gln Tyr Thr Gln
450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
            500                 505                 510

Gly Arg Ile Arg Tyr Ala Ala Gly Gly Gln Asp Met Lys Val Asn Tyr
        515                 520                 525

Ile Gly Tyr Gly Asn Thr Asn Gly Trp Asp Ala Ala Gly Val Leu Thr
530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
                565                 570                 575

Ala Leu Arg Leu Thr Ser Asn Leu Thr Ile Asn Met Gly Ala Ala His
            580                 585                 590

Arg Asn Gln Ala Tyr Arg Pro Leu Leu Leu Thr Thr Asn Asp Gly Val
        595                 600                 605

Ala Thr Tyr Leu Asn Asp Ser Asp Ala Asn Gly Ile Val Lys Tyr Thr
610                 615                 620

Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
                645                 650                 655

Ala Ser Glu Asn Gln Asp Val Arg Val Ala Pro Ser Lys Glu Lys Asn
            660                 665                 670

Ser Ser Gly Leu Val Tyr Glu Ser Asn Ala Ala Leu Asp Ser Gln Val
        675                 680                 685

Ile Tyr Glu Gly Phe Ser Asn Phe Gln Asp Phe Val Gln Asn Pro Ser
690                 695                 700
```

```
Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
            740                 745                 750

Asp Arg Tyr Asp Ile Gly Met Ser Lys Asp Asn Lys Tyr Gly Ser Leu
        755                 760                 765

Ala Asp Leu Lys Ala Ala Leu Lys Ser Leu His Ala Val Gly Ile Ser
    770                 775                 780

Ala Ile Ala Asp Trp Val Pro Asp Gln Ile Tyr Asn Leu Pro Gly Asp
785                 790                 795                 800

Glu Val Val Thr Ala Thr Arg Val Asn Asn Tyr Gly Glu Thr Lys Asp
                805                 810                 815

Gly Ala Ile Ile Asp His Ser Leu Tyr Ala Ala Lys Thr Arg Thr Phe
            820                 825                 830

Gly Asn Asp Tyr Gln Gly Lys Tyr Gly Gly Ala Phe Leu Asp Glu Leu
        835                 840                 845

Lys Arg Leu Tyr Pro Gln Ile Phe Asp Arg Val Gln Ile Ser Thr Gly
    850                 855                 860

Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
                885                 890                 895

Asn Gly Leu Asn Gly Tyr Tyr Gly Thr Asn Gly Gly Lys Val Ser Leu
            900                 905                 910

Pro Lys Val Val Gly Ser Asn Gln Ser Thr Asn Gly Asp Asn Gln Asn
        915                 920                 925

Gly Asp Gly Ser Gly Lys Phe Glu Lys Arg Leu Phe Ser Val Arg Tyr
    930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
                965                 970                 975

Glu Lys Thr Ile Asp Gly Lys Gln Tyr Phe Phe Leu Ala Asn Gly Val
            980                 985                 990

Gln Leu Arg Asp Gly Tyr Arg Gln Asn Arg Arg Gly Gln Val Phe Tyr
        995                 1000                1005

Tyr Asp Gln Asn Gly Val Leu Asn Ala Asn Gly Lys Gln Asp Pro
    1010                1015                1020

Lys Pro Asp Asn Asn Asn Ala Ser Gly Arg Asn Gln Phe Val
    1025                1030                1035

Gln Ile Gly Asn Asn Val Trp Ala Tyr Tyr Asp Gly Asn Gly Lys
    1040                1045                1050

Arg Val Thr Gly His Gln Asn Ile Asn Gly Gln Glu Leu Phe Phe
    1055                1060                1065

Asp Asn Asn Gly Val Gln Val Lys Gly Arg Thr Val Asn Glu Asn
    1070                1075                1080

Gly Ala Ile Arg Tyr Tyr Asp Ala Asn Ser Gly Glu Met Ala Arg
    1085                1090                1095

Asn Arg Phe Ala Glu Ile Glu Pro Gly Val Trp Ala Tyr Phe Asn
    1100                1105                1110
```

```
Asn Asp Gly Thr Ala Val Lys Gly Ser Gln Asn Ile Asn Gly Gln
    1115            1120                1125

Asp Leu Tyr Phe Asp Gln Asn Gly Arg Gln Val Lys Gly Ala Leu
    1130            1135                1140

Ala Asn Val Asp Gly Asn Leu Arg Tyr Tyr Asp Val Asn Ser Gly
    1145            1150                1155

Glu Leu Tyr Arg Asn Arg Phe His Glu Ile Asp Gly Ser Trp Tyr
    1160            1165                1170

Tyr Phe Asp Gly Asn Gly Asn Ala Val Lys Gly Met Val Asn Ile
    1175            1180                1185

Asn Gly Gln Asn Leu Leu Phe Asp Asn Asn Gly Lys Gln Ile Lys
    1190            1195                1200

Gly His Leu Val Arg Val Asn Gly Val Val Arg Tyr Phe Asp Pro
    1205            1210                1215

Asn Ser Gly Glu Met Ala Val Asn Arg Trp Val Glu Val Ser Pro
    1220            1225                1230

Gly Trp Trp Val Tyr Phe Asp Gly Glu Gly Arg Gly Gln Ile
    1235            1240                1245
```

<210> SEQ ID NO 7
<211> LENGTH: 4434
<212> TYPE: DNA
<213> ORGANISM: Streptococcus salivarius

<400> SEQUENCE: 7

```
atggacgaaa cgcaggataa gaccgtgacg cagagcaaca gcggcaccac cgcttccctg      60
gtcactagcc ctgaagccac gaaagaggcg gacaaacgca cgaacactaa agaggccgac     120
gttctgacgc ctgcaaaaga aacgaacgca gtcgagactg cgaccaccac taacacccag     180
gcgacggcgg aggccgccac gaccgcgacc accgcgacg tcgcggtggc tgcggtgccg      240
aacaaagaag cggtcgttac cacggatgct ccggcggtca cgaccgagaa agcggaagaa     300
cagccggcta ccgttaaagc agaagtcgtc aatacggaag tgaaagcgcc ggaagcggct     360
ctgaaagaca cgcgaggttga ggcagcgctg agcctgaaga acatcaagaa cattgatggc     420
aagtattact atgttaatga ggatggcagc cacaaagaga atttcgctat taccgtgaat     480
ggccagctgc tgtactttgg taaagacggt gcgctgacgt cctctagcac gtattctttt     540
accccaggca ctaccaatat cgtggacggt tttagcatta caaccgcgc ttacgacagc      600
agcgaggcga gctttgagct gatcgacggt tacttgaccg cagacagctg gtatcgtccg     660
gctagcatca tcaaagatgg tgttacgtgg caagcgtcca ccgccgagga ttttcgtccg     720
ctgctgatgg catggtggcc gaatgtggat acgcaggtga actatttgaa ttacatgtcc     780
aaagttttca acctggacgc gaaatactct agcaccgaca acaggaaac cctgaaagtg     840
gcagcaaag acattcaat caagattgaa caaaagattc aagcggagaa gagcacgcag     900
tggctgcgtg aaactatcag cgcctttgt aaaacccagc cgcagtggaa caaagaaacc     960
gagaattaca gcaagggtgg tggtgaggac cacctgcaag gtggcgcact gctgtatgtt    1020
aacgacagcc gtaccccttg ggcgaatagc gattaccgtc gtctgaatcg caccgcaacc    1080
aatcagacgg gcacgatcga taagtctatt ctggacgagc agtctgaccc aaaccacatg    1140
ggcggtttcg actttctgct ggcgaacgac gtcgacctga gcaatccggt cgtgcaggct    1200
gagcagctga tcaaatcca ctatctgatg aattggggtt ccattgtgat gggtgacaag    1260
gatgcgaact tgacggcat tcgtgtcgat gcagttgaca acgtggacgc ggacatgttg    1320
```

```
caactgtata ccaattactt ccgtgagtac tacggtgtga acaagagcga agctaacgca    1380
ctggctcaca tcagcgttct ggaggcgtgg agcctgaatg ataatcatta caatgacaag    1440
accgatggtg cggcactggc aatggagaat aagcaacgtc tggcgctgtt gttttcgttg    1500
gcgaaaccga tcaaagagcg tacccccggca gtgagcccgc tgtataacaa caccttcaat    1560
accacccagc gtgatgaaaa gaccgattgg attaacaaag acggtagcaa ggcttacaac    1620
gaagatggca cggtcaaaca atcgaccatc ggtaagtaca acgagaaata cggtgacgca    1680
tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga gcgacaaaaa gtatacccctg    1860 aataacattc cggcagcgta tgccgtgatg ttgcagaata tggaaacgat acccgcgtc    1920 tattacggtg atctgtatac ggacgacggt cactacatgg aaaccaaatc tccgtattac    1980
gataccatcg tgaatttgat gaagagccgt atcaagtatg tttcgggtgg ccaggcgcaa    2040
cgtagctatt ggctgccgac cgacggtaag atggacaata gcgacgttga gctgtaccgc    2100
acgaatgagg tttacacgag cgtgcgctat ggtaaggata tcatgaccgc taatgatacc    2160
gaaggctcta agtattcccg caccagcggc caagtcacct ggtcgcgaa caatccgaag    2220 ctgaatctgg accaaagcgc caagttgaat gtggagatgg gcaaaatcca tgcgaatcag    2280
aagtatcgcg cactgattgt cggcactgcg gacggcatta gaactttac ttccgacgcg    2340 gacgccattg cagcgggtta tgtgaaagaa accgatagca acggcgtgct gaccttcggt    2400
gctaacgaca ttaagggcta cgaaacgttt gatatgagcg gtttcgtggc ggtgtgggtt    2460
ccggtgggtg catctgacaa tcaggacatt cgtgttgcgc cgagcaccga ggcaaagaaa    2520
gaaggtgagc tgaccttgaa ggcgacggaa gcgtatgata ccagctgat ttacgaaggc    2580 tttagcaatt ccagacgat cccagatggc agcgatccgt ccgtgtatac gaaccgcaag    2640
attgcggaga acgtggatct gttcaaaagc tggggtgtca ccagctttga gatggcaccg    2700
caatttgtct cggcggatga tggcacccttt ctggatagcg ttattcagaa tggctacgcc    2760
ttcgccgacc gttatgacct ggccatgtcc aagaacaaca gtatggtag caaagaggac    2820 ctgcgtgatg cactgaaagc actgcataag gcgggtattc aagctatcgc agactgggtt    2880
ccagaccaga tctaccagct gccgggcaaa gaagttgtca ccgccacccg tacgatggt    2940 gctggccgta agatcgcaga cgcgattatc gaccattctc tgtatgttgc aaacagcaaa    3000
agcagcggca agattatca agcaaagtac ggtggcgagt tcctggccga gctgaaagcc    3060
aaatacccgg aaatgttcaa agttaacatg attagcacgg gtaagccgat tgatgactcc    3120
gtgaaattga agcaatggaa agccgagtac ttcaatggca ccaacgtttt ggaacgtggt    3180
gtcggctatg ttctgagcga cgaggcgacc ggtaagtatt tcacggtgac caaagaaggc    3240
aatttcattc cgctgcaact gacgggtaaa gagaaagtta tcacgggttt ctccagcgat    3300
ggtaagggta tcacctatt cggtacgagc ggtacgcagg cgaagtctgc gtttgttacc    3360
ttcaatggta acacctacta tttcgacgcg cgtggccaca tggttaccaa tagcgaatac    3420
agcccgaatg caaggacgt ctaccgtttt ctgccgaacg tatcatgct gagcaatgcg    3480 ttttacattg atgcgaacgg taatacctac ctgtacaact ctaagggtca aatgtacaaa    3540
ggcggttaca cgaaattcga tgtttctgaa acggataagg acggtaaaga gtccaaggtc    3600
gtcaagttcc gctactttac gaacgaaggc gtcatggcca agggtgttac cgtcattgat    3660
ggttttaccc aatacttcgg tgaggacggc tttcaagcga aggataagct ggtcaccttc    3720
```

```
aagggcaaga cgtattactt cgacgcacac actggtaatg gtatcaaaga tacctggcgc   3780
aatatcaatg gtaaatggta ctatttcgac gcgaatggcg ttgctgcgac cggtgcgcag   3840
gtgattaacg ccagaaaact gtacttcaac gaggatggct cccaagtcaa aggcggcgtg   3900
gttaagaacg cagacggcac ctatagcaaa tacaaagaag ttttggtga gctggttact    3960 aacgagtttt tcacgactga tggcaatgtt tggtactacg ccggtgcaaa tggtaaaacc   4020
gttaccggtg cacaagtgat caacggccaa catttgtact caatgcgga cggttcccag    4080 gtgaagggtg gcgttgtcaa gaacgcggat ggcacctaca gcaagtacaa tgctagcact   4140
ggtgaacgtc tgacgaacga gttctttacg accggtgata acaattggta ttacattggc   4200
gcaaacggta agagcgtgac gggtgaggtc aagattggtg atgatactta cttttcgcg    4260 aaggatggca acaagttaa aggtcaaacc gtcagcgccg gtaatggtcg cattagctac    4320
tactacggtg acagcggcaa gcgtgcggtt agcacctgga ttgagattca gccgggtgtt   4380
tatgtgtatt tcgacaaaaa cggtttggcg taccctccgc gtgttctgaa ttaa          4434
```

<210> SEQ ID NO 8
<211> LENGTH: 1477
<212> TYPE: PRT
<213> ORGANISM: Streptococcus salivarius

<400> SEQUENCE: 8

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

Asn Ala Val Glu Thr Ala Thr Thr Asn Thr Gln Ala Thr Ala Glu
    50                  55                  60

Ala Ala Thr Thr Ala Thr Thr Ala Asp Val Ala Val Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
            100                 105                 110

Glu Val Lys Ala Pro Glu Ala Ala Leu Lys Asp Ser Glu Val Glu Ala
        115                 120                 125

Ala Leu Ser Leu Lys Asn Ile Lys Asn Ile Asp Gly Lys Tyr Tyr Tyr
    130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Asn Ile Val Asp Gly Phe Ser
            180                 185                 190

Ile Asn Asn Arg Ala Tyr Asp Ser Ser Glu Ala Ser Phe Glu Leu Ile
        195                 200                 205

Asp Gly Tyr Leu Thr Ala Asp Ser Trp Tyr Arg Pro Ala Ser Ile Ile
    210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
```

```
                    245                 250                 255
Asn Tyr Met Ser Lys Val Phe Asn Leu Asp Ala Lys Tyr Ser Ser Thr
                260                 265                 270

Asp Lys Gln Glu Thr Leu Lys Val Ala Ala Lys Asp Ile Gln Ile Lys
            275                 280                 285

Ile Glu Gln Lys Ile Gln Ala Glu Lys Ser Thr Gln Trp Leu Arg Glu
        290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Glu Asp His Leu Gln Gly Gly Ala
                325                 330                 335

Leu Leu Tyr Val Asn Asp Ser Arg Thr Pro Trp Ala Asn Ser Asp Tyr
                340                 345                 350

Arg Arg Leu Asn Arg Thr Ala Thr Asn Gln Thr Gly Thr Ile Asp Lys
            355                 360                 365

Ser Ile Leu Asp Glu Gln Ser Asp Pro Asn His Met Gly Gly Phe Asp
        370                 375                 380

Phe Leu Leu Ala Asn Asp Val Asp Leu Ser Asn Pro Val Val Gln Ala
385                 390                 395                 400

Glu Gln Leu Asn Gln Ile His Tyr Leu Met Asn Trp Gly Ser Ile Val
                405                 410                 415

Met Gly Asp Lys Asp Ala Asn Phe Asp Gly Ile Arg Val Asp Ala Val
                420                 425                 430

Asp Asn Val Asp Ala Asp Met Leu Gln Leu Tyr Thr Asn Tyr Phe Arg
            435                 440                 445

Glu Tyr Tyr Gly Val Asn Lys Ser Glu Ala Asn Ala Leu Ala His Ile
        450                 455                 460

Ser Val Leu Glu Ala Trp Ser Leu Asn Asp Asn His Tyr Asn Asp Lys
465                 470                 475                 480

Thr Asp Gly Ala Ala Leu Ala Met Glu Asn Lys Gln Arg Leu Ala Leu
                485                 490                 495

Leu Phe Ser Leu Ala Lys Pro Ile Lys Glu Arg Thr Pro Ala Val Ser
                500                 505                 510

Pro Leu Tyr Asn Asn Thr Phe Asn Thr Thr Gln Arg Asp Glu Lys Thr
            515                 520                 525

Asp Trp Ile Asn Lys Asp Gly Ser Lys Ala Tyr Asn Glu Asp Gly Thr
        530                 535                 540

Val Lys Gln Ser Thr Ile Gly Lys Tyr Asn Glu Lys Tyr Gly Asp Ala
545                 550                 555                 560

Ser Gly Asn Tyr Val Phe Ile Arg Ala His Asp Asn Asn Val Gln Asp
                565                 570                 575

Ile Ile Ala Glu Ile Ile Lys Lys Glu Ile Asn Pro Lys Ser Asp Gly
                580                 585                 590

Phe Thr Ile Thr Asp Ala Glu Met Lys Gln Ala Phe Glu Ile Tyr Asn
            595                 600                 605

Lys Asp Met Leu Ser Ser Asp Lys Lys Tyr Thr Leu Asn Asn Ile Pro
        610                 615                 620

Ala Ala Tyr Ala Val Met Leu Gln Asn Met Glu Thr Ile Thr Arg Val
625                 630                 635                 640

Tyr Tyr Gly Asp Leu Tyr Thr Asp Asp Gly His Tyr Met Glu Thr Lys
                645                 650                 655

Ser Pro Tyr Tyr Asp Thr Ile Val Asn Leu Met Lys Ser Arg Ile Lys
                660                 665                 670
```

-continued

```
Tyr Val Ser Gly Gly Gln Ala Gln Arg Ser Tyr Trp Leu Pro Thr Asp
            675                 680                 685
Gly Lys Met Asp Asn Ser Asp Val Glu Leu Tyr Arg Thr Asn Glu Val
        690                 695                 700
Tyr Thr Ser Val Arg Tyr Gly Lys Asp Ile Met Thr Ala Asn Asp Thr
705                 710                 715                 720
Glu Gly Ser Lys Tyr Ser Arg Thr Ser Gly Gln Val Thr Leu Val Ala
                725                 730                 735
Asn Asn Pro Lys Leu Asn Leu Asp Gln Ser Ala Lys Leu Asn Val Glu
            740                 745                 750
Met Gly Lys Ile His Ala Asn Gln Lys Tyr Arg Ala Leu Ile Val Gly
            755                 760                 765
Thr Ala Asp Gly Ile Lys Asn Phe Thr Ser Asp Ala Asp Ala Ile Ala
        770                 775                 780
Ala Gly Tyr Val Lys Glu Thr Asp Ser Asn Gly Val Leu Thr Phe Gly
785                 790                 795                 800
Ala Asn Asp Ile Lys Gly Tyr Glu Thr Phe Asp Met Ser Gly Phe Val
                805                 810                 815
Ala Val Trp Val Pro Val Gly Ala Ser Asp Asn Gln Asp Ile Arg Val
            820                 825                 830
Ala Pro Ser Thr Glu Ala Lys Lys Glu Gly Glu Leu Thr Leu Lys Ala
            835                 840                 845
Thr Glu Ala Tyr Asp Ser Gln Leu Ile Tyr Glu Gly Phe Ser Asn Phe
850                 855                 860
Gln Thr Ile Pro Asp Gly Ser Asp Pro Ser Val Tyr Thr Asn Arg Lys
865                 870                 875                 880
Ile Ala Glu Asn Val Asp Leu Phe Lys Ser Trp Gly Val Thr Ser Phe
                885                 890                 895
Glu Met Ala Pro Gln Phe Val Ser Ala Asp Gly Thr Phe Leu Asp
            900                 905                 910
Ser Val Ile Gln Asn Gly Tyr Ala Phe Ala Asp Arg Tyr Asp Leu Ala
            915                 920                 925
Met Ser Lys Asn Lys Tyr Gly Ser Lys Glu Asp Leu Arg Asp Ala
        930                 935                 940
Leu Lys Ala Leu His Lys Ala Gly Ile Gln Ala Ile Ala Asp Trp Val
945                 950                 955                 960
Pro Asp Gln Ile Tyr Gln Leu Pro Gly Lys Glu Val Val Thr Ala Thr
                965                 970                 975
Arg Thr Asp Gly Ala Gly Arg Lys Ile Ala Asp Ala Ile Ile Asp His
            980                 985                 990
Ser Leu Tyr Val Ala Asn Ser Lys Ser Ser Gly Lys Asp Tyr Gln Ala
            995                1000                1005
Lys Tyr Gly Gly Glu Phe Leu Ala Glu Leu Lys Ala Lys Tyr Pro
        1010                1015                1020
Glu Met Phe Lys Val Asn Met Ile Ser Thr Gly Lys Pro Ile Asp
        1025                1030                1035
Asp Ser Val Lys Leu Lys Gln Trp Lys Ala Glu Tyr Phe Asn Gly
        1040                1045                1050
Thr Asn Val Leu Glu Arg Gly Val Gly Tyr Val Leu Ser Asp Glu
        1055                1060                1065
Ala Thr Gly Lys Tyr Phe Thr Val Thr Lys Glu Gly Asn Phe Ile
        1070                1075                1080
```

```
Pro Leu Gln Leu Thr Gly Lys Glu Lys Val Ile Thr Gly Phe Ser
    1085                1090                1095

Ser Asp Gly Lys Gly Ile Thr Tyr Phe Gly Thr Ser Gly Thr Gln
    1100                1105                1110

Ala Lys Ser Ala Phe Val Thr Phe Asn Gly Asn Thr Tyr Tyr Phe
    1115                1120                1125

Asp Ala Arg Gly His Met Val Thr Asn Ser Glu Tyr Ser Pro Asn
    1130                1135                1140

Gly Lys Asp Val Tyr Arg Phe Leu Pro Asn Gly Ile Met Leu Ser
    1145                1150                1155

Asn Ala Phe Tyr Ile Asp Ala Asn Gly Asn Thr Tyr Leu Tyr Asn
    1160                1165                1170

Ser Lys Gly Gln Met Tyr Lys Gly Gly Tyr Thr Lys Phe Asp Val
    1175                1180                1185

Ser Glu Thr Asp Lys Asp Gly Lys Glu Ser Lys Val Val Lys Phe
    1190                1195                1200

Arg Tyr Phe Thr Asn Glu Gly Val Met Ala Lys Gly Val Thr Val
    1205                1210                1215

Ile Asp Gly Phe Thr Gln Tyr Phe Gly Glu Asp Gly Phe Gln Ala
    1220                1225                1230

Lys Asp Lys Leu Val Thr Phe Lys Gly Lys Thr Tyr Tyr Phe Asp
    1235                1240                1245

Ala His Thr Gly Asn Gly Ile Lys Asp Thr Trp Arg Asn Ile Asn
    1250                1255                1260

Gly Lys Trp Tyr Tyr Phe Asp Ala Asn Gly Val Ala Ala Thr Gly
    1265                1270                1275

Ala Gln Val Ile Asn Gly Gln Lys Leu Tyr Phe Asn Glu Asp Gly
    1280                1285                1290

Ser Gln Val Lys Gly Gly Val Val Lys Asn Ala Asp Gly Thr Tyr
    1295                1300                1305

Ser Lys Tyr Lys Glu Gly Phe Gly Glu Leu Val Thr Asn Glu Phe
    1310                1315                1320

Phe Thr Thr Asp Gly Asn Val Trp Tyr Tyr Ala Gly Ala Asn Gly
    1325                1330                1335

Lys Thr Val Thr Gly Ala Gln Val Ile Asn Gly Gln His Leu Tyr
    1340                1345                1350

Phe Asn Ala Asp Gly Ser Gln Val Lys Gly Gly Val Val Lys Asn
    1355                1360                1365

Ala Asp Gly Thr Tyr Ser Lys Tyr Asn Ala Ser Thr Gly Glu Arg
    1370                1375                1380

Leu Thr Asn Glu Phe Phe Thr Thr Gly Asp Asn Trp Tyr Tyr
    1385                1390                1395

Ile Gly Ala Asn Gly Lys Ser Val Thr Gly Glu Val Lys Ile Gly
    1400                1405                1410

Asp Asp Thr Tyr Phe Phe Ala Lys Asp Gly Lys Gln Val Lys Gly
    1415                1420                1425

Gln Thr Val Ser Ala Gly Asn Gly Arg Ile Ser Tyr Tyr Tyr Gly
    1430                1435                1440

Asp Ser Gly Lys Arg Ala Val Ser Thr Trp Ile Glu Ile Gln Pro
    1445                1450                1455

Gly Val Tyr Val Tyr Phe Asp Lys Asn Gly Leu Ala Tyr Pro Pro
    1460                1465                1470

Arg Val Leu Asn
```

<210> SEQ ID NO 9
<211> LENGTH: 4311
<212> TYPE: DNA
<213> ORGANISM: Streptococcus downei

<400> SEQUENCE: 9

```
atggttgacg gcaaatacta ctactacgat caggacggca acgtaaagaa aaacttcgcg      60
gttagcgtgg gcgagaaaat ctattacttt gacgaaactg gcgcctacaa agacaccagc     120
aaagttgagg cggacaaaag cggcagcgac attagcaagg aagagactac cttcgcggca     180
aacaaccgcg cctacagcac cagcgcggag aattttgagg cgatcgacaa ttatctgacc     240
gcggactcct ggtatcgtcc taaatccatc ctgaaggatg gcaaaacgtg gacgaaagc      300 agcaaagatg actttcgtcc gctgctgatg gcgtggtggc cggataccga aacgaagcgc     360
aattacgtga actacatgaa caaagttgtt ggcatcgaca agacctatac cgcggaaacc     420
agccaggccg acttgaccgc tgcggcggaa ctggtgcaag cacgcattga gcagaagatc     480
acgaccgaac agaacacgaa atggctgcgt gaggcaatct cggcatttgt aaaaacgcaa     540
ccgcagtgga acggtgaaag cgagaagccg tacgacgatc acctgcaaaa cggtgctctg     600
aaatttgata tcagagcga cctgaccccg atacgcaaa gcaactaccg tctgttgaac      660
cgtaccccga ctaatcagac gggtagcctg acagccgct tcacttataa cgcgaacgac      720
cctttgggcg ttatgagct gctgctggca aatgacgtcg ataacagcaa tccgatcgtg      780
caggcggagc agctgaactg gctgcattac ctgctgaatt ttggtacgat ctacgccaaa     840
gatgccgacg ctaacttcga tagcattcgt gtggacgcgg ttgataacgt cgatgcggat     900
ctgctgcaaa ttagcagcga ttacctgaaa gcagcctacg gcattgataa gaataacaaa     960
aacgcgaaca ccacgtgag cattgtcgaa gcctggagcg ataatgatac cccgtacctg     1020
catgacgatg tgacaacct gatgaatatg ataacaaat ttcgcctgtc catgctgtgg      1080
tcgctggcca aaccgctgga caagcgtagc ggtctgaacc cgctgattca taacagcttg     1140
gtggatcgtg aagttgatga ccgcgaggtt gaaacggttc cgagctattc ttttgcacgt     1200
gcgcatgata gcgaggtcca ggacttgatc cgtgacatca tcaaggcaga gatcaatccg     1260
aacgcattcg ttatagctt tacccaagac gagattgacc aggcctttaa gatttacaat     1320
gaggatctga agaaaacgga taagaaatac acccactata atgtgccgtt gagctacacc     1380
ctgctgctga cgaataaggg tagcatccca cgtgtctact atggtgatat gtttaccgac     1440
gatggtcagt atatggcgaa caaaaccgtc aactatgacg ccattgaatc tctgctgaaa     1500
gcgcgtatga gtatgtcgc tggcggtcaa gcaatgcaga actaccaaat cggtaatggt     1560
gagatcctga ccagcgttcg ttatggtaag ggtgccctga acagagcga caaaggtgat     1620 gcgaccacgc gcaccagcgg tgtcggtgtc gttatgggca atcagccaaa ctttagcttg     1680
gacggcaaag tggtggctct gaacatgggc gcagctcatg cgaatcagga gtatcgtgcg     1740
ctgatggtta gcacgaaaga cggtgttgcc acgtatgcga ccgatgcaga tgcgagcaaa     1800
gccggtctgg tcaaacgtac cgacgaaaac ggctacctgt atttcctgaa tgacgacctg     1860
aagggtgtgg ccaatcctca ggtgagcggt ttcttgcagg tgtgggttcc ggtgggtgcc     1920
gcggatgatc aagatatccg tgttgcagct agcgataccg catccaccga tggcaagagc     1980
ctgcaccaag acgccgcgat ggatagccgt gttatgtttg aaggcttctc taactttcag     2040 tccttttgcca cgaaagaaga ggaatatacc aacgtcgtta tcgccaacaa tgtggataag     2100
```

-continued

```
ttcgttagct ggggtatcac ggatttcgag atggccccac aatatgtttc cagcaccgac    2160
ggtcaattcc tggactctgt cattcagaac ggttatgctt ttacgaccg ttatgacttg    2220 ggcatgtcta aggcaaacaa atacggcacg gccgatcaac tggttaaggc cattaaggcc    2280
ctgcacgcga agggcctgaa ggttatggca gattgggtgc cggatcagat gtataccttc    2340
ccgaaacagg aagtcgtgac cgttacccgt accgacaaat ttggcaaacc gatcgcaggt    2400
tcccaaatca atcatagcct gtatgttacc gataccaagt ccagcggcga tgactatcag    2460
gccaaatatg gtggtgcgtt tctggacgag ctgaaggaga aatatccgga gctgttcacg    2520
aagaaacaaa tcagcacggg tcaagctatt gacccgagcg tgaaaatcaa acagtggtct    2580
gctaagtatt tcaatggctc caacatcctg ggtcgcggtg cggactacgt actgtcggat    2640
caggcgagca acaaatacct gaacgtgtct gacgataaac tgttcctgcc gaaaaccttg    2700
ctgggccaag ttgtcgagag cggtatccgc tttgacggca ctggttatgt gtacaactct    2760
agcactacgg gtgaaaaagt taccgattcc ttcattacgg aggcaggtaa tctgtactac    2820
ttcggtcaag acggctatat ggtgaccggc gcacagaaca ttaagggcag caactattac    2880
ttcctggcca atggtgcggc cctgcgtaac accgtttaca ccgatgcgca aggtcagaat    2940
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt tcgataaaga tggtgtccag gccaaggata agatcattgt caccccgcgat    3120 ggcaaagtcc gctatttcga ccagcacaac ggtaatgcgg ttactaacac gttcgttgcg    3180
gacaagacgg gtcactggta ctatctgggc aaagacggcg tcgcggttac cggtgcgcag    3240
actgtgggta acagcatttt gtactttgaa gcgaacggtc aacaagtcaa gggtgacttc    3300
gtgacggcta agacggtaa actgtacttc tatgatgtgg acagcggcga catgtggacc    3360
aataccttta tcgaggataa agcgggtaat tggttctacc tgggtaagga cggtgcggcc    3420
gtcaccggtg cacagacgat caaaggccag aaattgtatt tcaaagccaa cggtcagcaa    3480
gttaaaggtg acattgtcaa ggacgcggac ggtaagatcc gttattacga cgctcagacc    3540
ggtgaacagg tctttaacaa gtccgttagc gtcaacggta agacctacta tttcggtagc    3600
gacggcaccg cgcaaaccca ggcgaatccg aaaggccaaa cctttaagga tggtagcggc    3660
gttctgcgtt tctacaattt ggagggccag tatgtctcgg gcagcggctg gtacgaaacg    3720
gccgagcacg agtgggtata tgtgaaatcc ggtaaagttc tgaccggtgc ccagacgatt    3780
ggtaatcaac gtgtttactt caaggacaat ggtcaccagg tgaaaggcca gctggtcacg    3840
ggtaatgacg gtaaattgcg ttactacgac gcgaacagcg tgatcaagc attcaacaaa    3900 tccgtcacgg ttaacggtaa aacctactac tttggcagcg atggtacggc gcagacgcag    3960
gctaatccta agggtcagac cttcaaagat ggtagcggcg tgctgcgttt ttacaacttg    4020
gaaggccaat acgtgtctgg cagcggttgg tacaagaatg cgcagggcca gtggctgtac    4080
gtgaaagatg gcaaggtcct gaccggtctg caaacggtcg gcaatcagaa ggtctacttc    4140
gacaaaaatg gcatccaagc aaagggtaag gccgttcgca cgtccgatgg taaagtgcgc    4200
tactttgatg agaatagcgg tagcatgatt acgaaccaat ggaagttcgt ttacggtcaa    4260
tactattact tcggttctga cggcgcagcg gtttaccgtg gttggaacta a             4311
```

<210> SEQ ID NO 10
<211> LENGTH: 1436
<212> TYPE: PRT

<213> ORGANISM: Streptococcus downei

<400> SEQUENCE: 10

| | | | | | | | | | | | | | | |
|---|---|---|---|---|---|---|---|---|---|---|---|---|---|---|
|Met|Val|Asp|Gly|Lys|Tyr|Tyr|Tyr|Asp|Gln|Asp|Gly|Asn|Val|Lys|
|1| | | |5| | | |10| | | | |15| |
|Lys|Asn|Phe|Ala|Val|Ser|Val|Gly|Glu|Lys|Ile|Tyr|Tyr|Phe|Asp|Glu|
| | | |20| | | |25| | | |30| | | |
|Thr|Gly|Ala|Tyr|Lys|Asp|Thr|Ser|Lys|Val|Glu|Ala|Asp|Lys|Ser|Gly|
| | | |35| | | |40| | | |45| | | |
|Ser|Asp|Ile|Ser|Lys|Glu|Glu|Thr|Phe|Ala|Ala|Asn|Asn|Arg|Ala|
| |50| | | |55| | | |60| | | | | |
|Tyr|Ser|Thr|Ser|Ala|Glu|Asn|Phe|Glu|Ala|Ile|Asp|Asn|Tyr|Leu|Thr|
|65| | | |70| | | |75| | | | | |80|
|Ala|Asp|Ser|Trp|Tyr|Arg|Pro|Lys|Ser|Ile|Leu|Lys|Asp|Gly|Lys|Thr|
| | | |85| | | |90| | | |95| | | |
|Trp|Thr|Glu|Ser|Ser|Lys|Asp|Asp|Phe|Arg|Pro|Leu|Leu|Met|Ala|Trp|
| | |100| | | |105| | | |110| | | | |
|Trp|Pro|Asp|Thr|Glu|Thr|Lys|Arg|Asn|Tyr|Val|Asn|Tyr|Met|Asn|Lys|
| | |115| | | |120| | | |125| | | | |
|Val|Val|Gly|Ile|Asp|Lys|Thr|Tyr|Thr|Ala|Glu|Thr|Ser|Gln|Ala|Asp|
| |130| | | |135| | | |140| | | | | |
|Leu|Thr|Ala|Ala|Ala|Glu|Leu|Val|Gln|Ala|Arg|Ile|Glu|Gln|Lys|Ile|
|145| | | |150| | | |155| | | | | |160|
|Thr|Thr|Glu|Gln|Asn|Thr|Lys|Trp|Leu|Arg|Glu|Ala|Ile|Ser|Ala|Phe|
| | | |165| | | |170| | | |175| | | |
|Val|Lys|Thr|Gln|Pro|Gln|Trp|Asn|Gly|Glu|Ser|Glu|Lys|Pro|Tyr|Asp|
| | |180| | | |185| | | |190| | | | |
|Asp|His|Leu|Gln|Asn|Gly|Ala|Leu|Lys|Phe|Asp|Asn|Gln|Ser|Asp|Leu|
| | |195| | | |200| | | |205| | | | |
|Thr|Pro|Asp|Thr|Gln|Ser|Asn|Tyr|Arg|Leu|Leu|Asn|Arg|Thr|Pro|Thr|
| |210| | | |215| | | |220| | | | | |
|Asn|Gln|Thr|Gly|Ser|Leu|Asp|Ser|Arg|Phe|Thr|Tyr|Asn|Ala|Asn|Asp|
|225| | | |230| | | |235| | | | | |240|
|Pro|Leu|Gly|Gly|Tyr|Glu|Leu|Leu|Leu|Ala|Asn|Asp|Val|Asp|Asn|Ser|
| | | |245| | | |250| | | |255| | | |
|Asn|Pro|Ile|Val|Gln|Ala|Glu|Gln|Leu|Asn|Trp|Leu|His|Tyr|Leu|Leu|
| | |260| | | |265| | | |270| | | | |
|Asn|Phe|Gly|Thr|Ile|Tyr|Ala|Lys|Asp|Ala|Asp|Ala|Asn|Phe|Asp|Ser|
| | |275| | | |280| | | |285| | | | |
|Ile|Arg|Val|Asp|Ala|Val|Asp|Asn|Val|Asp|Ala|Asp|Leu|Leu|Gln|Ile|
| |290| | | |295| | | |300| | | | | |
|Ser|Ser|Asp|Tyr|Leu|Lys|Ala|Ala|Tyr|Gly|Ile|Asp|Lys|Asn|Asn|Lys|
|305| | | |310| | | |315| | | | | |320|
|Asn|Ala|Asn|Asn|His|Val|Ser|Ile|Val|Glu|Ala|Trp|Ser|Asp|Asn|Asp|
| | | |325| | | |330| | | |335| | | |
|Thr|Pro|Tyr|Leu|His|Asp|Asp|Gly|Asp|Asn|Leu|Met|Asn|Met|Asp|Asn|
| | |340| | | |345| | | |350| | | | |
|Lys|Phe|Arg|Leu|Ser|Met|Leu|Trp|Ser|Leu|Ala|Lys|Pro|Leu|Asp|Lys|
| | |355| | | |360| | | |365| | | | |
|Arg|Ser|Gly|Leu|Asn|Pro|Leu|Ile|His|Asn|Ser|Leu|Val|Asp|Arg|Glu|
| |370| | | |375| | | |380| | | | | |
|Val|Asp|Asp|Arg|Glu|Val|Glu|Thr|Val|Pro|Ser|Tyr|Ser|Phe|Ala|Arg|
|385| | | |390| | | |395| | | | | |400|

```
Ala His Asp Ser Glu Val Gln Asp Leu Ile Arg Asp Ile Ile Lys Ala
            405                 410                 415
Glu Ile Asn Pro Asn Ala Phe Gly Tyr Ser Phe Thr Gln Asp Glu Ile
        420                 425                 430
Asp Gln Ala Phe Lys Ile Tyr Asn Glu Asp Leu Lys Lys Thr Asp Lys
            435                 440                 445
Lys Tyr Thr His Tyr Asn Val Pro Leu Ser Tyr Thr Leu Leu Leu Thr
        450                 455                 460
Asn Lys Gly Ser Ile Pro Arg Val Tyr Tyr Gly Asp Met Phe Thr Asp
465                 470                 475                 480
Asp Gly Gln Tyr Met Ala Asn Lys Thr Val Asn Tyr Asp Ala Ile Glu
                485                 490                 495
Ser Leu Leu Lys Ala Arg Met Lys Tyr Val Ala Gly Gly Gln Ala Met
            500                 505                 510
Gln Asn Tyr Gln Ile Gly Asn Gly Glu Ile Leu Thr Ser Val Arg Tyr
        515                 520                 525
Gly Lys Gly Ala Leu Lys Gln Ser Asp Lys Gly Asp Ala Thr Thr Arg
    530                 535                 540
Thr Ser Gly Val Gly Val Met Gly Asn Gln Pro Asn Phe Ser Leu
545                 550                 555                 560
Asp Gly Lys Val Val Ala Leu Asn Met Gly Ala Ala His Ala Asn Gln
                565                 570                 575
Glu Tyr Arg Ala Leu Met Val Ser Thr Lys Asp Gly Val Ala Thr Tyr
            580                 585                 590
Ala Thr Asp Ala Asp Ala Ser Lys Ala Gly Leu Val Lys Arg Thr Asp
        595                 600                 605
Glu Asn Gly Tyr Leu Tyr Phe Leu Asn Asp Asp Leu Lys Gly Val Ala
    610                 615                 620
Asn Pro Gln Val Ser Gly Phe Leu Gln Val Trp Val Pro Val Gly Ala
625                 630                 635                 640
Ala Asp Asp Gln Asp Ile Arg Val Ala Ala Ser Asp Thr Ala Ser Thr
                645                 650                 655
Asp Gly Lys Ser Leu His Gln Asp Ala Ala Met Asp Ser Arg Val Met
            660                 665                 670
Phe Glu Gly Phe Ser Asn Phe Gln Ser Phe Ala Thr Lys Glu Glu Glu
        675                 680                 685
Tyr Thr Asn Val Val Ile Ala Asn Asn Val Asp Lys Phe Val Ser Trp
    690                 695                 700
Gly Ile Thr Asp Phe Glu Met Ala Pro Gln Tyr Val Ser Ser Thr Asp
705                 710                 715                 720
Gly Gln Phe Leu Asp Ser Val Ile Gln Asn Gly Tyr Ala Phe Thr Asp
                725                 730                 735
Arg Tyr Asp Leu Gly Met Ser Lys Ala Asn Lys Tyr Gly Thr Ala Asp
            740                 745                 750
Gln Leu Val Lys Ala Ile Lys Ala Leu His Ala Lys Gly Leu Lys Val
        755                 760                 765
Met Ala Asp Trp Val Pro Asp Gln Met Tyr Thr Phe Pro Lys Gln Glu
    770                 775                 780
Val Val Thr Val Thr Arg Thr Asp Lys Phe Gly Lys Pro Ile Ala Gly
785                 790                 795                 800
Ser Gln Ile Asn His Ser Leu Tyr Val Thr Thr Lys Ser Ser Gly
                805                 810                 815
Asp Asp Tyr Gln Ala Lys Tyr Gly Gly Ala Phe Leu Asp Glu Leu Lys
```

-continued

```
            820                 825                 830
Glu Lys Tyr Pro Glu Leu Phe Thr Lys Lys Gln Ile Ser Thr Gly Gln
            835                 840                 845
Ala Ile Asp Pro Ser Val Lys Ile Lys Gln Trp Ser Ala Lys Tyr Phe
850                 855                 860
Asn Gly Ser Asn Ile Leu Gly Arg Gly Ala Asp Tyr Val Leu Ser Asp
865                 870                 875                 880
Gln Ala Ser Asn Lys Tyr Leu Asn Val Ser Asp Asp Lys Leu Phe Leu
            885                 890                 895
Pro Lys Thr Leu Leu Gly Gln Val Val Glu Ser Gly Ile Arg Phe Asp
            900                 905                 910
Gly Thr Gly Tyr Val Tyr Asn Ser Ser Thr Thr Gly Glu Lys Val Thr
            915                 920                 925
Asp Ser Phe Ile Thr Glu Ala Gly Asn Leu Tyr Tyr Phe Gly Gln Asp
            930                 935                 940
Gly Tyr Met Val Thr Gly Ala Gln Asn Ile Lys Gly Ser Asn Tyr Tyr
945                 950                 955                 960
Phe Leu Ala Asn Gly Ala Ala Leu Arg Asn Thr Val Tyr Thr Asp Ala
            965                 970                 975
Gln Gly Gln Asn His Tyr Tyr Gly Asn Asp Gly Lys Arg Tyr Glu Asn
            980                 985                 990
Gly Tyr Gln Gln Phe Gly Asn Asp Ser Trp Arg Tyr Phe Lys Asn Gly
            995                 1000                1005
Val Met Ala Leu Gly Leu Thr Thr Val Asp Gly His Val Gln Tyr
    1010                1015                1020
Phe Asp Lys Asp Gly Val Gln Ala Lys Asp Lys Ile Ile Val Thr
    1025                1030                1035
Arg Asp Gly Lys Val Arg Tyr Phe Asp Gln His Asn Gly Asn Ala
    1040                1045                1050
Val Thr Asn Thr Phe Val Ala Asp Lys Thr Gly His Trp Tyr Tyr
    1055                1060                1065
Leu Gly Lys Asp Gly Val Ala Val Thr Gly Ala Gln Thr Val Gly
    1070                1075                1080
Lys Gln His Leu Tyr Phe Glu Ala Asn Gly Gln Gln Val Lys Gly
    1085                1090                1095
Asp Phe Val Thr Ala Lys Asp Gly Lys Leu Tyr Phe Tyr Asp Val
    1100                1105                1110
Asp Ser Gly Asp Met Trp Thr Asn Thr Phe Ile Glu Asp Lys Ala
    1115                1120                1125
Gly Asn Trp Phe Tyr Leu Gly Lys Asp Gly Ala Ala Val Thr Gly
    1130                1135                1140
Ala Gln Thr Ile Lys Gly Gln Lys Leu Tyr Phe Lys Ala Asn Gly
    1145                1150                1155
Gln Gln Val Lys Gly Asp Ile Val Lys Asp Ala Asp Gly Lys Ile
    1160                1165                1170
Arg Tyr Tyr Asp Ala Gln Thr Gly Glu Gln Val Phe Asn Lys Ser
    1175                1180                1185
Val Ser Val Asn Gly Lys Thr Tyr Tyr Phe Gly Ser Asp Gly Thr
    1190                1195                1200
Ala Gln Thr Gln Ala Asn Pro Lys Gly Gln Thr Phe Lys Asp Gly
    1205                1210                1215
Ser Gly Val Leu Arg Phe Tyr Asn Leu Glu Gly Gln Tyr Val Ser
    1220                1225                1230
```

Gly Ser Gly Trp Tyr Glu Thr Ala Glu His Glu Trp Val Tyr Val
        1235                1240                1245

Lys Ser Gly Lys Val Leu Thr Gly Ala Gln Thr Ile Gly Asn Gln
    1250                1255                1260

Arg Val Tyr Phe Lys Asp Asn Gly His Gln Val Lys Gly Gln Leu
    1265                1270                1275

Val Thr Gly Asn Asp Gly Lys Leu Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Ser Asp Gly Thr Ala Gln Thr Gln Ala Asn Pro
    1310                1315                1320

Lys Gly Gln Thr Phe Lys Asp Gly Ser Gly Val Leu Arg Phe Tyr
    1325                1330                1335

Asn Leu Glu Gly Gln Tyr Val Ser Gly Ser Gly Trp Tyr Lys Asn
    1340                1345                1350

Ala Gln Gly Gln Trp Leu Tyr Val Lys Asp Gly Lys Val Leu Thr
    1355                1360                1365

Gly Leu Gln Thr Val Gly Asn Gln Lys Val Tyr Phe Asp Lys Asn
    1370                1375                1380

Gly Ile Gln Ala Lys Gly Lys Ala Val Arg Thr Ser Asp Gly Lys
    1385                1390                1395

Val Arg Tyr Phe Asp Glu Asn Ser Gly Ser Met Ile Thr Asn Gln
    1400                1405                1410

Trp Lys Phe Val Tyr Gly Gln Tyr Tyr Tyr Phe Gly Ser Asp Gly
    1415                1420                1425

Ala Ala Val Tyr Arg Gly Trp Asn
    1430                1435

<210> SEQ ID NO 11
<211> LENGTH: 3942
<212> TYPE: DNA
<213> ORGANISM: Streptococcus mutans

<400> SEQUENCE: 11
atgattgacg gcaaatacta ctactatgac aacaacggca agtacgcac caatttcacg        60
ttgatcgcgg acggtaaaat cctgcatttt gatgaaactg gcgcgtacac cgacactagc      120
attgataccg tgaacaagga tattgtcacg acgcgtagca acctgtataa gaaatacaat      180
caagtgtatg atcgcagcgc gcagagcttc gagcatgttg atcactacct gacggcggaa      240
tcttggtacc gtccgaaata cattctgaaa gatggcaaga cctggaccca gagcaccgag      300
aaggacttcc gtcctctgct gatgacctgg tggccgagcc aggaaacgca cgccagtat       360
gtcaacttca tgaacgccca gttgggtatc aacaaaacgt acgacgacac cagcaatcag      420
ctgcaattga acatcgctgc tgcaacgatc aagcaaaga tcgaagccaa atcacgacg        480
ctgaagaaca ccgattggct gcgtcaaacg atcagcgcgt tcgtcaaaac ccaaagcgct      540
tggaatagcg acagcgaaaa gccgtttgat gaccatctgc aaaacggtgc ggttctgtat      600
gataacgaag gtaaattgac gccgtatgcc aatagcaact atcgtattct gaaccgcacg      660
ccgaccaacc agaccggtaa gaaggacccg cgttataccg ccgacaacac gatcggcggc      720
tacgagtttc tgctggccaa cgacgtggat aatagcaacc cggtggttca ggccgagcag      780
ctgaactggc tgcacttcct gatgaacttt ggtaatatct acgcaaacga ccctgacgct      840

```
aacttcgact ccatccgcgt tgacgctgtc gataatgtgg acgccgatct gttacagatc    900
gcgggtgact atctgaaagc ggcaaagggc atccataaga atgacaaagc ggcgaacgac    960
cacctgtcca ttctggaagc gtggagcgac aatgacactc cgtatctgca tgatgatggc   1020
gacaacatga ttaacatgga taacaaactg cgcctgagcc tgctgttctc cctggcgaaa   1080
ccgctgaatc agcgtagcgg tatgaacccg ttgattacga acagcctggt caaccgtact   1140
gatgataatg ccgaaacggc ggcagtgcca agctactctt ttatccgtgc ccacgatagc   1200
gaggtccagg atttgattcg tgatatcatt aaggctgaga ttaacccgaa cgtcgtcggt   1260
tacagcttca cgatggaaga gattaagaag gcatttgaga tctacaataa ggacctgttg   1320
gccacggaga agaagtatac ccactataac accgcattga gctacgcgtt gctgctgacg   1380
aacaagagca gcgtgccgcg tgtctactat ggtgatatgt ttacggacga tggtcaatac   1440
atggcccaca agaccattaa ctacgaggca atcgaaaccc tgctgaaagc acgtatcaag   1500
tacgtgtccg gtggtcaggc tatgcgcaac cagcaagtgg gtaattcgga gatcatcacc   1560
agcgtgcgtt acggtaaagg tgcgctgaag gcgatggata cgggtgaccg cactacccgt   1620
acctctggtg tggcggtcat tgagggcaac aacccgagct tgcgcctgaa ggcttctgat   1680
cgtgtggttg tgaatatggg tgcggcccac aaaaatcaag cctatcgccc gctgctgttg   1740
acgaccgata acggcattaa ggcctatcac agcgaccaag aagcggcagg cctggtgcgt   1800
tacaccaacg accgtggcga actgatcttt accgcagccg acattaaggg ctacgcaaat   1860
ccgcaagtta gcggctacct gggcgtctgg gtccctgttg gcgcagcagc tgatcaggac   1920
gttcgtgttg cggcgagcac cgcgccaagc acggacggca agagcgttca ccagaacgcg   1980
gctctggaca gccgtgtgat gttcgagggt ttctcgaact tccaggcatt gctaccaag    2040
aaagaagagt ataccaatgt ggtcatcgct aagaatgtgg ataagttcgc ggagtggggt   2100
gtcaccgatt tcgagatggc tccgcaatac gtttctagca ccgacggtag cttttttggat  2160
agcgtgattc aaaacggtta tgcttttacc gaccgttacg acctgggcat cagcaagccg   2220
aacaaatatg gcaccgcgga cgatctggtt aaagcgatta aggcattgca cagcaaaggc   2280
atcaaagtta tggcggattg ggttccggac cagatgtatg ccctgccgga aaagaggtt    2340
gtgacggcaa cccgtgttga caaatacggt acgccggtag ctggcagcca gatcaaaaac   2400
acgctgtacg tggtcgatgg taaatctagc ggtaaggacc agcaggcgaa gtacggtggt   2460
gccttcctgg aagagctgca agcgaagtat ccggaactgt tcgcgcgcaa acagattagc   2520
accggtgttc cgatggaccc gagcgtcaag attaagcaat ggagcgcaaa atacttcaac   2580
ggcacgaata tcctgggtcg tggtgctggt tacgtgctga agatcaggc aaccaacacc     2640
tactttaaca tcagcgacaa taaagagatc aatttcctgc caaagacgtt gctgaaccag   2700
gattctcaag ttggctttag ctacgacggt aagggctatg tgtactacag cacctcgggc   2760
taccaggcta aaaacacgtt catcagcgag ggtgacaagt ggtattactt cgacaataac   2820
ggttatatgg ttaccggcgc acagagcatt aatggtgtga actattactt cctgccgaat   2880
ggtttacagc tgcgtgatgc gattctgaaa aatgaggacg tacgtacgc gtattatggc    2940
aatgatggtc gccgctacga gaatggctat tatcagttta tgagcggtgt ttggcgccat   3000
ttcaataatg gcgagatgtc cgttggtctg accgtcattg acggtcaagt tcaatacttt   3060
gacgagatgg gttaccaggc gaaaggcaaa ttcgttacca ccgcggatgg taagatccgt   3120
tacttcgata agcagagcgg caatatgtat cgtaatcgtt tcattgagaa cgaagagggc   3180
aaatggctgt acctgggtga ggacggcgcg gcagtcaccg gtagccagac gatcaatggt   3240
```

```
cagcacctgt attttcgtgc taacggcgtt caggttaagg gtgagttcgt gaccgatcgt    3300
catggccgca tctcttatta cgacggcaac agcggtgatc agatccgcaa ccgtttcgtc    3360
cgcaatgcgc aaggccagtg gttttacttt gacaacaatg gctatgcagt aactggtgct    3420
cgtacgatca acggccagca cctgtatttc cgcgcgaacg tgttcaggt aaaaggtgag     3480 tttgttacgg accgccacgg ccgcattagc tattatgatg gtaatagcgg tgaccaaatt    3540
cgcaatcgtt tcgtgcgtaa tgcacagggt cagtggttct acttcgacaa taatggttat    3600
gcagtcacgg gtgcacgtac cattaacggc caacacctgt actttcgcgc caatggtgtg    3660
caagtgaaag gcgaatttgt tactgatcgt tatggtcgta tcagctacta tgatggcaat    3720
tctggcgacc aaattcgcaa tcgctttgtt cgtaacgccc aaggtcaatg gttctatttc    3780
gacaacaacg gttacgcggt gaccggtgcc gcacgatta atggtcaaca cttgtacttc     3840
cgtgccaacg tgtccaggt gaagggtgaa tttgtgaccg accgctatgg tcgcatttct     3900
tactacgacg caaattccgg tgaacgcgtc cgtatcaatt aa                       3942
```

<210> SEQ ID NO 12
<211> LENGTH: 1313
<212> TYPE: PRT
<213> ORGANISM: Streptococcus mutans

<400> SEQUENCE: 12

```
Met Ile Asp Gly Lys Tyr Tyr Tyr Asp Asn Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
    50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110

Ser Gln Glu Thr Gln Arg Gln Tyr Val Asn Phe Met Asn Ala Gln Leu
        115                 120                 125

Gly Ile Asn Lys Thr Tyr Asp Asp Thr Ser Asn Gln Leu Gln Leu Asn
    130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
            180                 185                 190

Leu Gln Asn Gly Ala Val Leu Tyr Asp Asn Glu Gly Lys Leu Thr Pro
        195                 200                 205

Tyr Ala Asn Ser Asn Tyr Arg Ile Leu Asn Arg Thr Pro Thr Asn Gln
    210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
```

```
                          245                 250                 255
        Gln Ala Glu Gln Leu Asn Trp Leu His Phe Leu Met Asn Phe Gly Asn
                        260                 265                 270

Ile Tyr Ala Asn Asp Pro Asp Ala Asn Phe Asp Ser Ile Arg Val Asp
                        275                 280                 285

Ala Val Asp Asn Val Asp Ala Asp Leu Leu Gln Ile Ala Gly Asp Tyr
                        290                 295                 300

Leu Lys Ala Ala Lys Gly Ile His Lys Asn Asp Lys Ala Ala Asn Asp
        305                 310                 315                 320

His Leu Ser Ile Leu Glu Ala Trp Ser Asp Asn Asp Thr Pro Tyr Leu
                        325                 330                 335

His Asp Asp Gly Asp Asn Met Ile Asn Met Asp Asn Lys Leu Arg Leu
                        340                 345                 350

Ser Leu Leu Phe Ser Leu Ala Lys Pro Leu Asn Gln Arg Ser Gly Met
                        355                 360                 365

Asn Pro Leu Ile Thr Asn Ser Leu Val Asn Arg Thr Asp Asp Asn Ala
                        370                 375                 380

Glu Thr Ala Ala Val Pro Ser Tyr Ser Phe Ile Arg Ala His Asp Ser
        385                 390                 395                 400

Glu Val Gln Asp Leu Ile Arg Asp Ile Ile Lys Ala Glu Ile Asn Pro
                        405                 410                 415

Asn Val Val Gly Tyr Ser Phe Thr Met Glu Glu Ile Lys Lys Ala Phe
                        420                 425                 430

Glu Ile Tyr Asn Lys Asp Leu Leu Ala Thr Glu Lys Lys Tyr Thr His
                        435                 440                 445

Tyr Asn Thr Ala Leu Ser Tyr Ala Leu Leu Leu Thr Asn Lys Ser Ser
        450                 455                 460

Val Pro Arg Val Tyr Tyr Gly Asp Met Phe Thr Asp Asp Gly Gln Tyr
        465                 470                 475                 480

Met Ala His Lys Thr Ile Asn Tyr Glu Ala Ile Glu Thr Leu Leu Lys
                        485                 490                 495

Ala Arg Ile Lys Tyr Val Ser Gly Gln Ala Met Arg Asn Gln Gln
                        500                 505                 510

Val Gly Asn Ser Glu Ile Ile Thr Ser Val Arg Tyr Gly Lys Gly Ala
                        515                 520                 525

Leu Lys Ala Met Asp Thr Gly Asp Arg Thr Thr Arg Thr Ser Gly Val
                        530                 535                 540

Ala Val Ile Glu Gly Asn Asn Pro Ser Leu Arg Leu Lys Ala Ser Asp
        545                 550                 555                 560

Arg Val Val Asn Met Gly Ala Ala His Lys Asn Gln Ala Tyr Arg
                        565                 570                 575

Pro Leu Leu Leu Thr Thr Asp Asn Gly Ile Lys Ala Tyr His Ser Asp
                        580                 585                 590

Gln Glu Ala Ala Gly Leu Val Arg Tyr Thr Asn Asp Arg Gly Glu Leu
                        595                 600                 605

Ile Phe Thr Ala Ala Asp Ile Lys Gly Tyr Ala Asn Pro Gln Val Ser
                        610                 615                 620

Gly Tyr Leu Gly Val Trp Val Pro Val Gly Ala Ala Asp Gln Asp
        625                 630                 635                 640

Val Arg Val Ala Ala Ser Thr Ala Pro Ser Thr Asp Gly Lys Ser Val
                        645                 650                 655

His Gln Asn Ala Ala Leu Asp Ser Arg Val Met Phe Glu Gly Phe Ser
                        660                 665                 670
```

```
Asn Phe Gln Ala Phe Ala Thr Lys Lys Glu Glu Tyr Thr Asn Val Val
            675                 680                 685

Ile Ala Lys Asn Val Asp Lys Phe Ala Glu Trp Gly Val Thr Asp Phe
        690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                725                 730                 735

Ile Ser Lys Pro Asn Lys Tyr Gly Thr Ala Asp Asp Leu Val Lys Ala
            740                 745                 750

Ile Lys Ala Leu His Ser Lys Gly Ile Lys Val Met Ala Asp Trp Val
            755                 760                 765

Pro Asp Gln Met Tyr Ala Leu Pro Glu Lys Glu Val Val Thr Ala Thr
        770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
                805                 810                 815

Lys Tyr Gly Gly Ala Phe Leu Glu Glu Leu Gln Ala Lys Tyr Pro Glu
            820                 825                 830

Leu Phe Ala Arg Lys Gln Ile Ser Thr Gly Val Pro Met Asp Pro Ser
        835                 840                 845

Val Lys Ile Lys Gln Trp Ser Ala Lys Tyr Phe Asn Gly Thr Asn Ile
850                 855                 860

Leu Gly Arg Gly Ala Gly Tyr Val Leu Lys Asp Gln Ala Thr Asn Thr
865                 870                 875                 880

Tyr Phe Asn Ile Ser Asp Asn Lys Glu Ile Asn Phe Leu Pro Lys Thr
                885                 890                 895

Leu Leu Asn Gln Asp Ser Gln Val Gly Phe Ser Tyr Asp Gly Lys Gly
            900                 905                 910

Tyr Val Tyr Tyr Ser Thr Ser Gly Tyr Gln Ala Lys Asn Thr Phe Ile
        915                 920                 925

Ser Glu Gly Asp Lys Trp Tyr Tyr Phe Asp Asn Asn Gly Tyr Met Val
        930                 935                 940

Thr Gly Ala Gln Ser Ile Asn Gly Val Asn Tyr Tyr Phe Leu Pro Asn
945                 950                 955                 960

Gly Leu Gln Leu Arg Asp Ala Ile Leu Lys Asn Glu Asp Gly Thr Tyr
                965                 970                 975

Ala Tyr Tyr Gly Asn Asp Gly Arg Arg Tyr Glu Asn Gly Tyr Tyr Gln
            980                 985                 990

Phe Met Ser Gly Val Trp Arg His Phe Asn Asn Gly Glu Met Ser Val
        995                 1000                 1005

Gly Leu Thr Val Ile Asp Gly Gln Val Gln Tyr Phe Asp Glu Met
        1010                 1015                 1020

Gly Tyr Gln Ala Lys Gly Lys Phe Val Thr Thr Ala Asp Gly Lys
        1025                 1030                 1035

Ile Arg Tyr Phe Asp Lys Gln Ser Gly Asn Met Tyr Arg Asn Arg
        1040                 1045                 1050

Phe Ile Glu Asn Glu Glu Gly Lys Trp Leu Tyr Leu Gly Glu Asp
        1055                 1060                 1065

Gly Ala Ala Val Thr Gly Ser Gln Thr Ile Asn Gly Gln His Leu
        1070                 1075                 1080
```

-continued

| | | | | | | | | | | |
|---|---|---|---|---|---|---|---|---|---|---|
| Tyr | Phe | Arg | Ala | Asn | Gly | Val | Gln | Val | Lys | Gly | Glu | Phe | Val | Thr |
| | 1085 | | | | 1090 | | | | 1095 | |

Asp Arg His Gly Arg Ile Ser Tyr Tyr Asp Gly Asn Ser Gly Asp
    1100                1105                1110

Gln Ile Arg Asn Arg Phe Val Arg Asn Ala Gln Gly Gln Trp Phe
    1115                1120                1125

Tyr Phe Asp Asn Asn Gly Tyr Ala Val Thr Gly Ala Arg Thr Ile
    1130                1135                1140

Asn Gly Gln His Leu Tyr Phe Arg Ala Asn Gly Val Gln Val Lys
    1145                1150                1155

Gly Glu Phe Val Thr Asp Arg His Gly Arg Ile Ser Tyr Tyr Asp
    1160                1165                1170

Gly Asn Ser Gly Asp Gln Ile Arg Asn Arg Phe Val Arg Asn Ala
    1175                1180                1185

Gln Gly Gln Trp Phe Tyr Phe Asp Asn Asn Gly Tyr Ala Val Thr
    1190                1195                1200

Gly Ala Arg Thr Ile Asn Gly Gln His Leu Tyr Phe Arg Ala Asn
    1205                1210                1215

Gly Val Gln Val Lys Gly Glu Phe Val Thr Asp Arg Tyr Gly Arg
    1220                1225                1230

Ile Ser Tyr Tyr Asp Gly Asn Ser Gly Asp Gln Ile Arg Asn Arg
    1235                1240                1245

Phe Val Arg Asn Ala Gln Gly Gln Trp Phe Tyr Phe Asp Asn Asn
    1250                1255                1260

Gly Tyr Ala Val Thr Gly Ala Arg Thr Ile Asn Gly Gln His Leu
    1265                1270                1275

Tyr Phe Arg Ala Asn Gly Val Gln Val Lys Gly Glu Phe Val Thr
    1280                1285                1290

Asp Arg Tyr Gly Arg Ile Ser Tyr Tyr Asp Ala Asn Ser Gly Glu
    1295                1300                1305

Arg Val Arg Ile Asn
    1310

<210> SEQ ID NO 13
<211> LENGTH: 3972
<212> TYPE: DNA
<213> ORGANISM: Streptococcus dentirousetti

<400> SEQUENCE: 13
atggttgacg gcaaatacta ctactacgat gcagacggca acgtaaagaa aaacttcgcg     60
gttagcgttg gcgatgccat tttctatttt gatgaaacgg gtgcctacaa agataccagc    120
aaagttgatg cggataagac cagctctagc gtcaatcaga ccacggaaac gttcgcagcg    180
aataaccgtg cgtatagcac cgcagccgag aactttgaag cgattgataa ctacctgact    240
gcggatagct ggtatcgtcc gaagtctatc ttgaaagatg gtacgacgtg gaccgaaagc    300
accaaggatg atttttcgccc gctgctgatg cgtggtggc cggataccga aaccaaacgt    360
aactacgtga actatatgaa caaggtggtc ggtatcgaca aaacgtacac cgcggaaacg    420
tcccaagctg acctgacggc ggcagccgaa ctggtgcagg cgcgtatcga gcagaaaatc    480
actagcgaaa agaatacgaa gtggctgcgt gaggcgattt ccgcgttcgt taagactcaa    540
ccgcagtgga atggcgagag cgagaaacct tatgatgacc acctgcaaaa tggtgcgctg    600
aagttcgaca atgaaaccag cctgaccccg gatacgcaga gcggctatcg catcctgaac    660
cgtaccccga cgaatcaaac cggtagcctg gacccgcgct tcacctttaa tcagaatgac    720

```
ccgctgggtg gttatgagta tttgctggct aatgatgtcg ataacagcaa cccggtcgtt    780
caggccgaga gcctgaactg gctgcattac ctgctgaatt ttggtagcat ttacgcgaat    840
gatccggagg ccaatttcga cagcatccgt gtggacgcgg tggacaatgt tgacgcagac    900
ctgctgcaaa ttagctcgga ttacctgaaa tcggcgtaca aaattgacaa gaacaacaaa    960
aatgcgaacg accacgttag catcgtcgag gcgtggagcg acaatgatac cccgtacctg   1020
aatgatgatg cgacaatctg atgaacatgg ataacaagtt tcgtctgagc atgctgtgg    1080
agcctggcga agccaaccaa tgtccgtagc ggcttgaatc cgctgatcca acagcgtg    1140
gttgaccgtg aggtggacga ccgtgaagtt gaggctaccc cgaattacag ctttgcacgc   1200
gcacacgaca gcgaagttca agatttgatt cgcgacatca tcaaagctga gatcaaccca   1260
aacagcttcg gttatagctt tacccaagag gaaatcgacc aggccttcaa gatctacaat   1320
gaggatttga agaaaaccaa taagaagtat acccactaca acgtcccgct gagctacacc   1380
ctgctgctga cgaacaaggg cagcattcca cgcatttact acggtgacat gtttacggat   1440
gacggtcagt atatggccaa caaaaccgtt aactatgacg ccattgagag cctgctgaaa   1500
gcacgtatga agtatgttag cggtggccaa gcgatgcaga attacaacat cggcaacggc   1560
gagattctga ccagcgtccg ttacggtaag ggtgccctga acagagcga caaaggcgat    1620
aagactactc gtaccagcgg tattggcgtt gtgatgggta accagagcaa tttcagcctg   1680
gagggcaagg tggtggccct gaatatgggt gcaacgcata ccaaacagaa gtatcgtgca   1740
ttgatggtgt ctacggaaac cggcgtggcg atttacaata gcgatgaaga agcagaggca   1800
gcaggcctga tcaaaacgac cgatgagaat ggttatttgt actttctgaa tgacgatctg   1860
aagggcgtgg ctaacccgca ggtcagcggc ttcctgcaag tgtgggttcc ggttggtgca   1920
ccggctgacc aggacattcg tgtggcggcg accgatgcgg cttctaccga cggtaagagc   1980
ctgcatcagg acgcagctct ggattctcgc gtcatgtttg aaggtttcag caacttccag   2040
agcttcgcaa ccaaggaaga ggaatacacc aacgttgtta ttgcaaagaa cgtggataag   2100
ttcgtgagct ggggtatcac cgacttcgag atggcaccgc agtacgttag ctctaccgat   2160
ggcacctttc tggatagcgt gattcaaaat ggctatgcct ttacggaccg ttacgacctg   2220
ggtatgagca aagcaaacaa gtatggtact gctgaccaac tggtggccgc gattaaagcg   2280
ctgcatgcga agggtctgcg tgtgatggcg gattgggtcc cagatcaaat gtacactttc   2340
cctaagaagg aagtggttac cgttacccgt acggacaaat ttggcaatcc agtggcaggc   2400
agccaaatca ccacaccctt gtacgtcact gatactaagg gtagcggtga cgactaccag   2460
gcgaagtacg gtggcgcatt cctggatgaa ctgaagaaa agtacccgga gctgtttacc   2520
aagaagcaaa tcagcaccgg tcaggcaatc gacccgagcg tgaaaatcaa gcagtggagc   2580
gcgaagtact tcaacggtag caatatcttg ggtcgcggtg cgaactacgt gctgtccgac   2640
caggcgtcta acaagtactt taacgtgcc gaaggtaaag tctttctgcc agcggcgatg   2700
ctgggtaagg tcgtcgagag cggtatccgt ttcgacggta aaggttatat ctataacagc   2760
agcaccactg gcgaacaagt gaaggacagc ttcattaccg aagcgggtaa cttgtactat   2820
tttggcaaag atggttatat ggtcatgggt gcacagaata tccagggtgc taactactac   2880
ttcttggcga atggtgcggc cctgcgcaat agcatcctga cggatcagga tggcaaaagc   2940
cactattatg caaatgacgg caagcgttat gagaacggct actatcaatt cggtaacgac   3000
tcctggcgct atttttgaaaa cggcgttatg gccgttggtt tgacgcgcgt tgcgggccac   3060
```

-continued

```
gaccaatact ttgataagga tggtatccaa gcgaagaata agatcattgt tacgcgtgac    3120
ggtaaggtcc gctacttcga cgaacacaac ggcaatgctg ccacgaatac gtttatcagc    3180
gatcaagccg gccattggta ctacctgggt aaagatggtg tcgccgtgac gggtgcgcag    3240
accgttggca agcaacacct gtacttcgag gctaacggcc aacaagtaaa aggcgatttt    3300
gttaccgcca aggacggtaa gttgtatttt ctggacggtg actctggcga catgtggacc    3360
gataccttcg tccaggataa ggctggtcat tggttctatc tgggcaaaga cggtgcggcg    3420
gtaaccggtg cccagaccgt ccgtggtcag aagctgtact caaagcgaa tggccagcag     3480 gttaaggtg acattgtgaa aggcgcggat ggtaaaatcc gttactatga tgcaaattcc     3540
ggtgaccagg tttacaatcg cacggtgaaa ggctccgacg gcaagaccta tatcattggt    3600
aatgacggcg tcgcaatcac gcaaaccatc gccaaaggcc agaccatcaa ggatggcagc    3660
gttctgcgct tctatagcat ggagggtcag ctggtgaccg gcagcggctg gtattccaac    3720
gcgaaaggtc aatggttgta tgtcaagaac ggtcaagtcc tgacgggttt gcagacggtg    3780
ggcagccagc gtgtgtactt tgacgcaaat ggtattcaag cgaaaggtaa agcagtgcgt    3840
acctccgatg gcaaactgcg ttacttcgat gcgaacagcg gcagcatgat caccaatcag    3900
tggaaagaag ttaatggtca gtactactat ttcgacaaca acggtgttgc gatctatcgc    3960
ggttggaact aa                                                        3972
```

<210> SEQ ID NO 14
<211> LENGTH: 1323
<212> TYPE: PRT
<213> ORGANISM: Streptococcus dentirousetti

<400> SEQUENCE: 14

```
Met Val Asp Gly Lys Tyr Tyr Tyr Asp Ala Asp Gly Asn Val Lys
1               5                   10                  15

Lys Asn Phe Ala Val Ser Val Gly Asp Ala Ile Phe Tyr Phe Asp Glu
            20                  25                  30

Thr Gly Ala Tyr Lys Asp Thr Ser Lys Val Asp Ala Asp Lys Thr Ser
        35                  40                  45

Ser Ser Val Asn Gln Thr Thr Glu Thr Phe Ala Ala Asn Asn Arg Ala
    50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Thr Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205
```

```
Thr Pro Asp Thr Gln Ser Gly Tyr Arg Ile Leu Asn Arg Thr Pro Thr
    210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu Asn Asp Asp Gly Asp Asn Leu Met Asn Met Asp Asn
                340                 345                 350

Lys Phe Arg Leu Ser Met Leu Trp Ser Leu Ala Lys Pro Thr Asn Val
            355                 360                 365

Arg Ser Gly Leu Asn Pro Leu Ile His Asn Ser Val Asp Arg Glu
    370                 375                 380

Val Asp Asp Arg Glu Val Glu Ala Thr Pro Asn Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
                420                 425                 430

Asp Gln Ala Phe Lys Ile Tyr Asn Glu Asp Leu Lys Lys Thr Asn Lys
            435                 440                 445

Lys Tyr Thr His Tyr Asn Val Pro Leu Ser Tyr Thr Leu Leu Leu Thr
    450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gln Ala Met
            500                 505                 510

Gln Asn Tyr Asn Ile Gly Asn Gly Glu Ile Leu Thr Ser Val Arg Tyr
    515                 520                 525

Gly Lys Gly Ala Leu Lys Gln Ser Asp Lys Gly Asp Lys Thr Thr Arg
530                 535                 540

Thr Ser Gly Ile Gly Val Val Met Gly Asn Gln Ser Asn Phe Ser Leu
545                 550                 555                 560

Glu Gly Lys Val Val Ala Leu Asn Met Gly Ala Thr His Thr Lys Gln
                565                 570                 575

Lys Tyr Arg Ala Leu Met Val Ser Thr Glu Thr Gly Val Ala Ile Tyr
            580                 585                 590

Asn Ser Asp Glu Glu Ala Glu Ala Gly Leu Ile Lys Thr Thr Asp
    595                 600                 605

Glu Asn Gly Tyr Leu Tyr Phe Leu Asn Asp Asp Leu Lys Gly Val Ala
610                 615                 620

Asn Pro Gln Val Ser Gly Phe Leu Gln Val Trp Val Pro Val Gly Ala
```

-continued

```
            625                 630                 635                 640
    Pro Ala Asp Gln Asp Ile Arg Val Ala Ala Thr Asp Ala Ala Ser Thr
                    645                 650                 655
    Asp Gly Lys Ser Leu His Gln Asp Ala Ala Leu Asp Ser Arg Val Met
                    660                 665                 670
    Phe Glu Gly Phe Ser Asn Phe Gln Ser Phe Ala Thr Lys Glu Glu Glu
                    675                 680                 685
    Tyr Thr Asn Val Val Ile Ala Lys Asn Val Asp Lys Phe Val Ser Trp
                    690                 695                 700
    Gly Ile Thr Asp Phe Glu Met Ala Pro Gln Tyr Val Ser Ser Thr Asp
    705                 710                 715                 720
    Gly Thr Phe Leu Asp Ser Val Ile Gln Asn Gly Tyr Ala Phe Thr Asp
                    725                 730                 735
    Arg Tyr Asp Leu Gly Met Ser Lys Ala Asn Lys Tyr Gly Thr Ala Asp
                    740                 745                 750
    Gln Leu Val Ala Ala Ile Lys Ala Leu His Ala Lys Gly Leu Arg Val
                    755                 760                 765
    Met Ala Asp Trp Val Pro Asp Gln Met Tyr Thr Phe Pro Lys Lys Glu
                    770                 775                 780
    Val Val Thr Val Thr Arg Thr Asp Lys Phe Gly Asn Pro Val Ala Gly
    785                 790                 795                 800
    Ser Gln Ile Asn His Thr Leu Tyr Val Thr Asp Thr Lys Gly Ser Gly
                    805                 810                 815
    Asp Asp Tyr Gln Ala Lys Tyr Gly Gly Ala Phe Leu Asp Glu Leu Lys
                    820                 825                 830
    Glu Lys Tyr Pro Glu Leu Phe Thr Lys Lys Gln Ile Ser Thr Gly Gln
                    835                 840                 845
    Ala Ile Asp Pro Ser Val Lys Ile Lys Gln Trp Ser Ala Lys Tyr Phe
                    850                 855                 860
    Asn Gly Ser Asn Ile Leu Gly Arg Gly Ala Asn Tyr Val Leu Ser Asp
    865                 870                 875                 880
    Gln Ala Ser Asn Lys Tyr Phe Asn Val Ala Glu Gly Lys Val Phe Leu
                    885                 890                 895
    Pro Ala Ala Met Leu Gly Lys Val Val Glu Ser Gly Ile Arg Phe Asp
                    900                 905                 910
    Gly Lys Gly Tyr Ile Tyr Asn Ser Ser Thr Thr Gly Glu Gln Val Lys
                    915                 920                 925
    Asp Ser Phe Ile Thr Glu Ala Gly Asn Leu Tyr Tyr Phe Gly Lys Asp
                    930                 935                 940
    Gly Tyr Met Val Met Gly Ala Gln Asn Ile Gln Gly Ala Asn Tyr Tyr
    945                 950                 955                 960
    Phe Leu Ala Asn Gly Ala Ala Leu Arg Asn Ser Ile Leu Thr Asp Gln
                    965                 970                 975
    Asp Gly Lys Ser His Tyr Tyr Ala Asn Asp Gly Lys Arg Tyr Glu Asn
                    980                 985                 990
    Gly Tyr Tyr Gln Phe Gly Asn Asp Ser Trp Arg Tyr Phe Glu Asn Gly
                    995                1000                1005
    Val Met Ala Val Gly Leu Thr Arg Val Ala Gly His Asp Gln Tyr
                   1010                1015                1020
    Phe Asp Lys Asp Gly Ile Gln Ala Lys Asn Lys Ile Ile Val Thr
                   1025                1030                1035
    Arg Asp Gly Lys Val Arg Tyr Phe Asp Glu His Asn Gly Asn Ala
                   1040                1045                1050
```

| | | | | | | | | | | |
|---|---|---|---|---|---|---|---|---|---|---|
| Ala | Thr | Asn | Thr | Phe | Ile | Ser | Asp | Gln | Ala | Gly | His | Trp | Tyr | Tyr |
| | 1055 | | | | 1060 | | | | 1065 | |

Leu Gly Lys Asp Gly Val Ala Val Thr Gly Ala Gln Thr Val Gly
    1070            1075                1080

Lys Gln His Leu Tyr Phe Glu Ala Asn Gly Gln Gln Val Lys Gly
    1085            1090                1095

Asp Phe Val Thr Ala Lys Asp Gly Lys Leu Tyr Phe Leu Asp Gly
    1100            1105                1110

Asp Ser Gly Asp Met Trp Thr Asp Thr Phe Val Gln Asp Lys Ala
    1115            1120                1125

Gly His Trp Phe Tyr Leu Gly Lys Asp Gly Ala Ala Val Thr Gly
    1130            1135                1140

Ala Gln Thr Val Arg Gly Gln Lys Leu Tyr Phe Lys Ala Asn Gly
    1145            1150                1155

Gln Gln Val Lys Gly Asp Ile Val Lys Gly Ala Asp Gly Lys Ile
    1160            1165                1170

Arg Tyr Tyr Asp Ala Asn Ser Gly Asp Gln Val Tyr Asn Arg Thr
    1175            1180                1185

Val Lys Gly Ser Asp Gly Lys Thr Tyr Ile Ile Gly Asn Asp Gly
    1190            1195                1200

Val Ala Ile Thr Gln Thr Ile Ala Lys Gly Gln Thr Ile Lys Asp
    1205            1210                1215

Gly Ser Val Leu Arg Phe Tyr Ser Met Glu Gly Gln Leu Val Thr
    1220            1225                1230

Gly Ser Gly Trp Tyr Ser Asn Ala Lys Gly Gln Trp Leu Tyr Val
    1235            1240                1245

Lys Asn Gly Gln Val Leu Thr Gly Leu Gln Thr Val Gly Ser Gln
    1250            1255                1260

Arg Val Tyr Phe Asp Ala Asn Gly Ile Gln Ala Lys Gly Lys Ala
    1265            1270                1275

Val Arg Thr Ser Asp Gly Lys Leu Arg Tyr Phe Asp Ala Asn Ser
    1280            1285                1290

Gly Ser Met Ile Thr Asn Gln Trp Lys Glu Val Asn Gly Gln Tyr
    1295            1300                1305

Tyr Tyr Phe Asp Asn Asn Gly Val Ala Ile Tyr Arg Gly Trp Asn
    1310            1315                1320

<210> SEQ ID NO 15
<211> LENGTH: 4047
<212> TYPE: DNA
<213> ORGANISM: Streptococcus oralis

<400> SEQUENCE: 15

```
atgatcgacg gcaaaaacta ctacgtacag gatgatggca cggtaaagaa gaatttcgcg      60
gtagaactga tggtcgtat cctgtatttt gatgcagaaa ccggcgctct ggttgatagc     120
aacgagtatc agttccaaca gggtacgagc agcctgaaca tgaatttttc tcagaagaac     180
gcattctatg gtacgaccga taaggatatt gagactgtgg atggctacct gaccgcagat     240
agctggtatc gcccgaaatt catcctgaag gatggcaaga cgtggaccgc gagcacggaa     300
acggatctgc gtccgctgtt gatggcatgg tggccggaca agcgtaccca aatcaactat     360
ctgaactaca tgaaccagca gggtctgggt gcgggtgcgt ttgagaacaa agtggagcag     420
gccctgctga cgggtgcaag ccaacaggta caacgcaaga tcgaagagaa gattggtaaa     480
```

```
gagggtgata ccaagtggct gcgcaccctg atgggtgcgt tcgtgaaaac gcaaccaaac    540
tggaatatca aaaccgagtc tgaaacgacc ggcacgaaaa aggaccatct gcaaggcggt    600
gcactgctgt atacgaacaa cgagaaatcc ccgcacgcgg acagcaaatt tcgtctgctg    660
aatcgtaccc cgaccagcca aaccggcacg ccgaagtatt tcatcgacaa gtctaacggt    720
ggctacgaat ttctgctggc gaacgatttt gacaatagca atcctgcggt acaagctgag    780
cagctgaatt ggctgcacta catgatgaac tttggcagca ttgttgcgaa tgatccgacc    840
gcgaatttcg acggcgttcg tgtggatgct gttgataacg tcaatgcgga cttgttgcaa    900
attgcaagcg attactttaa gagccgttac aaagtcggtg agagcgaaga agaagcgatc    960
aagcacctgt ccatcctgga agcatggagc gataacgacc cggactacaa caaagatacc   1020
aagggtgcac agttggcgat tgataacaaa ctgcgcctga gcctgctgta ctctttcatg   1080
cgtaatctga gcatccgtag cggtgttgaa ccgacgatta ccaatagcct gaatgaccgt   1140
tccagcgaaa agaagaacgg cgagcgtatg gcaaattaca tcttcgtgcg tgcccacgat   1200
agcgaggtcc aaacggtgat cgccgacatc attcgcgaaa acatcaatcc gaacaccgac   1260
ggcctgacgt ttacgatgga cgagctgaag caggcattca agatttacaa cgaggacatg   1320
cgcaaggcgg acaaaaagta tacccagttt aacattccta ccgcacacgc gctgatgctg   1380
tctaataagg attctattac ccgcgtgtac tatggtgatc tgtatactga cgatggtcag   1440
tacatggaga gaaaagcccc gtatcacgat gcgattgacg ctctgctgcg tgcacgtatt   1500
aaatacgtcg cgggtggcca ggatatgaaa gtgacctata tgggcgtgcc gcgtgaagcg   1560
gataagtgga gctataacgg cattctgacc agcgtgcgct atggcacggg cgctaacgaa   1620
gccacggatg agggcactgc ggaaacgcgc acgcaaggta tggcagtgat tgcgagcaat   1680
aatccaaatc tgaaactgaa tgaatgggac aagttgcaag tcaacatggg tgcggcgcat   1740
aagaatcaat attaccgtcc ggttctgctg accactaagg acggtatcag ccgttatctg   1800
accgatgaag aagtgcctca gagcctgtgg aaaaagacgg acgcaaacgg tattctgacc   1860
ttcgacatga atgatattgc tggctacagc aacgtgcaag ttagcggtta cctggccgtc   1920
tgggtcccgg tcggtgcgaa ggcggatcaa gatgcgcgca cgaccgcatc caagaagaaa   1980
aatgcgtcgg gtcaggtgta cgaaagcagc gcggctctgg atagccagct gatttacgaa   2040
ggtttcagca actttcaaga cttttgccact cgcgatgatc agtacacgaa caaggtcatt   2100
gcgaaaaacg tgaatctgtt caaagaatgg ggtgtgacca gcttcgagct gccgccgcag   2160
tacgtgagca gccaagatgg caccttttctg gacagcatta tccaaaacgg ctatgcattt   2220
gaagaccgtt acgatatggc tgatgagcaag aataacaagt atggtagcct gaaagacctg   2280
ttgaacgcgc tgcgcgcact gcacagcgtc aacattcaag caatcgccga ttgggtgccg   2340
gaccaaattt acaacttgcc gggcaaagag gtggtgaccg caactcgtgt caacaactac   2400
ggcacctacc gtgagggtgc tgaaatcaaa gaaaagctgt atgtcgccaa tagcaagacc   2460
aacgaaaccg atttccaagg taaatacggt ggtgcgttcc tggatgagct gaaggcgaag   2520
tacccggaga ttttcgagcg tgtccaaatc agcaacggcc aaaagatgac taccgatgaa   2580
aagatcacca aatggagcgc gaaatacttt aatggcacca atattctggg tcgtggcgcg   2640
tactatgtcc tgaaagattg ggccagcaat gattacctga cgaaccgtaa cggcgagatt   2700
gttttgccga agcaactggt taacaagaat agctataccg gctttgtcag cgacgcgaac   2760
ggcacgaagt tctattctac ctctggctac caggcgaaga acagcttcat tcaagacgaa   2820
aacggtaatt ggtattactt tgacaaacgt ggttatctgg ttacgggcgc acacgagatt   2880
```

-continued

```
gatggcaagc atgtctactt cctgaaaaac ggtatccaac tgcgtgacag catccgtgag    2940
gatgagaacg gtaatcaata ctattacgac cagaccggcg cacaagtgct gaaccgttac    3000
tacacgacgg acggtcagaa ttggcgctat ttcgatgcga aaggtgttat ggcacgcggc    3060
ctggtaaaga ttggtgacgg ccaacagttt ttcgatgaaa acggttacca ggtcaagggc    3120
aagattgtta gcgcaaaaga cggcaagctg cgctactttg ataaagactc tggcaatgct    3180
gtcattaatc gtttcgcgca gggtgacaat ccgagcgact ggtactattt cggtgtggaa    3240
tttgctaaac tgacgggttt gcaaaagatc ggccagcaga cgctgtattt tgaccaagac    3300
ggtaagcaag tcaaaggtaa gatcgtaact ctgtcggaca aaagcattcg ttacttcgat    3360
gccaacagcg gtgaaatggc ggttggcaag ttcgcggaag gtgcaaagaa tgagtggtat    3420
tatttcgata aaaccggcaa agcgttact ggtttgcaga aaattggtaa gcagaccctg    3480
tactttgacc aggacggtaa acaggttaaa ggcaaggttg tcacgctggc tgataaaagc    3540
atccgctact tcgacgcaga ctccggcgag atggcggtcg gtaagtttgc agagggtgcg    3600
aagaacgagt ggtactattt tgatcagact ggcaaggccg tgactggttt gcaaaagatt    3660
gacaagcaaa ccttgtactt cgaccaggac ggtaaacaag tcaagggtaa gattgtgacg    3720
ttgagcgaca agtcgatccg ttactttgat gctaatagcg gtgagatggc tactaacaaa    3780
ttcgtcgagg gctcgcagaa tgaatggtac tacttcgatc aagcgggtaa ggctgttacg    3840
ggcttgcaac aggtcggtca gcaaactctg tacttcaccc aggatggtaa gcaagtgaag    3900
ggtaaggtcg tggacgtgaa cggtgtttct cgttatttcg acgcaaactc cggtgacatg    3960
gctcgttcta aatggattca actggaagat ggcagctgga tgtatttcga ccgtgacggt    4020
cgtggccaga attttggccg taactaa                                        4047
```

<210> SEQ ID NO 16
<211> LENGTH: 1348
<212> TYPE: PRT
<213> ORGANISM: Streptococcus oralis

<400> SEQUENCE: 16

```
Met Ile Asp Gly Lys Asn Tyr Tyr Val Gln Asp Asp Gly Thr Val Lys
1               5                  10                  15

Lys Asn Phe Ala Val Glu Leu Asn Gly Arg Ile Leu Tyr Phe Asp Ala
            20                  25                  30

Glu Thr Gly Ala Leu Val Asp Ser Asn Glu Tyr Gln Phe Gln Gln Gly
        35                  40                  45

Thr Ser Ser Leu Asn Asn Glu Phe Ser Gln Lys Asn Ala Phe Tyr Gly
    50                  55                  60

Thr Thr Asp Lys Asp Ile Glu Thr Val Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Thr Asp Leu Arg Pro Leu Met Ala Trp Trp Pro
            100                 105                 110

Asp Lys Arg Thr Gln Ile Asn Tyr Leu Asn Tyr Met Asn Gln Gln Gly
        115                 120                 125

Leu Gly Ala Gly Ala Phe Glu Asn Lys Val Glu Gln Ala Leu Leu Thr
    130                 135                 140

Gly Ala Ser Gln Gln Val Gln Arg Lys Ile Glu Glu Lys Ile Gly Lys
145                 150                 155                 160
```

```
Glu Gly Asp Thr Lys Trp Leu Arg Thr Leu Met Gly Ala Phe Val Lys
            165                 170                 175

Thr Gln Pro Asn Trp Asn Ile Lys Thr Glu Ser Glu Thr Thr Gly Thr
        180                 185                 190

Lys Lys Asp His Leu Gln Gly Gly Ala Leu Leu Tyr Thr Asn Asn Glu
        195                 200                 205

Lys Ser Pro His Ala Asp Ser Lys Phe Arg Leu Leu Asn Arg Thr Pro
        210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Tyr Met Met Asn Phe Gly
            260                 265                 270

Ser Ile Val Ala Asn Asp Pro Thr Ala Asn Phe Asp Gly Val Arg Val
                275                 280                 285

Asp Ala Val Asp Asn Val Asn Ala Asp Leu Leu Gln Ile Ala Ser Asp
        290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Ala Ile Asp Asn Lys Leu Arg
                340                 345                 350

Leu Ser Leu Leu Tyr Ser Phe Met Arg Asn Leu Ser Ile Arg Ser Gly
            355                 360                 365

Val Glu Pro Thr Ile Thr Asn Ser Leu Asn Asp Arg Ser Ser Glu Lys
        370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
                420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
        450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
        530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
```

```
                  580                 585                 590
Lys Asp Gly Ile Ser Arg Tyr Leu Thr Asp Glu Glu Val Pro Gln Ser
            595                 600                 605
Leu Trp Lys Lys Thr Asp Ala Asn Gly Ile Leu Thr Phe Asp Met Asn
610                 615                 620
Asp Ile Ala Gly Tyr Ser Asn Val Gln Val Ser Gly Tyr Leu Ala Val
625                 630                 635                 640
Trp Val Pro Val Gly Ala Lys Ala Asp Gln Asp Ala Arg Thr Thr Ala
            645                 650                 655
Ser Lys Lys Asn Ala Ser Gly Gln Val Tyr Glu Ser Ser Ala Ala
            660                 665                 670
Leu Asp Ser Gln Leu Ile Tyr Glu Gly Phe Ser Asn Phe Gln Asp Phe
            675                 680                 685
Ala Thr Arg Asp Asp Gln Tyr Thr Asn Lys Val Ile Ala Lys Asn Val
            690                 695                 700
Asn Leu Phe Lys Glu Trp Gly Val Thr Ser Phe Glu Leu Pro Pro Gln
705                 710                 715                 720
Tyr Val Ser Ser Gln Asp Gly Thr Phe Leu Asp Ser Ile Ile Gln Asn
            725                 730                 735
Gly Tyr Ala Phe Glu Asp Arg Tyr Asp Met Ala Met Ser Lys Asn Asn
            740                 745                 750
Lys Tyr Gly Ser Leu Lys Asp Leu Leu Asn Ala Leu Arg Ala Leu His
            755                 760                 765
Ser Val Asn Ile Gln Ala Ile Ala Asp Trp Val Pro Asp Gln Ile Tyr
770                 775                 780
Asn Leu Pro Gly Lys Glu Val Val Thr Ala Thr Arg Val Asn Asn Tyr
785                 790                 795                 800
Gly Thr Tyr Arg Glu Gly Ala Glu Ile Lys Lys Leu Tyr Val Ala
            805                 810                 815
Asn Ser Lys Thr Asn Glu Thr Asp Phe Gln Gly Lys Tyr Gly Gly Ala
            820                 825                 830
Phe Leu Asp Glu Leu Lys Ala Lys Tyr Pro Glu Ile Phe Glu Arg Val
            835                 840                 845
Gln Ile Ser Asn Gly Gln Lys Met Thr Thr Asp Glu Lys Ile Thr Lys
            850                 855                 860
Trp Ser Ala Lys Tyr Phe Asn Gly Thr Asn Ile Leu Gly Arg Gly Ala
865                 870                 875                 880
Tyr Tyr Val Leu Lys Asp Trp Ala Ser Asn Asp Tyr Leu Thr Asn Arg
            885                 890                 895
Asn Gly Glu Ile Val Leu Pro Lys Gln Leu Val Asn Lys Asn Ser Tyr
            900                 905                 910
Thr Gly Phe Val Ser Asp Ala Asn Gly Thr Lys Phe Tyr Ser Thr Ser
            915                 920                 925
Gly Tyr Gln Ala Lys Asn Ser Phe Ile Gln Asp Glu Asn Gly Asn Trp
            930                 935                 940
Tyr Tyr Phe Asp Lys Arg Gly Tyr Leu Val Thr Gly Ala His Glu Ile
945                 950                 955                 960
Asp Gly Lys His Val Tyr Phe Leu Lys Asn Gly Ile Gln Leu Arg Asp
            965                 970                 975
Ser Ile Arg Glu Asp Glu Asn Gly Asn Gln Tyr Tyr Asp Gln Thr
            980                 985                 990
Gly Ala Gln Val Leu Asn Arg Tyr  Tyr Thr Thr Asp Gly  Gln Asn Trp
            995                 1000                1005
```

| Arg | Tyr | Phe | Asp | Ala | Lys | Gly | Val | Met | Ala | Arg | Gly | Leu | Val | Lys |
| | 1010 | | | | 1015 | | | | 1020 | | | | | |

| Ile | Gly | Asp | Gly | Gln | Gln | Phe | Phe | Asp | Glu | Asn | Gly | Tyr | Gln | Val |
| 1025 | | | | | 1030 | | | | | 1035 | | | | |

| Lys | Gly | Lys | Ile | Val | Ser | Ala | Lys | Asp | Gly | Lys | Leu | Arg | Tyr | Phe |
| | 1040 | | | | | 1045 | | | | | 1050 | | | |

| Asp | Lys | Asp | Ser | Gly | Asn | Ala | Val | Ile | Asn | Arg | Phe | Ala | Gln | Gly |
| | 1055 | | | | | 1060 | | | | | 1065 | | | |

| Asp | Asn | Pro | Ser | Asp | Trp | Tyr | Tyr | Phe | Gly | Val | Glu | Phe | Ala | Lys |
| | 1070 | | | | | 1075 | | | | | 1080 | | | |

| Leu | Thr | Gly | Leu | Gln | Lys | Ile | Gly | Gln | Gln | Thr | Leu | Tyr | Phe | Asp |
| | 1085 | | | | | 1090 | | | | | 1095 | | | |

| Gln | Asp | Gly | Lys | Gln | Val | Lys | Gly | Lys | Ile | Val | Thr | Leu | Ser | Asp |
| | 1100 | | | | | 1105 | | | | | 1110 | | | |

| Lys | Ser | Ile | Arg | Tyr | Phe | Asp | Ala | Asn | Ser | Gly | Glu | Met | Ala | Val |
| | 1115 | | | | | 1120 | | | | | 1125 | | | |

| Gly | Lys | Phe | Ala | Glu | Gly | Ala | Lys | Asn | Glu | Trp | Tyr | Tyr | Phe | Asp |
| | 1130 | | | | | 1135 | | | | | 1140 | | | |

| Lys | Thr | Gly | Lys | Ala | Val | Thr | Gly | Leu | Gln | Lys | Ile | Gly | Lys | Gln |
| | 1145 | | | | | 1150 | | | | | 1155 | | | |

| Thr | Leu | Tyr | Phe | Asp | Gln | Asp | Gly | Lys | Gln | Val | Lys | Gly | Lys | Val |
| | 1160 | | | | | 1165 | | | | | 1170 | | | |

| Val | Thr | Leu | Ala | Asp | Lys | Ser | Ile | Arg | Tyr | Phe | Asp | Ala | Asp | Ser |
| | 1175 | | | | | 1180 | | | | | 1185 | | | |

| Gly | Glu | Met | Ala | Val | Gly | Lys | Phe | Ala | Glu | Gly | Ala | Lys | Asn | Glu |
| | 1190 | | | | | 1195 | | | | | 1200 | | | |

| Trp | Tyr | Tyr | Phe | Asp | Gln | Thr | Gly | Lys | Ala | Val | Thr | Gly | Leu | Gln |
| | 1205 | | | | | 1210 | | | | | 1215 | | | |

| Lys | Ile | Asp | Lys | Gln | Thr | Leu | Tyr | Phe | Asp | Gln | Asp | Gly | Lys | Gln |
| | 1220 | | | | | 1225 | | | | | 1230 | | | |

| Val | Lys | Gly | Lys | Ile | Val | Thr | Leu | Ser | Asp | Lys | Ser | Ile | Arg | Tyr |
| | 1235 | | | | | 1240 | | | | | 1245 | | | |

| Phe | Asp | Ala | Asn | Ser | Gly | Glu | Met | Ala | Thr | Asn | Lys | Phe | Val | Glu |
| | 1250 | | | | | 1255 | | | | | 1260 | | | |

| Gly | Ser | Gln | Asn | Glu | Trp | Tyr | Tyr | Phe | Asp | Gln | Ala | Gly | Lys | Ala |
| | 1265 | | | | | 1270 | | | | | 1275 | | | |

| Val | Thr | Gly | Leu | Gln | Gln | Val | Gly | Gln | Gln | Thr | Leu | Tyr | Phe | Thr |
| | 1280 | | | | | 1285 | | | | | 1290 | | | |

| Gln | Asp | Gly | Lys | Gln | Val | Lys | Gly | Lys | Val | Val | Asp | Val | Asn | Gly |
| | 1295 | | | | | 1300 | | | | | 1305 | | | |

| Val | Ser | Arg | Tyr | Phe | Asp | Ala | Asn | Ser | Gly | Asp | Met | Ala | Arg | Ser |
| | 1310 | | | | | 1315 | | | | | 1320 | | | |

| Lys | Trp | Ile | Gln | Leu | Glu | Gly | Ser | Trp | Met | Tyr | Phe | Asp | Arg |
| | 1325 | | | | | 1330 | | | | | 1335 | | |

| Asp | Gly | Arg | Gly | Gln | Asn | Phe | Gly | Arg | Asn |
| | 1340 | | | | | 1345 | | | |

<210> SEQ ID NO 17
<211> LENGTH: 4047
<212> TYPE: DNA
<213> ORGANISM: Streptococcus sanguinis

<400> SEQUENCE: 17
atgattgatg gtaaaaagta ttacgtacag gacgacggca cggttaagaa gaatttcgcg    60

```
gttgagctga atggcaagat cctgtacttc gatgcagaga ctggtgcgtt gattgacagc      120
gcggagtatc aattccaaca aggcaccagc agcctgaata atgagttcac tcaaaagaac      180
gccttttacg gtacgaccga taaggatgtg gaaaccattg atggttactt gaccgccgat      240
tcctggtatc gtccgaagtt cattctgaaa gatggcaaaa cctggacggc gagcacggaa      300
attgacttgc gtccgttgtt gatggcgtgg tggccggaca acagaccca ggttagctac       360 ctgaattaca tgaaccagca aggcttgggt gcaggcgcct tcgaaaacaa agtagagcag      420
gcaattctga ccggtgcgtc ccaacaggta caacgtaaaa tcgaagaacg catcggtaaa      480
gagggtgata ccaagtggct gcgtaccctg atgggtgcat ttgtaaagac ccagccgaac      540
tggaacatta agaccgagtc cgaaaccact ggcacgaata agatcatct gcaaggtggc       600 gcactgctgt atagcaattc cgacaagacg agccatgcca actctaagta ccgtatcctg      660
aaccgcaccc cgaccaacca aacgggcacg ccgaaatact ttattgacaa gagcaatggt      720
ggttatgaat ttctgctggc gaatgacttt gacaatagca atccggcagt gcaagcggaa      780
cagctgaact ggttgcactt tatgatgaat tttggctcca tcgttgcaaa tgatccgacg      840
gccaacttcg acggcgtccg cgttgacgct gtggataacg tgaatgcgga tctgttgcaa      900
attgcgagcg actatttcaa gagccgctat aaagtcggcg aaagcgaaga agaggccatt      960
aagcacctgt ccatcctgga agcgtggagc gacaacgacc cggactacaa caaggatact     1020
aaaggtgccc aactgccgat cgacaacaaa ctgcgtctga gcctgctgta ctccttcatg     1080
cgtaagctga gcatccgtag cggcgtcgag ccgaccatca ccaactctct gaatgatcgc     1140
agcacggaga agaagaatgg tgagcgtatg gcaaactata tcttcgttcg tgcacatgat     1200
agcgaggtgc aaacggtcat cgccgacatt atccgtgaga acatcaatcc gaataccgac     1260
ggcctgacgt tcacgatgga tgaactgaag caggcctttta aaatttacaa tgaggatatg     1320
cgtaaagccg acaaaaagta cacgcagttc aatatcccga ccgcgcacgc gctgatgctg     1380
agcaacaaag attctatcac ccgcgtttac tacggtgacc tgtatacgga tgacggtcag     1440
tatatggaaa agaaaagccc gtatcacgac gccattgacg ctctgctgcg tgcgcgtatc     1500
aaatatgttg cgggtggtca ggacatgaag gtgacctata tgggcgtgcc gcgtgaggca     1560
gataaatgga gctataacgg catcctgacc agcgttcgtt atggtacggg tgccaacgag     1620
gcaaccgacg agggtacggc agaaacccgt acccagggca tggccgtcat tgccagcaac     1680
aatccgaacc tgaaactgaa cgagtgggac aagttgcagg tcaacatggg tgcagctcac     1740
aaaaaccaat actatcgtcc ggtgctgctg accaccaagg acggcatctc cgctacctg      1800 accgacgaag aagtcccgca gagcctgtgg aaaaagaccg atgcgaacgg catcttgacg     1860
tttgacatga atgatatttgc gggttacagc aacgtccaag tgagcggtta tctggccgtc    1920
tgggttcctg tgggtgcgaa ggcggaccag gacgctcgtg ttacggcatc taagaagaaa    1980
aatgcctctg gccaagttta cgaaagcagc gcagccctgg actcccagct gatctatgag    2040
ggcttcagca tttttcagga ctttgccacc cgtgacgacc agtacactaa caaggttatc    2100
gcgaaaaacg tcaatctgtt taaagagtgg ggcgtcacca gcttcgaatt gccgccacag    2160
tatgtgagca gccaagacgg tacgttcctg gatagcatca tccagaatgg ttatgcattc    2220
gaagatcgct atgatatggc gatgagcaaa aacaataagt acggtagctt gaacgacctg    2280
ttgaacgcct tgcgtgcact gcatagcgtg aatatccaag cgattgcgga ttgggtgccg    2340
gaccagattt acaatctgcc gggtaaagaa gttgtcactg caacccgtgt taacaattat    2400
```

```
ggcacgtatc gtgagggtag cgagattaaa gagaacctgt acgttgctaa caccaaaacc    2460
aatggtacgg actaccaagg taagtatggt ggtgcgttct tggacgagct gaaagccaaa    2520
taccctgaga tttttgagcg cgtccaaatc agcaacggcc agaagatgac caccgacgag    2580
aagattacga aatggtccgc caaacacttt aacggcacga acattctggg tcgtggtgcg    2640
tattatgtgc tgaaagactg ggcgagcaac gagtacctga ataacaaaaa tggcgagatg    2700
gttctgccga agcagctggt taataaaaat gcatataccg gcttcgtcag cgacgcgagc    2760
ggcaccaaat actattctac cagcggctat caggctcgta atagctttat tcaagatgaa    2820
aatggtaatt ggtactactt caataaccgt ggttatttgg tgacgggtgc acaggaaatc    2880
gacggtaagc aactgtattt cctgaaaaac ggcattcagc tgcgtgattc tctgcgtgag    2940
gacgaaaacg gcaaccagta ttactatgat aagacgggtg cgcaagttct gaatcgttat    3000
tacactacgg acggccaaaa ttggcgctac ttcgacgtta aaggcgtcat ggcccgtggt    3060
ctggtcacga tggtggtaa ccaacaattc tttgaccaaa acggttacca ggttaaaggc    3120
aaaattgcgc gtgcaaaaga cggtaaactg cgttacttcg ataaagacag cggtaatgcg    3180
gcagctaacc gtttcgccca aggcgataac cctagcgact ggtactattt cggtgcagat    3240
ggtgttgcgc ttacgggcct gcaaaaggtt ggtcagcaaa ctctgtactt tgatcaggac    3300
ggcaagcagg tgaaaggtaa agttgttacc ttggcggaca aaagcattcg ttatttcgat    3360
gcaaacagcg gcgagatggc ggtgaacaag tttgtggaag gtgctaagaa cgtgtggtac    3420
tacttcgatc aagcaggcaa agcggtgacc ggcctgcaaa ccatcaataa acaagtgctg    3480
tatttcgacc aggatggtaa acaagtcaaa ggtaaggtgg tcacgctggc tgataagtct    3540
atccgctact tcgacgcgaa cagcggtgag atggcagtgg gcaaattcgc cgaaggcgca    3600
aagaatgagt ggtattactt tgaccaggcg gcaaggctg ttaccggtct gcaaaagatc    3660
ggccaacaga cgctgtatttt cgaccagaac ggtaaacagg ttaagggtaa agtggtcacc    3720
ctggcggata gagcatccg ctatttcgac gctaactctg gcgaaatggc aagcaataag    3780
ttcgttgagg gtgccaaaaa tgaatggtac tatttcgatc aggctggcaa ggcagtgacg    3840
ggtctgcaac aaattggcca gcagaccctg tattttgacc agaatggcaa acaggtgaag    3900
ggtaagattg tgtatgttaa tggtgcgaat cgctactttg atgccaatag cggtgaaatg    3960
gcgcgtaaca gtggattca gctggaagat ggcagctgga tgtattttga ccgcaatggt    4020
cgtggtcgtc gtttcggttg gaactaa                                         4047
```

<210> SEQ ID NO 18
<211> LENGTH: 1348
<212> TYPE: PRT
<213> ORGANISM: Streptococcus sanguinis

<400> SEQUENCE: 18

```
Met Ile Asp Gly Lys Lys Tyr Tyr Val Gln Asp Asp Gly Thr Val Lys
1               5                   10                  15

Lys Asn Phe Ala Val Glu Leu Asn Gly Lys Ile Leu Tyr Phe Asp Ala
            20                  25                  30

Glu Thr Gly Ala Leu Ile Asp Ser Ala Glu Tyr Gln Phe Gln Gln Gly
        35                  40                  45

Thr Ser Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80
```

```
Ser Trp Tyr Arg Pro Lys Phe Ile Leu Lys Asp Gly Lys Thr Trp Thr
                 85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
            115                 120                 125

Leu Gly Ala Gly Ala Phe Glu Asn Lys Val Glu Gln Ala Ile Leu Thr
            130                 135                 140

Gly Ala Ser Gln Gln Val Gln Arg Lys Ile Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
            195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
            275                 280                 285

Asp Ala Val Asp Asn Val Asn Ala Asp Leu Leu Gln Ile Ala Ser Asp
            290                 295                 300

Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
            355                 360                 365

Val Glu Pro Thr Ile Thr Asn Ser Leu Asn Asp Arg Ser Thr Glu Lys
            370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
```

-continued

```
                500                 505                 510
Tyr Met Gly Val Pro Arg Glu Ala Asp Lys Trp Ser Tyr Asn Gly Ile
            515                 520                 525
Leu Thr Ser Val Arg Tyr Gly Thr Gly Ala Asn Glu Ala Thr Asp Glu
            530                 535                 540
Gly Thr Ala Glu Thr Arg Thr Gln Gly Met Ala Val Ile Ala Ser Asn
545                 550                 555                 560
Asn Pro Asn Leu Lys Leu Asn Glu Trp Asp Lys Leu Gln Val Asn Met
            565                 570                 575
Gly Ala Ala His Lys Asn Gln Tyr Tyr Arg Pro Val Leu Leu Thr Thr
            580                 585                 590
Lys Asp Gly Ile Ser Arg Tyr Leu Thr Asp Glu Val Pro Gln Ser
            595                 600                 605
Leu Trp Lys Lys Thr Asp Ala Asn Gly Ile Leu Thr Phe Asp Met Asn
            610                 615                 620
Asp Ile Ala Gly Tyr Ser Asn Val Gln Val Ser Gly Tyr Leu Ala Val
625                 630                 635                 640
Trp Val Pro Val Gly Ala Lys Ala Asp Gln Asp Ala Arg Val Thr Ala
            645                 650                 655
Ser Lys Lys Asn Ala Ser Gly Gln Val Tyr Glu Ser Ser Ala Ala
            660                 665                 670
Leu Asp Ser Gln Leu Ile Tyr Glu Gly Phe Ser Asn Phe Gln Asp Phe
            675                 680                 685
Ala Thr Arg Asp Asp Gln Tyr Thr Asn Lys Val Ile Ala Lys Asn Val
            690                 695                 700
Asn Leu Phe Lys Glu Trp Gly Val Thr Ser Phe Glu Leu Pro Pro Gln
705                 710                 715                 720
Tyr Val Ser Ser Gln Asp Gly Thr Phe Leu Asp Ser Ile Ile Gln Asn
            725                 730                 735
Gly Tyr Ala Phe Glu Asp Arg Tyr Asp Met Ala Met Ser Lys Asn Asn
            740                 745                 750
Lys Tyr Gly Ser Leu Asn Asp Leu Leu Asn Ala Leu Arg Ala Leu His
            755                 760                 765
Ser Val Asn Ile Gln Ala Ile Ala Asp Trp Val Pro Asp Gln Ile Tyr
            770                 775                 780
Asn Leu Pro Gly Lys Glu Val Thr Ala Thr Arg Val Asn Asn Tyr
785                 790                 795                 800
Gly Thr Tyr Arg Glu Gly Ser Glu Ile Lys Glu Asn Leu Tyr Val Ala
            805                 810                 815
Asn Thr Lys Thr Asn Gly Thr Asp Tyr Gln Gly Lys Tyr Gly Gly Ala
            820                 825                 830
Phe Leu Asp Glu Leu Lys Ala Lys Tyr Pro Glu Ile Phe Glu Arg Val
            835                 840                 845
Gln Ile Ser Asn Gly Gln Lys Met Thr Thr Asp Glu Lys Ile Thr Lys
            850                 855                 860
Trp Ser Ala Lys His Phe Asn Gly Thr Asn Ile Leu Gly Arg Gly Ala
865                 870                 875                 880
Tyr Tyr Val Leu Lys Asp Trp Ala Ser Asn Glu Tyr Leu Asn Asn Lys
            885                 890                 895
Asn Gly Glu Met Val Leu Pro Lys Gln Leu Val Asn Lys Asn Ala Tyr
            900                 905                 910
Thr Gly Phe Val Ser Asp Ala Ser Gly Thr Lys Tyr Tyr Ser Thr Ser
            915                 920                 925
```

```
Gly Tyr Gln Ala Arg Asn Ser Phe Ile Gln Asp Glu Asn Gly Asn Trp
        930                 935                 940

Tyr Tyr Phe Asn Asn Arg Gly Tyr Leu Val Thr Gly Ala Gln Glu Ile
945                 950                 955                 960

Asp Gly Lys Gln Leu Tyr Phe Leu Lys Asn Gly Ile Gln Leu Arg Asp
                965                 970                 975

Ser Leu Arg Glu Asp Glu Asn Gly Asn Gln Tyr Tyr Tyr Asp Lys Thr
            980                 985                 990

Gly Ala Gln Val Leu Asn Arg Tyr Tyr Thr Thr Asp Gly Gln Asn Trp
        995                 1000                1005

Arg Tyr Phe Asp Val Lys Gly Val Met Ala Arg Gly Leu Val Thr
    1010                1015                1020

Met Gly Gly Asn Gln Gln Phe Phe Asp Gln Asn Gly Tyr Gln Val
    1025                1030                1035

Lys Gly Lys Ile Ala Arg Ala Lys Asp Gly Lys Leu Arg Tyr Phe
    1040                1045                1050

Asp Lys Asp Ser Gly Asn Ala Ala Ala Asn Arg Phe Ala Gln Gly
    1055                1060                1065

Asp Asn Pro Ser Asp Trp Tyr Tyr Phe Gly Ala Asp Gly Val Ala
    1070                1075                1080

Val Thr Gly Leu Gln Lys Val Gly Gln Gln Thr Leu Tyr Phe Asp
    1085                1090                1095

Gln Asp Gly Lys Gln Val Lys Gly Lys Val Val Thr Leu Ala Asp
    1100                1105                1110

Lys Ser Ile Arg Tyr Phe Asp Ala Asn Ser Gly Glu Met Ala Val
    1115                1120                1125

Asn Lys Phe Val Glu Gly Ala Lys Asn Val Trp Tyr Tyr Phe Asp
    1130                1135                1140

Gln Ala Gly Lys Ala Val Thr Gly Leu Gln Thr Ile Asn Lys Gln
    1145                1150                1155

Val Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asn Ser
    1175                1180                1185

Gly Glu Met Ala Val Gly Lys Phe Ala Glu Gly Ala Lys Asn Glu
    1190                1195                1200

Trp Tyr Tyr Phe Asp Gln Ala Gly Lys Ala Val Thr Gly Leu Gln
    1205                1210                1215

Lys Ile Gly Gln Gln Thr Leu Tyr Phe Asp Gln Asn Gly Lys Gln
    1220                1225                1230

Val Lys Gly Lys Val Val Thr Leu Ala Asp Lys Ser Ile Arg Tyr
    1235                1240                1245

Phe Asp Ala Asn Ser Gly Glu Met Ala Ser Asn Lys Phe Val Glu
    1250                1255                1260

Gly Ala Lys Asn Glu Trp Tyr Tyr Phe Asp Gln Ala Gly Lys Ala
    1265                1270                1275

Val Thr Gly Leu Gln Gln Ile Gly Gln Gln Thr Leu Tyr Phe Asp
    1280                1285                1290

Gln Asn Gly Lys Gln Val Lys Gly Lys Ile Val Tyr Val Asn Gly
    1295                1300                1305

Ala Asn Arg Tyr Phe Asp Ala Asn Ser Gly Glu Met Ala Arg Asn
    1310                1315                1320
```

| Lys | Trp | Ile | Gln | Leu | Glu | Asp | Gly | Ser | Trp | Met | Tyr | Phe | Asp | Arg |
|---|---|---|---|---|---|---|---|---|---|---|---|---|---|---|
| 1325 | | | | | 1330 | | | | | | 1335 | | | |

| Asn | Gly | Arg | Gly | Arg | Arg | Phe | Gly | Trp | Asn |
|---|---|---|---|---|---|---|---|---|---|
| 1340 | | | | | 1345 | | | | |

<210> SEQ ID NO 19
<211> LENGTH: 4023
<212> TYPE: DNA
<213> ORGANISM: unknown
<220> FEATURE:
<223> OTHER INFORMATION: unknown Streptococcus sp. C150

<400> SEQUENCE: 19

| | | | | | |
|---|---|---|---|---|---|
| atgatcgacg | gcaaatacta | ctacgtaaac | gaggacggca | gccacaaaga | gaatttcgcg | 60 |
| atcacggtta | atggtcaact | gctgtatttt | ggtaaggatg | gcgcgctgac | cagcagcagc | 120 |
| acgtacagct | tcacccaagg | cactaccaat | attgtggacg | gttttagcat | taacaaccgt | 180 |
| gcgtatgact | ccagcgaggc | ctctttcgag | ctgattgacg | gttatctgac | tgcggactct | 240 |
| tggtaccgtc | cggcgagcat | tatcaaagac | ggtgtgacgt | ggcaagcatc | caccgccgag | 300 |
| gacttccgcc | cgttgctgat | ggcgtggtgg | ccgaacgttg | atactcaggt | gaactacctg | 360 |
| aactacatgt | ccaaagtctt | taatctggat | gctaaataca | gctcgactga | taaacaggaa | 420 |
| accctgaagg | tggcggcgaa | agatatccag | atcaaaattg | aacaaaagat | tcaggcggaa | 480 |
| aagtccacgc | aatggctgcg | tgaaacgatc | agcgcctttg | taaaacccca | gccgcaatgg | 540 |
| aacaaagaga | ctgagaacta | cagcaagggc | ggtggtgagg | accatctgca | aggtggtgcc | 600 |
| ctgctgtatg | ttaatgactc | tcgtaccccg | tgggcgaaca | gcaactatcg | tttgctgaac | 660 |
| cgcacggcga | ccaaccagac | cggtacgatc | gacaagagca | tcctggacga | gcagagcgat | 720 |
| ccgaatcaca | tgggtggttt | tgatttcttg | ctggctaatg | acgttgactt | gagcaatccg | 780 |
| gtcgtccagg | cggaacaact | gaatcagatc | cactacctga | tgaattgggg | ttctattgtc | 840 |
| atgggtgata | agacgcgaa | ttttgacggt | attcgtgtag | acgcggtgga | taatgttgat | 900 |
| gcggacatgc | tgcaattgta | caccaactat | ttccgcgaat | actatggtgt | caacaaaagc | 960 |
| gaggcaaacg | cgctggcgca | cattagcgtc | ctggaagcct | ggagcctgaa | tgacaaccat | 1020 |
| tacaatgata | agactgatgt | tgcggcgctg | gcaatggaga | ataagcagcg | cttggcactg | 1080 |
| ttgtttagcc | tggcgaaacc | gattaaagaa | cgcacgcctg | ccgtgtctcc | gctgtacaac | 1140 |
| aatacgttta | acaccactca | gcgtgatgaa | aagacggact | ggatcaataa | agatggttcg | 1200 |
| aaagcctaca | atgaggatgg | cactgtcaag | aaaagcacca | tcggcaagta | taacgagaag | 1260 |
| tatggtgatg | ctagcggcaa | ctacgttttc | atccgcgctc | acgacaataa | cgtgcaagac | 1320 |
| atcatcgcgg | agatcattaa | gaaagagatt | aacgagaaat | ctgacggttt | taccattacg | 1380 |
| gattcggaga | tgaagcgtgc | atttgagatc | tataacaaag | acatgctgtc | taatgacaaa | 1440 |
| aagtacacgc | tgaataacat | cccggcggcg | tacgcggtta | tgctgcaaaa | catggaaacg | 1500 |
| attacccgcg | tgtattacgg | cgatctgtac | acggacgacg | taattacat | ggaagcgaaa | 1560 |
| agcccgtact | acgatacgat | tgttaacttg | atgaagtctc | gcatcaaata | cgtgagcggt | 1620 |
| ggccaggcgc | agcgcagcta | ctggctgccg | accgatggta | agatggataa | gtcggatgtt | 1680 |
| gagctgtacc | gtacgaacga | agtgtacacg | agcgtccgtt | acggcaaaga | cattatgacc | 1740 |
| gccgatgaca | cgcaaggtag | caaatacagc | cgtaccagcg | gtcaggtgac | cctggtcgtc | 1800 |
| aacaacccaa | aactgacctt | ggaccaaagc | gcaaagctga | acgtggttat | gggcaagatt | 1860 |
| catgctaatc | agaagtaccg | cgcactgatt | gtcggtaccc | cgaacggtat | taagaatttc | 1920 |

```
accagcgacg cagaggctat tgccgcaggc tatgtcaaag aaaccgatgg caatggcgtg    1980
ctgaccttcg gtgcaaacga catcaagggt tatgaaactt tcgatatgag cggcttcgtc    2040
gctgtttggg ttccggtcgg tgcgagcgac gaccaagata ttcgtgtggc ggcgtctacg    2100
gcagcaaaga aagagggtga gctgacgctg aaagcgaccg aagcctatga ctcccaactg    2160
atctatgaag gctttagcaa tttccagacc atcccagatg gcagcgatcc ttctgtttat    2220
accaatcgta agatcgcgga aaatgttgat ttgttcaaga gctggggtgt cacgagcttc    2280
gaaatggctc cgcagttcgt ttctgcggac gatggcacgt ttctggacag cgtcattcaa    2340
aacggctatg cgttcgcaga ccgttatgat ctggccatga gcaaaaacaa taagtacggt    2400
agcaaagaag atctgcgtaa cgcgctgaag gcactgcaca aagcaggcat tcaggcgatt    2460
gcagattggg tgccagacca aatctaccag ctgcctggca agaagttgt tactgccacc      2520 cgcacggacg gtgctggtcg caaaatcagc gatgcaatca tcgatcattc cctgtacgtt    2580
gcgaactcca agagctccgg taaggactac caagcgaagt acgtggcga gttcttggcg      2640 gaactgaagg cgaaatacc ggaaatgttc aaagtgaaca tgattagcac cggcaaaccg      2700
attgatgata gcgtgaaact gaagcagtgg aaagcagaat acttcaacgg caccaatgtg    2760
ctggatcgcg gtgtcggtta tgttctgagc gatgaggcaa ccggtaagta tttcaccgtt    2820
accaaagagg gtaactttat cccgttgcag ctgaagggta acaagaaggt gattaccggc    2880
ttttccagcg acggtaaggg cattacctat ttcggtacta gcggtaacca agctaaatcc    2940
gcgttcgtca cttttaacgg taacacgtac tacttcgacg cacgtggcca catggttacc    3000
aacggtgagt actcgccgaa tggtaaagat gtgtatcgtt ttctgccgaa cggcattatg    3060
ctgagcaacg cgttctatgt tgacggcaat ggcaacacct acctgtacaa ctccaaaggc    3120
caaatgtata aggtggcta tagcaaattt gacgtcacga aaacgaagga cggtaaagag      3180
agcaaagttg tcaagttccg ctactttacg aacgagggcg tgatggcgaa aggtgtcacg    3240
gttgtggatg gcttcactca gtactttaac gaggatggca ttcaaagcaa agacgagctg    3300
gtcacttaca atggcaagac ctattacttc gaagcacaca cgggcaatgc cattaagaat    3360
acgtggcgta atatcaaggg caaatggtac cattttgatg ctaacggtgt cgcggctact    3420
ggcgcacagg ttatcaacgg tcagcacctg tacttcaatg aagatggctc tcaagtaaaa    3480
ggtagcatcg tcaaaaacgc tgatggtacg ttcagcaagt acaaggacag ctctggcgat    3540
ctggtggtga acgagttttt cacgacgggt gataacgtct ggtactatgc tggtgccaat    3600
ggcaaaacgt tactggtgc acaggtgatt aatggccagc acttgttctt caaagaggat      3660
ggcagccagg tcaagggcga ctttgtgaag aatagcgacg gcacctactc caagtatgac    3720
gctgcgagcg cgaacgtct gaccaacgag ttcttcacta cgggcgacaa tcattggtac      3780
tatattggcg ccaacggtaa gaccgttacc ggtgaagtta agattggtga cgacacgtat    3840
ttcttcgcaa aagacggtaa gcaactgaaa ggtcaaatcg ttaccacccg tagcggtcgt    3900
atcagctact actttggtga tagcggtaag aaggctatta gcacgtgggt ggagatccag    3960
ccgggtgtgt ttgttttctt cgacaaaaac ggcctggctt acccaccgga gaatatgaac    4020
tga                                                                  4023
```

<210> SEQ ID NO 20
<211> LENGTH: 1340
<212> TYPE: PRT
<213> ORGANISM: unknown
<220> FEATURE:

<223> OTHER INFORMATION: unknown Streptococcus sp. C150

<400> SEQUENCE: 20

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
            35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
                115                 120                 125

Leu Asp Ala Lys Tyr Ser Ser Thr Asp Lys Gln Glu Thr Leu Lys Val
            130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
            195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
            275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
                340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400
```

-continued

Lys Ala Tyr Asn Glu Asp Gly Thr Val Lys Lys Ser Thr Ile Gly Lys
            405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Glu Lys Ser Asp Gly Phe Thr Ile Thr Asp Ser Glu Met
            450                 455                 460

Lys Arg Ala Phe Glu Ile Tyr Asn Lys Asp Met Leu Ser Asn Asp Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
            500                 505                 510

Asp Gly Asn Tyr Met Glu Ala Lys Ser Pro Tyr Tyr Asp Thr Ile Val
            515                 520                 525

Asn Leu Met Lys Ser Arg Ile Lys Tyr Val Ser Gly Gly Gln Ala Gln
            530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
            565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Thr Leu Asp
            595                 600                 605

Gln Ser Ala Lys Leu Asn Val Val Met Gly Lys Ile His Ala Asn Gln
610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
            645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
            675                 680                 685

Ser Asp Asp Gln Asp Ile Arg Val Ala Ala Ser Thr Ala Ala Lys Lys
            690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
            725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
            770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
            805                 810                 815

Ile Gln Ala Ile Ala Asp Trp Val Pro Asp Gln Ile Tyr Gln Leu Pro

```
                  820                 825                 830
Gly Lys Glu Val Val Thr Ala Thr Arg Thr Asp Gly Ala Gly Arg Lys
            835                 840                 845
Ile Ser Asp Ala Ile Ile Asp His Ser Leu Tyr Val Ala Asn Ser Lys
850                 855                 860
Ser Ser Gly Lys Asp Tyr Gln Ala Lys Tyr Gly Gly Glu Phe Leu Ala
865                 870                 875                 880
Glu Leu Lys Ala Lys Tyr Pro Glu Met Phe Lys Val Asn Met Ile Ser
            885                 890                 895
Thr Gly Lys Pro Ile Asp Asp Ser Val Lys Leu Lys Gln Trp Lys Ala
            900                 905                 910
Glu Tyr Phe Asn Gly Thr Asn Val Leu Asp Arg Gly Val Gly Tyr Val
            915                 920                 925
Leu Ser Asp Glu Ala Thr Gly Lys Tyr Phe Thr Val Thr Lys Glu Gly
            930                 935                 940
Asn Phe Ile Pro Leu Gln Leu Lys Gly Asn Lys Lys Val Ile Thr Gly
945                 950                 955                 960
Phe Ser Ser Asp Gly Lys Gly Ile Thr Tyr Phe Gly Thr Ser Gly Asn
                965                 970                 975
Gln Ala Lys Ser Ala Phe Val Thr Phe Asn Gly Asn Thr Tyr Tyr Phe
                980                 985                 990
Asp Ala Arg Gly His Met Val Thr Asn Gly Glu Tyr Ser Pro Asn Gly
                995                 1000                1005
Lys Asp Val Tyr Arg Phe Leu Pro Asn Gly Ile Met Leu Ser Asn
            1010                1015                1020
Ala Phe Tyr Val Asp Gly Asn Gly Asn Thr Tyr Leu Tyr Asn Ser
            1025                1030                1035
Lys Gly Gln Met Tyr Lys Gly Gly Tyr Ser Lys Phe Asp Val Thr
            1040                1045                1050
Glu Thr Lys Asp Gly Lys Glu Ser Lys Val Val Lys Phe Arg Tyr
            1055                1060                1065
Phe Thr Asn Glu Gly Val Met Ala Lys Gly Val Thr Val Val Asp
            1070                1075                1080
Gly Phe Thr Gln Tyr Phe Asn Glu Asp Gly Ile Gln Ser Lys Asp
            1085                1090                1095
Glu Leu Val Thr Tyr Asn Gly Lys Thr Tyr Tyr Phe Glu Ala His
            1100                1105                1110
Thr Gly Asn Ala Ile Lys Asn Thr Trp Arg Asn Ile Lys Gly Lys
            1115                1120                1125
Trp Tyr His Phe Asp Ala Asn Gly Val Ala Ala Thr Gly Ala Gln
            1130                1135                1140
Val Ile Asn Gly Gln His Leu Tyr Phe Asn Glu Asp Gly Ser Gln
            1145                1150                1155
Val Lys Gly Ser Ile Val Lys Asn Ala Asp Gly Thr Phe Ser Lys
            1160                1165                1170
Tyr Lys Asp Ser Ser Gly Asp Leu Val Val Asn Glu Phe Phe Thr
            1175                1180                1185
Thr Gly Asp Asn Val Trp Tyr Tyr Ala Gly Ala Asn Gly Lys Thr
            1190                1195                1200
Val Thr Gly Ala Gln Val Ile Asn Gly Gln His Leu Phe Phe Lys
            1205                1210                1215
Glu Asp Gly Ser Gln Val Lys Gly Asp Phe Val Lys Asn Ser Asp
            1220                1225                1230
```

-continued

| | | | | | | | | | | |
|---|---|---|---|---|---|---|---|---|---|---|
| Gly | Thr | Tyr | Ser | Lys | Tyr | Asp | Ala | Ala | Ser | Gly | Glu | Arg | Leu | Thr |
| | 1235 | | | | 1240 | | | | 1245 | |

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile
    1280                1285                1290

Val Thr Thr Arg Ser Gly Arg Ile Ser Tyr Tyr Phe Gly Asp Ser
    1295                1300                1305

Gly Lys Lys Ala Ile Ser Thr Trp Val Glu Ile Gln Pro Gly Val
    1310                1315                1320

Phe Val Phe Phe Asp Lys Asn Gly Leu Ala Tyr Pro Pro Glu Asn
    1325                1330                1335

Met Asn
    1340

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25
<211> LENGTH: 4308
<212> TYPE: DNA
<213> ORGANISM: Streptococcus sobrinus

<400> SEQUENCE: 25
atggttgacg gcaaatacta ctattatgat caggatggca acgttaagaa gaatttcgcg      60
gttagcgttg gtgacaagat ctactacttt gacgagactg gtgcctacaa agacacctct     120
aaagtggacg cggacaagtc tagcagcgcc gttagccaaa atgcgacgat ctttgcggct     180
aacaatcgtg cgtatagcac ctctgctgag aactttgagg ccgttgataa ctatctgacg     240
gcagatagct ggtatcgtcc taaatctatt ctgaaagatg caagacgtg  gaccgagtcg     300 ggtaaggacg acttccgtcc gctgctgatg cgtggtggc  cggacacgga gactaaacgc     360
aattacgtga attacatgaa cctggttgtc ggcatcgaca agacgtacac cgcggaaacc     420
tctcaagcag atttgaccgc agcggcggag ctggtccagg cgcgtattga acagaaaatc     480
accacggaac agaatacgaa atggctgcgc gaggcgatct ctgctttcgt caagacccag     540

```
ccgcagtgga atggtgaaag cgagaagccg tatgacgacc acctgcaaaa cggtgctctg      600
aaattcgata atcagagcga cctgaccccg gacacccaga gcaactatcg cctgctgaat      660
cgcaccccga ctaaccagac tggcagcctg gacagccgtt tcacctataa tgcgaacgat      720
ccgttgggtg gctacgaatt tctgctggct aacgacgtgg ataatagcaa ccctgtggtg      780
caggcagaac aactgaactg gttgcattac ctgttgaatt ttggtagcat ttacgcgaaa      840
gatgcggatc aaacttcga ttccatccgt gtggacgccg tggacaacgt cgatgcagat       900
ctgttgcaga ttagcagcga ttacctgaag gcagcctatg gcattgacaa gaacaataag      960
aacgcgaaca accatgttag cattgttgag gcttggagcg ataacgatac gccgtacctg     1020
cacgatgacg gtgataacct gatgaacatg gacaataagt tccgcttgag catgctgtgg     1080
agcctggcca agccgctgga caagcgcagc ggtctgaatc ctctgattca taacagcctg     1140
gtggaccgtg aggttgatga ccgtgaagtg gaaacggttc cgagctactc ttttgcgcgt     1200
gcgcatgatt ccgaggtcca agacattatc cgcgacatta tcaaggccga aatcaacccg     1260
aatagctttg gttatagctt cacccaagaa gagattgacc aggcgtttaa gatctataat     1320
gaagatctga agaaaaccga caagaaatac acccactata atgtcccgtt gagctatact     1380
ttgctgctga cgaataaagg ttcgattccg cgtgtgtatt acggtgatat gttcaccgat     1440
gatggtcaat acatggcgaa caaaacggtt aactatgatg ccattgagtc gctgctgaaa     1500
gcgcgcatga agtacgttag cggcggtcaa gcgatgcaaa actatcaaat cggcaatggt     1560
gagattctga ccagcgttcg ttatggtaag ggtgcattga agcaatccga caagggtgac     1620
gcgaccacgc gtacgtccgg tgtgggcgtc gtgatgggca accagccgaa ctttagcctg     1680
gacggcaagg tggtggcatt gaacatgggt gccgctcatg caaatcagga gtatcgtgcg     1740
ctgatggtga gcaccaagga tggcgttgcc acgtatgcca ccgacgcgga cgcaagcaag     1800
gcaggtctgg tcaaacgcac cgatgaaaat ggttatttgt actttctgaa cgacgatctg     1860
aagggtgtgg caaacccaca agtcagcggt tccttgcagg tgtgggtccc agtgggtgcg     1920
gctgacgatc aggacattcg tgttgcagcg agcgacacgg ctagcacgga cggtaagtcc     1980
ctgcatcaag atgcggcaat ggatagccgt gttatgtttg aggggttttag caacttccag     2040 agctttgcaa ccaaagaaga agagtacacc aacgtagtta ttgcgaacaa cgtggacaaa     2100
ttcgttagct gggtattac cgactttgag atggcaccgc aatatgtcag ctccaccgat      2160
ggccagtttc tggatagcgt tatccagaat ggttacgcgt tcaccgaccg ttatgatctg     2220
ggtatgagca aagccaacaa atacggtacc gcggatcagc tggttaaagc aatcaaagcg     2280
ttgcacgcga agggtctgaa ggtgatggcg gactgggttc cagaccagat gtacacgttt     2340
ccgaagcagg aagttgtcac tgtcacgcgc accgacaaat tggtaagcc gattgcgggc      2400 agccaaatca atcacagcct gtacgtgacg gacaccaaat ccagcggtga tgattaccag     2460
gccaaatatg gtggtgcgtt cctggatgag ctgaaagaga atacccgga gctgttcacc      2520 aaaaagcaga tctcgaccgg tcaggcgatc gacccgagct gaagattaa gcagtggagc      2580 gcgaaatact ttaatggtag caacattctg ggtcgtggtg ccgactacgt cctgtccgat     2640
caagttagca caagtatttt caatgtgcc agcgacacgc tgtttctgcc gtctagcctg      2700
ttgggtaagg ttgtcgaaag cggtattcgt tacgatggca aaggttatat ctataacagc     2760
agcgcgactg cgaccaagt caaggcgtct tttatcacgg aagcaggcaa tctgtactac      2820
ttcggcaaag acgttacat ggttactggt gcgcagacca ttaacggtgc gaattacttc      2880 ttccttggaaa atggtacggc cctgcgtaat accatctaca ccgatgcaca gggcaactcc     2940
```

```
cactattatg ctaatgatgg caagcgttac gagaacggtt accagcagtt cggcaacgat    3000
tggcgttact tcaaagatgg taacatggcc gtcggtctga ccacggtgga tggtaacgtt    3060
cagtatttcg acaaggacgg tgtccaagct aaagacaaga ttattgtgac ccgcgatggt    3120
aaggtgcgct actttgatca acacaatggc aacgcggtca cgaataccttt tatcgccgac    3180
aagaccggtc actggtacta cctgggcaaa gatggcgtcg cggtcaccgg cgctcaaacc    3240
gtcggtaagc aaaaactgta ttttgaggcg aacggtgagc aggtgaaagg cgactttgtg    3300
actagccatg aaggcaaact gtacttttat gatgttgaca gcggcgacat gtggaccgat    3360
accttcatcg aggataaggc cggcaactgg ttctacctgg gtaaagacgg cgcagcagtt    3420
agcggtgcac agaccattcg cggtcaaaag ctgtacttca aggcgtacgg tcaacaggtc    3480
aaaggtgaca tcgttaaagg caccgacggc aagatccgtt actacgatgc gaaatccggc    3540
gagcaggttt tcaataagac ggtcaaagcc gctgatggca aaacctatgt gatcggcaac    3600
aatggtgtgg cggtcgatcc gagcgttgtt aagggtcaga cgttcaaaga cgccagcggc    3660
gcactgcgtt tttacaatct gaaaggtcaa ctggttacgg gctccggttg gtatgaaacg    3720
gccaatcacg attgggtgta tattcagagc ggtaaagcac tgaccggtga gcaaaccatc    3780
aatggtcagc acctgtactt taaagaagat ggccaccaag ttaaaggtca gctggtcacc    3840
cgtacggacg gcaaagtgcg ttactatgac gcaaattctg gcgatcaagc gttcaacaag    3900
tccgtgacgg ttaacggcaa aacgtattac ttcggtaatg atggtaccgc gcaaaccgcg    3960
ggtaacccga aaggccaaat cttcaaggac ggcagcgttc tgcgtttcta tagcatggaa    4020
ggccagctgg taattggcag cggctggtat ccaacgcgc aaggccaatg gctgtatgtg    4080
aagaatggta agtgttgac cggtttgcag accgtcggtt cccagcgcgt gtactttgat    4140
gagaatggca ttcaagcaaa aggcaaagcg gttcgcacga gcgacggcaa aattcgctac    4200
ttcgacgaga acagcggtag catgatcacc aatcaatgga gtttgtttta cggtcaatac    4260
tattactttg gtaatgacgg tgcggcaatc taccgtggtt ggaattaa                4308
```

<210> SEQ ID NO 26
<211> LENGTH: 1435
<212> TYPE: PRT
<213> ORGANISM: Streptococcus sobrinus

<400> SEQUENCE: 26

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
            20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
    50                  55                  60

Tyr Ser Thr Ser Ala Glu Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Leu
        115                 120                 125
```

```
Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Lys Pro Tyr Asp
                180                 185                 190

Asp His Leu Gln Asn Gly Ala Leu Lys Phe Asp Asn Gln Ser Asp Leu
            195                 200                 205

Thr Pro Asp Thr Gln Ser Asn Tyr Arg Leu Leu Asn Arg Thr Pro Thr
        210                 215                 220

Asn Gln Thr Gly Ser Leu Asp Ser Arg Phe Thr Tyr Asn Ala Asn Asp
225                 230                 235                 240

Pro Leu Gly Gly Tyr Glu Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
        290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
                340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
        370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Ile
                420                 425                 430

Asp Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
        450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
530                 535                 540

Thr Ser Gly Val Gly Val Val Met Gly Asn Gln Pro Asn Phe Ser Leu
```

```
545                 550                 555                 560
Asp Gly Lys Val Val Ala Leu Asn Met Gly Ala His Ala Asn Gln
                565                 570                 575

Glu Tyr Arg Ala Leu Met Val Ser Thr Lys Asp Gly Val Ala Thr Tyr
                580                 585                 590

Ala Thr Asp Ala Asp Ala Ser Lys Ala Gly Leu Val Lys Arg Thr Asp
                595                 600                 605

Glu Asn Gly Tyr Leu Tyr Phe Leu Asn Asp Asp Leu Lys Gly Val Ala
                610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
                660                 665                 670

Phe Glu Gly Phe Ser Asn Phe Gln Ser Phe Ala Thr Lys Glu Glu Glu
                675                 680                 685

Tyr Thr Asn Val Val Ile Ala Asn Asn Val Asp Lys Phe Val Ser Trp
                690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
                740                 745                 750

Gln Leu Val Lys Ala Ile Lys Ala Leu His Ala Lys Gly Leu Lys Val
                755                 760                 765

Met Ala Asp Trp Val Pro Asp Gln Met Tyr Thr Phe Pro Lys Gln Glu
                770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
                900                 905                 910

Gly Lys Gly Tyr Ile Tyr Asn Ser Ser Ala Thr Gly Asp Gln Val Lys
                915                 920                 925

Ala Ser Phe Ile Thr Glu Ala Gly Asn Leu Tyr Phe Gly Lys Asp
                930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975
```

-continued

```
Gln Gly Asn Ser His Tyr Tyr Ala Asn Asp Gly Lys Arg Tyr Glu Asn
            980                 985                 990

Gly Tyr Gln Gln Phe Gly Asn Asp  Trp Arg Tyr Phe Lys  Asp Gly Asn
            995                1000                1005

Met Ala Val Gly Leu Thr Thr  Val Asp Gly Asn Val  Gln Tyr Phe
    1010                1015                1020

Asp Lys Asp Gly Val Gln Ala  Lys Asp Lys Ile Ile  Val Thr Arg
    1025                1030                1035

Asp Gly Lys Val Arg Tyr Phe  Asp Gln His Asn Gly  Asn Ala Val
    1040                1045                1050

Thr Asn Thr Phe Ile Ala Asp  Lys Thr Gly His Trp  Tyr Tyr Leu
    1055                1060                1065

Gly Lys Asp Gly Val Ala Val  Thr Gly Ala Gln Thr  Val Gly Lys
    1070                1075                1080

Gln Lys Leu Tyr Phe Glu Ala  Asn Gly Glu Gln Val  Lys Gly Asp
    1085                1090                1095

Phe Val Thr Ser His Glu Gly  Lys Leu Tyr Phe Tyr  Asp Val Asp
    1100                1105                1110

Ser Gly Asp Met Trp Thr Asp  Thr Phe Ile Glu Asp  Lys Ala Gly
    1115                1120                1125

Asn Trp Phe Tyr Leu Gly Lys  Asp Gly Ala Ala Val  Ser Gly Ala
    1130                1135                1140

Gln Thr Ile Arg Gly Gln Lys  Leu Tyr Phe Lys Ala  Tyr Gly Gln
    1145                1150                1155

Gln Val Lys Gly Asp Ile Val  Lys Gly Thr Asp Gly  Lys Ile Arg
    1160                1165                1170

Tyr Tyr Asp Ala Lys Ser Gly  Glu Gln Val Phe Asn  Lys Thr Val
    1175                1180                1185

Lys Ala Ala Asp Gly Lys Thr  Tyr Val Ile Gly Asn  Asn Gly Val
    1190                1195                1200

Ala Val Asp Pro Ser Val Val  Lys Gly Gln Thr Phe  Lys Asp Ala
    1205                1210                1215

Ser Gly Ala Leu Arg Phe Tyr  Asn Leu Lys Gly Gln  Leu Val Thr
    1220                1225                1230

Gly Ser Gly Trp Tyr Glu Thr  Ala Asn His Asp Trp  Val Tyr Ile
    1235                1240                1245

Gln Ser Gly Lys Ala Leu Thr  Gly Glu Gln Thr Ile  Asn Gly Gln
    1250                1255                1260

His Leu Tyr Phe Lys Glu Asp  Gly His Gln Val Lys  Gly Gln Leu
    1265                1270                1275

Val Thr Arg Thr Asp Gly Lys  Val Arg Tyr Tyr Asp  Ala Asn Ser
    1280                1285                1290

Gly Asp Gln Ala Phe Asn Lys  Ser Val Thr Val Asn  Gly Lys Thr
    1295                1300                1305

Tyr Tyr Phe Gly Asn Asp Gly  Thr Ala Gln Thr Ala  Gly Asn Pro
    1310                1315                1320

Lys Gly Gln Ile Phe Lys Asp  Gly Ser Val Leu Arg  Phe Tyr Ser
    1325                1330                1335

Met Glu Gly Gln Leu Val Ile  Gly Ser Gly Trp Tyr  Ser Asn Ala
    1340                1345                1350

Gln Gly Gln Trp Leu Tyr Val  Lys Asn Gly Lys Val  Leu Thr Gly
    1355                1360                1365
```

```
Leu Gln Thr Val Gly Ser Gln Arg Val Tyr Phe Asp Glu Asn Gly
    1370            1375                1380

Ile Gln Ala Lys Gly Lys Ala Val Arg Thr Ser Asp Gly Lys Ile
    1385            1390                1395

Arg Tyr Phe Asp Glu Asn Ser Gly Ser Met Ile Thr Asn Gln Trp
    1400            1405                1410

Lys Phe Val Tyr Gly Gln Tyr Tyr Tyr Phe Gly Asn Asp Gly Ala
    1415            1420                1425

Ala Ile Tyr Arg Gly Trp Asn
    1430            1435

<210> SEQ ID NO 27
<211> LENGTH: 4023
<212> TYPE: DNA
<213> ORGANISM: Streptococcus salivarius PS4

<400> SEQUENCE: 27
```

| | | | | | |
|---|---|---|---|---|---|
| atgattgacg | gcaaatacta | ctacgtaaac | aaagatggct | cgcacaaaga | gaatttcgca | 60 |
| attaccgtga | atggtcagtt | gttgtatttc | ggtaaggacg | gtgcattgac | gtctagcagc | 120 |
| acctacagct | ttacgcaggg | caccaccaac | atcgttgatg | ctttagcaa | aaacaaccgt | 180 |
| gcgtacgatt | ccagcgaggc | gagctttgaa | ctgatcgacg | gttatctgac | cgcggactcc | 240 |
| tggtatcgtc | cggtgagcat | tatcaaggac | ggcgttacgt | ggcaagccag | caccaaagag | 300 |
| gactttcgcc | cgctgctgat | ggcctggtgg | ccgaatgttg | acacccaggt | caactacctg | 360 |
| aattacatgt | cgaaggtgtt | taacctggac | gcgaagtata | cgagcaccga | caaacaggtt | 420 |
| gacctgaatc | gcgcagccaa | ggacattcag | gttaagattg | agcaaaagat | tcaggccgag | 480 |
| aagagcactc | aatggctgcg | tgaagcgatt | tcggccttcg | tcaaaaccca | gccgcagtgg | 540 |
| aataaagaaa | cggagaactt | ctccaagggt | ggtggtgagg | atcatctgca | aggtggtgca | 600 |
| ctgctgtacg | ttaacgaccc | gcgtaccccg | tgggctaact | ccaactaccg | cctgctgaat | 660 |
| cgtactgcga | ccaaccagac | cggcacgatc | gacaagagcg | ttctggacga | acagagcgat | 720 |
| cctaaccaca | tgggcggctt | cgattttctg | ctggcgaatg | acgtcgatac | cagcaatccg | 780 |
| gtggtgcagg | cggaacaact | gaatcagatc | cactacctga | tgaattgggg | ttccattgtt | 840 |
| atgggcgaca | agatgcaaa | cttcgatggt | atccgcgtgg | acgcggtcga | taacgttgac | 900 |
| gcagatatgc | tgcaactgta | caccaactac | tttcgtgagt | attatggcgt | gaacaaaagc | 960 |
| gaggcaaacg | ctttggcgca | catctcggtg | ctggaagcgt | ggagcttgaa | tgataatcac | 1020 |
| tataatgaca | agactgacgg | tgcggccctg | gcgatggaga | caaacagcg | tttgccctg | 1080 |
| ctgtttagct | tggcgaaacc | gatcaaagaa | cgtacccctg | cggtgagccc | gctgtacaac | 1140 |
| aacactttca | cacgacgca | gcgtgacgaa | aagaccgatt | ggattaacaa | agacggtagc | 1200 |
| aaagcctata | tgaggacgg | caccgtcaag | cagtccacca | tcggcaagta | caacgagaaa | 1260 |
| tacggcgacg | cgtccggcaa | ttatgtgttc | attcgcgccc | acgataacaa | cgtccaagac | 1320 |
| attattgcag | agatcattaa | gaaagaaatc | aatccgaaaa | gcgacggttt | caccattacc | 1380 |
| gacgccgaaa | tgaaaaaggc | attcgaaatc | tacaacaaag | atatgctgtc | ctctgataag | 1440 |
| aaatacaccc | tgaacaacat | cccagcggcc | tacgcggtga | tgctgcaaaa | catggaaacc | 1500 |
| attactcgtg | tgtattacgg | cgatctgtat | accgacgatg | ccattacat | ggaaaccaag | 1560 |
| agcccgtact | acgacaccat | tgtgaacctg | atgaagaacc | gtatcaaata | cgtgtccggt | 1620 |
| ggtcaagcgc | aacgttccta | ttggctgccg | accgacggta | agatggataa | aagcgatgtc | 1680 |

-continued

```
gaactgtatc gcaccaacga ggtgtacacc agcgtccgtt acggtaagga catcatgact   1740
gccgatgaca cccaaggtag caagtacagc cgtaccagcg gtcaggtgac cctggtggtg   1800
aacaacccga agctgtcttt ggataagagc gcgaagctgg acgtcgaaat gggcaagatc   1860
catgcaaacc agaaataccg tgctctgatc gtgggtacgc cgaacggcat caaaaacttc   1920
acgagcgacg ccgaggcaat cgcggctggc tacgtgaaag aaaccgacgg caatggtgtg   1980
ctgaccttcg gtgcaaatga catcaaaggt tacgaaacgt ttgacatgag cggtttcgtt   2040
gcagtttggg ttccggtagg tgcaagcgat gatcaagaca tccgtgtcgc cgcaagcacc   2100
gcggcaaaga aagaaggtga gctgactttg aaggcaactg aggcgtatga ctctcagctg   2160
atttacgaag gttttttcgaa ttttcagacc attccggatg gtagcgatcc gagcgtttac   2220
accaatcgta agatcgcgga aaatgttgat ttgttcaaga gctggggtgt gacctctttc   2280
gaaatggcgc cacagtttgt gagcgcagac gacggtacgt ttctggacag cgttatccag   2340
aacggctatg cgtttgcgga ccgttatgat ctggcgatgt ccaaaaacaa taagtacggt   2400
tcgaaagaag atctgcgtaa cgcgttgaag gctttgcaca aggccggcat ccaagccatt   2460
gcggactggg ttccggatca gatctaccaa ctgccgggca agaagtagt gaccgccact   2520 cgtaccgatg gtgccggtcg taagattagc gatgcaatta tcgatcacag cctgtacgtc   2580
gcaaacagca agtcgtctgg caaagactat caagctaaat acggtggtga gttcctggcc   2640
gagctgaaag caaagtaccc ggaaatgttt aaagtcaaca tgattagcac gggtaaaccg   2700
atcgacgact ctgtcaaact gaagcaatgg aaggcggagt actttaacgg tacgaatgtt   2760
ctggaccgtg tgttggtta cgtcctgagc gatgaggcga cgggcaagta ctttaccgtt   2820
acgaaagagg gtaactttat cccactgcaa ttgaaaggta acgagaaagt tatcacgggc   2880
ttcagctctg acggcaaggg cattacctat ttcggcaccct cgggtaatca agcgaaaagc   2940
gcttttgtca cgttcaatgg taatacctac tattttgacg cgcgtggcca catggttacc   3000
aacggcgaat atagccctaa tggtaaggat gtgtatcgtt tcctgccgaa tggtattatg   3060
ttgagcaatg cattctacgt tgacggtaac ggcaatacct acctgtacaa ctccaagggc   3120
caaatgtaca aggtggtta tagcaaattc gacgttacgg aaaccaaaga tggtaaagag   3180
agcaaagtgg tgaaatttcg ctactttacc aatgaaggtg tgatggcaaa aggtgttacc   3240
gtggtggacg gcttcactca atacttcaac gaagatggca ttcagagcaa ggacgaactg   3300
gtgacctaca atggtaaaac ctattacttc gaagcgcata ccggtaatgc gatcaaaaac   3360
acgtggcgca atatcaaggg taagtggtat cactttgatg cgaatggcgt ggcggcaacg   3420
ggtgcacagg ttatcaatgg tcagcacctg tactttaatg aggatggttc ccaggtgaag   3480
ggtggcgtcg tgaagaatgc ggatggtacc ttcagcaagt ataaagatgg ttccggtgac   3540
ctggtggtca atgagttctt cactactggt gataacgtgt ggtactacgc tggtgccaac   3600
ggcaaaactg tgacgggtgc ccaggtcatc aatggccaac acctgttttt caaagaggac   3660
ggtagccagg ttaagggtga tttcgttaag aacagcgacg gcacctactc taagtatgat   3720
gcggccagcg gcgaacgcct gacgaatgag ttttcacga ccggtgacaa ccactggtac   3780
tatattggtg ccaatggcaa aaccgttacc ggcgaagtca agatcggtga tgatacgtac   3840
ttcttcgcaa aagatggcaa gcagctgaag ggccagatcg tgacgacccg cagcggtcgt   3900
atcagctact acttcggcga ctctggtaag aaggcgatta gcacctgggt ggagattcag   3960
ccgggtgttt tcgtgttttt cgacaaaaat ggcctggcat atccgccgga aaacatgaat   4020
taa                                                                  4023
```

<210> SEQ ID NO 28
<211> LENGTH: 1340
<212> TYPE: PRT
<213> ORGANISM: Streptococcus salivarius PS4

<400> SEQUENCE: 28

```
Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Gln Gly Thr
            35                  40                  45

Thr Asn Ile Val Asp Gly Phe Ser Lys Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Lys Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
            115                 120                 125

Leu Asp Ala Lys Tyr Thr Ser Thr Asp Lys Gln Val Asp Leu Asn Arg
130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Ala Ile Ser Ala Phe Val Lys Thr
                165                 170                 175

Gln Pro Gln Trp Asn Lys Glu Thr Glu Asn Phe Ser Lys Gly Gly Gly
            180                 185                 190

Glu Asp His Leu Gln Gly Gly Ala Leu Leu Tyr Val Asn Asp Pro Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Thr Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
```

```
              370                 375                 380
Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Asn Val Gln Asp Ile Ile Ala Glu Ile Ile Lys Lys
                435                 440                 445

Glu Ile Asn Pro Lys Ser Asp Gly Phe Thr Ile Thr Asp Ala Glu Met
            450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
                500                 505                 510

Asp Gly His Tyr Met Glu Thr Lys Ser Pro Tyr Tyr Asp Thr Ile Val
            515                 520                 525

Asn Leu Met Lys Asn Arg Ile Lys Tyr Val Ser Gly Gly Gln Ala Gln
            530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
                580                 585                 590

Ser Gly Gln Val Thr Leu Val Val Asn Asn Pro Lys Leu Ser Leu Asp
            595                 600                 605

Lys Ser Ala Lys Leu Asp Val Glu Met Gly Lys Ile His Ala Asn Gln
            610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
            675                 680                 685

Ser Asp Asp Gln Asp Ile Arg Val Ala Ala Ser Thr Ala Ala Lys Lys
            690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
            770                 775                 780

Phe Ala Asp Arg Tyr Asp Leu Ala Met Ser Lys Asn Asn Lys Tyr Gly
785                 790                 795                 800
```

```
Ser Lys Glu Asp Leu Arg Asn Ala Leu Lys Ala Leu His Lys Ala Gly
            805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
            835                 840                 845

Ile Ser Asp Ala Ile Ile Asp His Ser Leu Tyr Val Ala Asn Ser Lys
            850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
            915                 920                 925

Leu Ser Asp Glu Ala Thr Gly Lys Tyr Phe Thr Val Thr Lys Glu Gly
            930                 935                 940

Asn Phe Ile Pro Leu Gln Leu Lys Gly Asn Glu Lys Val Ile Thr Gly
945                 950                 955                 960

Phe Ser Ser Asp Gly Lys Gly Ile Thr Tyr Phe Gly Thr Ser Gly Asn
            965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155

Val Lys Gly Gly Val Val Lys Asn Ala Asp Gly Thr Phe Ser Lys
    1160                1165                1170

Tyr Lys Asp Gly Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200
```

| | | | | | | | | | | |
|---|---|---|---|---|---|---|---|---|---|---|
|Val|Thr|Gly|Ala|Gln|Val|Ile|Asn|Gly|Gln|His|Leu|Phe|Phe|Lys|
| |1205| | | |1210| | | |1215| |
|Glu|Asp|Gly|Ser|Gln|Val|Lys|Gly|Asp|Phe|Val|Lys|Asn|Ser|Asp|
| |1220| | | |1225| | | |1230| |
|Gly|Thr|Tyr|Ser|Lys|Tyr|Asp|Ala|Ala|Ser|Gly|Glu|Arg|Leu|Thr|
| |1235| | | |1240| | | |1245| |
|Asn|Glu|Phe|Phe|Thr|Thr|Gly|Asp|Asn|His|Trp|Tyr|Tyr|Ile|Gly|
| |1250| | | |1255| | | |1260| |
|Ala|Asn|Gly|Lys|Thr|Val|Thr|Gly|Glu|Val|Lys|Ile|Gly|Asp|Asp|
| |1265| | | |1270| | | |1275| |
|Thr|Tyr|Phe|Phe|Ala|Lys|Asp|Gly|Lys|Gln|Leu|Lys|Gly|Gln|Ile|
| |1280| | | |1285| | | |1290| |
|Val|Thr|Thr|Arg|Ser|Gly|Arg|Ile|Ser|Tyr|Tyr|Phe|Gly|Asp|Ser|
| |1295| | | |1300| | | |1305| |
|Gly|Lys|Lys|Ala|Ile|Ser|Thr|Trp|Val|Glu|Ile|Gln|Pro|Gly|Val|
| |1310| | | |1315| | | |1320| |
|Phe|Val|Phe|Phe|Asp|Lys|Asn|Gly|Leu|Ala|Tyr|Pro|Pro|Glu|Asn|
| |1325| | | |1330| | | |1335| |
|Met|Asn| | | | | | | | | |
| |1340| | | | | | | | | |

<210> SEQ ID NO 29
<211> LENGTH: 4026
<212> TYPE: DNA
<213> ORGANISM: Streptococcus salivarius K12

<400> SEQUENCE: 29

```
atgacggacg gtaaatacta ttatgtaaat gaggacggca gccacaaaga gaatttcgca      60
attacggtaa acgtcaact gttgtacttt ggcaaggacg gcgctctgac gagcagcagc     120
acgcacagct tcacgccggg tactacgaat attgtggacg gtttctcgat caacaaccgt     180
gcgtacgata gcagcgaagc gagctttgag ctgatcaacg ttacctgac ggcggattcc      240
tggtatcgcc cggtttctat catcaaggat ggcgtcacgt ggcaggcaag cactgccgag     300
gattttcgtc cgctgttgat ggcctggtgg ccgaacgttg atacccaggt gaactatctg     360
aactatatgt ccaaggtctt taacctggaa gccaagtaca ccagcaccga taaacaggct     420
gatctgaacc gtgctgcaaa ggatatccag gtcaagatcg aacagaagat ccaggcggaa     480
aagagcacgc agtggctgcg tgagactatc tccgcgtttg ttaaaaccca gccgcaatgg     540
aacaaagaga ctgagaatta ctccaagggt ggtggcgaag atcatctgca aggcggtgcg     600
ctgttgtacg tgaacgacag ccgtaccccg tgggcgaata gcaattaccg cctgctgaat     660
cgcacggcaa cgaaccagac cggtaccatt aacaagtcgg tgttggacga gcaatccgat     720
ccaaatcaca tgggtggctt cgacttcctg ctggcaaacg atgtggatct gagcaatcct     780
gttgtgcagg ccgagcagct gaatcaaatc cattatctga tgaactgggg cagcattgtt     840
atgggtgaca agacgcgaa ttttgatggt atccgtgtgg acgccgttga caacgtgaac      900
gctgacatgt tgcagctgta cacgaactac tttcgtgagt attacggcgt caacaaaagc     960
gaagcgcaag cgctggcgca cattagcgtt ctggaagcgt ggagcttgaa cgataaccac    1020
tataacgaca aaaccgatgg tgcggcactg gcgatggaga ataagcaacg tctggccttg    1080
ctgttctctc tggccaagcc gatcaaagat cgtactccgg cagtgagccc actgtataac    1140
aatactttca ataccaccca acgtgacttc aagacggatt ggattaacaa ggacggtagc    1200
accgcctaca tgaggatgg caccgcgaaa caatctacca tcggtaagta caatgagaaa    1260
```

```
tatggtgatg caagcggtaa ctatgtgttt attcgtgccc atgacaataa cgtccaagac    1320
attattgcgg agatcattaa gaaagaaatc aataagaaga gcgatggttt taccatcagc    1380
gatagcgaaa tgaaacaggc gttcgaaatc tacaacaaag atatgctgag cagcaataag    1440
aaatacactc tgaataacat tccggcagcg tacgccgtga tgctgcaaaa catggagact    1500
atcacccgtg tgtattatgg tgacctgtac accgacgacg gtcactatat ggaaaccaag    1560
agcccgtatc atgacaccat tgtgaacctg atgaaaaacc gtatcaagta cgtttctggt    1620
ggccaggccc aacgctccta ttggctgccg accgacggta aaatggacaa tagcgatgtc    1680
gaactgtacc gtactagcga ggtctatacc agcgttcgct acggtaagga cattatgacg    1740
gcggatgaca ccgagggtag caagtactcc cgcacgagcg gtcaggttac cctggttgtt    1800
aacaacccga agctgactct gcatgaaagc gccaaactga acgtcgagat gggtaagatc    1860
cacgcaaacc agaaataccg tgcgctgatt gtgggtaccg ccgatggcat caaaaacttt    1920
acgtctgatg ccgaagcgat cgcggcaggc tacgtaaaag aaacggacag caatggtgtt    1980
ctgaccttcg gcgcaaatga tatcaaaggt tacgagactt tcgatatgag cggtttcgtc    2040
gcagtttggg tgccggtggg tgcgagcgat gatcaggaca tccgcgtggc gccgtcgacg    2100
gaagcgaaga agaaggtga actgacgctg aaagccacgg aagcgtatga tagccagttg    2160 attatgaag gcttctccaa tttccagacc attccggatg gcagcgaccc gagcgtttat    2220
accaaccgca aaattgctga gaatgttgat ctgtttaagt cctggggtgt cactagcttc    2280
gaaatggctc gcagtttgt ttcggcggac gacggcacct tcctggatag cgttatccag    2340
aacggttacg cctttgcgga ccgttatgat ttggccatga gcaagaacaa caagtacggt    2400
tctaaagagg atctgcgcga cgcactgaaa gcgctgcaca aagctggcat tcaggcaatc    2460
gcggactggg tcccagacca aatctaccaa ctgccaggca agaagtggt tacggcgacg    2520 cgcacggacg gtgcggtcg caagatcgcg gacgccatca ttgatcatag cctgtatgtt    2580
gctaactcca agagctccgg tcgcgattac caagcgcagt atggtggcga gtttctggca    2640
gagctgaaag cgaagtaccc gaaaatgttc acggaaaaca tgattagcac gggtaagccg    2700
atcgatgaca gcgtcaaact gaagcaatgg aaagccaagt atttcaatgg tacgaatgtg    2760
ctggaccgtg gtgtcggtta cgtcctgtcc gacgaggcga ccggcaaata cttcaccgtt    2820
accaaagagg gtaacttcat tccgctgcaa ctgaccggca atgaaaaagc ggtgaccggt    2880
ttcagcaacg acggcaaggg tatcacctac tttggtacga gcggtaatca ggccaagagc    2940
gcgttcgtca cctttaacgg caatacgtac tatttcgacg cgcgtggcca catggtcacg    3000
aacggcgagt atagcccgaa cggcaaagat gtctaccgtt ttctgccaaa tggtattatg    3060
ttgtcgaacg cgtttatgt cgacgcaaac ggtaatacgc acttgtacaa ctacaagggc    3120
cagatgtaca aggtggtta tacgaaattt gatgtcaccg aaactgataa agatggtaat    3180
gagagcaagg tggtcaagtt tcgttatttc accaatgagg cgtcatggc taagggtctg    3240 accgtcattg acggtagcac ccagtacttt ggtgaggatg gttttcaaac gaaggacaag    3300
ctggcgacct ataaaggtaa gacttattac ttcgaggcac acacgggcaa tgcgatcaaa    3360
aacacctggc gtaacatcga cggtaagtgg tatcacttcg atgagaatgg cgttgccgcg    3420
accggtgcac aagtgattaa cggtcaaaaa ctgtatttca cgaggatgg ctcgcaagtg    3480 aagggcggtg ttgttaagaa cgccgacggt acctacagca aatacaaaga gggcagcggt    3540
gagctggtta ccaacgagtt tttcacgacc gacggtaatg tgtggtacta tgctggtgcg    3600
```

```
gatggcaaga ctgtgaccgg tgctcaggtc attaatggtc agcacctgta ctttaaagaa    3660
gatggcagcc aggtgaaagg tggtgtggtg aaaaacgcgg acggtacgta cagcaagtat    3720
gacgccgcca ccggtgaacg cttgaccaat gagttcttta ccacgggcga taacaattgg    3780
tactatattg gttctaatgg taagaccgta accggtgaag tcaaaatcgg tgcggacacc    3840
tattactttg ccaaagatgg caaacaggtc aagggccaaa ccgtcaccgc aggcaatggc    3900
cgcatctcct attactacgg cgattctggt aagaaagcaa tcagcacgtg gatcgaaatt    3960
caaccgggta tctatgtcta ttttgataag acgggcatcg cgtacccacc gcgtgtgctg    4020
aattaa                                                               4026
```

<210> SEQ ID NO 30
<211> LENGTH: 1341
<212> TYPE: PRT
<213> ORGANISM: Streptococcus salivarius K12

<400> SEQUENCE: 30

```
Met Thr Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr His Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asn Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Glu Ala Lys Tyr Thr Ser Thr Asp Lys Gln Ala Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asn Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asn Ala Asp Met Leu
```

```
            290                 295                 300
Gln Leu Tyr Thr Asn Tyr Phe Arg Glu Tyr Tyr Gly Val Asn Lys Ser
305                 310                 315                 320

Glu Ala Gln Ala Leu Ala His Ile Ser Val Leu Glu Ala Trp Ser Leu
            325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Asp Arg Thr Pro Ala Val Ser Pro Leu Tyr Asn Asn Thr Phe Asn
        370                 375                 380

Thr Thr Gln Arg Asp Phe Lys Thr Asp Trp Ile Asn Lys Asp Gly Ser
385                 390                 395                 400

Thr Ala Tyr Asn Glu Asp Gly Thr Ala Lys Gln Ser Thr Ile Gly Lys
            405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Lys Lys Ser Asp Gly Phe Thr Ile Ser Asp Ser Glu Met
        450                 455                 460

Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr His Asp Thr Ile Val
        515                 520                 525

Asn Leu Met Lys Asn Arg Ile Lys Tyr Val Ser Gly Gly Gln Ala Gln
        530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
            565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
        595                 600                 605

Glu Ser Ala Lys Leu Asn Val Glu Met Gly Lys Ile His Ala Asn Gln
        610                 615                 620

Lys Tyr Arg Ala Leu Ile Val Gly Thr Ala Asp Gly Ile Lys Asn Phe
625                 630                 635                 640

Thr Ser Asp Ala Glu Ala Ile Ala Ala Gly Tyr Val Lys Glu Thr Asp
            645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
        690                 695                 700

Glu Gly Glu Leu Thr Leu Lys Ala Thr Glu Ala Tyr Asp Ser Gln Leu
705                 710                 715                 720
```

```
Ile Tyr Glu Gly Phe Ser Asn Phe Gln Thr Ile Pro Asp Gly Ser Asp
            725                 730                 735

Pro Ser Val Tyr Thr Asn Arg Lys Ile Ala Glu Asn Val Asp Leu Phe
        740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
            805                 810                 815

Ile Gln Ala Ile Ala Asp Trp Val Pro Asp Gln Ile Tyr Gln Leu Pro
        820                 825                 830

Gly Lys Glu Val Val Thr Ala Thr Arg Thr Asp Gly Ala Gly Arg Lys
            835                 840                 845

Ile Ala Asp Ala Ile Ile Asp His Ser Leu Tyr Val Ala Asn Ser Lys
        850                 855                 860

Ser Ser Gly Arg Asp Tyr Gln Ala Gln Tyr Gly Gly Glu Phe Leu Ala
865                 870                 875                 880

Glu Leu Lys Ala Lys Tyr Pro Lys Met Phe Thr Glu Asn Met Ile Ser
            885                 890                 895

Thr Gly Lys Pro Ile Asp Asp Ser Val Lys Leu Lys Gln Trp Lys Ala
            900                 905                 910

Lys Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
930                 935                 940

Asn Phe Ile Pro Leu Gln Leu Thr Gly Asn Glu Lys Ala Val Thr Gly
945                 950                 955                 960

Phe Ser Asn Asp Gly Lys Gly Ile Thr Tyr Phe Gly Thr Ser Gly Asn
            965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
        995                 1000                1005

Lys Asp Val Tyr Arg Phe Leu Pro Asn Gly Ile Met Leu Ser Asn
        1010                1015                1020

Ala Phe Tyr Val Asp Ala Asn Gly Asn Thr Tyr Leu Tyr Asn Tyr
        1025                1030                1035

Lys Gly Gln Met Tyr Lys Gly Gly Tyr Thr Lys Phe Asp Val Thr
        1040                1045                1050

Glu Thr Asp Lys Asp Gly Asn Glu Ser Lys Val Val Lys Phe Arg
        1055                1060                1065

Tyr Phe Thr Asn Glu Gly Val Met Ala Lys Gly Leu Thr Val Ile
        1070                1075                1080

Asp Gly Ser Thr Gln Tyr Phe Gly Glu Asp Gly Phe Gln Thr Lys
        1085                1090                1095

Asp Lys Leu Ala Thr Tyr Lys Gly Lys Thr Tyr Tyr Phe Glu Ala
        1100                1105                1110

His Thr Gly Asn Ala Ile Lys Asn Thr Trp Arg Asn Ile Asp Gly
        1115                1120                1125
```

| | | | | | | | | | | |
|---|---|---|---|---|---|---|---|---|---|---|
| Lys | Trp | Tyr | His | Phe | Asp | Glu | Asn | Gly | Val | Ala | Ala | Thr | Gly | Ala |
| | 1130 | | | | 1135 | | | | 1140 | |

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asp Gly Lys
    1190                1195                1200

Thr Val Thr Gly Ala Gln Val Ile Asn Gly Gln His Leu Tyr Phe
    1205                1210                1215

Lys Glu Asp Gly Ser Gln Val Lys Gly Gly Val Val Lys Asn Ala
    1220                1225                1230

Asp Gly Thr Tyr Ser Lys Tyr Asp Ala Ala Thr Gly Glu Arg Leu
    1235                1240                1245

Thr Asn Glu Phe Phe Thr Thr Gly Asp Asn Asn Trp Tyr Tyr Ile
    1250                1255                1260

Gly Ser Asn Gly Lys Thr Val Thr Gly Glu Val Lys Ile Gly Ala
    1265                1270                1275

Asp Thr Tyr Tyr Phe Ala Lys Asp Gly Lys Gln Val Lys Gly Gln
    1280                1285                1290

Thr Val Thr Ala Gly Asn Gly Arg Ile Ser Tyr Tyr Tyr Gly Asp
    1295                1300                1305

Ser Gly Lys Lys Ala Ile Ser Thr Trp Ile Glu Ile Gln Pro Gly
    1310                1315                1320

Ile Tyr Val Tyr Phe Asp Lys Thr Gly Ile Ala Tyr Pro Pro Arg
    1325                1330                1335

Val Leu Asn
    1340

<210> SEQ ID NO 31

<400> SEQUENCE: 31

000

<210> SEQ ID NO 32

<400> SEQUENCE: 32

000

<210> SEQ ID NO 33
<211> LENGTH: 4026
<212> TYPE: DNA
<213> ORGANISM: Streptococcus salivarius JIM8777

<400> SEQUENCE: 33
atgatcgacg gcaaatacta ctatgtaaac gaggacggca gccacaaaga gaatttcgcg       60
attacggtaa acggtcagct gctgtacttt ggtaaggacg gtgctctgac gagcagctcc      120
acgtacagct ttaccccggg tacgaccaat attgtcgatg gcttcagcat taacaaccgt      180
gcgtatgaca gcagcgaggc atcctttgag ctgatcgatg gttatttgac cgcggatagc      240
tggtatcgtc cggcgagcat cattaaggac ggcgttacgt ggcaggcctc gaccgcagaa      300
gattttcgtc gctgctgat ggcttggtgg ccgaatgttg cacccaggt gaattatctg      360

```
aattacatgt ccaaggtttt caacctggat gcaaagtaca ccagcaccga caagcaggaa    420
accctgaacg tggctgcgaa agatatccaa gtcaagattg agcaaaagat tcaggcagag    480
aaatctaccc agtggctgcg tgaaacgatt agcgcgtttg ttaaaactca gccgcaatgg    540
aataaagaaa cggaaaacta ttccaagggt ggtggcgagg accatctgca aggcggtgcc    600
ctgttgtacg ttaacgattc gcgcaccccg tgggcgaact cgaactatcg cttgctgaac    660
cataccgcta ccaatcaaaa aggcactatt gacaaatctg tcctggacga gcagagcgac    720
ccgaaccaca tgggcggttt cgattttctg ctggcgaacg acgtcgacct gagcaacccg    780
gtggtgcagg ccgaacaact gaaccagatt cactacctga tgaattgggg tagcatcgtg    840
atgggtgata agatgcgaa ctttgacggc attcgtgtcg atgcggtcga taacgtggac    900
gccgacatgt tgcagctgta cacgaactac tttcgtgagt actacggcgt taacaagagc    960
gaagcaaatg ccctggcgca tatcagcgtt ctggaagcgt ggagcctgaa tgacaatcac   1020
tataacgata gacggacgg tgcggccctg gcaatggaga ataaacaacg tctggcgctg   1080
ctgttcagcc tggcgaaacc gatcaaagag cgtacgccgg ctgtgagccc actgtataac   1140
aacaccttca atactacgca gcgtgacgag aaaacggact ggattaacaa agacggtagc   1200
aaagcgtata acgaggatgg taccgtcaag caatcgacca ttggtaagta caatgagaag   1260
tatggcgacg caagcggtaa ttacgtgttc attcgtgccc acgacaacaa tgttcaagac   1320
atcatcgccg aaatcatcaa gaaagagatc aaccctaaga gcgacggttt caccatcacc   1380
gacgcagaga tgaagaaggc ctttgaaatc tacaacaagg acatgttgag cagcgataag   1440
aagtatactc tgaacaacat tccggctgcg tacgcggtga tgttgcagaa tatggaaacc   1500
atcacgcgtg tttactatgg tgatctgtat accgataatg caactacat ggaaacgaaa   1560 agcccgtact atgacaccat tgttaatctg atgaagaatc gcatcaagta tgtgtctggc   1620
ggtcaagcgc agcgttctta ctggctgccg accgatggta agatggacaa tagcgatgtg   1680
gaactgtacc gcaccaacga ggtatacgct tctgtgcgct atggtaaaga cattatgacc   1740
gccgatgata ccgagggttc caagtactcc cgtacgagcg ccaagttac cttggtggca   1800 aacaacccga aattgaccct ggaccaaagc gcgaaactga agtggagat gggtaagatc   1860 cacgcaaatc aaaagtaccg tgcactgatt gtcggtaccg ccgacggtat caagaatttc   1920
accagcgatg cggatgcgat tgcagcaggc tatgttaaag agactgatag caatggtgtg   1980
ctgacgtttg gtgcgaacga cattaaaggc tatgaaacgt ttgacatgag cggtttcgtt   2040
gcggtgtggg tgcctgtggg tgctagcgat gatcaggata tccgtgtcgc gccgagcacc   2100
gaggcaaaga aagaaggtga gctgacgttg aaagcgaccg aggcctatga cagccagttg   2160
atttacgaag gtttcagcaa tttccaaacc attccagacg gttccgatcc gagcgtctac   2220
accaatcgca aaatcgcgga aaacgttgat ctgttcaaaa gctgggtgt gaccagcttc   2280 gaaatggcac cgcaattcgt tagcgcggac gatggtacgt tcttggacag cgttatccaa   2340
aatggctatg cgttcgccga tcgttatgac ttggcgatga gcaaaaacaa caaatacggc   2400
agcaaagagg atctgcgcga cgccctgaaa gcgctgcata agcgggtat tcaagccatc   2460 gctgactggg ttccggacca gatctaccag ctgccgggta agaagtcgt taccgcgacc   2520 cgcaccgatg gcgctggccg taagatcgcg gatgcaatta tcgatcatag cttgtatgtg   2580
gccaatacta aaagctccgg taaggattac caggcgaaat atggtggtga atttctggct   2640
gagctgaagg ccaaataccc ggagatgttc aaggtcaaca tgattagcac cggcaaacct   2700
attgatgact ctgtcaaatt gaaacaatgg aaggcagagt atttcaatgg cactaacgtc   2760
```

-continued

```
ctggaacgtg gtgttggtta cgtgctgagc gacgaggcga ccggtaaata cttcaccgtt   2820
acgaaggacg gcaatttcat cccgctgcaa ctgaccggta atgagaaggt tgtgacgggt   2880
tttctaatg acggtaaggg cattacctac ttcggtacct cgggtaccca ggcaaagagc    2940
gcattcgtga cgtttaacgg taacacctac tactttgatg cacgcggcca catggtgacg   3000
aacggcgagt acagcccgaa cggcaaggat gtttatcgct tcctgccgaa tggcatcatg   3060
ctgtccaatg cgttttacgt cgatgcaaat ggtaatactt acctgtacaa cagcaagggt   3120
cagatgtata agggcggtta taccaagttc gacgttactg aaacggacaa ggacggtaaa   3180
gagagcaaag tagtgaagtt tcgttatttc acgaacgaag gcgtcatggc gaaaggtgtc   3240
accgttattg atggctttac ccagtatttc ggtgaagatg ctttcaagc gaaggacaag    3300
ctggtgacct ttaagggcaa aacctactat tttgacgcgc acacgggcaa cgccatcaag   3360
aacacctggc gtaatatcga cggtaagtgg tatcattttg atgcgaacgg tgtggcggcg   3420
accggcgcac aggtcattaa tggtcaaaaa ctgtacttta atgaggacgg tagccaagtc   3480
aaaggtggcg tcgtcaagaa tgcagatggc acctatagca aatacaaaga gggctccggt   3540
gagctggtta ccaacgagtt ctttaccacg gatggtaacg tctggtacta tgctggtgcg   3600
aatggcaaga ccgttaccgg tgcacaggtt atcaacggcc agcacctgta cttcaatgcg   3660
gatggctctc aagtgaaggg cggtgtcgtc aaaaacgcgg acggtacgta ctccaaatac   3720
gatgccgcga ccggtgaacg tctgaccaat gagtttttca cgactggtga acaacaattgg  3780
tactacatcg gcgccaacgg taagacggtt acgggcgaag tgaaaattgg cgacgatacg   3840
tactacttcg caaaagatgg taaacaggtg aaaggtcaga cggtttccgc tggtaatggc   3900
cgcatcagct actattacgg tgactctggt aaacgtgcgg ttagcacgtg ggttgaaatt   3960
caaccgggcg tgtatgtcta ttttgataag aatggcctgg catatccacc gcgcgttttg   4020
aattaa                                                             4026
```

<210> SEQ ID NO 34
<211> LENGTH: 1341
<212> TYPE: PRT
<213> ORGANISM: Streptococcus salivarius JIM8777

<400> SEQUENCE: 34

```
Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Glu Thr Leu Asn Val
    130                 135                 140
```

```
Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn His Thr Ala Thr
    210                 215                 220

Asn Gln Lys Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asn Gly Asn Tyr Met Glu Thr Lys Ser Pro Tyr Tyr Asp Thr Ile Val
        515                 520                 525

Asn Leu Met Lys Asn Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560
```

-continued

```
Glu Leu Tyr Arg Thr Asn Glu Val Tyr Ala Ser Val Arg Tyr Gly Lys
                565                 570                 575

Asp Ile Met Thr Ala Asp Thr Glu Gly Ser Lys Tyr Ser Arg Thr
    580                 585                 590

Ser Gly Gln Val Thr Leu Val Ala Asn Asn Pro Lys Leu Thr Leu Asp
        595                 600                 605

Gln Ser Ala Lys Leu Lys Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
        915                 920                 925

Leu Ser Asp Glu Ala Thr Gly Lys Tyr Phe Thr Val Thr Lys Asp Gly
    930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
```

```
                    980             985              990
Asp Ala Arg Gly His Met Val Thr Asn Gly Glu Tyr Ser Pro Asn Gly
            995              1000             1005
Lys Asp Val Tyr Arg Phe Leu Pro Asn Gly Ile Met Leu Ser Asn
    1010             1015             1020
Ala Phe Tyr Val Asp Ala Asn Gly Asn Thr Tyr Leu Tyr Asn Ser
    1025             1030             1035
Lys Gly Gln Met Tyr Lys Gly Gly Tyr Thr Lys Phe Asp Val Thr
    1040             1045             1050
Glu Thr Asp Lys Asp Gly Lys Glu Ser Lys Val Val Lys Phe Arg
    1055             1060             1065
Tyr Phe Thr Asn Glu Gly Val Met Ala Lys Gly Val Thr Val Ile
    1070             1075             1080
Asp Gly Phe Thr Gln Tyr Phe Gly Glu Asp Gly Phe Gln Ala Lys
    1085             1090             1095
Asp Lys Leu Val Thr Phe Lys Gly Lys Thr Tyr Tyr Phe Asp Ala
    1100             1105             1110
His Thr Gly Asn Ala Ile Lys Asn Thr Trp Arg Asn Ile Asp Gly
    1115             1120             1125
Lys Trp Tyr His Phe Asp Ala Asn Gly Val Ala Ala Thr Gly Ala
    1130             1135             1140
Gln Val Ile Asn Gly Gln Lys Leu Tyr Phe Asn Glu Asp Gly Ser
    1145             1150             1155
Gln Val Lys Gly Gly Val Val Lys Asn Ala Asp Gly Thr Tyr Ser
    1160             1165             1170
Lys Tyr Lys Glu Gly Ser Gly Glu Leu Val Thr Asn Glu Phe Phe
    1175             1180             1185
Thr Thr Asp Gly Asn Val Trp Tyr Tyr Ala Gly Ala Asn Gly Lys
    1190             1195             1200
Thr Val Thr Gly Ala Gln Val Ile Asn Gly Gln His Leu Tyr Phe
    1205             1210             1215
Asn Ala Asp Gly Ser Gln Val Lys Gly Gly Val Val Lys Asn Ala
    1220             1225             1230
Asp Gly Thr Tyr Ser Lys Tyr Asp Ala Ala Thr Gly Glu Arg Leu
    1235             1240             1245
Thr Asn Glu Phe Phe Thr Thr Gly Asp Asn Asn Trp Tyr Tyr Ile
    1250             1255             1260
Gly Ala Asn Gly Lys Thr Val Thr Gly Glu Val Lys Ile Gly Asp
    1265             1270             1275
Asp Thr Tyr Tyr Phe Ala Lys Asp Gly Lys Gln Val Lys Gly Gln
    1280             1285             1290
Thr Val Ser Ala Gly Asn Gly Arg Ile Ser Tyr Tyr Tyr Gly Asp
    1295             1300             1305
Ser Gly Lys Arg Ala Val Ser Thr Trp Val Glu Ile Gln Pro Gly
    1310             1315             1320
Val Tyr Val Tyr Phe Asp Lys Asn Gly Leu Ala Tyr Pro Pro Arg
    1325             1330             1335
Val Leu Asn
    1340

<210> SEQ ID NO 35

<400> SEQUENCE: 35
```

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

```
<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
```

<400> SEQUENCE: 58

000

<210> SEQ ID NO 59
<211> LENGTH: 1242
<212> TYPE: PRT
<213> ORGANISM: Streptococcus sp. C150

<400> SEQUENCE: 59

```
Met Ile Asn Gly Lys Glu Tyr Tyr Val Glu Asp Asp Gly Thr Val Arg
1               5                   10                  15

Lys Asn Tyr Val Leu Glu Arg Asn Gly Gly Ser Gln Tyr Phe Asn Ala
            20                  25                  30

Glu Thr Gly Glu Leu Ser Asn Gln Lys Asp Tyr Arg Phe Asp Lys Asn
        35                  40                  45

Gly Gly Thr Gly Ser Ala Ala Asp Ser Thr Thr Asn Thr Asn Val Thr
    50                  55                  60

Val Asn Gly Asp Lys Asn Ala Phe Tyr Gly Thr Thr Glu Lys Asp Ile
65                  70                  75                  80

Glu Leu Val Asp Gly Tyr Phe Thr Ala Asn Thr Trp Tyr Arg Pro Lys
                85                  90                  95

Glu Ile Leu Lys Asp Gly Lys Glu Trp Thr Ala Ser Thr Glu Asn Asp
            100                 105                 110

Lys Arg Pro Leu Leu Thr Val Trp Trp Pro Ser Lys Ala Ile Gln Ala
        115                 120                 125

Ser Tyr Leu Asn Tyr Met Arg Glu Glu Gly Leu Gly Thr Asn Gln Thr
    130                 135                 140

Phe Thr Ser Tyr Ser Ser Gln Thr Gln Met Asp Gln Ala Ala Leu Glu
145                 150                 155                 160

Val Gln Lys Arg Ile Glu Glu Arg Ile Ala Arg Glu Gly Asn Thr Asp
                165                 170                 175

Trp Leu Arg Thr Thr Ile Lys Asn Phe Val Lys Thr Gln Pro Gly Trp
            180                 185                 190

Asn Ser Thr Ser Glu Asn Leu Asp Asn Ser Asp His Leu Gln Gly Gly
        195                 200                 205

Ala Leu Leu Tyr Asn Asn Ser Asn Arg Thr Ser Tyr Ala Asn Ser Asp
    210                 215                 220

Tyr Arg Leu Leu Asn Arg Thr Pro Thr Gln Gln Asp Gly Thr Arg Arg
225                 230                 235                 240

Tyr Phe Lys Asp Asn Ser Ser Gly Gly Phe Glu Phe Leu Leu Ala Asn
                245                 250                 255

Asp Ile Asp Asn Ser Asn Pro Ala Val Gln Ala Glu Gln Leu Asn Trp
            260                 265                 270

Leu His Tyr Ile Met Asn Ile Gly Ser Leu Thr Gly Gly Ser Glu Asp
        275                 280                 285

Glu Asn Phe Asp Gly Val Arg Val Asp Ala Val Asp Asn Val Asn Ala
    290                 295                 300

Asp Leu Leu Gln Ile Ala Ser Asp Tyr Phe Lys Ala Lys Tyr Gly Val
305                 310                 315                 320

Glu Lys Ser Glu Glu Glu Ala Ile Lys His Leu Ser Ile Leu Glu Ala
                325                 330                 335

Trp Ser His Asn Asp Ala Tyr Tyr Asn Glu Asp Thr Lys Gly Ala Gln
            340                 345                 350
```

```
Leu Pro Met Asp Asp Pro Leu Arg Leu Ala Met Val Phe Ser Phe Leu
            355                 360                 365

Arg Pro Ile Gly Asn Arg Ser Gly Leu Glu Pro Leu Ile Thr Asn Ser
370                 375                 380

Leu Asn Asp Arg Ser Glu Ser Lys Lys Asn Thr Lys Arg Met Ala Asn
385                 390                 395                 400

Tyr Thr Phe Val Arg Ala His Asp Ser Glu Val Gln Ser Val Ile Gly
                405                 410                 415

Gln Ile Ile Lys Asn Glu Ile Asn Pro Gln Ser Thr Gly Asn Thr Phe
            420                 425                 430

Thr Leu Asp Glu Met Lys Lys Ala Phe Lys Ile Tyr Asn Ala Asp Met
            435                 440                 445

Arg Ser Ala Asn Lys Arg Tyr Thr Gln Tyr Asn Ile Pro Ser Ala Tyr
450                 455                 460

Ala Phe Met Leu Thr Asn Lys Asp Thr Val Pro Arg Val Tyr Tyr Gly
465                 470                 475                 480

Asp Leu Tyr Thr Asp Asp Gly Gln Tyr Met Ala Gln Lys Ser Pro Tyr
                485                 490                 495

His Asp Ala Ile Ser Thr Leu Leu Gln Ala Arg Ile Arg Tyr Ala Ala
            500                 505                 510

Gly Gly Gln Asp Met Lys Met Ser Tyr Val Gly Ser Gly Asn Thr Asn
            515                 520                 525

Gly Trp Asp Ala Ser Gly Val Leu Thr Ser Val Arg Tyr Gly Lys Gly
            530                 535                 540

Ala Asn Asn Ala Ser Asp Ala Gly Thr Ala Glu Thr Arg Asn Gln Gly
545                 550                 555                 560

Met Ala Val Ile Leu Ser Asn Gln Pro Ala Leu Arg Leu Asn Ser Asn
                565                 570                 575

Leu Thr Ile Asn Met Gly Ala Ala His Arg Asn Gln Ala Tyr Arg Pro
            580                 585                 590

Leu Leu Leu Thr Thr Ser Asn Gly Val Ala Ser Tyr Leu Asn Asp Gly
            595                 600                 605

Asp Ala Asn Gly Ile Val Lys Tyr Thr Asp Ala Asn Gly Tyr Leu Thr
610                 615                 620

Phe Asn Pro Gly Glu Ile Ser Gly Val Arg Asn Ala Gln Val Asp Gly
625                 630                 635                 640

Tyr Leu Ala Val Trp Val Pro Leu Gly Ala Ser Glu Asn Gln Asp Val
                645                 650                 655

Arg Val Ala Ala Ser Lys Ser Lys Asn Ser Ser Gly Leu Val Tyr Asp
            660                 665                 670

Ser Ser Ala Ala Leu Asp Ser Gln Val Ile Tyr Glu Gly Phe Ser Asn
            675                 680                 685

Phe Gln Asp Phe Val Gln Asp Pro Ser Gln Tyr Thr Asn Lys Lys Ile
            690                 695                 700

Ala Glu Asn Ala Asn Leu Phe Lys Ser Trp Gly Ile Thr Ser Phe Glu
705                 710                 715                 720

Phe Ala Pro Gln Tyr Val Ser Ser Asp Asp Gly Thr Phe Leu Asp Ser
                725                 730                 735

Val Ile Gln Asn Gly Tyr Ala Phe Ser Asp Arg Tyr Asp Ile Gly Met
            740                 745                 750

Ser Lys Asp Asn Lys Tyr Gly Ser Leu Ala Asp Leu Lys Ala Ala Leu
            755                 760                 765

Lys Ser Leu His Ala Val Gly Ile Ser Ala Ile Ala Asp Trp Val Pro
```

-continued

```
            770                 775                 780
Asp Gln Ile Tyr Asn Leu Pro Gly Asp Glu Val Thr Ala Thr Arg
785                 790                 795                 800

Val Asn Asn Tyr Gly Glu Thr Lys Asp Gly Ala Ile Ile Asp His Ser
                805                 810                 815

Leu Tyr Val Ala Lys Thr Arg Thr Phe Gly Asn Asp Tyr Gln Gly Lys
                820                 825                 830

Tyr Gly Gly Ala Tyr Leu Asp Glu Leu Lys Arg Leu Tyr Pro Gln Phe
                835                 840                 845

Phe Asp Arg Val Gln Ile Ser Thr Gly Lys Arg Leu Thr Thr Asp Glu
850                 855                 860

Lys Ile Thr Lys Trp Ser Ala Lys Tyr Met Asn Gly Thr Asn Ile Leu
865                 870                 875                 880

Asp Arg Gly Ser Glu Tyr Val Leu Lys Asn Gly Leu Ser Gly Tyr Tyr
                885                 890                 895

Gly Thr Asn Gly Gly Lys Val Ser Leu Pro Lys Val Val Gly Ser Asn
                900                 905                 910

Gln Ser Thr Asn Asn Asn Gln Asn Gly Asp Gly Ser Gly Arg Phe
                915                 920                 925

Glu Lys Ser Trp Gly Ser Val Tyr Arg Tyr Asn Asp Gly Gln Arg
                930                 935                 940

Ala Arg Asn Ala Phe Ile Lys Asp Asn Asp Gly Asn Val Tyr Tyr Phe
945                 950                 955                 960

Asp Asn Thr Gly Arg Met Ala Ile Gly Glu Lys Thr Ile Asp Gly Lys
                965                 970                 975

Gln Tyr Phe Phe Leu Ala Asn Gly Val Gln Leu Arg Asp Gly Tyr Arg
                980                 985                 990

Gln Asn Arg Arg Gly Gln Val Phe Tyr Tyr Asp Glu Asn Gly Ile Met
                995                 1000                1005

Ser Gln Thr Gly Lys Pro Ser Pro Lys Pro Glu Pro Lys Pro Asp
    1010                1015                1020

Asn Asn Thr Phe Ser Arg Asn Gln Phe Ile Gln Ile Gly Asn Asn
    1025                1030                1035

Val Trp Ala Tyr Tyr Asp Gly Asn Gly Lys Arg Val Ile Gly Arg
    1040                1045                1050

Gln Asn Ile Asn Gly Gln Glu Leu Phe Phe Asp Asn Asn Gly Val
    1055                1060                1065

Gln Val Lys Gly Arg Thr Ala Gln Val Asp Gly Val Thr Arg Tyr
    1070                1075                1080

Phe Asp Ala Asn Ser Gly Glu Met Ala Arg Asn Arg Phe Ala Glu
    1085                1090                1095

Val Glu Pro Gly Val Trp Ala Tyr Phe Asn Asn Asp Gly Ala Ala
    1100                1105                1110

Val Thr Gly Ser Gln Asn Ile Asn Gly Gln Thr Leu Tyr Phe Asp
    1115                1120                1125

Gln Asn Gly His Gln Val Lys Gly Ala Leu Val Thr Val Asp Gly
    1130                1135                1140

Asn Leu Arg Tyr Tyr Asp Ala Asn Ser Gly Asp Leu Tyr Arg Asn
    1145                1150                1155

Arg Phe Gln Glu Val Asn Gly Ser Trp Tyr Tyr Phe Asp Gly Asn
    1160                1165                1170

Gly Asn Ala Val Lys Gly Met Val Asn Ile Asn Gly Gln Asn Leu
    1175                1180                1185
```

```
Leu Phe Asp Asn Asp Gly Lys Gln Val Lys Gly His Leu Val Arg
    1190            1195                1200

Val Asn Gly Val Ile Arg Tyr Tyr Asp Pro Asn Ser Gly Glu Met
    1205            1210                1215

Ala Val Asn Arg Trp Val Glu Ile Ser Ser Gly Trp Trp Val Tyr
    1220            1225                1230

Phe Asp Gly Glu Gly Arg Gly Gln Ile
    1235            1240

<210> SEQ ID NO 60
<211> LENGTH: 1518
<212> TYPE: PRT
<213> ORGANISM: Streptococcus salivarius

<400> SEQUENCE: 60

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45

Thr Val Thr Gln Ser Asn Ser Gly Thr Thr Ala Ser Leu Val Thr Ser
        50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
```

-continued

```
305                 310                 315                 320
Val Ala Ala Lys Asp Ile Gln Ile Lys Ile Glu Gln Lys Ile Gln Ala
                325                 330                 335
Glu Lys Ser Thr Gln Trp Leu Arg Glu Thr Ile Ser Ala Phe Val Lys
                340                 345                 350
Thr Gln Pro Gln Trp Asn Lys Glu Thr Glu Asn Tyr Ser Lys Gly Gly
                355                 360                 365
Gly Glu Asp His Leu Gln Gly Gly Ala Leu Leu Tyr Val Asn Asp Ser
                370                 375                 380
Arg Thr Pro Trp Ala Asn Ser Asp Tyr Arg Arg Leu Asn Arg Thr Ala
385                 390                 395                 400
Thr Asn Gln Thr Gly Thr Ile Asp Lys Ser Ile Leu Asp Glu Gln Ser
                405                 410                 415
Asp Pro Asn His Met Gly Gly Phe Asp Phe Leu Leu Ala Asn Asp Val
                420                 425                 430
Asp Leu Ser Asn Pro Val Val Gln Ala Glu Gln Leu Asn Gln Ile His
                435                 440                 445
Tyr Leu Met Asn Trp Gly Ser Ile Val Met Gly Asp Lys Asp Ala Asn
                450                 455                 460
Phe Asp Gly Ile Arg Val Asp Ala Val Asp Asn Val Asp Ala Asp Met
465                 470                 475                 480
Leu Gln Leu Tyr Thr Asn Tyr Phe Arg Glu Tyr Tyr Gly Val Asn Lys
                485                 490                 495
Ser Glu Ala Asn Ala Leu Ala His Ile Ser Val Leu Glu Ala Trp Ser
                500                 505                 510
Leu Asn Asp Asn His Tyr Asn Asp Lys Thr Asp Gly Ala Ala Leu Ala
                515                 520                 525
Met Glu Asn Lys Gln Arg Leu Ala Leu Leu Phe Ser Leu Ala Lys Pro
                530                 535                 540
Ile Lys Glu Arg Thr Pro Ala Val Ser Pro Leu Tyr Asn Asn Thr Phe
545                 550                 555                 560
Asn Thr Thr Gln Arg Asp Glu Lys Thr Asp Trp Ile Asn Lys Asp Gly
                565                 570                 575
Ser Lys Ala Tyr Asn Glu Asp Gly Thr Val Lys Gln Ser Thr Ile Gly
                580                 585                 590
Lys Tyr Asn Glu Lys Tyr Gly Asp Ala Ser Gly Asn Tyr Val Phe Ile
                595                 600                 605
Arg Ala His Asp Asn Asn Val Gln Asp Ile Ile Ala Glu Ile Ile Lys
                610                 615                 620
Lys Glu Ile Asn Pro Lys Ser Asp Gly Phe Thr Ile Thr Asp Ala Glu
625                 630                 635                 640
Met Lys Gln Ala Phe Glu Ile Tyr Asn Lys Asp Met Leu Ser Ser Asp
                645                 650                 655
Lys Lys Tyr Thr Leu Asn Asn Ile Pro Ala Ala Tyr Ala Val Met Leu
                660                 665                 670
Gln Asn Met Glu Thr Ile Thr Arg Val Tyr Tyr Gly Asp Leu Tyr Thr
                675                 680                 685
Asp Asp Gly His Tyr Met Glu Thr Lys Ser Pro Tyr Tyr Asp Thr Ile
                690                 695                 700
Val Asn Leu Met Lys Ser Arg Ile Lys Tyr Val Ser Gly Gly Gln Ala
705                 710                 715                 720
Gln Arg Ser Tyr Trp Leu Pro Thr Asp Gly Lys Met Asp Asn Ser Asp
                725                 730                 735
```

```
Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
            755                 760                 765

Thr Ser Gly Gln Val Thr Leu Val Ala Asn Asn Pro Lys Leu Asn Leu
            770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
            805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
            835                 840                 845

Glu Thr Phe Asp Met Ser Gly Phe Val Ala Val Trp Val Pro Val Gly
            850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
            885                 890                 895

Leu Ile Tyr Glu Gly Phe Ser Asn Phe Gln Thr Ile Pro Asp Gly Ser
            900                 905                 910

Asp Pro Ser Val Tyr Thr Asn Arg Lys Ile Ala Glu Asn Val Asp Leu
            915                 920                 925

Phe Lys Ser Trp Gly Val Thr Ser Phe Glu Met Ala Pro Gln Phe Val
            930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
            965                 970                 975

Gly Ser Lys Glu Asp Leu Arg Asp Ala Leu Lys Ala Leu His Lys Ala
            980                 985                 990

Gly Ile Gln Ala Ile Ala Asp Trp Val Pro Asp Gln Ile Tyr Gln Leu
            995                 1000                1005

Pro Gly Lys Glu Val Val Thr Ala Thr Arg Thr Asp Gly Ala Gly
    1010                1015                1020

Arg Lys Ile Ala Asp Ala Ile Ile Asp His Ser Leu Tyr Val Ala
    1025                1030                1035

Asn Ser Lys Ser Ser Gly Lys Asp Tyr Gln Ala Lys Tyr Gly Gly
    1040                1045                1050

Glu Phe Leu Ala Glu Leu Lys Ala Lys Tyr Pro Glu Met Phe Lys
    1055                1060                1065

Val Asn Met Ile Ser Thr Gly Lys Pro Ile Asp Ser Val Lys
    1070                1075                1080

Leu Lys Gln Trp Lys Ala Glu Tyr Phe Asn Gly Thr Asn Val Leu
    1085                1090                1095

Glu Arg Gly Val Gly Tyr Val Leu Ser Asp Glu Ala Thr Gly Lys
    1100                1105                1110

Tyr Phe Thr Val Thr Lys Glu Gly Asn Phe Ile Pro Leu Gln Leu
    1115                1120                1125

Thr Gly Lys Glu Lys Val Ile Thr Gly Phe Ser Ser Asp Gly Lys
    1130                1135                1140
```

Gly Ile Thr Tyr Phe Gly Thr Ser Gly Thr Gln Ala Lys Ser Ala
    1145                1150                1155

Phe Val Thr Phe Asn Gly Asn Thr Tyr Tyr Phe Asp Ala Arg Gly
    1160                1165                1170

His Met Val Thr Asn Ser Glu Tyr Ser Pro Asn Gly Lys Asp Val
    1175                1180                1185

Tyr Arg Phe Leu Pro Asn Gly Ile Met Leu Ser Asn Ala Phe Tyr
    1190                1195                1200

Ile Asp Ala Asn Gly Asn Thr Tyr Leu Tyr Asn Ser Lys Gly Gln
    1205                1210                1215

Met Tyr Lys Gly Gly Tyr Thr Lys Phe Asp Val Ser Glu Thr Asp
    1220                1225                1230

Lys Asp Gly Lys Glu Ser Lys Val Val Lys Phe Arg Tyr Phe Thr
    1235                1240                1245

Asn Glu Gly Val Met Ala Lys Gly Val Thr Val Ile Asp Gly Phe
    1250                1255                1260

Thr Gln Tyr Phe Gly Glu Asp Gly Phe Gln Ala Lys Asp Lys Leu
    1265                1270                1275

Val Thr Phe Lys Gly Lys Thr Tyr Tyr Phe Asp Ala His Thr Gly
    1280                1285                1290

Asn Gly Ile Lys Asp Thr Trp Arg Asn Ile Asn Gly Lys Trp Tyr
    1295                1300                1305

Tyr Phe Asp Ala Asn Gly Val Ala Ala Thr Gly Ala Gln Val Ile
    1310                1315                1320

Asn Gly Gln Lys Leu Tyr Phe Asn Glu Asp Gly Ser Gln Val Lys
    1325                1330                1335

Gly Gly Val Val Lys Asn Ala Asp Gly Thr Tyr Ser Lys Tyr Lys
    1340                1345                1350

Glu Gly Phe Gly Glu Leu Val Thr Asn Glu Phe Phe Thr Thr Asp
    1355                1360                1365

Gly Asn Val Trp Tyr Tyr Ala Gly Ala Asn Gly Lys Thr Val Thr
    1370                1375                1380

Gly Ala Gln Val Ile Asn Gly Gln His Leu Tyr Phe Asn Ala Asp
    1385                1390                1395

Gly Ser Gln Val Lys Gly Gly Val Val Lys Asn Ala Asp Gly Thr
    1400                1405                1410

Tyr Ser Lys Tyr Asn Ala Ser Thr Gly Glu Arg Leu Thr Asn Glu
    1415                1420                1425

Phe Phe Thr Thr Gly Asp Asn Trp Tyr Tyr Ile Gly Ala Asn
    1430                1435                1440

Gly Lys Ser Val Thr Gly Glu Val Lys Ile Gly Asp Asp Thr Tyr
    1445                1450                1455

Phe Phe Ala Lys Asp Gly Lys Gln Val Lys Gly Gln Thr Val Ser
    1460                1465                1470

Ala Gly Asn Gly Arg Ile Ser Tyr Tyr Tyr Gly Asp Ser Gly Lys
    1475                1480                1485

Arg Ala Val Ser Thr Trp Ile Glu Ile Gln Pro Gly Val Tyr Val
    1490                1495                1500

Tyr Phe Asp Lys Asn Gly Leu Ala Tyr Pro Pro Arg Val Leu Asn
    1505                1510                1515

<210> SEQ ID NO 61
<211> LENGTH: 1528
<212> TYPE: PRT

<213> ORGANISM: Streptococcus salivarius K12

<400> SEQUENCE: 61

| | | | | | | | | | | | | | | |
|---|---|---|---|---|---|---|---|---|---|---|---|---|---|---|
| Met | Thr | Asn | Lys | Ile | Thr | Gly | Lys | Ile | Ile | Met | Glu | Asn | Lys | Val | His |
| 1 | | | | 5 | | | | | 10 | | | | | 15 | |
| Tyr | Lys | Leu | His | Lys | Val | Lys | Lys | Gln | Trp | Val | Thr | Ile | Ala | Val | Ala |
| | | | 20 | | | | | 25 | | | | | 30 | | |
| Ser | Ala | Ala | Leu | Ala | Thr | Val | Val | Gly | Gly | Leu | Ser | Ala | Thr | Thr | Ser |
| | | 35 | | | | | 40 | | | | | 45 | | | |
| Ser | Val | Ser | Ala | Asp | Glu | Thr | Gln | Asp | Lys | Ile | Val | Thr | Gln | Pro | Asn |
| 50 | | | | | 55 | | | | | 60 | | | | | |
| Leu | Asp | Thr | Thr | Ala | Asp | Leu | Val | Thr | Ser | Thr | Glu | Ala | Thr | Lys | Glu |
| 65 | | | | | 70 | | | | | 75 | | | | | 80 |
| Val | Asp | Lys | Arg | Thr | Asn | Thr | Lys | Glu | Ala | Asp | Val | Leu | Thr | Pro | Ala |
| | | | | 85 | | | | | 90 | | | | | 95 | |
| Lys | Glu | Thr | Asn | Ala | Val | Glu | Thr | Ala | Thr | Thr | Asn | Thr | Gln | Ala |
| | | | 100 | | | | | 105 | | | | | 110 | | |
| Thr | Ala | Glu | Ala | Ala | Thr | Thr | Ala | Thr | Thr | Ser | Asp | Val | Ala | Val | Ala |
| | | | 115 | | | | | 120 | | | | | 125 | | |
| Ala | Val | Pro | Asn | Lys | Glu | Ala | Val | Val | Thr | Thr | Asp | Ala | Pro | Ala | Val |
| | | 130 | | | | | 135 | | | | | 140 | | | |
| Thr | Thr | Glu | Lys | Ala | Glu | Glu | Gln | Pro | Ala | Thr | Val | Lys | Ala | Glu | Val |
| 145 | | | | | 150 | | | | | 155 | | | | | 160 |
| Val | Asn | Thr | Glu | Val | Lys | Ala | Pro | Gln | Ala | Ala | Leu | Lys | Asp | Ser | Glu |
| | | | | 165 | | | | | 170 | | | | | 175 | |
| Val | Glu | Ala | Ala | Leu | Ser | Leu | Lys | Asn | Ile | Lys | Tyr | Thr | Asp | Gly | Lys |
| | | | 180 | | | | | 185 | | | | | 190 | | |
| Tyr | Tyr | Tyr | Val | Asn | Glu | Asp | Gly | Ser | His | Lys | Glu | Asn | Phe | Ala | Ile |
| | | | 195 | | | | | 200 | | | | | 205 | | |
| Thr | Val | Asn | Gly | Gln | Leu | Leu | Tyr | Phe | Gly | Lys | Asp | Gly | Ala | Leu | Thr |
| | | 210 | | | | | 215 | | | | | 220 | | | |
| Ser | Ser | Ser | Thr | His | Ser | Phe | Thr | Pro | Gly | Thr | Thr | Asn | Ile | Val | Asp |
| 225 | | | | | 230 | | | | | 235 | | | | | 240 |
| Gly | Phe | Ser | Ile | Asn | Asn | Arg | Ala | Tyr | Asp | Ser | Ser | Glu | Ala | Ser | Phe |
| | | | | 245 | | | | | 250 | | | | | 255 | |
| Glu | Leu | Ile | Asn | Gly | Tyr | Leu | Thr | Ala | Asp | Ser | Trp | Tyr | Arg | Pro | Val |
| | | | 260 | | | | | 265 | | | | | 270 | | |
| Ser | Ile | Ile | Lys | Asp | Gly | Val | Thr | Trp | Gln | Ala | Ser | Thr | Ala | Glu | Asp |
| | | 275 | | | | | 280 | | | | | 285 | | | |
| Phe | Arg | Pro | Leu | Leu | Met | Ala | Trp | Trp | Pro | Asn | Val | Asp | Thr | Gln | Val |
| | 290 | | | | | 295 | | | | | 300 | | | | |
| Asn | Tyr | Leu | Asn | Tyr | Met | Ser | Lys | Val | Phe | Asn | Leu | Glu | Ala | Lys | Tyr |
| 305 | | | | | 310 | | | | | 315 | | | | | 320 |
| Thr | Ser | Thr | Asp | Lys | Gln | Ala | Asp | Leu | Asn | Arg | Ala | Ala | Lys | Asp | Ile |
| | | | | 325 | | | | | 330 | | | | | 335 | |
| Gln | Val | Lys | Ile | Glu | Gln | Lys | Ile | Gln | Ala | Glu | Lys | Ser | Thr | Gln | Trp |
| | | | 340 | | | | | 345 | | | | | 350 | | |
| Leu | Arg | Glu | Thr | Ile | Ser | Ala | Phe | Val | Lys | Thr | Gln | Pro | Gln | Trp | Asn |
| | | | 355 | | | | | 360 | | | | | 365 | | |
| Lys | Glu | Thr | Glu | Asn | Tyr | Ser | Lys | Gly | Gly | Glu | Asp | His | Leu | Gln |
| | 370 | | | | | 375 | | | | | 380 | | | | |
| Gly | Gly | Ala | Leu | Leu | Tyr | Val | Asn | Asp | Ser | Arg | Thr | Pro | Trp | Ala | Asn |
| 385 | | | | | 390 | | | | | 395 | | | | | 400 |

```
Ser Asn Tyr Arg Leu Leu Asn Arg Thr Ala Thr Asn Gln Thr Gly Thr
                405                 410                 415

Ile Asn Lys Ser Val Leu Asp Glu Gln Ser Asp Pro Asn His Met Gly
            420                 425                 430

Gly Phe Asp Phe Leu Leu Ala Asn Asp Val Asp Leu Ser Asn Pro Val
        435                 440                 445

Val Gln Ala Glu Gln Leu Asn Gln Ile His Tyr Leu Met Asn Trp Gly
450                 455                 460

Ser Ile Val Met Gly Asp Lys Asp Ala Asn Phe Asp Gly Ile Arg Val
465                 470                 475                 480

Asp Ala Val Asp Asn Val Asn Ala Asp Met Leu Gln Leu Tyr Thr Asn
                485                 490                 495

Tyr Phe Arg Glu Tyr Tyr Gly Val Asn Lys Ser Glu Ala Gln Ala Leu
            500                 505                 510

Ala His Ile Ser Val Leu Glu Ala Trp Ser Leu Asn Asp Asn His Tyr
        515                 520                 525

Asn Asp Lys Thr Asp Gly Ala Ala Leu Ala Met Glu Asn Lys Gln Arg
        530                 535                 540

Leu Ala Leu Leu Phe Ser Leu Ala Lys Pro Ile Lys Asp Arg Thr Pro
545                 550                 555                 560

Ala Val Ser Pro Leu Tyr Asn Asn Thr Phe Asn Thr Thr Gln Arg Asp
                565                 570                 575

Phe Lys Thr Asp Trp Ile Asn Lys Asp Gly Ser Thr Ala Tyr Asn Glu
            580                 585                 590

Asp Gly Thr Ala Lys Gln Ser Thr Ile Gly Lys Tyr Asn Glu Lys Tyr
        595                 600                 605

Gly Asp Ala Ser Gly Asn Tyr Val Phe Ile Arg Ala His Asp Asn Asn
        610                 615                 620

Val Gln Asp Ile Ile Ala Glu Ile Ile Lys Lys Glu Ile Asn Lys Lys
625                 630                 635                 640

Ser Asp Gly Phe Thr Ile Ser Asp Ser Glu Met Lys Gln Ala Phe Glu
                645                 650                 655

Ile Tyr Asn Lys Asp Met Leu Ser Ser Asn Lys Lys Tyr Thr Leu Asn
            660                 665                 670

Asn Ile Pro Ala Ala Tyr Ala Val Met Leu Gln Asn Met Glu Thr Ile
        675                 680                 685

Thr Arg Val Tyr Tyr Gly Asp Leu Tyr Thr Asp Asp Gly His Tyr Met
        690                 695                 700

Glu Thr Lys Ser Pro Tyr His Asp Thr Ile Val Asn Leu Met Lys Asn
705                 710                 715                 720

Arg Ile Lys Tyr Val Ser Gly Gln Ala Gln Arg Ser Tyr Trp Leu
                725                 730                 735

Pro Thr Asp Gly Lys Met Asp Asn Ser Asp Val Glu Leu Tyr Arg Thr
            740                 745                 750

Ser Glu Val Tyr Thr Ser Val Arg Tyr Gly Lys Asp Ile Met Thr Ala
        755                 760                 765

Asp Asp Thr Glu Gly Ser Lys Tyr Ser Arg Thr Ser Gly Gln Val Thr
        770                 775                 780

Leu Val Val Asn Asn Pro Lys Leu Thr Leu His Glu Ser Ala Lys Leu
785                 790                 795                 800

Asn Val Glu Met Gly Lys Ile His Ala Asn Gln Lys Tyr Arg Ala Leu
                805                 810                 815

Ile Val Gly Thr Ala Asp Gly Ile Lys Asn Phe Thr Ser Asp Ala Glu
```

```
                820             825             830
Ala Ile Ala Ala Gly Tyr Val Lys Glu Thr Asp Ser Asn Gly Val Leu
                835             840             845

Thr Phe Gly Ala Asn Asp Ile Lys Gly Tyr Glu Thr Phe Asp Met Ser
850             855             860

Gly Phe Val Ala Val Trp Val Pro Val Gly Ala Ser Asp Asp Gln Asp
865             870             875             880

Ile Arg Val Ala Pro Ser Thr Glu Ala Lys Glu Gly Glu Leu Thr
                885             890             895

Leu Lys Ala Thr Glu Ala Tyr Asp Ser Gln Leu Ile Tyr Glu Gly Phe
                900             905             910

Ser Asn Phe Gln Thr Ile Pro Asp Gly Ser Asp Pro Ser Val Tyr Thr
                915             920             925

Asn Arg Lys Ile Ala Glu Asn Val Asp Leu Phe Lys Ser Trp Gly Val
                930             935             940

Thr Ser Phe Glu Met Ala Pro Gln Phe Val Ser Ala Asp Gly Thr
945             950             955             960

Phe Leu Asp Ser Val Ile Gln Asn Gly Tyr Ala Phe Ala Asp Arg Tyr
                965             970             975

Asp Leu Ala Met Ser Lys Asn Asn Lys Tyr Gly Ser Lys Glu Asp Leu
                980             985             990

Arg Asp Ala Leu Lys Ala Leu His Lys Ala Gly Ile Gln Ala Ile Ala
                995             1000            1005

Asp Trp Val Pro Asp Gln Ile Tyr Gln Leu Pro Gly Lys Glu Val
    1010            1015            1020

Val Thr Ala Thr Arg Thr Asp Gly Ala Gly Arg Lys Ile Ala Asp
    1025            1030            1035

Ala Ile Ile Asp His Ser Leu Tyr Val Ala Asn Ser Lys Ser Ser
    1040            1045            1050

Gly Arg Asp Tyr Gln Ala Gln Tyr Gly Gly Glu Phe Leu Ala Glu
    1055            1060            1065

Leu Lys Ala Lys Tyr Pro Lys Met Phe Thr Glu Asn Met Ile Ser
    1070            1075            1080

Thr Gly Lys Pro Ile Asp Asp Ser Val Lys Leu Lys Gln Trp Lys
    1085            1090            1095

Ala Lys Tyr Phe Asn Gly Thr Asn Val Leu Asp Arg Gly Val Gly
    1100            1105            1110

Tyr Val Leu Ser Asp Glu Ala Thr Gly Lys Tyr Phe Thr Val Thr
    1115            1120            1125

Lys Glu Gly Asn Phe Ile Pro Leu Gln Leu Thr Gly Asn Glu Lys
    1130            1135            1140

Ala Val Thr Gly Phe Ser Asn Asp Gly Lys Gly Ile Thr Tyr Phe
    1145            1150            1155

Gly Thr Ser Gly Asn Gln Ala Lys Ser Ala Phe Val Thr Phe Asn
    1160            1165            1170

Gly Asn Thr Tyr Tyr Phe Asp Ala Arg Gly His Met Val Thr Asn
    1175            1180            1185

Gly Glu Tyr Ser Pro Asn Gly Lys Asp Val Tyr Arg Phe Leu Pro
    1190            1195            1200

Asn Gly Ile Met Leu Ser Asn Ala Phe Tyr Val Asp Ala Asn Gly
    1205            1210            1215

Asn Thr Tyr Leu Tyr Asn Tyr Lys Gly Gln Met Tyr Lys Gly Gly
    1220            1225            1230
```

-continued

```
Tyr Thr Lys Phe Asp Val Thr Glu Thr Asp Lys Asp Gly Asn Glu
    1235                1240                1245

Ser Lys Val Val Lys Phe Arg Tyr Phe Thr Asn Glu Gly Val Met
    1250                1255                1260

Ala Lys Gly Leu Thr Val Ile Asp Gly Ser Thr Gln Tyr Phe Gly
    1265                1270                1275

Glu Asp Gly Phe Gln Thr Lys Asp Lys Leu Ala Thr Tyr Lys Gly
    1280                1285                1290

Lys Thr Tyr Tyr Phe Glu Ala His Thr Gly Asn Ala Ile Lys Asn
    1295                1300                1305

Thr Trp Arg Asn Ile Asp Gly Lys Trp Tyr His Phe Asp Glu Asn
    1310                1315                1320

Gly Val Ala Ala Thr Gly Ala Gln Val Ile Asn Gly Gln Lys Leu
    1325                1330                1335

Tyr Phe Asn Glu Asp Gly Ser Gln Val Lys Gly Val Val Lys
    1340                1345                1350

Asn Ala Asp Gly Thr Tyr Ser Lys Tyr Lys Glu Gly Ser Gly Glu
    1355                1360                1365

Leu Val Thr Asn Glu Phe Phe Thr Thr Asp Gly Asn Val Trp Tyr
    1370                1375                1380

Tyr Ala Gly Ala Asp Gly Lys Thr Val Thr Gly Ala Gln Val Ile
    1385                1390                1395

Asn Gly Gln His Leu Tyr Phe Lys Glu Asp Gly Ser Gln Val Lys
    1400                1405                1410

Gly Gly Val Val Lys Asn Ala Asp Gly Thr Tyr Ser Lys Tyr Asp
    1415                1420                1425

Ala Ala Thr Gly Glu Arg Leu Thr Asn Glu Phe Phe Thr Thr Gly
    1430                1435                1440

Asp Asn Asn Trp Tyr Tyr Ile Gly Ser Asn Gly Lys Thr Val Thr
    1445                1450                1455

Gly Glu Val Lys Ile Gly Ala Asp Thr Tyr Tyr Phe Ala Lys Asp
    1460                1465                1470

Gly Lys Gln Val Lys Gly Gln Thr Val Thr Ala Gly Asn Gly Arg
    1475                1480                1485

Ile Ser Tyr Tyr Tyr Gly Asp Ser Gly Lys Lys Ala Ile Ser Thr
    1490                1495                1500

Trp Ile Glu Ile Gln Pro Gly Ile Tyr Val Tyr Phe Asp Lys Thr
    1505                1510                1515

Gly Ile Ala Tyr Pro Pro Arg Val Leu Asn
    1520                1525
```

<210> SEQ ID NO 62
<211> LENGTH: 1518
<212> TYPE: PRT
<213> ORGANISM: Streptococcus salivarius SK126

<400> SEQUENCE: 62

```
Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45

Thr Val Thr Gln Ser Asn Ser Gly Thr Thr Ala Ser Leu Val Thr Ser
```

-continued

```
             50                  55                  60
Pro Glu Ala Thr Lys Glu Ala Asp Lys Arg Thr Asn Thr Lys Glu Ala
 65                  70                  75                  80

Asp Val Leu Thr Pro Ala Lys Glu Thr Asn Ala Val Glu Thr Ala Thr
                 85                  90                  95

Thr Thr Asn Thr Gln Ala Thr Ala Glu Ala Ala Thr Thr Ala Thr Thr
            100                 105                 110

Ala Asp Val Ala Val Ala Ala Val Pro Asn Lys Glu Ala Val Val Thr
            115                 120                 125

Thr Asp Ala Pro Ala Val Thr Thr Glu Lys Ala Glu Glu Gln Pro Ala
130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Val Asn Glu Asp Gly Ser His
                180                 185                 190

Lys Glu Asn Phe Ala Ile Thr Val Asn Gly Gln Leu Leu Tyr Phe Gly
            195                 200                 205

Lys Asp Gly Ala Leu Thr Ser Ser Thr Tyr Ser Phe Thr Pro Gly
            210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
                260                 265                 270

Ala Ser Thr Ala Glu Asp Phe Arg Pro Leu Leu Met Ala Trp Trp Pro
            275                 280                 285

Asn Val Asp Thr Gln Val Asn Tyr Leu Asn Tyr Met Ser Lys Val Phe
290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
            355                 360                 365

Gly Glu Asp His Leu Gln Gly Gly Ala Leu Leu Tyr Val Asn Asp Ser
            370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
            420                 425                 430

Asp Leu Ser Asn Pro Val Gln Ala Glu Gln Leu Asn Gln Ile His
            435                 440                 445

Tyr Leu Met Asn Trp Gly Ser Ile Val Met Gly Asp Lys Asp Ala Asn
            450                 455                 460

Phe Asp Gly Ile Arg Val Asp Ala Val Asp Asn Val Asp Ala Asp Met
465                 470                 475                 480
```

```
Leu Gln Leu Tyr Thr Asn Tyr Phe Arg Glu Tyr Tyr Gly Val Asn Lys
            485                 490                 495

Ser Glu Ala Asn Ala Leu Ala His Ile Ser Val Leu Glu Ala Trp Ser
            500                 505                 510

Leu Asn Asp Asn His Tyr Asn Asp Lys Thr Asp Gly Ala Ala Leu Ala
            515                 520                 525

Met Glu Asn Lys Gln Arg Leu Ala Leu Leu Phe Ser Leu Ala Lys Pro
            530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
            565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
            595                 600                 605

Arg Ala His Asp Asn Asn Val Gln Asp Ile Ile Ala Glu Ile Ile Lys
            610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
            645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
            675                 680                 685

Asp Asp Gly His Tyr Met Glu Thr Lys Ser Pro Tyr Tyr Asp Thr Ile
            690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
            725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
            755                 760                 765

Thr Ser Gly Gln Val Thr Leu Val Ala Asn Asn Pro Lys Leu Thr Leu
770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
            805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
            835                 840                 845

Glu Thr Phe Asp Met Ser Gly Phe Val Ala Val Trp Val Pro Val Gly
            850                 855                 860

Ala Ser Asp Asp Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
            885                 890                 895
```

```
Leu Ile Tyr Glu Gly Phe Ser Asn Phe Gln Thr Ile Pro Asp Gly Ser
                900                 905                 910

Asp Pro Ser Val Tyr Thr Asn Arg Lys Ile Ala Glu Asn Val Asp Leu
        915                 920                 925

Phe Lys Ser Trp Gly Val Thr Ser Phe Glu Met Ala Pro Gln Phe Val
        930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
                980                 985                 990

Gly Ile Gln Ala Ile Ala Asp Trp Val Pro Asp Gln Ile Tyr Gln Leu
                995                 1000                1005

Pro Gly Lys Glu Val Val Thr Ala Thr Arg Thr Asp Gly Ala Gly
    1010                1015                1020

Arg Lys Ile Ala Asp Ala Ile Ile Asp His Ser Leu Tyr Val Ala
    1025                1030                1035

Asn Thr Lys Ser Ser Gly Lys Asp Tyr Gln Ala Lys Tyr Gly Gly
    1040                1045                1050

Glu Phe Leu Ala Glu Leu Lys Ala Lys Tyr Pro Glu Met Phe Lys
    1055                1060                1065

Val Asn Met Ile Ser Thr Gly Lys Pro Ile Asp Asp Ser Val Lys
    1070                1075                1080

Leu Lys Gln Trp Lys Ala Glu Tyr Phe Asn Gly Thr Asn Val Leu
    1085                1090                1095

Glu Arg Gly Val Gly Tyr Val Leu Ser Asp Glu Ala Thr Gly Lys
    1100                1105                1110

Tyr Phe Thr Val Thr Lys Asp Gly Asn Phe Ile Pro Leu Gln Leu
    1115                1120                1125

Thr Gly Asn Glu Lys Val Val Thr Gly Phe Ser Asn Asp Gly Lys
    1130                1135                1140

Gly Ile Thr Tyr Phe Gly Thr Ser Gly Thr Gln Ala Lys Ser Ala
    1145                1150                1155

Phe Val Thr Phe Asn Gly Asn Thr Tyr Tyr Phe Asp Ala Arg Gly
    1160                1165                1170

His Met Val Thr Asn Gly Glu Tyr Ser Pro Asn Gly Lys Asp Val
    1175                1180                1185

Tyr Arg Phe Leu Pro Asn Gly Ile Met Leu Ser Asn Ala Phe Tyr
    1190                1195                1200

Val Asp Ala Asn Gly Asn Thr Tyr Leu Tyr Asn Ser Lys Gly Gln
    1205                1210                1215

Met Tyr Lys Gly Gly Tyr Thr Lys Phe Asp Val Thr Glu Thr Asp
    1220                1225                1230

Lys Asp Gly Lys Glu Ser Lys Val Val Lys Phe Arg Tyr Phe Thr
    1235                1240                1245

Asn Glu Gly Val Met Ala Lys Gly Val Thr Val Ile Asp Gly Phe
    1250                1255                1260

Thr Gln Tyr Phe Gly Glu Asp Gly Phe Gln Ala Lys Asp Lys Leu
    1265                1270                1275

Val Thr Phe Lys Gly Lys Thr Tyr Tyr Phe Asp Ala His Thr Gly
    1280                1285                1290

Asn Ala Ile Lys Asp Thr Trp Arg Asn Ile Asn Gly Lys Trp Tyr
```

```
                1295                1300                1305

His Phe Asp Ala Asn Gly Val Ala Ala Thr Gly Ala Gln Val Ile
    1310                1315                1320

Asn Gly Gln Lys Leu Tyr Phe Asn Glu Asp Gly Ser Gln Val Lys
    1325                1330                1335

Gly Gly Val Val Lys Asn Ala Asp Gly Thr Tyr Ser Lys Tyr Lys
    1340                1345                1350

Glu Gly Ser Gly Glu Leu Val Thr Asn Glu Phe Phe Thr Thr Asp
    1355                1360                1365

Gly Asn Val Trp Tyr Tyr Ala Gly Ala Asn Gly Lys Thr Val Thr
    1370                1375                1380

Gly Ala Gln Val Ile Asn Gly Gln His Leu Tyr Phe Asn Ala Asp
    1385                1390                1395

Gly Ser Gln Val Lys Gly Gly Val Val Lys Asn Ala Asp Gly Thr
    1400                1405                1410

Tyr Ser Lys Tyr Asp Ala Ser Thr Gly Glu Arg Leu Thr Asn Glu
    1415                1420                1425

Phe Phe Thr Thr Gly Asp Asn Asn Trp Tyr Tyr Ile Gly Ala Asn
    1430                1435                1440

Gly Lys Ser Val Thr Gly Glu Val Lys Ile Gly Asp Asp Thr Tyr
    1445                1450                1455

Phe Phe Ala Lys Asp Gly Lys Gln Val Lys Gly Gln Thr Val Ser
    1460                1465                1470

Ala Gly Asn Gly Arg Ile Ser Tyr Tyr Tyr Gly Asp Ser Gly Lys
    1475                1480                1485

Arg Ala Val Ser Thr Trp Ile Glu Ile Gln Pro Gly Val Tyr Val
    1490                1495                1500

Tyr Phe Asp Lys Asn Gly Ile Ala Tyr Pro Pro Arg Val Leu Asn
    1505                1510                1515

<210> SEQ ID NO 63
<211> LENGTH: 1431
<212> TYPE: PRT
<213> ORGANISM: Streptococcus salivarius PS4

<400> SEQUENCE: 63

Met Thr Lys Glu Thr Asn Thr Val Asp Ala Ala Thr Thr Asn Thr
1               5                   10                  15

Gln Ala Ala Asp Ala Ala Thr Lys Thr Asp Ala Ala Val Thr
            20                  25                  30

Ala Leu Pro Asn Lys Glu Ala Val Thr Thr Asp Ala Pro Ala Val
            35                  40                  45

Thr Thr Glu Lys Ala Ala Glu Gln Pro Ala Thr Val Lys Ser Glu Val
        50                  55                  60

Val Asn Thr Glu Val Lys Ala Pro Glu Ala Ala Leu Lys Asp Ser Glu
65                  70                  75                  80

Val Glu Ala Ala Leu Ser Leu Lys Asn Ile Lys Asn Ile Asp Gly Lys
                85                  90                  95

Tyr Tyr Tyr Val Asn Lys Asp Gly Ser His Lys Glu Asn Phe Ala Ile
                100                 105                 110

Thr Val Asn Gly Gln Leu Leu Tyr Phe Gly Lys Asp Gly Ala Leu Thr
                115                 120                 125

Ser Ser Ser Thr Tyr Ser Phe Thr Gln Gly Thr Thr Asn Ile Val Asp
                130                 135                 140
```

-continued

```
Gly Phe Ser Lys Asn Asn Arg Ala Tyr Asp Ser Ser Glu Ala Ser Phe
145                 150                 155                 160

Glu Leu Ile Asp Gly Tyr Leu Thr Ala Asp Ser Trp Tyr Arg Pro Val
            165                 170                 175

Ser Ile Ile Lys Asp Gly Val Thr Trp Gln Ala Ser Thr Lys Glu Asp
            180                 185                 190

Phe Arg Pro Leu Leu Met Ala Trp Trp Pro Asn Val Asp Thr Gln Val
            195                 200                 205

Asn Tyr Leu Asn Tyr Met Ser Lys Val Phe Asn Leu Asp Ala Lys Tyr
            210                 215                 220

Thr Ser Thr Asp Lys Gln Val Asp Leu Asn Arg Ala Ala Lys Asp Ile
225                 230                 235                 240

Gln Val Lys Ile Glu Gln Lys Ile Gln Ala Glu Lys Ser Thr Gln Trp
            245                 250                 255

Leu Arg Glu Ala Ile Ser Ala Phe Val Lys Thr Gln Pro Gln Trp Asn
            260                 265                 270

Lys Glu Thr Glu Asn Phe Ser Lys Gly Gly Glu Asp His Leu Gln
            275                 280                 285

Gly Gly Ala Leu Leu Tyr Val Asn Asp Pro Arg Thr Pro Trp Ala Asn
            290                 295                 300

Ser Asn Tyr Arg Leu Leu Asn Arg Thr Ala Thr Asn Gln Thr Gly Thr
305                 310                 315                 320

Ile Asp Lys Ser Val Leu Asp Glu Gln Ser Asp Pro Asn His Met Gly
            325                 330                 335

Gly Phe Asp Phe Leu Leu Ala Asn Asp Val Asp Thr Ser Asn Pro Val
            340                 345                 350

Val Gln Ala Glu Gln Leu Asn Gln Ile His Tyr Leu Met Asn Trp Gly
            355                 360                 365

Ser Ile Val Met Gly Asp Lys Asp Ala Asn Phe Asp Gly Ile Arg Val
            370                 375                 380

Asp Ala Val Asp Asn Val Asp Ala Asp Met Leu Gln Leu Tyr Thr Asn
385                 390                 395                 400

Tyr Phe Arg Glu Tyr Tyr Gly Val Asn Lys Ser Glu Ala Asn Ala Leu
            405                 410                 415

Ala His Ile Ser Val Leu Glu Ala Trp Ser Leu Asn Asp Asn His Tyr
            420                 425                 430

Asn Asp Lys Thr Asp Gly Ala Ala Leu Ala Met Glu Asn Lys Gln Arg
            435                 440                 445

Leu Ala Leu Leu Phe Ser Leu Ala Lys Pro Ile Lys Glu Arg Thr Pro
            450                 455                 460

Ala Val Ser Pro Leu Tyr Asn Asn Thr Phe Asn Thr Thr Gln Arg Asp
465                 470                 475                 480

Glu Lys Thr Asp Trp Ile Asn Lys Asp Gly Ser Lys Ala Tyr Asn Glu
            485                 490                 495

Asp Gly Thr Val Lys Gln Ser Thr Ile Gly Lys Tyr Asn Glu Lys Tyr
            500                 505                 510

Gly Asp Ala Ser Gly Asn Tyr Val Phe Ile Arg Ala His Asp Asn Asn
            515                 520                 525

Val Gln Asp Ile Ile Ala Glu Ile Lys Lys Glu Ile Asn Pro Lys
            530                 535                 540

Ser Asp Gly Phe Thr Ile Thr Asp Ala Glu Met Lys Lys Ala Phe Glu
545                 550                 555                 560

Ile Tyr Asn Lys Asp Met Leu Ser Ser Asp Lys Lys Tyr Thr Leu Asn
```

-continued

```
                565                 570                 575
Asn Ile Pro Ala Ala Tyr Ala Val Met Leu Gln Asn Met Glu Thr Ile
                580                 585                 590

Thr Arg Val Tyr Tyr Gly Asp Leu Tyr Thr Asp Asp Gly His Tyr Met
                595                 600                 605

Glu Thr Lys Ser Pro Tyr Tyr Asp Thr Ile Val Asn Leu Met Lys Asn
            610                 615                 620

Arg Ile Lys Tyr Val Ser Gly Gln Ala Gln Arg Ser Tyr Trp Leu
625                 630                 635                 640

Pro Thr Asp Gly Lys Met Asp Lys Ser Asp Val Glu Leu Tyr Arg Thr
                645                 650                 655

Asn Glu Val Tyr Thr Ser Val Arg Tyr Gly Lys Asp Ile Met Thr Ala
                660                 665                 670

Asp Asp Thr Gln Gly Ser Lys Tyr Ser Arg Thr Ser Gly Gln Val Thr
                675                 680                 685

Leu Val Val Asn Asn Pro Lys Leu Ser Leu Asp Lys Ser Ala Lys Leu
            690                 695                 700

Asp Val Glu Met Gly Lys Ile His Ala Asn Gln Lys Tyr Arg Ala Leu
705                 710                 715                 720

Ile Val Gly Thr Pro Asn Gly Ile Lys Asn Phe Thr Ser Asp Ala Glu
                725                 730                 735

Ala Ile Ala Ala Gly Tyr Val Lys Glu Thr Asp Gly Asn Gly Val Leu
                740                 745                 750

Thr Phe Gly Ala Asn Asp Ile Lys Gly Tyr Glu Thr Phe Asp Met Ser
            755                 760                 765

Gly Phe Val Ala Val Trp Val Pro Val Gly Ala Ser Asp Asp Gln Asp
            770                 775                 780

Ile Arg Val Ala Ala Ser Thr Ala Ala Lys Lys Glu Gly Glu Leu Thr
785                 790                 795                 800

Leu Lys Ala Thr Glu Ala Tyr Asp Ser Gln Leu Ile Tyr Glu Gly Phe
                805                 810                 815

Ser Asn Phe Gln Thr Ile Pro Asp Gly Ser Asp Pro Ser Val Tyr Thr
            820                 825                 830

Asn Arg Lys Ile Ala Glu Asn Val Asp Leu Phe Lys Ser Trp Gly Val
            835                 840                 845

Thr Ser Phe Glu Met Ala Pro Gln Phe Val Ser Ala Asp Asp Gly Thr
            850                 855                 860

Phe Leu Asp Ser Val Ile Gln Asn Gly Tyr Ala Phe Ala Asp Arg Tyr
865                 870                 875                 880

Asp Leu Ala Met Ser Lys Asn Asn Lys Tyr Gly Ser Lys Glu Asp Leu
                885                 890                 895

Arg Asn Ala Leu Lys Ala Leu His Lys Ala Gly Ile Gln Ala Ile Ala
                900                 905                 910

Asp Trp Val Pro Asp Gln Ile Tyr Gln Leu Pro Gly Lys Glu Val Val
            915                 920                 925

Thr Ala Thr Arg Thr Asp Gly Ala Gly Arg Lys Ile Ser Asp Ala Ile
            930                 935                 940

Ile Asp His Ser Leu Tyr Val Ala Asn Ser Lys Ser Ser Gly Lys Asp
945                 950                 955                 960

Tyr Gln Ala Lys Tyr Gly Gly Glu Phe Leu Ala Glu Leu Lys Ala Lys
                965                 970                 975

Tyr Pro Glu Met Phe Lys Val Asn Met Ile Ser Thr Gly Lys Pro Ile
            980                 985                 990
```

```
Asp Asp Ser Val Lys Leu Lys Gln Trp Lys Ala Glu Tyr Phe Asn Gly
        995                 1000                1005

Thr Asn Val Leu Asp Arg Gly Val Gly Tyr Val Leu Ser Asp Glu
    1010            1015            1020

Ala Thr Gly Lys Tyr Phe Thr Val Thr Lys Glu Gly Asn Phe Ile
    1025            1030            1035

Pro Leu Gln Leu Lys Gly Asn Glu Lys Val Ile Thr Gly Phe Ser
    1040            1045            1050

Ser Asp Gly Lys Gly Ile Thr Tyr Phe Gly Thr Ser Gly Asn Gln
    1055            1060            1065

Ala Lys Ser Ala Phe Val Thr Phe Asn Gly Asn Thr Tyr Tyr Phe
    1070            1075            1080

Asp Ala Arg Gly His Met Val Thr Asn Gly Glu Tyr Ser Pro Asn
    1085            1090            1095

Gly Lys Asp Val Tyr Arg Phe Leu Pro Asn Gly Ile Met Leu Ser
    1100            1105            1110

Asn Ala Phe Tyr Val Asp Gly Asn Gly Asn Thr Tyr Leu Tyr Asn
    1115            1120            1125

Ser Lys Gly Gln Met Tyr Lys Gly Gly Tyr Ser Lys Phe Asp Val
    1130            1135            1140

Thr Glu Thr Lys Asp Gly Lys Glu Ser Lys Val Val Lys Phe Arg
    1145            1150            1155

Tyr Phe Thr Asn Glu Gly Val Met Ala Lys Gly Val Thr Val Val
    1160            1165            1170

Asp Gly Phe Thr Gln Tyr Phe Asn Glu Asp Gly Ile Gln Ser Lys
    1175            1180            1185

Asp Glu Leu Val Thr Tyr Asn Gly Lys Thr Tyr Tyr Phe Glu Ala
    1190            1195            1200

His Thr Gly Asn Ala Ile Lys Asn Thr Trp Arg Asn Ile Lys Gly
    1205            1210            1215

Lys Trp Tyr His Phe Asp Ala Asn Gly Val Ala Ala Thr Gly Ala
    1220            1225            1230

Gln Val Ile Asn Gly Gln His Leu Tyr Phe Asn Glu Asp Gly Ser
    1235            1240            1245

Gln Val Lys Gly Gly Val Val Lys Asn Ala Asp Gly Thr Phe Ser
    1250            1255            1260

Lys Tyr Lys Asp Gly Ser Gly Asp Leu Val Val Asn Glu Phe Phe
    1265            1270            1275

Thr Thr Gly Asp Asn Val Trp Tyr Tyr Ala Gly Ala Asn Gly Lys
    1280            1285            1290

Thr Val Thr Gly Ala Gln Val Ile Asn Gly Gln His Leu Phe Phe
    1295            1300            1305

Lys Glu Asp Gly Ser Gln Val Lys Gly Asp Phe Val Lys Asn Ser
    1310            1315            1320

Asp Gly Thr Tyr Ser Lys Tyr Asp Ala Ala Ser Gly Glu Arg Leu
    1325            1330            1335

Thr Asn Glu Phe Phe Thr Thr Gly Asp Asn His Trp Tyr Tyr Ile
    1340            1345            1350

Gly Ala Asn Gly Lys Thr Val Thr Gly Glu Val Lys Ile Gly Asp
    1355            1360            1365

Asp Thr Tyr Phe Phe Ala Lys Asp Gly Lys Gln Leu Lys Gly Gln
    1370            1375            1380
```

-continued

```
Ile Val Thr Thr Arg Ser Gly Arg Ile Ser Tyr Tyr Phe Gly Asp
    1385                1390                1395

Ser Gly Lys Lys Ala Ile Ser Thr Trp Val Glu Ile Gln Pro Gly
1400                1405                1410

Val Phe Val Phe Phe Asp Lys Asn Gly Leu Ala Tyr Pro Pro Glu
    1415                1420                1425

Asn Met Asn
    1430

<210> SEQ ID NO 64
<211> LENGTH: 1532
<212> TYPE: PRT
<213> ORGANISM: unknown
<220> FEATURE:
<223> OTHER INFORMATION: unknown Streptococcus sp. C150

<400> SEQUENCE: 64

Met Glu Asn Lys Val His Tyr Lys Leu His Lys Val Lys Lys Gln Trp
1               5                   10                  15

Val Thr Ile Ala Val Ala Ser Ala Ala Leu Ala Thr Val Val Gly Gly
                20                  25                  30

Leu Ser Ala Thr Thr Ser Ser Val Ser Ala Asp Glu Thr Gln Asp Lys
            35                  40                  45

Thr Val Thr Gln Pro Asn Ser Asp Thr Thr Ala Asp Leu Val Thr Ser
        50                  55                  60

Thr Glu Ala Thr Lys Glu Val Asp Lys Arg Thr Asn Thr Lys Glu Ala
65                  70                  75                  80

Asp Val Leu Thr Pro Ala Lys Glu Thr Asn Thr Val Glu Thr Ala Ala
                85                  90                  95

Thr Thr Asn Thr Gln Ala Thr Ala Glu Ala Ala Lys Thr Ala Thr Thr
            100                 105                 110

Thr Asn Thr Gln Ala Thr Ala Glu Val Ala Lys Thr Ala Thr Thr Ala
        115                 120                 125

Asp Val Ala Val Ala Val Pro Asn Lys Glu Ala Val Val Thr Thr
130                 135                 140

Asp Ala Pro Ala Val Thr Thr Glu Lys Ala Glu Glu Gln Pro Ala Thr
145                 150                 155                 160

Val Lys Ala Glu Val Val Asn Thr Glu Val Lys Ala Pro Glu Ala Ala
                165                 170                 175

Leu Lys Asp Ser Glu Val Glu Ala Ala Leu Ser Leu Lys Asn Ile Lys
            180                 185                 190

Asn Ile Asp Gly Lys Tyr Tyr Val Asn Glu Asp Gly Ser His Lys
        195                 200                 205

Glu Asn Phe Ala Ile Thr Val Asn Gly Gln Leu Leu Tyr Phe Gly Lys
    210                 215                 220

Asp Gly Ala Leu Thr Ser Ser Thr Tyr Ser Phe Thr Gln Gly Thr
225                 230                 235                 240

Thr Asn Ile Val Asp Gly Phe Ser Ile Asn Asn Arg Ala Tyr Asp Ser
                245                 250                 255

Ser Glu Ala Ser Phe Glu Leu Ile Asp Gly Tyr Leu Thr Ala Asp Ser
            260                 265                 270

Trp Tyr Arg Pro Ala Ser Ile Ile Lys Asp Gly Val Thr Trp Gln Ala
        275                 280                 285

Ser Thr Ala Glu Asp Phe Arg Pro Leu Leu Met Ala Trp Trp Pro Asn
    290                 295                 300
```

-continued

Val Asp Thr Gln Val Asn Tyr Leu Asn Tyr Met Ser Lys Val Phe Asn
305                 310                 315                 320

Leu Asp Ala Lys Tyr Ser Ser Thr Asp Lys Gln Glu Thr Leu Lys Val
            325                 330                 335

Ala Ala Lys Asp Ile Gln Ile Lys Ile Glu Gln Lys Ile Gln Ala Glu
                340                 345                 350

Lys Ser Thr Gln Trp Leu Arg Glu Thr Ile Ser Ala Phe Val Lys Thr
        355                 360                 365

Gln Pro Gln Trp Asn Lys Thr Glu Asn Tyr Ser Lys Gly Gly
    370                 375                 380

Glu Asp His Leu Gln Gly Gly Ala Leu Leu Tyr Val Asn Asp Ser Arg
385                 390                 395                 400

Thr Pro Trp Ala Asn Ser Asn Tyr Arg Leu Leu Asn Arg Thr Ala Thr
                405                 410                 415

Asn Gln Thr Gly Thr Ile Asp Lys Ser Ile Leu Asp Glu Gln Ser Asp
                420                 425                 430

Pro Asn His Met Gly Gly Phe Asp Phe Leu Leu Ala Asn Asp Val Asp
            435                 440                 445

Leu Ser Asn Pro Val Val Gln Ala Glu Gln Leu Asn Gln Ile His Tyr
450                 455                 460

Leu Met Asn Trp Gly Ser Ile Val Met Gly Asp Lys Asp Ala Asn Phe
465                 470                 475                 480

Asp Gly Ile Arg Val Asp Ala Val Asp Asn Val Asp Ala Asp Met Leu
                485                 490                 495

Gln Leu Tyr Thr Asn Tyr Phe Arg Glu Tyr Tyr Gly Val Asn Lys Ser
            500                 505                 510

Glu Ala Asn Ala Leu Ala His Ile Ser Val Leu Glu Ala Trp Ser Leu
        515                 520                 525

Asn Asp Asn His Tyr Asn Asp Lys Thr Asp Val Ala Ala Leu Ala Met
        530                 535                 540

Glu Asn Lys Gln Arg Leu Ala Leu Leu Phe Ser Leu Ala Lys Pro Ile
545                 550                 555                 560

Lys Glu Arg Thr Pro Ala Val Ser Pro Leu Tyr Asn Asn Thr Phe Asn
                565                 570                 575

Thr Thr Gln Arg Asp Glu Lys Thr Asp Trp Ile Asn Lys Asp Gly Ser
            580                 585                 590

Lys Ala Tyr Asn Glu Asp Gly Thr Val Lys Lys Ser Thr Ile Gly Lys
        595                 600                 605

Tyr Asn Glu Lys Tyr Gly Asp Ala Ser Gly Asn Tyr Val Phe Ile Arg
    610                 615                 620

Ala His Asp Asn Asn Val Gln Asp Ile Ile Ala Glu Ile Ile Lys Lys
625                 630                 635                 640

Glu Ile Asn Glu Lys Ser Asp Gly Phe Thr Ile Thr Asp Ser Glu Met
                645                 650                 655

Lys Arg Ala Phe Glu Ile Tyr Asn Lys Asp Met Leu Ser Asn Asp Lys
            660                 665                 670

Lys Tyr Thr Leu Asn Asn Ile Pro Ala Ala Tyr Ala Val Met Leu Gln
        675                 680                 685

Asn Met Glu Thr Ile Thr Arg Val Tyr Tyr Gly Asp Leu Tyr Thr Asp
        690                 695                 700

Asp Gly Asn Tyr Met Glu Ala Lys Ser Pro Tyr Tyr Asp Thr Ile Val
705                 710                 715                 720

Asn Leu Met Lys Ser Arg Ile Lys Tyr Val Ser Gly Gly Gln Ala Gln

```
                    725                 730                 735
Arg Ser Tyr Trp Leu Pro Thr Asp Gly Lys Met Asp Lys Ser Asp Val
                740                 745                 750

Glu Leu Tyr Arg Thr Asn Glu Val Tyr Thr Ser Val Arg Tyr Gly Lys
            755                 760                 765

Asp Ile Met Thr Ala Asp Thr Gln Gly Ser Lys Tyr Ser Arg Thr
        770                 775                 780

Ser Gly Gln Val Thr Leu Val Val Asn Asn Pro Lys Leu Thr Leu Asp
785                 790                 795                 800

Gln Ser Ala Lys Leu Asn Val Val Met Gly Lys Ile His Ala Asn Gln
                805                 810                 815

Lys Tyr Arg Ala Leu Ile Val Gly Thr Pro Asn Gly Ile Lys Asn Phe
                820                 825                 830

Thr Ser Asp Ala Glu Ala Ile Ala Ala Gly Tyr Val Lys Glu Thr Asp
                835                 840                 845

Gly Asn Gly Val Leu Thr Phe Gly Ala Asn Asp Ile Lys Gly Tyr Glu
850                 855                 860

Thr Phe Asp Met Ser Gly Phe Val Ala Val Trp Val Pro Val Gly Ala
865                 870                 875                 880

Ser Asp Asp Gln Asp Ile Arg Val Ala Ala Ser Thr Ala Ala Lys Lys
                885                 890                 895

Glu Gly Glu Leu Thr Leu Lys Ala Thr Glu Ala Tyr Asp Ser Gln Leu
                900                 905                 910

Ile Tyr Glu Gly Phe Ser Asn Phe Gln Thr Ile Pro Asp Gly Ser Asp
                915                 920                 925

Pro Ser Val Tyr Thr Asn Arg Lys Ile Ala Glu Asn Val Asp Leu Phe
930                 935                 940

Lys Ser Trp Gly Val Thr Ser Phe Glu Met Ala Pro Gln Phe Val Ser
945                 950                 955                 960

Ala Asp Asp Gly Thr Phe Leu Asp Ser Val Ile Gln Asn Gly Tyr Ala
                965                 970                 975

Phe Ala Asp Arg Tyr Asp Leu Ala Met Ser Lys Asn Asn Lys Tyr Gly
                980                 985                 990

Ser Lys Glu Asp Leu Arg Asn Ala   Leu Lys Ala Leu His   Lys Ala Gly
            995                 1000                1005

Ile Gln Ala Ile Ala Asp Trp  Val Pro Asp Gln Ile   Tyr Gln Leu
        1010                1015                1020

Pro Gly Lys Glu Val Val Thr  Ala Thr Arg Thr Asp   Gly Ala Gly
        1025                1030                1035

Arg Lys Ile Ser Asp Ala Ile  Ile Asp His Ser Leu   Tyr Val Ala
        1040                1045                1050

Asn Ser Lys Ser Ser Gly Lys  Asp Tyr Gln Ala Lys   Tyr Gly Gly
        1055                1060                1065

Glu Phe Leu Ala Glu Leu Lys  Ala Lys Tyr Pro Glu   Met Phe Lys
        1070                1075                1080

Val Asn Met Ile Ser Thr Gly  Lys Pro Ile Asp Asp   Ser Val Lys
        1085                1090                1095

Leu Lys Gln Trp Lys Ala Glu  Tyr Phe Asn Gly Thr   Asn Val Leu
        1100                1105                1110

Asp Arg Gly Val Gly Tyr Val  Leu Ser Asp Glu Ala   Thr Gly Lys
        1115                1120                1125

Tyr Phe Thr Val Thr Lys Glu  Gly Asn Phe Ile Pro   Leu Gln Leu
        1130                1135                1140
```

```
Lys Gly Asn Lys Lys Val Ile Thr Gly Phe Ser Ser Asp Gly Lys
1145                1150                1155

Gly Ile Thr Tyr Phe Gly Thr Ser Gly Asn Gln Ala Lys Ser Ala
1160                1165                1170

Phe Val Thr Phe Asn Gly Asn Thr Tyr Tyr Phe Asp Ala Arg Gly
1175                1180                1185

His Met Val Thr Asn Gly Glu Tyr Ser Pro Asn Gly Lys Asp Val
1190                1195                1200

Tyr Arg Phe Leu Pro Asn Gly Ile Met Leu Ser Asn Ala Phe Tyr
1205                1210                1215

Val Asp Gly Asn Gly Asn Thr Tyr Leu Tyr Asn Ser Lys Gly Gln
1220                1225                1230

Met Tyr Lys Gly Gly Tyr Ser Lys Phe Asp Val Thr Glu Thr Lys
1235                1240                1245

Asp Gly Lys Glu Ser Lys Val Val Lys Phe Arg Tyr Phe Thr Asn
1250                1255                1260

Glu Gly Val Met Ala Lys Gly Val Thr Val Val Asp Gly Phe Thr
1265                1270                1275

Gln Tyr Phe Asn Glu Asp Gly Ile Gln Ser Lys Asp Glu Leu Val
1280                1285                1290

Thr Tyr Asn Gly Lys Thr Tyr Tyr Phe Glu Ala His Thr Gly Asn
1295                1300                1305

Ala Ile Lys Asn Thr Trp Arg Asn Ile Lys Gly Lys Trp Tyr His
1310                1315                1320

Phe Asp Ala Asn Gly Val Ala Ala Thr Gly Ala Gln Val Ile Asn
1325                1330                1335

Gly Gln His Leu Tyr Phe Asn Glu Asp Gly Ser Gln Val Lys Gly
1340                1345                1350

Ser Ile Val Lys Asn Ala Asp Gly Thr Phe Ser Lys Tyr Lys Asp
1355                1360                1365

Ser Ser Gly Asp Leu Val Val Asn Glu Phe Phe Thr Thr Gly Asp
1370                1375                1380

Asn Val Trp Tyr Tyr Ala Gly Ala Asn Gly Lys Thr Val Thr Gly
1385                1390                1395

Ala Gln Val Ile Asn Gly Gln His Leu Phe Phe Lys Glu Asp Gly
1400                1405                1410

Ser Gln Val Lys Gly Asp Phe Val Lys Asn Ser Asp Gly Thr Tyr
1415                1420                1425

Ser Lys Tyr Asp Ala Ala Ser Gly Glu Arg Leu Thr Asn Glu Phe
1430                1435                1440

Phe Thr Thr Gly Asp Asn His Trp Tyr Tyr Ile Gly Ala Asn Gly
1445                1450                1455

Lys Thr Val Thr Gly Glu Val Lys Ile Gly Asp Thr Tyr Phe
1460                1465                1470

Phe Ala Lys Asp Gly Lys Gln Leu Lys Gly Gln Ile Val Thr Thr
1475                1480                1485

Arg Ser Gly Arg Ile Ser Tyr Tyr Phe Gly Asp Ser Gly Lys Lys
1490                1495                1500

Ala Ile Ser Thr Trp Val Glu Ile Gln Pro Gly Val Phe Val Phe
1505                1510                1515

Phe Asp Lys Asn Gly Leu Ala Tyr Pro Pro Glu Asn Met Asn
1520                1525                1530
```

<210> SEQ ID NO 65
<211> LENGTH: 1341
<212> TYPE: PRT
<213> ORGANISM: Streptococcus salivarius

<400> SEQUENCE: 65

```
Met Ile Asp Gly Lys Tyr Tyr Tyr Val Asn Glu Asp Gly Ser His Lys
1               5                   10                  15
Glu Asn Phe Ala Ile Thr Val Asn Gly Gln Leu Leu Tyr Phe Gly Lys
            20                  25                  30
Asp Gly Ala Leu Thr Ser Ser Thr Tyr Ser Phe Thr Pro Gly Thr
        35                  40                  45
Thr Asn Ile Val Asp Gly Phe Ser Ile Asn Asn Arg Ala Tyr Asp Ser
    50                  55                  60
Ser Glu Ala Ser Phe Glu Leu Ile Asp Gly Tyr Leu Thr Ala Asp Ser
65                  70                  75                  80
Trp Tyr Arg Pro Ala Ser Ile Ile Lys Asp Gly Val Thr Trp Gln Ala
                85                  90                  95
Ser Thr Ala Glu Asp Phe Arg Pro Leu Leu Met Ala Trp Trp Pro Asn
            100                 105                 110
Val Asp Thr Gln Val Asn Tyr Leu Asn Tyr Met Ser Lys Val Phe Asn
        115                 120                 125
Leu Asp Ala Lys Tyr Ser Ser Thr Asp Lys Gln Glu Thr Leu Lys Val
    130                 135                 140
Ala Ala Lys Asp Ile Gln Ile Lys Ile Glu Gln Lys Ile Gln Ala Glu
145                 150                 155                 160
Lys Ser Thr Gln Trp Leu Arg Glu Thr Ile Ser Ala Phe Val Lys Thr
                165                 170                 175
Gln Pro Gln Trp Asn Lys Glu Thr Glu Asn Tyr Ser Lys Gly Gly Gly
            180                 185                 190
Glu Asp His Leu Gln Gly Gly Ala Leu Leu Tyr Val Asn Asp Ser Arg
        195                 200                 205
Thr Pro Trp Ala Asn Ser Asp Tyr Arg Arg Leu Asn Arg Thr Ala Thr
    210                 215                 220
Asn Gln Thr Gly Thr Ile Asp Lys Ser Ile Leu Asp Glu Gln Ser Asp
225                 230                 235                 240
Pro Asn His Met Gly Gly Phe Asp Phe Leu Leu Ala Asn Asp Val Asp
                245                 250                 255
Leu Ser Asn Pro Val Val Gln Ala Glu Gln Leu Asn Gln Ile His Tyr
            260                 265                 270
Leu Met Asn Trp Gly Ser Ile Val Met Gly Asp Lys Asp Ala Asn Phe
        275                 280                 285
Asp Gly Ile Arg Val Asp Ala Val Asp Asn Val Asp Ala Asp Met Leu
    290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
            340                 345                 350
Glu Asn Lys Gln Arg Leu Ala Leu Leu Phe Ser Leu Ala Lys Pro Ile
        355                 360                 365
Lys Glu Arg Thr Pro Ala Val Ser Pro Leu Tyr Asn Asn Thr Phe Asn
    370                 375                 380
```

```
Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
            405                 410                 415

Tyr Asn Glu Lys Tyr Gly Asp Ala Ser Gly Asn Tyr Val Phe Ile Arg
        420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Asn Leu Asp
        595                 600                 605

Gln Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asn Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800
```

```
Ser Lys Glu Asp Leu Arg Asp Ala Leu Lys Ala Leu His Lys Ala Gly
            805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
            835                 840                 845

Ile Ala Asp Ala Ile Ile Asp His Ser Leu Tyr Val Ala Asn Ser Lys
850                 855                 860

Ser Ser Gly Lys Asp Tyr Gln Ala Lys Tyr Gly Glu Phe Leu Ala
865                 870                 875                 880

Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
            915                 920                 925

Leu Ser Asp Glu Ala Thr Gly Lys Tyr Phe Thr Val Thr Lys Glu Gly
930                 935                 940

Asn Phe Ile Pro Leu Gln Leu Thr Gly Lys Glu Lys Val Ile Thr Gly
945                 950                 955                 960

Phe Ser Ser Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Ser Glu Tyr Ser Pro Asn Gly
            995                 1000                1005

Lys Asp Val Tyr Arg Phe Leu Pro Asn Gly Ile Met Leu Ser Asn
            1010                1015                1020

Ala Phe Tyr Ile Asp Ala Asn Gly Asn Thr Tyr Leu Tyr Asn Ser
            1025                1030                1035

Lys Gly Gln Met Tyr Lys Gly Gly Tyr Thr Lys Phe Asp Val Ser
            1040                1045                1050

Glu Thr Asp Lys Asp Gly Lys Glu Ser Lys Val Val Lys Phe Arg
            1055                1060                1065

Tyr Phe Thr Asn Glu Gly Val Met Ala Lys Gly Val Thr Val Ile
            1070                1075                1080

Asp Gly Phe Thr Gln Tyr Phe Gly Glu Asp Gly Phe Gln Ala Lys
            1085                1090                1095

Asp Lys Leu Val Thr Phe Lys Gly Lys Thr Tyr Tyr Phe Asp Ala
            1100                1105                1110

His Thr Gly Asn Gly Ile Lys Asp Thr Trp Arg Asn Ile Asn Gly
            1115                1120                1125

Lys Trp Tyr Tyr Phe Asp Ala Asn Gly Val Ala Ala Thr Gly Ala
            1130                1135                1140

Gln Val Ile Asn Gly Gln Lys Leu Tyr Phe Asn Glu Asp Gly Ser
            1145                1150                1155

Gln Val Lys Gly Gly Val Val Lys Asn Ala Asp Gly Thr Tyr Ser
            1160                1165                1170

Lys Tyr Lys Glu Gly Phe Gly Glu Leu Val Thr Asn Glu Phe Phe
            1175                1180                1185

Thr Thr Asp Gly Asn Val Trp Tyr Tyr Ala Gly Ala Asn Gly Lys
            1190                1195                1200

Thr Val Thr Gly Ala Gln Val Ile Asn Gly Gln His Leu Tyr Phe
```

```
                    1205                1210                1215

Asn Ala Asp Gly Ser Gln Val Lys Gly Gly Val Val Lys Asn Ala
            1220                1225                1230

Asp Gly Thr Tyr Ser Lys Tyr Asn Ala Ser Thr Gly Glu Arg Leu
        1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
    1265                1270                1275

Asp Thr Tyr Phe Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Ile Glu Ile Gln Pro Gly
    1310                1315                1320

Val Tyr Val Tyr Phe Asp Lys Asn Gly Leu Ala Tyr Pro Pro Arg
    1325                1330                1335

Val Leu Asn
    1340

<210> SEQ ID NO 66

<400> SEQUENCE: 66

000

<210> SEQ ID NO 67
<211> LENGTH: 93
<212> TYPE: DNA
<213> ORGANISM: Unknown
<220> FEATURE:
<223> OTHER INFORMATION: terminator sequence added to pHYT

<400> SEQUENCE: 67
ggttaccttg aatgtatata aacattctca aagggatttc taataaaaaa cgctcggttg      60
ccgccgggcg ttttttatgc atcgatggaa ttc                                  93

<210> SEQ ID NO 68
<211> LENGTH: 971
<212> TYPE: PRT
<213> ORGANISM: Aspergillus clavatus

<400> SEQUENCE: 68

Ala Ala Val His Ser Phe Ala Pro Ser Thr Thr Ala Thr Ala Ala Tyr
1               5                   10                  15

Ser Gln His Thr Leu Pro Ser Ser Ile Asp Asn Gly Ala Gln Leu Ile
            20                  25                  30

Ala Asn Ile Asp Asp Pro Leu Ala Val Asn Ala Gln Ser Val Cys Pro
        35                  40                  45

Gly Tyr Lys Ala Ser Asp Val Gln Gln Thr Ser Arg Gly Phe Thr Ala
    50                  55                  60

Ser Leu Gln Leu Ala Gly Glu Pro Cys Asn Ala Tyr Gly Ile Asp Val
65                  70                  75                  80

Asp Ser Leu Ser Leu Ser Val Glu Val Leu Ala Lys Asp Arg Leu Asn
                85                  90                  95

Ile Gln Ile Val Pro Thr His Val Asp Ser Ser Asn Ala Ser Trp Tyr
            100                 105                 110
```

```
Ile Leu Pro Glu Asp Arg Val Pro Lys Ala Gln Ala Ser Ala Asp Ala
            115                 120                 125
Ser Val Ser Gln Ser Asp Phe Glu Ile Glu Trp Ser Asn Asp Pro Ser
        130                 135                 140
Phe Asn Ile Lys Ile Ile Arg Lys Ala Thr Gly Asp Ala Leu Phe Asp
145                 150                 155                 160
Thr Ala Asp Ser Val Leu Val Phe Gln Asn Gln Phe Ile Glu Phe Val
                165                 170                 175
Ser Ala Leu Pro Glu Gly Tyr Asn Leu Tyr Gly Leu Gly Glu Arg Met
            180                 185                 190
Ala Gln Leu Arg Leu Leu Arg Asn Ala Thr Leu Thr Thr Tyr Ala Ala
        195                 200                 205
Asp Val Gly Asp Pro Ile Asp Asp Asn Ile Tyr Gly Gln His Pro Phe
    210                 215                 220
Tyr Leu Asp Thr Arg Tyr Tyr Thr Lys Asp Ala Asn Gly Ser Tyr Ser
225                 230                 235                 240
Leu Val Asn Thr Asp Asp Ala Asp Ala Ser Gly Asp Tyr Glu Ser Phe
                245                 250                 255
Ser His Gly Val Phe Leu Arg Asn Ala His Gly Gln Glu Val Ile Leu
            260                 265                 270
Gln Ser Arg Asn Ile Thr Trp Arg Thr Ile Gly Gly Ser Ile Asp Leu
        275                 280                 285
Thr Phe Tyr Ser Gly Pro Thr Gln Ala Asp Val Thr Lys Ser Tyr Gln
    290                 295                 300
Leu Thr Thr Ile Gly Leu Pro Ala Met Gln Gln Tyr Ser Ala Leu Gly
305                 310                 315                 320
Phe His Gln Cys Arg Trp Gly Tyr Arg Ser Trp Ser Glu Leu Glu Glu
                325                 330                 335
Val Val Asn Thr Phe Glu Gln Phe Glu Ile Pro Leu Glu Tyr Ile Trp
            340                 345                 350
Thr Asp Ile Asp Tyr Met Arg Gly Tyr Arg Asp Phe Asp Asn Asp Gln
        355                 360                 365
Val His Phe Pro Tyr Asp Glu Gly Glu Phe Leu Asp Arg Leu His
    370                 375                 380
Lys Ser Gly Arg His Trp Val Pro Ile Val Asp Ser Ala Ile Tyr Ile
385                 390                 395                 400
Pro Asn Pro Asp Asn Ala Ser Asp Ala Tyr Asp Thr Tyr Ala Arg Gly
                405                 410                 415
Ala Lys Asp Asp Val Phe Ile Lys Asn Pro Asp Gly Ser Leu Tyr Ile
            420                 425                 430
Gly Ala Val Trp Pro Gly Phe Thr Val Phe Pro Asp Trp His Asn Pro
        435                 440                 445
Lys Ala Ala Glu Trp Trp Ser Asn Glu Leu Val Thr Trp Phe Glu Lys
    450                 455                 460
Val Gln Tyr Asp Gly Ile Trp Ile Asp Met Ser Glu Val Ser Ser Phe
465                 470                 475                 480
Cys Val Gly Ser Cys Gly Thr Gly Asn Leu His Leu Asn Pro Ala His
                485                 490                 495
Pro Pro Phe Gln Leu Pro Gly Glu Pro Gly Asn Ile Glu Tyr Thr Tyr
            500                 505                 510
Pro Glu Ala Phe Asn Val Thr Asn Ser Thr Glu Ala Ala Ser Ala Ser
        515                 520                 525
Ala Ala Ser Ala Ser Gln Ser Ser Ala Ala Ala Ala Thr Gln Thr Asp
```

```
                530             535             540
Val Ser Ser Thr Thr Thr Ser Tyr Leu Arg Thr Thr Pro Thr Pro Gly
545                 550                 555                 560

Val Arg Asp Ile Asn Tyr Pro Pro Tyr Val Ile Asn His Val Gln Ser
                565                 570                 575

Gly His Asp Leu Ala Val His Ala Ile Ser Pro Asn Ala Thr His Val
                580                 585                 590

Asp Gly Val Gln Glu Tyr Asp Val His Ser Leu Trp Gly His Gln Ile
                595                 600                 605

Leu Asn Ala Thr Tyr Gln Gly Leu Leu Glu Val Phe Thr Glu Lys Arg
                610                 615                 620

Pro Phe Ile Ile Gly Arg Ser Thr Phe Ala Gly Ser Gly Lys Trp Ala
625                 630                 635                 640

Gly His Trp Gly Gly Asp Asn Asn Ser Arg Trp Gly Ser Met Phe His
                645                 650                 655

Ser Ile Ser Gln Ala Leu Ser Phe Ser Leu Phe Gly Ile Pro Met Phe
                660                 665                 670

Gly Val Asp Thr Cys Gly Phe Asn Gly Asn Thr Asp Glu Glu Leu Cys
                675                 680                 685

Asn Arg Trp Met Gln Leu Ser Ala Phe Phe Pro Phe Tyr Arg Asn His
                690                 695                 700

Asn Thr Leu Ala Ala Leu Ser Gln Glu Pro Tyr Arg Trp Ala Ser Val
705                 710                 715                 720

Thr Glu Ala Ala Lys Thr Ala Met Ser Ile Arg Tyr Ala Leu Leu Pro
                725                 730                 735

Tyr Phe Tyr Thr Leu Phe His Gln Ala His Thr Thr Gly Ser Thr Val
                740                 745                 750

Met Arg Ala Leu Ala Trp Glu Phe Pro Asn Asp Pro Ser Leu Ala Ala
                755                 760                 765

Val Asp Thr Gln Phe Met Val Gly Pro Ser Ile Leu Val Thr Pro Val
                770                 775                 780

Leu Glu Pro Leu Ala Lys Thr Val Lys Gly Val Phe Pro Gly Val Gly
785                 790                 795                 800

Lys Gly Gln Val Trp Tyr Asp Trp Tyr Thr Gln Ala Ala Val Asp Ala
                805                 810                 815

Lys Pro Gly Val Asn Thr Thr Ile Pro Ala Pro Leu Gly His Ile Pro
                820                 825                 830

Val Tyr Val Arg Gly Gly Ser Ile Leu Pro Met Gln Glu Pro Ala Leu
                835                 840                 845

Thr Thr Arg Asp Ala Arg Lys Thr Pro Trp Ser Leu Leu Ala Ala Leu
850                 855                 860

Asp Gly Asn Gln Thr Ala Ser Gly Gln Leu Tyr Leu Asp Asp Gly Ser
865                 870                 875                 880

Ser Val Asn Pro Ser Ser Thr Leu Asn Val Glu Phe Ala Ala Thr His
                885                 890                 895

Ser Ser Ile Lys Val Ser Ala Lys Gly Asp Trp Arg Glu Lys Asn Ser
                900                 905                 910

Leu Asp Ser Val Thr Val Leu Gly Val Ala Lys Glu Pro Ala Arg Val
                915                 920                 925

Thr Phe Asn Arg Arg Val Pro Pro Glu Ser Val Glu Tyr Asn Ala
                930                 935                 940

Thr Ser Gln Val Leu Thr Val Ser Gly Leu Gln Lys Leu Thr Pro Arg
945                 950                 955                 960
```

```
<210> SEQ ID NO 69
<211> LENGTH: 969
<212> TYPE: PRT
<213> ORGANISM: Neosartorya fischeri

<400> SEQUENCE: 69
```

Gly Ala Trp Ala Glu Asp Trp Ile Leu Lys Trp
              965                 970

Ala Ser His Ser Leu Ala Pro Ser Thr Ser Ala Thr Ser Ala His Ala
1               5                   10                  15

Gln Tyr Thr Leu Pro Ser Ser Ile Asp Val Gly Ala Gln Leu Val Ala
            20                  25                  30

Asn Ile Asp Asp Pro Leu Ala Val Asp Ala Gln Ser Val Cys Pro Gly
        35                  40                  45

Tyr Lys Ala Ser Asn Val His Gln Thr Ser Gln Gly Phe Thr Ala Ser
    50                  55                  60

Leu Gln Leu Ala Gly Asp Pro Cys Asn Val Tyr Gly Thr Asp Val Asp
65                  70                  75                  80

Ser Leu Ser Leu Thr Val Asp Tyr Leu Ala Lys Asp Arg Leu Asn Ile
                85                  90                  95

Gln Ile Val Pro Thr Tyr Val Asp Ala Ser Asn Ala Ser Trp Tyr Leu
            100                 105                 110

Leu Ser Glu Asp Leu Val Pro Arg Ala Gln Gly Ser Gly Val Ser Ala
        115                 120                 125

Ser Gln Ser Asp Phe Asp Val Lys Trp Ser Asn Glu Pro Ser Phe Asn
130                 135                 140

Leu Lys Val Ile Arg Lys Ala Thr Gly Asp Val Leu Phe Asp Thr Glu
145                 150                 155                 160

Gly Ser Val Leu Val Phe Glu Asn Gln Phe Ile Glu Phe Val Ser Ser
                165                 170                 175

Leu Pro Glu Gly Tyr Asn Leu Tyr Gly Leu Gly Glu Arg Met Ala Gln
            180                 185                 190

Leu Arg Leu Leu Arg Asn Ala Thr Leu Thr Thr Tyr Ala Ala Asp Val
        195                 200                 205

Gly Asp Pro Ile Asp Ser Asn Ile Tyr Gly Gln His Pro Phe Tyr Leu
    210                 215                 220

Asp Thr Arg Tyr Tyr Thr Lys Gly Thr Asn Gly Ser Tyr Ser Leu Val
225                 230                 235                 240

Asn Thr Asp Glu Ala Asp Leu Ser Glu Asp Tyr Glu Ser Phe Ser His
                245                 250                 255

Gly Val Phe Leu Arg Asn Ser His Gly Gln Glu Val Leu Leu Gln Pro
            260                 265                 270

Arg Asn Ile Thr Trp Arg Thr Ile Gly Gly Ser Ile Asp Leu Thr Phe
        275                 280                 285

Tyr Ser Gly Pro Thr Gln Ala Asp Val Thr Lys Ser Tyr Gln Leu Ser
    290                 295                 300

Thr Ile Gly Leu Pro Ala Met Gln Gln Tyr Ser Thr Leu Gly Phe His
305                 310                 315                 320

Gln Cys Arg Trp Gly Tyr Gln Asn Trp Ser Gln Leu Glu Glu Val Val
                325                 330                 335

Asn Asn Phe Glu Arg Phe Glu Ile Pro Leu Glu Tyr Ile Trp Ser Asp
            340                 345                 350

Ile Asp Tyr Met Leu Gly Tyr Arg Asp Phe Glu Asn Asp Pro Glu Arg

```
                355                 360                 365
Phe Ser Tyr Asp Glu Gly Glu Phe Leu Asn Lys Leu His Lys Ser
370                 375                 380
Gly Arg His Tyr Val Pro Ile Val Asp Ser Ala Ile Tyr Ile Pro Asn
385                 390                 395                 400
Pro Asp Asn Ala Ser Asp Ala Tyr Glu Pro Tyr Ala Arg Gly Ala Lys
                405                 410                 415
Asp Asp Val Phe Ile Lys Asn Pro Asp Gly Thr Leu Tyr Ile Gly Ala
                420                 425                 430
Val Trp Pro Gly Phe Thr Val Phe Pro Asp Trp Leu Asn Pro Lys Ala
                435                 440                 445
Phe Asp Tyr Trp Ala Asn Glu Leu Val Ile Trp Ser Lys Lys Val Ala
                450                 455                 460
Phe Asp Gly Ile Trp Ile Asp Met Ser Glu Val Ser Ser Phe Cys Val
465                 470                 475                 480
Gly Ser Cys Gly Thr Gly Lys Leu His Leu Asn Pro Val His Pro Pro
                485                 490                 495
Phe Gln Leu Pro Gly Glu Pro Gly Asn Ile Gly Tyr Asp Tyr Pro Glu
                500                 505                 510
Ala Phe Asn Val Thr Asn Ser Thr Glu Ala Ala Ser Ala Ser Ala Ala
                515                 520                 525
Ser Ala Ser Gln Ala Ser Ala Ala Ala Thr Gln Thr Ala Thr Thr
                530                 535                 540
Ser Thr Ser Thr Ser Tyr Leu Arg Thr Pro Thr Pro Gly Val Arg
545                 550                 555                 560
Asp Val Asn Tyr Pro Pro Tyr Val Ile Asn His Val Gln Glu Gly His
                565                 570                 575
Asp Leu Ala Val His Ala Ile Ser Pro Asn Ser Thr His Ala Asp Gly
                580                 585                 590
Val Gln Glu Tyr Asp Val His Ser Leu Trp Gly His Gln Ile Leu Asn
                595                 600                 605
Ala Thr Tyr Tyr Gly Leu Arg Gln Val Phe Thr Glu Lys Arg Pro Phe
                610                 615                 620
Ile Ile Gly Arg Ser Thr Phe Ala Gly Ser Gly Lys Trp Ala Gly His
625                 630                 635                 640
Trp Gly Gly Asp Asn Asn Ser Lys Trp Gly Ser Met Phe Leu Ser Ile
                645                 650                 655
Ser Gln Gly Leu Ser Phe Ser Leu Phe Gly Ile Pro Met Phe Gly Val
                660                 665                 670
Asp Thr Cys Gly Phe Asn Gly Asn Thr Asp Glu Glu Leu Cys Ser Arg
                675                 680                 685
Trp Met Gln Leu Ser Ala Phe Phe Pro Phe Tyr Arg Asn His Asn Val
                690                 695                 700
Leu Gly Ala Ile Pro Gln Glu Pro Tyr Arg Trp Ala Ser Val Thr Gln
705                 710                 715                 720
Ala Ser Lys Ala Ala Met Lys Ile Arg Tyr Ser Ile Leu Pro Tyr Phe
                725                 730                 735
Tyr Thr Leu Phe His Gln Ala His Thr Thr Gly Ser Thr Val Met Arg
                740                 745                 750
Ala Leu Ala Trp Glu Phe Pro Thr Asp Pro Ser Leu Ala Ala Val Asp
                755                 760                 765
Thr Gln Phe Met Val Gly Pro Ser Ile Met Val Val Pro Val Leu Glu
                770                 775                 780
```

```
Pro Leu Ala Asp Thr Val Lys Gly Ala Phe Pro Gly Val Gly Lys Gly
785                 790                 795                 800

Glu Val Trp Tyr Asp Trp Tyr Thr Gln Thr Ala Val Asp Ala Lys Pro
            805                 810                 815

Gly Val Asn Thr Thr Ile Pro Ala Pro Leu Gly His Ile Pro Val Tyr
        820                 825                 830

Val Arg Gly Gly Ser Ile Leu Pro Met Gln Glu Pro Ala Leu Thr Thr
            835                 840                 845

Arg Asp Ala Arg Asn Thr Pro Trp Ser Leu Leu Val Ala Leu Ser Gly
850                 855                 860

Asn Gln Thr Ala Ser Gly Ser Leu Tyr Leu Asp Asp Gly Thr Ser Leu
865                 870                 875                 880

Asn Pro Ser Arg Thr Leu Asp Val Asp Phe Gln Ala Thr Ala Trp Ser
            885                 890                 895

Ile Lys Val Ser Val Lys Gly Thr Trp Glu Glu Lys Asn Arg Leu Asp
            900                 905                 910

Lys Val Thr Val Leu Gly Val Gly Glu Lys Pro Ser Ala Val Thr Phe
            915                 920                 925

Asn Gly Arg Asn Val His Pro Gly Ser Val His Tyr Asn Ala Thr Ser
            930                 935                 940

Lys Val Leu Ser Val Gln Gly Leu His Ser Met Thr Pro His Gly Ala
945                 950                 955                 960

Trp Ala Gly Asn Trp Val Leu Lys Trp
                965

<210> SEQ ID NO 70
<211> LENGTH: 1022
<212> TYPE: PRT
<213> ORGANISM: Neurospora crassa

<400> SEQUENCE: 70

Gln His Val Ser Val Val Ala Thr Ser Ser Gly Pro Gly Val Leu Ser
1               5                   10                  15

Gly Thr Val Ala Gly Asp Ser Pro Met Phe Thr Phe Pro Ala Ser Ala
            20                  25                  30

Asp Ile Gly Pro Asn Val Leu Pro Asn Ile Phe Asp Pro Gln Ala Val
        35                  40                  45

Asn Val Gln Ser Val Cys Pro Gly Tyr Thr Ala Ala Asn Ala Gln Lys
    50                  55                  60

Thr Glu Lys Gly Leu Thr Ala Asp Leu Thr Leu Ala Gly Pro Pro Cys
65                  70                  75                  80

Asn Val Tyr Gly Asn Asp Ile Glu His Leu Lys Leu Thr Ile Glu Phe
                85                  90                  95

Gln Ala Asp Asn Arg Ile Asn Val Gln Ile Gln Pro Arg Tyr Thr Gly
            100                 105                 110

Pro Gly Asn Glu Thr Trp Phe Ile Leu Pro Glu Val Leu Val Pro Arg
        115                 120                 125

Pro Glu Ala Glu Pro Asp Ala Asn Ala Ala Arg Ser Lys Leu Glu Ile
    130                 135                 140

Ser Trp Ser Asn Glu Pro Thr Phe Ser Phe Thr Val Lys Arg Lys Glu
145                 150                 155                 160

Thr Gly Asp Val Leu Phe Thr Thr Glu Gly Arg Val Leu Val Tyr Glu
                165                 170                 175

Asp Gln Phe Ile Glu Phe Gly Ser Ser Leu Pro Glu Asn Tyr Asn Leu
```

```
            180                 185                 190
Tyr Gly Leu Gly Glu Val Met His Gly Phe Arg Leu Gly Asn Asn Leu
        195                 200                 205

Thr Arg Thr Leu Phe Ala Ala Asp Val Gly Asp Asn Leu Asp Ala Asn
210                 215                 220

Ile Tyr Gly Asn His Pro Ile Tyr Leu Asp Thr Arg Tyr Phe Thr Lys
225                 230                 235                 240

Asp Glu Ser Gly Lys Leu Ser Tyr Val Ser Asp Pro Ala Asp Lys Asn
                245                 250                 255

Ala Lys Tyr Val Ser Tyr Thr Asn Gly Val Phe Leu Arg Asn Ala His
                260                 265                 270

Ala Gln Glu Val Leu Leu Arg Pro Glu Gly Ile Thr Trp Arg Thr Leu
            275                 280                 285

Gly Gly Ser Ile Asp Leu Tyr Phe Phe Glu Gly Pro Phe Ala Gln Asp
        290                 295                 300

Ile Ile Lys Ser Tyr Gln Leu Ser Thr Val Gly Leu Pro Ala Met Gln
305                 310                 315                 320

Gln Tyr Trp Thr Leu Gly Phe His Gln Cys Arg Trp Gly Tyr Ser Asn
                325                 330                 335

Trp Thr Val Val Lys Asp Val Val Asp Asn Phe Arg Lys Phe Gly Ile
                340                 345                 350

Pro Leu Glu Thr Ile Trp Thr Asp Ile Asp Tyr Met Lys Gly Tyr Arg
            355                 360                 365

Asp Phe Glu Asn Asp Pro Asp Gln Phe Ser Tyr Glu Glu Gly Ala Arg
        370                 375                 380

Phe Leu Glu Glu Leu His Lys Asn His Gln His Tyr Val Pro Ile Val
385                 390                 395                 400

Asp Ser Ala Ile Tyr Val Pro Asn Pro Asp Lys Pro Glu Asp Asp Tyr
                405                 410                 415

Glu Pro Tyr His Arg Gly Leu Glu Ala Asp Ala Phe Ile Met Asn Pro
                420                 425                 430

Asp Gly Ser Leu Tyr Ile Gly Ala Val Trp Pro Gly Tyr Thr Val Phe
            435                 440                 445

Pro Asp Trp Ile Gly Ala Ala Leu Asn Gly Thr Gly Thr Val Gly Trp
        450                 455                 460

Trp Thr Asp Glu Phe Val Arg Tyr Tyr Lys Lys Val Ala Phe Asp Gly
465                 470                 475                 480

Ile Trp Ile Asp Met Ser Glu Val Ala Ser Phe Cys Ile Gly Ser Cys
                485                 490                 495

Gly Thr Gly Asn Leu Thr Leu Asn Pro Val His Pro Pro Trp Gly Leu
                500                 505                 510

Pro Gly Glu Pro Gly Ala Leu Val Leu Asp Tyr Pro Glu Gly Phe Glu
            515                 520                 525

Lys Thr Asn Ala Ser Glu Ala Ser Ser Ala Thr Ser Val Tyr Lys Thr
        530                 535                 540

Gln Asn Pro Asp Pro Thr Thr Ala Ser Thr Ser Thr Thr Ser
545                 550                 555                 560

Tyr Leu Arg Thr Thr Pro Thr Pro Gly Val Arg Asn Ile Asn Tyr Pro
                565                 570                 575

Pro Tyr Val Ile Asn Asn Phe His Gly Asp Ile Gly Thr His Ala Leu
                580                 585                 590

Ser Pro Asn Gly Thr His His Gly Gly Thr Val Asp Tyr Asp Phe His
            595                 600                 605
```

-continued

```
Asn Leu Phe Gly His Gln Ile Leu His Ala Thr Tyr Gln Ala Leu Leu
    610                 615                 620
Lys Val Phe Glu Gly Lys Arg Pro Phe Ile Ile Gly Arg Ser Thr Phe
625                 630                 635                 640
Ala Gly Ser Gly Lys Trp Ala Gly His Trp Gly Gly Asp Asn Tyr Ser
                645                 650                 655
Leu Trp Ala Phe Leu Tyr Phe Ser Ile Pro Gln Ala Leu Ser Phe Ser
                660                 665                 670
Ile Phe Gly Phe Pro Met Phe Gly Val Asp Thr Cys Gly Phe Asn Gly
            675                 680                 685
Asn Thr Asp His Glu Leu Cys Ser Arg Trp Met Gln Leu Ser Ala Phe
    690                 695                 700
Phe Pro Phe Tyr Arg Asn His Asn Val Arg Gly Ala Ile Ser Gln Glu
705                 710                 715                 720
Pro Tyr Val Trp Ser Ser Val Ile Asp Ala Ser Lys Lys Ala Met Arg
                725                 730                 735
Ile Arg Tyr Leu Leu Pro Tyr Met Tyr Thr Leu Met Ala Gln Ala
                740                 745                 750
Ser Leu Ser Gly Asp Thr Val Met Arg Ala Leu Ser Trp Glu Phe Pro
    755                 760                 765
Gln Glu Pro Trp Leu Ala Asp Ala Asp Arg Gln Phe Met Leu Gly Ser
770                 775                 780
Ala Val Met Val Thr Pro Cys Leu Val Gln Gly Ala Asn Thr Val Asp
785                 790                 795                 800
Gly Val Phe Pro Gly Val Gly Asp Gly Thr Ile Trp Tyr Asp Trp Tyr
                805                 810                 815
Thr Tyr Lys Ala Ala Ser Glu Gly Val Gln Pro Gly Glu Asn Val Thr
            820                 825                 830
Ile Asp Ala Pro Leu Gly His Ile Pro Val Phe Leu Arg Gly Gly His
    835                 840                 845
Val Ile Pro Val Gln Glu Pro Gly Met Thr Thr Thr Glu Ser Arg Gln
    850                 855                 860
Asn Glu Trp Ser Val Ile Val Ala Leu Asp Gly Ala Gly Lys Ala Asn
865                 870                 875                 880
Gly Thr Leu Tyr Leu Asp Asp Gly Glu Ser Leu Glu Pro Gly Glu Asn
                885                 890                 895
Val Lys Trp Val Asp Phe Thr Val Glu Lys Asn Ser Phe Arg Val Thr
            900                 905                 910
Pro Gln Gly Lys Tyr Leu Asp Arg Asn Ser Leu Ala Asn Val Thr Ile
            915                 920                 925
Leu Gly Val Ala Glu Ala Pro Leu Gly Val Ala Ile Asn Ser His Leu
    930                 935                 940
Leu Gly Ser Ala Ser Trp Ser Tyr Asp Ser Glu Gly Lys Phe Leu Ser
945                 950                 955                 960
Val Thr Glu Leu Gln Asp Asn Phe Lys Glu Gly Ala Trp Ala Ser Asn
                965                 970                 975
Trp Thr Leu Ser Trp Asn Ser Ala Ser Asn Ser Gly Ser Ser Pro Val
            980                 985                 990
Gln Gly Gly Gly Gly Arg Leu Glu  Phe Ser Thr Pro Asn  Leu Leu His
    995                 1000                1005
Ala Ala  Ala Phe Gly Ile Leu  Phe Gly Arg Met Phe  Val Val
    1010            1015                1020
```

<210> SEQ ID NO 71
<211> LENGTH: 1012
<212> TYPE: PRT
<213> ORGANISM: Artificial sequence
<220> FEATURE:
<223> OTHER INFORMATION: Derived from Rasamsonia composticola.

<400> SEQUENCE: 71

```
Ala Ile Val Arg Arg Asn Gly Ala Ser Pro Ser Cys Pro Gly Tyr Lys
 1               5                  10                  15

Ala Ser Asn Val Lys Thr Val Asp Gly Glu Ile Val Ser Ala Asp Leu
            20                  25                  30

Asn Leu Ala Gly Pro Ala Cys Asn Val Tyr Gly Thr Asp Leu Asp Asp
        35                  40                  45

Leu Lys Leu Gln Val Glu Tyr Gln Ser Gly Pro Gly Val Arg Ala Asp
50                  55                  60

Cys Leu Leu Pro Phe Asp Val Thr Gly Thr Val Arg Leu Val Asp Asn
65                  70                  75                  80

Asp Leu Thr Ser Ala Glu Gln Arg Leu His Val Lys Ile Tyr Asp Ala
                85                  90                  95

Ala Glu Gln Val Tyr Gln Val Pro Thr Ala Val Leu Pro Arg Pro Ser
            100                 105                 110

Ser Ala Asn Ile Pro Pro Ala Lys Ser Asp Leu Lys Phe Ser Met Thr
        115                 120                 125

Asn Asp Pro Phe Ser Phe Thr Ile Lys Arg Arg Ser Asn Gly Glu Ile
130                 135                 140

Leu Phe Asp Thr Ser Gly His Pro Leu Ile Phe Glu Ser Gln Tyr Leu
145                 150                 155                 160

Gly Leu Arg Thr Lys Leu Pro Asp Ser Pro Asn Ile Tyr Gly Leu Gly
                165                 170                 175

Glu His Thr Gly Ser Phe Arg Leu Pro Thr Lys Asn Tyr Thr Arg Thr
            180                 185                 190

Leu Trp Ser Arg Asp Ala Tyr Gly Thr Pro Lys Asp Thr Asn Leu Tyr
        195                 200                 205

Gly Asn His Pro Val Tyr Phe Asp Tyr Arg Gly Ser Asn Gly Thr His
210                 215                 220

Gly Val Phe Leu Leu Asn Ser Asn Gly Met Asp Val Asp Ile Asp Val
225                 230                 235                 240

Asp Ser Asp Gly Gln Tyr Leu Gln Tyr Asn Thr Leu Gly Gly Val Leu
                245                 250                 255

Asp Phe Tyr Phe Leu Ser Gly Pro Pro Lys Ala Val Ala Thr Gln
            260                 265                 270

Tyr Ala Glu Thr Val Gly Lys Pro Val Met Met Pro Tyr Trp Gly Phe
        275                 280                 285

Gly Phe His Asn Cys Arg Tyr Gly Tyr Gln Asp Ile Tyr Glu Val Ala
290                 295                 300

Glu Ile Ile Ala Asn Tyr Ser Ala Ala Asn Ile Pro Leu Glu Thr Gln
305                 310                 315                 320

Trp Thr Asp Ile Asp Tyr Met Asp Leu Arg Lys Val Phe Thr Leu Asp
                325                 330                 335

Pro Tyr Arg Tyr Pro Leu Lys Leu Val Gln Glu Val Val Ser Tyr Leu
            340                 345                 350

His Lys His Asn Gln His Tyr Ile Met Met Val Asp Pro Ala Val Ala
        355                 360                 365
```

```
Tyr Gln Asn Tyr Ser Ala Phe Asn Asn Gly Val Ala Ala Asp Ala Phe
    370                 375                 380

Leu Lys Phe Ser Asn Gly Ser Ile Tyr Gln Gly Val Val Trp Pro Gly
385                 390                 395                 400

Pro Thr Ala Phe Pro Asp Trp Phe Ala Pro Gln Thr Gln Glu Phe Trp
                405                 410                 415

Asn Ser Glu Phe Ser Thr Phe Phe Asp Pro Ala His Gly Val Asp Ile
            420                 425                 430

Asp Ala Leu Trp Ile Asp Met Asn Glu Ala Ser Asn Phe Cys Asp Phe
                435                 440                 445

Pro Cys Ser Asn Pro Ala Ala Tyr Ala Ala Ala Asn Gly Asp Pro Pro
            450                 455                 460

Thr Pro Pro Pro Val Arg Leu Ser Pro Pro Arg Pro Ile Pro Gly Phe
465                 470                 475                 480

Gly Pro Asp Phe Gln Pro Thr Cys Val Ala Thr Val Ser Phe Asp Cys
                485                 490                 495

Asp Ala Gln Thr Tyr Phe Gly Glu Asn Ile Leu Ile Leu Gly Asn Ser
                500                 505                 510

Thr Thr Leu Gly Ala Gly Asp Val His Met Ala Pro Val Met Ser Ala
            515                 520                 525

Asn Asn Tyr Pro Ile Trp Gln Leu Thr Val Gln Met Pro Pro Asn Gly
            530                 535                 540

Thr Phe Ser Tyr Gln Tyr Val Arg Lys Glu Ser Asp Gly Ser Tyr Ile
545                 550                 555                 560

Tyr Glu Gln Thr Asn Arg Thr Val Thr Thr Gly Asp Cys Thr Ser Gly
                565                 570                 575

Thr Leu Lys Val Ser Asp Thr Ile Thr Thr Ser Ser Gly Pro His Lys
            580                 585                 590

Arg Ser Glu Leu Arg Pro Leu Val Arg Ser Pro Phe Pro Ala Glu Asp
            595                 600                 605

Leu Thr Arg Arg Gln Ser Gly Ser Met Leu Gly Leu Pro Asn Arg Asn
            610                 615                 620

Leu Leu Asn Pro Pro Tyr Thr Ile His Asn Ala Ala Gly Asn Leu Ser
625                 630                 635                 640

Glu Lys Thr Ile Asn Thr Asp Leu Ile His Ala Gly Gly Tyr Ala Glu
                645                 650                 655

Tyr Asp Thr His Asn Leu Tyr Gly Thr Met Met Ser Ala Thr Ser Arg
                660                 665                 670

Glu Ala Met Leu Asn Arg Arg Pro Ala Val Arg Pro Leu Val Ile Thr
            675                 680                 685

Arg Ser Thr Phe Ala Gly Ala Gly Arg Gln Val Gly His Trp Leu Gly
            690                 695                 700

Asp Asn Phe Ala Asp Trp Asp His Tyr Arg Trp Thr Ile Ala Glu Leu
705                 710                 715                 720

Gln Glu Phe Ala Ala Leu Phe Gln Ile Pro Met Val Gly Ser Asp Ile
                725                 730                 735

Cys Gly Tyr Asp Gly Asn Thr Thr Asp Asn Leu Cys Ser Arg Trp Val
                740                 745                 750

Phe Leu Gly Ala Phe Ser Pro Phe Phe Arg Asp His Ser Asp Asn Gln
                755                 760                 765

Ser Pro Pro His Glu Leu Tyr Arg Thr Pro Gln Ile Ala Ala Ala Ala
            770                 775                 780

Arg Ala Ala Ile Asp Ile Arg Tyr Arg Leu Leu Asp Tyr Ala Tyr Thr
```

```
                785                 790                 795                 800
Val Leu Trp Thr Gln Thr Gln Thr Gly Ala Pro Met Leu Asn Pro Met
                805                 810                 815

Phe Phe Glu Tyr Pro Ala Asp Ser Asn Thr Ala Asp Leu Gln Tyr Gln
            820                 825                 830

Phe Phe Trp Gly Asp Ser Ile Met Val Ala Pro Val Thr Asp Asn Asp
            835                 840                 845

Ser Thr Thr Val Asn Val Tyr Phe Pro Lys Asp Gln Phe Tyr Asp Phe
    850                 855                 860

Tyr Thr Gly Ala Pro Val Ser Gly Glu Gly Asn Thr Val Thr Leu Thr
865                 870                 875                 880

Asp Val Gly Phe Asp Thr Ile Pro Leu Tyr Phe Lys Gly Gly Ser Ile
                885                 890                 895

Val Pro Met Arg Val Arg Ser Ala Asn Thr Thr Ala Glu Leu Arg Gln
                900                 905                 910

Gln Asp Phe Val Val Ile Ala Pro Asp Ser His Gly Asp Ala Thr
            915                 920                 925

Gly Gln Leu Tyr Leu Asp Asp Gly Glu Ser Ile Asn Gln Pro His Thr
        930                 935                 940

Ser Glu Ile Gln Phe Ser Tyr Arg Gly Gly His Phe Ser Met Thr Gly
945                 950                 955                 960

Lys Phe Asp Tyr Asp Pro Gly Asn Val Val Ile Ser Gln Ile Thr Leu
                965                 970                 975

Leu Gly Ala Asp Gly Ala Gly Lys Gly Gly Ser Tyr Asn Ser Thr Thr
            980                 985                 990

Lys Val Ala Thr Tyr Lys Val Asn  Ala Lys Leu Thr Gly  Lys Phe Glu
        995                 1000                1005

Ala Ser  Leu His
     1010

<210> SEQ ID NO 72
<211> LENGTH: 984
<212> TYPE: PRT
<213> ORGANISM: Rasamsonia composticola

<400> SEQUENCE: 72

Ala Ile Val Arg Arg Asn Gly Ala Ser Pro Ser Cys Pro Gly Tyr Lys
1               5                   10                  15

Ala Ser Asn Val Lys Thr Val Asp Gly Glu Ile Val Ser Ala Asp Leu
            20                  25                  30

Asn Leu Ala Gly Pro Ala Cys Asn Val Tyr Gly Thr Asp Leu Asp Asp
        35                  40                  45

Leu Lys Leu Gln Val Glu Tyr Gln Ser Glu Gln Arg Leu His Val Lys
    50                  55                  60

Ile Tyr Asp Ala Ala Glu Gln Val Tyr Gln Val Pro Thr Ala Val Leu
65                  70                  75                  80

Pro Arg Pro Ser Ser Ala Asn Ile Pro Ala Lys Ser Asp Leu Lys
                85                  90                  95

Phe Ser Met Thr Asn Asp Pro Phe Ser Phe Thr Ile Lys Arg Arg Ser
            100                 105                 110

Asn Gly Glu Ile Leu Phe Asp Thr Ser Gly His Pro Leu Ile Phe Glu
        115                 120                 125

Ser Gln Tyr Leu Gly Leu Arg Thr Lys Leu Pro Asp Ser Pro Asn Ile
    130                 135                 140
```

```
Tyr Gly Leu Gly Glu His Thr Gly Ser Phe Arg Leu Pro Thr Lys Asn
145                 150                 155                 160

Tyr Thr Arg Thr Leu Trp Ser Arg Asp Ala Tyr Gly Thr Pro Lys Asp
            165                 170                 175

Thr Asn Leu Tyr Gly Asn His Pro Val Tyr Phe Asp Tyr Arg Gly Ser
                180                 185                 190

Asn Gly Thr His Gly Val Phe Leu Leu Asn Ser Asn Gly Met Asp Val
        195                 200                 205

Asp Ile Asp Val Asp Ser Asp Gly Gln Tyr Leu Gln Tyr Asn Thr Leu
    210                 215                 220

Gly Gly Val Leu Asp Phe Tyr Phe Leu Ser Gly Pro Asp Pro Lys Ala
225                 230                 235                 240

Val Ala Thr Gln Tyr Ala Glu Thr Val Gly Lys Pro Val Met Met Pro
                245                 250                 255

Tyr Trp Gly Phe Gly Phe His Asn Cys Arg Tyr Gly Tyr Gln Asp Ile
                260                 265                 270

Tyr Glu Val Ala Glu Ile Ile Ala Asn Tyr Ser Ala Ala Asn Ile Pro
        275                 280                 285

Leu Glu Thr Gln Trp Thr Asp Ile Asp Tyr Met Asp Leu Arg Lys Val
    290                 295                 300

Phe Thr Leu Asp Pro Tyr Arg Tyr Pro Leu Lys Leu Val Gln Glu Val
305                 310                 315                 320

Val Ser Tyr Leu His Lys His Asn Gln His Tyr Ile Met Met Val Asp
                325                 330                 335

Pro Ala Val Ala Tyr Gln Asn Tyr Ser Ala Phe Asn Asn Gly Val Ala
                340                 345                 350

Ala Asp Ala Phe Leu Lys Phe Ser Asn Gly Ser Ile Tyr Gln Gly Val
        355                 360                 365

Val Trp Pro Gly Pro Thr Ala Phe Pro Asp Trp Phe Ala Pro Gln Thr
    370                 375                 380

Gln Glu Phe Trp Asn Ser Glu Phe Ser Thr Phe Phe Asp Pro Ala His
385                 390                 395                 400

Gly Val Asp Ile Asp Ala Leu Trp Ile Asp Met Asn Glu Ala Ser Asn
                405                 410                 415

Phe Cys Asp Phe Pro Cys Ser Asn Pro Ala Ala Tyr Ala Ala Ala Asn
                420                 425                 430

Gly Asp Pro Pro Thr Pro Pro Val Arg Leu Ser Pro Arg Pro
        435                 440                 445

Ile Pro Gly Phe Gly Pro Asp Phe Gln Pro Thr Cys Val Ala Thr Val
    450                 455                 460

Ser Phe Asp Cys Asp Ala Gln Thr Tyr Phe Gly Glu Asn Ile Leu Ile
465                 470                 475                 480

Leu Gly Asn Ser Thr Thr Leu Gly Ala Gly Asp Val His Met Ala Pro
                485                 490                 495

Val Met Ser Ala Asn Asn Tyr Pro Ile Trp Gln Leu Thr Val Gln Met
                500                 505                 510

Pro Pro Asn Gly Thr Phe Ser Tyr Gln Tyr Val Arg Lys Glu Ser Asp
                515                 520                 525

Gly Ser Tyr Ile Tyr Glu Gln Thr Asn Arg Thr Val Thr Thr Gly Asp
        530                 535                 540

Cys Thr Ser Gly Thr Leu Lys Val Ser Asp Thr Ile Thr Thr Ser Ser
545                 550                 555                 560

Gly Pro His Lys Arg Ser Glu Leu Arg Pro Leu Val Arg Ser Pro Phe
```

```
                565                 570                 575
Pro Ala Glu Asp Leu Thr Arg Arg Gln Ser Gly Ser Met Leu Gly Leu
                580                 585                 590

Pro Asn Arg Asn Leu Leu Asn Pro Pro Tyr Thr Ile His Asn Ala Ala
            595                 600                 605

Gly Asn Leu Ser Glu Lys Thr Ile Asn Thr Asp Leu Ile His Ala Gly
        610                 615                 620

Gly Tyr Ala Glu Tyr Asp Thr His Asn Leu Tyr Gly Thr Met Met Ser
625                 630                 635                 640

Ala Thr Ser Arg Glu Ala Met Leu Asn Arg Arg Pro Ala Val Arg Pro
                645                 650                 655

Leu Val Ile Thr Arg Ser Thr Phe Ala Gly Ala Gly Arg Gln Val Gly
            660                 665                 670

His Trp Leu Gly Asp Asn Phe Ala Asp Trp Asp His Tyr Arg Trp Thr
        675                 680                 685

Ile Ala Glu Leu Gln Glu Phe Ala Ala Leu Phe Gln Ile Pro Met Val
    690                 695                 700

Gly Ser Asp Ile Cys Gly Tyr Asp Gly Asn Thr Thr Asp Asn Leu Cys
705                 710                 715                 720

Ser Arg Trp Val Phe Leu Gly Ala Phe Ser Pro Phe Arg Asp His
                725                 730                 735

Ser Asp Asn Gln Ser Pro Pro His Glu Leu Tyr Arg Thr Pro Gln Ile
            740                 745                 750

Ala Ala Ala Ala Arg Ala Ala Ile Asp Ile Arg Tyr Arg Leu Leu Asp
        755                 760                 765

Tyr Ala Tyr Thr Val Leu Trp Thr Gln Thr Gln Thr Gly Ala Pro Met
770                 775                 780

Leu Asn Pro Met Phe Phe Glu Tyr Pro Ala Asp Ser Asn Thr Ala Asp
785                 790                 795                 800

Leu Gln Tyr Gln Phe Phe Trp Gly Asp Ser Ile Met Val Ala Pro Val
                805                 810                 815

Thr Asp Asn Asp Ser Thr Thr Val Asn Val Tyr Phe Pro Lys Asp Gln
            820                 825                 830

Phe Tyr Asp Phe Tyr Thr Gly Ala Pro Val Ser Gly Glu Gly Asn Thr
        835                 840                 845

Val Thr Leu Thr Asp Val Gly Phe Asp Thr Ile Pro Leu Tyr Phe Lys
850                 855                 860

Gly Gly Ser Ile Val Pro Met Arg Val Arg Ser Ala Asn Thr Thr Ala
865                 870                 875                 880

Glu Leu Arg Gln Gln Asp Phe Val Val Ile Ala Pro Asp Ser His
                885                 890                 895

Gly Asp Ala Thr Gly Gln Leu Tyr Leu Asp Asp Gly Glu Ser Ile Asn
            900                 905                 910

Gln Pro His Thr Ser Glu Ile Gln Phe Ser Tyr Arg Gly Gly His Phe
        915                 920                 925

Ser Met Thr Gly Lys Phe Asp Tyr Asp Pro Gly Asn Val Val Ile Ser
930                 935                 940

Gln Ile Thr Leu Leu Gly Ala Asp Gly Ala Gly Lys Gly Gly Ser Tyr
945                 950                 955                 960

Asn Ser Thr Thr Lys Val Ala Thr Tyr Lys Val Asn Ala Lys Leu Thr
                965                 970                 975

Gly Lys Phe Glu Ala Ser Leu His
            980
```

<210> SEQ ID NO 73
<211> LENGTH: 984
<212> TYPE: PRT
<213> ORGANISM: Artificial sequence
<220> FEATURE:
<223> OTHER INFORMATION: Derived from Rasamsonia composticola.

<400> SEQUENCE: 73

| | | | | | | | | | | | | | | |
|---|---|---|---|---|---|---|---|---|---|---|---|---|---|---|
| Ala | Ile | Val | Arg | Arg | Asn | Gly | Ala | Ser | Pro | Ser | Cys | Pro | Gly | Tyr | Lys |
| 1 | | | | 5 | | | | | 10 | | | | | 15 | |
| Ala | Ser | Asn | Val | Lys | Thr | Val | Asp | Gly | Glu | Ile | Val | Ser | Ala | Asp | Leu |
| | | | 20 | | | | | 25 | | | | | 30 | | |
| Asn | Leu | Ala | Gly | Pro | Ala | Cys | Asn | Val | Tyr | Gly | Thr | Asp | Leu | Asp | Asp |
| | | | 35 | | | | | 40 | | | | | 45 | | |
| Leu | Lys | Leu | Gln | Val | Glu | Tyr | Gln | Ser | Glu | Gln | Arg | Leu | His | Val | Lys |
| | 50 | | | | | 55 | | | | | 60 | | | | |
| Ile | Tyr | Asp | Ala | Ala | Glu | Gln | Val | Tyr | Gln | Val | Pro | Thr | Ala | Val | Leu |
| 65 | | | | | 70 | | | | | 75 | | | | | 80 |
| Pro | Arg | Pro | Ser | Ser | Ala | Asn | Ile | Pro | Pro | Ala | Lys | Ser | Asp | Leu | Lys |
| | | | | 85 | | | | | 90 | | | | | 95 | |
| Phe | Ser | Met | Thr | Asn | Asp | Pro | Phe | Ser | Phe | Thr | Ile | Lys | Arg | Arg | Ser |
| | | | 100 | | | | | 105 | | | | | 110 | | |
| Asn | Gly | Glu | Ile | Leu | Phe | Asp | Thr | Ser | Gly | His | Pro | Leu | Ile | Phe | Glu |
| | | | 115 | | | | | 120 | | | | | 125 | | |
| Ser | Gln | Tyr | Leu | Gly | Leu | Arg | Thr | Lys | Leu | Pro | Asp | Ser | Pro | Asn | Ile |
| | 130 | | | | | 135 | | | | | 140 | | | | |
| Tyr | Gly | Leu | Gly | Glu | His | Thr | Gly | Ser | Phe | Arg | Leu | Pro | Thr | Lys | Asn |
| 145 | | | | | 150 | | | | | 155 | | | | | 160 |
| Tyr | Thr | Arg | Thr | Leu | Trp | Ser | Arg | Asp | Ala | Tyr | Gly | Thr | Pro | Lys | Asp |
| | | | | 165 | | | | | 170 | | | | | 175 | |
| Thr | Asn | Leu | Tyr | Gly | Asn | His | Pro | Val | Tyr | Phe | Asp | Tyr | Arg | Gly | Ser |
| | | | 180 | | | | | 185 | | | | | 190 | | |
| Asn | Gly | Thr | His | Gly | Val | Phe | Leu | Leu | Asn | Ser | Asn | Gly | Met | Asp | Val |
| | | | 195 | | | | | 200 | | | | | 205 | | |
| Asp | Ile | Asp | Val | Asp | Ser | Asp | Gly | Gln | Tyr | Leu | Gln | Tyr | Asn | Thr | Leu |
| | 210 | | | | | 215 | | | | | 220 | | | | |
| Gly | Gly | Val | Leu | Asp | Phe | Tyr | Phe | Leu | Ser | Gly | Pro | Asp | Pro | Lys | Ala |
| 225 | | | | | 230 | | | | | 235 | | | | | 240 |
| Val | Ala | Thr | Gln | Tyr | Ala | Glu | Thr | Val | Gly | Lys | Pro | Val | Met | Met | Pro |
| | | | | 245 | | | | | 250 | | | | | 255 | |
| Tyr | Trp | Gly | Phe | Gly | Phe | His | Asn | Cys | Arg | Tyr | Gly | Tyr | Gln | Asp | Ile |
| | | | 260 | | | | | 265 | | | | | 270 | | |
| Tyr | Glu | Val | Ala | Glu | Ile | Ile | Ala | Asn | Tyr | Ser | Ala | Ala | Asn | Ile | Pro |
| | | | 275 | | | | | 280 | | | | | 285 | | |
| Leu | Glu | Thr | Gln | Trp | Thr | Asp | Ile | Asp | Tyr | Met | Asp | Leu | Arg | Lys | Val |
| | 290 | | | | | 295 | | | | | 300 | | | | |
| Phe | Thr | Leu | Asp | Pro | Tyr | Arg | Tyr | Pro | Leu | Lys | Leu | Val | Gln | Glu | Val |
| 305 | | | | | 310 | | | | | 315 | | | | | 320 |
| Val | Ser | Tyr | Leu | His | Lys | His | Asn | Gln | His | Tyr | Ile | Met | Met | Val | Asp |
| | | | | 325 | | | | | 330 | | | | | 335 | |
| Pro | Ala | Val | Ala | Tyr | Gln | Asn | Tyr | Ser | Ala | Phe | Asn | Asn | Gly | Val | Ala |
| | | | 340 | | | | | 345 | | | | | 350 | | |
| Ala | Asp | Ala | Phe | Leu | Lys | Phe | Ser | Asn | Gly | Ser | Ile | Tyr | Gln | Gly | Val |
| | | | 355 | | | | | 360 | | | | | 365 | | |

```
Val Trp Pro Gly Pro Thr Ala Phe Pro Asp Trp Phe Ala Pro Gln Thr
    370                 375                 380

Gln Glu Phe Trp Asn Ser Glu Phe Ser Thr Phe Phe Asp Pro Ala His
385                 390                 395                 400

Gly Val Asp Ile Asp Ala Leu Trp Ile Asp Met Asn Glu Ala Ser Asn
                405                 410                 415

Phe Cys Asp Phe Pro Cys Ser Asn Pro Ala Ala Tyr Ala Ala Ala Asn
                420                 425                 430

Gly Asp Pro Pro Thr Pro Pro Val Arg Leu Ser Pro Pro Arg Pro
            435                 440                 445

Ile Pro Gly Phe Gly Pro Asp Phe Gln Pro Thr Cys Val Ala Thr Val
    450                 455                 460

Ser Phe Asp Cys Asp Ala Gln Thr Tyr Phe Gly Glu Asn Ile Leu Ile
465                 470                 475                 480

Leu Gly Asn Ser Thr Thr Leu Gly Ala Gly Asp Val His Met Ala Pro
                485                 490                 495

Val Met Ser Ala Asn Asn Tyr Pro Ile Trp Gln Leu Thr Val Gln Met
                500                 505                 510

Pro Pro Asn Gly Thr Phe Ser Tyr Gln Tyr Val Arg Lys Glu Ser Asp
            515                 520                 525

Gly Ser Tyr Ile Tyr Glu Gln Thr Asn Arg Thr Val Thr Thr Gly Asp
    530                 535                 540

Cys Thr Ser Gly Thr Leu Lys Val Ser Asp Thr Ile Thr Thr Ser Ser
545                 550                 555                 560

Gly Pro His Lys Arg Ser Glu Leu Arg Pro Leu Val Arg Ser Pro Phe
                565                 570                 575

Pro Ala Glu Asp Leu Thr Arg Arg Gln Ser Gly Ser Met Leu Gly Leu
            580                 585                 590

Pro Asn Arg Asn Leu Leu Asn Pro Pro Tyr Thr Ile His Asn Ala Ala
    595                 600                 605

Gly Asn Leu Ser Glu Lys Thr Ile Asn Thr Asp Leu Ile His Ala Gly
        610                 615                 620

Gly Tyr Ala Glu Tyr Asp Thr His Asn Leu Tyr Gly Thr Met Met Ser
625                 630                 635                 640

Ala Thr Ser Arg Glu Ala Met Leu Asn Arg Arg Pro Ala Val Arg Pro
                645                 650                 655

Leu Val Ile Thr Arg Ser Thr Phe Ala Gly Ala Gly Arg Gln Val Gly
            660                 665                 670

His Trp Leu Gly Asp Asn Phe Ala Asp Trp Asp His Tyr Arg Trp Thr
    675                 680                 685

Ile Ala Glu Leu Gln Glu Phe Ala Ala Leu Phe Gln Ile Pro Met Val
    690                 695                 700

Gly Ser Asp Ile Cys Gly Tyr Asp Gly Asn Thr Thr Asp Asn Leu Cys
705                 710                 715                 720

Ser Arg Trp Val Phe Leu Gly Ala Phe Ser Pro Phe Phe Arg Asp His
                725                 730                 735

Ser Asp Asn Gln Ser Pro Pro His Glu Leu Tyr Arg Thr Pro Gln Ile
            740                 745                 750

Ala Ala Ala Ala Arg Ala Ala Ile Asp Ile Arg Tyr Arg Leu Leu Asp
        755                 760                 765

Tyr Ala Tyr Thr Val Leu Trp Thr Gln Thr Gln Thr Gly Ala Pro Met
    770                 775                 780
```

```
Leu Asn Pro Met Phe Phe Glu Tyr Pro Ala Asp Ser Asn Thr Ala Asp
785                 790                 795                 800

Leu Gln Tyr Gln Phe Phe Trp Gly Asp Ser Ile Met Val Ala Pro Val
            805                 810                 815

Thr Asp Asn Asp Ser Thr Thr Val Asn Val Tyr Phe Pro Lys Asp Gln
        820                 825                 830

Phe Tyr Asp Phe Tyr Thr Gly Ala Pro Val Ser Gly Glu Gly Asn Thr
    835                 840                 845

Val Thr Leu Thr Asp Val Gly Phe Asp Thr Ile Pro Leu Tyr Phe Lys
850                 855                 860

Gly Gly Ser Ile Val Pro Met Arg Val Arg Ser Ala Asn Thr Thr Ala
865                 870                 875                 880

Glu Leu Arg Gln Gln Asp Phe Val Val Ile Ala Pro Asp Ser His
            885                 890                 895

Gly Asp Ala Thr Gly Gln Leu Tyr Leu Asp Asp Gly Glu Ser Ile Asn
        900                 905                 910

Gln Pro His Thr Ser Glu Ile Gln Phe Ser Tyr Arg Gly Gly His Phe
    915                 920                 925

Ser Met Thr Gly Lys Phe Asp Tyr Asp Pro Gly Asn Val Val Ile Ser
930                 935                 940

Gln Ile Thr Leu Leu Gly Ala Asp Ser Ala Gly Lys Gly Ser Tyr
945                 950                 955                 960

Asn Ser Thr Thr Lys Val Ala Thr Tyr Lys Val Asn Ala Lys Leu Thr
            965                 970                 975

Gly Lys Phe Glu Ala Ser Leu His
            980

<210> SEQ ID NO 74
<211> LENGTH: 973
<212> TYPE: PRT
<213> ORGANISM: Rasamsonia composticola

<400> SEQUENCE: 74

Phe Asp Ala Leu Ala Gly Pro Val Ser Ser Thr Thr Ala Ala Ala Pro
1               5                   10                  15

Ser Ala Gln Phe Thr Val Pro Ala Ala Ala Asp Val Gly Ala Asn Leu
            20                  25                  30

Leu Ala Asn Ile Asp Asp Pro Asn Ala Val Asn Ala Gln Asp Val Cys
        35                  40                  45

Pro Gly Tyr Thr Ala Ser Asn Val Gln Asn Thr Glu Ser Gly Phe Val
    50                  55                  60

Ala Thr Leu Thr Leu Ala Gly Lys Pro Cys Asn Val Tyr Gly Thr Asp
65                  70                  75                  80

Val Glu Ser Leu Asn Leu Thr Val Glu Tyr Gln Ala Ala Asp Arg Leu
                85                  90                  95

Asn Ile Asn Ile Val Pro Thr His Val Asp Ser Ser Asn Gln Ser Trp
            100                 105                 110

Tyr Leu Leu Pro Glu Asn Val Val Pro Lys Pro Gly Val Asp Ala Gly
        115                 120                 125

Ala Gln Val Pro Glu Ser Asp Leu Val Phe Ser Trp Ser Asn Glu Pro
    130                 135                 140

Ser Phe Asn Phe Lys Val Ile Arg Lys Ala Thr Gly Asp Ile Leu Phe
145                 150                 155                 160

Asp Thr Glu Gly Ser Val Leu Val Phe Glu Asn Gln Phe Ile Glu Phe
                165                 170                 175
```

```
Ala Ser Ala Leu Pro Glu Asn Tyr Asn Leu Tyr Gly Leu Gly Glu Arg
            180                 185                 190

Ile His Gly Leu Arg Leu Gly Asn Asn Phe Thr Ala Thr Thr Tyr Ala
        195                 200                 205

Ala Asp Ser Ala Asp Pro Ile Asp Arg Asn Ile Tyr Gly Thr His Pro
210                 215                 220

Phe Tyr Leu Asp Thr Arg Tyr Tyr Glu Val Asp Ser Glu His Gly Arg
225                 230                 235                 240

Phe Thr Leu Val Thr Asp Asn Glu Thr Asp Phe Ser Lys Glu Tyr Leu
                245                 250                 255

Ser Leu Ser His Gly Val Phe Leu Arg Asn Ala His Gly Gln Glu Val
                260                 265                 270

Leu Leu Arg Pro Gln Ser Ile Thr Trp Arg Thr Leu Gly Gly Ser Ile
            275                 280                 285

Asp Leu Tyr Phe Tyr Ala Gly Pro Thr Gln Ala Asp Val Thr Arg Ser
        290                 295                 300

Tyr Gln Thr Ser Thr Val Gly Leu Pro Ala Met Gln Gln Tyr Phe Thr
305                 310                 315                 320

Leu Gly Tyr His Gln Cys Arg Trp Gly Tyr Arg Asn Trp Ser Glu Leu
                325                 330                 335

Ala Asp Val Val Ala Asn Phe Glu Lys Phe Glu Ile Pro Leu Glu Asn
                340                 345                 350

Ile Trp Ser Asp Ile Asp Tyr Met Asn Glu Tyr Arg Asp Phe Glu Asn
            355                 360                 365

Asp Pro Val Arg Phe Ser Tyr Ser Glu Gly Ala Lys Phe Leu Asp Gln
        370                 375                 380

Leu His Lys Ser Gly Arg His Tyr Ile Pro Ile Val Asp Ala Ala Ile
385                 390                 395                 400

Tyr Asp Pro Asn Pro Asn Asn Asp Ser Asp Ala Tyr Ala Thr Tyr Asp
                405                 410                 415

Arg Gly Ser Lys Asp Asp Ile Trp Leu Lys Asn Pro Asp Gly Ser Val
                420                 425                 430

Tyr Ile Gly Ala Val Trp Pro Gly Tyr Thr Val Phe Thr Asp Trp His
            435                 440                 445

His Pro Lys Ala Asn Glu Trp Trp Ala Asn Glu Leu Ala Leu Trp His
        450                 455                 460

Glu Lys Val Ala Phe Asp Gly Ile Trp Leu Asp Met Asn Glu Val Ser
465                 470                 475                 480

Ser Phe Cys Val Gly Ser Cys Gly Thr Gly Asn Leu Thr Leu Asn Pro
                485                 490                 495

Val His Pro Asn Phe Ala Leu Pro Gly Glu Pro Gly Ala Val Ile Tyr
                500                 505                 510

Asp Tyr Pro Glu Asp Phe Asn Val Thr Asn Ala Thr Ala Ala Ala Ser
            515                 520                 525

Ala Ser Ala Ala Ser Ser Gln Ala Ala Thr Ala Thr Ala Thr
        530                 535                 540

Ser Ser Ser Thr Thr Thr Ser Tyr Leu Val Thr Thr Pro Thr Pro Gly
545                 550                 555                 560

Val Arg Asn Val Asn Tyr Pro Pro Tyr Val Ile Asn His Val Gln Glu
                565                 570                 575

Gly His Asp Leu Ala Val His Ala Val Ser Pro Asn Ala Thr His Val
            580                 585                 590
```

```
Asp Gly Val Gln Glu Tyr Asp Val His Asn Leu Trp Gly Tyr Gln Glu
            595                 600                 605

Thr Asn Ala Thr Tyr His Ala Leu Leu Ser Ile Phe Pro Gly Lys Arg
    610                 615                 620

Pro Phe Ile Ile Ser Arg Ser Thr Phe Ala Gly Ser Gly Arg Trp Ala
625                 630                 635                 640

Gly His Trp Gly Gly Asp Asn Ala Ser Lys Trp Ala Tyr Met Phe Phe
                645                 650                 655

Ser Ile Pro Gln Ala Leu Ser Phe Ser Leu Phe Gly Ile Pro Met Phe
                660                 665                 670

Gly Val Asp Thr Cys Gly Phe Asn Gly Asn Ser Asp Glu Glu Leu Cys
                675                 680                 685

Asn Arg Trp Met Gln Leu Ser Ala Phe Phe Pro Phe Tyr Arg Asn His
            690                 695                 700

Asn Val Leu Ser Ala Ile Pro Gln Glu Pro Tyr Val Trp Ala Ser Val
705                 710                 715                 720

Ile Glu Ala Ser Lys Ser Ala Met Arg Ile Arg Tyr Thr Leu Leu Pro
                725                 730                 735

Tyr Leu Tyr Thr Leu Phe Tyr Leu Ala His Thr Thr Gly Ser Thr Val
                740                 745                 750

Met Arg Ala Leu Ala Trp Glu Phe Pro Asn Asp Pro Ser Leu Ala Ala
            755                 760                 765

Val Asp Arg Gln Phe Leu Leu Gly Pro Ser Leu Met Val Val Pro Val
            770                 775                 780

Leu Glu Pro Gln Val Asp Thr Val Lys Gly Val Phe Pro Gly Val Ala
785                 790                 795                 800

Gln Gly Gln Val Trp Tyr Asp Trp Tyr Thr Gln Thr Ala Phe Asp Ala
                805                 810                 815

Gln Pro Gly Val Asn Thr Thr Ile Ser Ala Pro Leu Gly His Ile Pro
                820                 825                 830

Val Phe Val Arg Gly Gly Ser Val Leu Pro Met Gln Gln Pro Ala Leu
            835                 840                 845

Val Thr Arg Asp Val Arg Asn Ser Pro Trp Ser Leu Leu Val Ala Leu
            850                 855                 860

Gly Ser Asp Gly Thr Ala Ser Gly Gln Leu Tyr Val Asp Asp Gly Glu
865                 870                 875                 880

Ser Ile Thr Pro Pro Ala Ser Leu His Val Asp Phe Val Ala Ala Asn
                885                 890                 895

Phe Ser Thr Leu Phe Ala Thr Ala Arg Gly Ala Phe Lys Asp Ser Asn
                900                 905                 910

Thr Leu Ala Asn Val Thr Val Leu Gly Val Pro Ala Ala Pro Ser Ser
            915                 920                 925

Ala Val Thr Trp Asn Asn Glu Thr Val Pro Ser Glu Ser Val Ser Tyr
930                 935                 940

Asn Ala Thr Ser Lys Val Leu Val Asn Gly Leu Gln Ser Leu Thr
945                 950                 955                 960

Arg Asp Gly Ala Trp Ser Ser Asp Trp Val Leu Lys Trp
                965                 970

<210> SEQ ID NO 75
<211> LENGTH: 604
<212> TYPE: PRT
<213> ORGANISM: Bifidobacterium longum

<400> SEQUENCE: 75
```

-continued

```
Met Thr Ala Asn Asn Leu Asn Asp Asp Trp Trp Lys Gln Ala Val Val
1               5                   10                  15

Tyr Gln Ile Tyr Pro Arg Ser Phe Lys Asp Val Asn Gly Asp Gly Leu
            20                  25                  30

Gly Asp Ile Ala Gly Val Thr Glu Lys Met Asp Tyr Leu Lys Asn Leu
        35                  40                  45

Gly Val Asp Ala Ile Trp Leu Ser Pro Phe Tyr Pro Ser Asp Leu Ala
    50                  55                  60

Asp Gly Gly Tyr Asp Val Ile Asp Tyr Arg Asn Val Asp Pro Arg Leu
65                  70                  75                  80

Gly Thr Met Glu Asp Phe Asp Ala Met Ala Lys Ala His Glu Ala
                85                  90                  95

Gly Ile Lys Val Ile Val Asp Ile Val Pro Asn His Thr Ala Asp Lys
            100                 105                 110

His Val Phe Phe Gln Glu Ala Leu Ala Ala Glu Pro Gly Ser Pro Ala
        115                 120                 125

Arg Asp Arg Tyr Ile Phe Arg Asp Arg Gly Glu His Gly Glu Leu
    130                 135                 140

Pro Pro Asn Asp Trp Gln Ser Phe Phe Gly Pro Ala Trp Ala Arg
145                 150                 155                 160

Val Ala Asp Gly Gln Trp Tyr Leu His Leu Phe Asp Lys Ala Gln Pro
            165                 170                 175

Asp Val Asn Trp Lys Asn Pro Asp Ile His Glu Glu Phe Lys Lys Thr
            180                 185                 190

Leu Arg Phe Trp Ser Asp His Gly Thr Asp Gly Phe Arg Ile Asp Val
        195                 200                 205

Ala His Gly Leu Ala Lys Asp Leu Glu Ser Lys Pro Leu Glu Glu Leu
    210                 215                 220

Gly Arg Glu Tyr Ser Val Val Gly Val Leu Asn His Asp Phe Ser His
225                 230                 235                 240

Pro Leu Phe Asp Arg Arg Glu Val His Asp Ile Tyr Arg Glu Trp Arg
            245                 250                 255

Lys Val Phe Asn Glu Tyr Asp Pro Pro Arg Phe Ala Val Ala Glu Ala
            260                 265                 270

Trp Val Val Pro Glu His Gln His Leu Tyr Ala Ser Met Asp Glu Leu
        275                 280                 285

Gly Gln Ser Phe Asn Phe Asp Phe Ala Gln Ala Asn Trp Tyr Ala Asp
    290                 295                 300

Glu Phe Arg Glu Ala Ile Ala Ala Gly Leu Lys Ala Ala Ala Glu Thr
305                 310                 315                 320

Gly Gly Ser Thr Thr Thr Trp Val Met Asn Asn His Asp Val Pro Arg
            325                 330                 335

Ser Pro Ser Arg Tyr Gly Leu Pro Gln Ile Lys Gly Ala Pro Tyr His
            340                 345                 350

Gln Leu Pro His Asp Trp Leu Leu Arg Asn Gly Thr Thr Tyr Pro Glu
        355                 360                 365

Asp Arg Glu Leu Gly Thr Arg Arg Ala Arg Ala Ala Leu Met Glu
    370                 375                 380

Leu Gly Leu Pro Gly Ala Ala Tyr Ile Tyr Gln Gly Glu Glu Leu Gly
385                 390                 395                 400

Leu Phe Glu Val Ala Asp Ile Pro Trp Asp His Leu Glu Asp Pro Thr
            405                 410                 415
```

```
Ala Phe His Thr Ala Gln Ala Thr Met Asp Lys Gly Arg Asp Gly Cys
            420                 425                 430

Arg Val Pro Leu Pro Trp Thr Ala Ala Asp Glu Pro Ala Leu Ala Asp
            435                 440                 445

Phe Ser Arg Pro Thr Pro Ala Asp Asp Gly Thr Gly Glu Asn His Val
450                 455                 460

Pro Leu Cys Ala Ala Gly Gln Phe Gly Thr Gly Ala Ser Phe Gly Phe
465                 470                 475                 480

Ser Pro Ala Thr Arg Ala Glu Gly Val Thr Pro Ala Ala Asp Pro His
            485                 490                 495

Leu Pro Gln Pro Leu Trp Phe Lys Asp Tyr Ala Val Asp Val Glu Gln
            500                 505                 510

Ala Asp Pro Asp Ser Met Leu Ala Leu Tyr Arg Ala Ala Leu Ala Ile
            515                 520                 525

Arg Gln Glu Ser Leu Thr Ala Thr Arg Asp Thr Thr Ala Glu Gln Val
            530                 535                 540

Asp Met Gly Asp Asp Val Val Ala Tyr Thr Arg Ala Ala Val Gly Gly
545                 550                 555                 560

Arg Val Phe Thr Ser Ile Thr Asn Phe Gly Asn Ala Pro Val Ala Leu
            565                 570                 575

Pro Asp Gly Ser Val Val Leu Ala Ser Gly Pro Leu Thr Pro Glu Ala
            580                 585                 590

Gln Leu Pro Thr Asp Thr Ser Ala Trp Val Val Gln
            595                 600

<210> SEQ ID NO 76
<211> LENGTH: 604
<212> TYPE: PRT
<213> ORGANISM: Bifidobacterium longum

<400> SEQUENCE: 76

Met Thr Ala Asn Asn Leu Asn Asp Asp Trp Trp Lys Gln Ala Val Val
1               5                   10                  15

Tyr Gln Ile Tyr Pro Arg Ser Phe Lys Asp Val Asn Gly Asp Gly Leu
            20                  25                  30

Gly Asp Ile Ala Gly Val Thr Glu Lys Met Asp Tyr Leu Lys Asn Leu
            35                  40                  45

Gly Val Asp Ala Ile Trp Leu Ser Pro Phe Tyr Pro Ser Asp Leu Ala
        50                  55                  60

Asp Gly Gly Tyr Asp Val Ile Asp Tyr Arg Asn Val Asp Pro Arg Leu
65                  70                  75                  80

Gly Thr Met Glu Asp Phe Asp Ala Met Ala Lys Ala Ala His Glu Ala
            85                  90                  95

Gly Ile Lys Val Ile Val Asp Ile Val Pro Asn His Thr Ala Asp Lys
            100                 105                 110

His Val Phe Phe Gln Glu Ala Leu Ala Ala Glu Pro Gly Ser Pro Ala
            115                 120                 125

Arg Asp Arg Tyr Ile Phe Arg Asp Gly Arg Gly Glu His Gly Glu Leu
            130                 135                 140

Pro Pro Asn Asp Trp Gln Ser Phe Phe Gly Gly Pro Ala Trp Ala Arg
145                 150                 155                 160

Val Ala Asp Gly Gln Trp Tyr Leu His Leu Phe Asp Lys Ala Gln Pro
            165                 170                 175

Asp Val Asn Trp Lys Asn Pro Asp Ile His Glu Glu Phe Lys Lys Thr
            180                 185                 190
```

```
Leu Arg Phe Trp Ser Asp His Gly Thr Asp Gly Phe Arg Ile Asp Val
            195                 200                 205

Ala His Gly Leu Ala Lys Asp Leu Glu Ser Lys Pro Leu Glu Glu Leu
        210                 215                 220

Gly Arg Glu Tyr Ser Val Val Gly Val Leu Asn His Asp Phe Ser His
225                 230                 235                 240

Pro Leu Phe Asp Arg Arg Glu Val His Asp Ile Tyr Arg Glu Trp Arg
                245                 250                 255

Lys Val Phe Asn Glu Tyr Asp Pro Pro Arg Phe Ala Val Ala Glu Ala
                260                 265                 270

Trp Val Val Pro Glu His Gln His Leu Tyr Ala Ser Met Asp Glu Leu
                275                 280                 285

Gly Gln Ser Phe Asn Phe Asp Phe Ala Gln Ala Asn Trp Tyr Ala Asp
            290                 295                 300

Glu Phe Arg Glu Ala Ile Ala Ala Gly Leu Lys Ala Ala Ala Glu Thr
305                 310                 315                 320

Gly Gly Ser Thr Thr Thr Trp Val Met Asn Asn His Asp Val Pro Arg
                325                 330                 335

Ser Pro Ser Arg Tyr Gly Leu Pro Gln Ile Lys Gly Ala Pro Tyr His
                340                 345                 350

Gln Leu Pro His Asp Trp Leu Leu Arg Asn Gly Thr Thr Tyr Pro Glu
            355                 360                 365

Asp Arg Glu Leu Gly Thr Arg Arg Ala Arg Ala Ala Ala Leu Met Glu
            370                 375                 380

Leu Gly Leu Pro Gly Ala Ala Tyr Ile Tyr Gln Gly Glu Glu Leu Gly
385                 390                 395                 400

Leu Phe Glu Val Ala Asp Ile Pro Trp Asp His Leu Glu Asp Pro Thr
                405                 410                 415

Ala Phe His Thr Ala Gln Ala Thr Met Asp Lys Gly Arg Asp Gly Cys
            420                 425                 430

Arg Val Pro Leu Pro Trp Thr Ala Ala Asp Glu Pro Ala Leu Ala Asp
            435                 440                 445

Phe Ser Arg Pro Thr Pro Ala Asp Asp Gly Thr Gly Glu Asn His Val
        450                 455                 460

Pro Leu Cys Ala Ala Gly Gln Phe Gly Thr Gly Ala Ser Phe Gly Phe
465                 470                 475                 480

Ser Pro Ala Thr Arg Ala Glu Gly Val Thr Pro Ala Ala Asp Pro His
                485                 490                 495

Leu Pro Gln Pro Leu Trp Phe Lys Asp Tyr Ala Val Asp Val Glu Gln
            500                 505                 510

Ala Asp Pro Asp Ser Met Leu Ala Leu Tyr Arg Ala Ala Leu Ala Ile
            515                 520                 525

Arg Gln Glu Ser Leu Thr Ala Thr Arg Asp Thr Thr Ala Glu Gln Val
        530                 535                 540

Asp Met Gly Asp Asp Val Val Ala Tyr Thr Arg Ala Ala Val Gly Gly
545                 550                 555                 560

Arg Val Phe Thr Ser Ile Thr Asn Phe Gly Asn Ala Pro Val Ala Leu
                565                 570                 575

Pro Asp Gly Ser Val Val Leu Ala Ser Gly Pro Leu Thr Pro Glu Ala
            580                 585                 590

Gln Leu Pro Thr Asp Thr Ser Ala Trp Val Val Gln
        595                 600
```

<210> SEQ ID NO 77
<211> LENGTH: 604
<212> TYPE: PRT
<213> ORGANISM: Bifidobacterium longum

<400> SEQUENCE: 77

| | | | | | | | | | | | | | | |
|---|---|---|---|---|---|---|---|---|---|---|---|---|---|---|
| Met | Thr | Ala | Asn | Asn | Leu | Asn | Asp | Asp | Trp | Trp | Lys | Gln | Ala | Val | Val |
| 1 | | | | 5 | | | | | 10 | | | | | 15 | |
| Tyr | Gln | Ile | Tyr | Pro | Arg | Ser | Phe | Lys | Asp | Val | Asn | Gly | Asp | Gly | Leu |
| | | | 20 | | | | | 25 | | | | | 30 | | |
| Gly | Asp | Ile | Ala | Gly | Val | Thr | Glu | Lys | Met | Asp | Tyr | Leu | Lys | Asn | Leu |
| | | 35 | | | | | 40 | | | | | 45 | | | |
| Gly | Val | Asp | Ala | Ile | Trp | Leu | Ser | Pro | Phe | Tyr | Pro | Ser | Asp | Leu | Ala |
| 50 | | | | | 55 | | | | | 60 | | | | | |
| Asp | Gly | Gly | Tyr | Asp | Val | Ile | Asp | Tyr | Arg | Asn | Val | Asp | Pro | Arg | Leu |
| 65 | | | | 70 | | | | | 75 | | | | | 80 | |
| Gly | Thr | Met | Asp | Asp | Phe | Asp | Ala | Met | Ala | Glu | Ala | Ala | His | Glu | Ala |
| | | | | 85 | | | | | 90 | | | | | 95 | |
| Gly | Ile | Lys | Val | Ile | Val | Asp | Ile | Val | Pro | Asn | His | Thr | Ala | Asp | Lys |
| | | | 100 | | | | | 105 | | | | | 110 | | |
| His | Val | Phe | Phe | Lys | Glu | Ala | Leu | Ala | Ser | Glu | Pro | Gly | Ser | Pro | Ala |
| | | 115 | | | | | 120 | | | | | 125 | | | |
| Arg | Asp | Arg | Tyr | Ile | Phe | Arg | Asp | Gly | Arg | Gly | Glu | His | Gly | Glu | Leu |
| 130 | | | | | 135 | | | | | 140 | | | | | |
| Pro | Pro | Asn | Asp | Trp | Gln | Ser | Phe | Phe | Gly | Gly | Pro | Ala | Trp | Ala | Arg |
| 145 | | | | 150 | | | | | 155 | | | | | 160 | |
| Val | Pro | Asp | Gly | Gln | Trp | Tyr | Leu | His | Leu | Phe | Asp | Lys | Ala | Gln | Pro |
| | | | | 165 | | | | | 170 | | | | | 175 | |
| Asp | Val | Asn | Trp | Lys | Asn | Pro | Asp | Ile | His | Glu | Glu | Phe | Lys | Lys | Thr |
| | | | 180 | | | | | 185 | | | | | 190 | | |
| Leu | Arg | Phe | Trp | Ser | Asp | His | Gly | Thr | Asp | Gly | Phe | Arg | Ile | Asp | Val |
| | | 195 | | | | | 200 | | | | | 205 | | | |
| Ala | His | Gly | Leu | Ala | Lys | Asp | Leu | Glu | Ser | Lys | Pro | Leu | Glu | Glu | Leu |
| 210 | | | | | 215 | | | | | 220 | | | | | |
| Gly | Arg | Glu | Tyr | Ser | Val | Val | Gly | Val | Leu | Asn | His | Asp | Phe | Ser | His |
| 225 | | | | | 230 | | | | | 235 | | | | | 240 |
| Pro | Leu | Phe | Asp | Arg | Arg | Glu | Val | His | Asp | Ile | Tyr | Arg | Glu | Trp | Arg |
| | | | | 245 | | | | | 250 | | | | | 255 | |
| Lys | Val | Phe | Asn | Glu | Tyr | Thr | Pro | Pro | Arg | Phe | Ala | Val | Ala | Glu | Ala |
| | | | 260 | | | | | 265 | | | | | 270 | | |
| Trp | Val | Val | Pro | Glu | His | Gln | His | Leu | Tyr | Ala | Ser | Met | Asp | Glu | Leu |
| | | 275 | | | | | 280 | | | | | 285 | | | |
| Gly | Gln | Ser | Phe | Asn | Phe | Asp | Phe | Ala | Gln | Ala | Asn | Trp | Tyr | Ala | Asp |
| | | 290 | | | | | 295 | | | | | 300 | | | |
| Glu | Phe | Arg | Lys | Ala | Ile | Ala | Ala | Gly | Leu | Lys | Ala | Ala | Ala | Glu | Thr |
| 305 | | | | | 310 | | | | | 315 | | | | | 320 |
| Gly | Gly | Ser | Thr | Thr | Thr | Trp | Val | Met | Asn | Asn | His | Asp | Val | Pro | Arg |
| | | | | 325 | | | | | 330 | | | | | 335 | |
| Ser | Pro | Ser | Arg | Tyr | Gly | Leu | Pro | Gln | Val | Lys | Gly | Ala | Pro | Tyr | His |
| | | | 340 | | | | | 345 | | | | | 350 | | |
| Gln | Leu | Pro | His | Asp | Trp | Leu | Leu | Arg | Asp | Gly | Thr | Thr | Tyr | Pro | Glu |
| | | 355 | | | | | 360 | | | | | 365 | | | |
| Asn | Arg | Glu | Leu | Gly | Thr | Arg | Arg | Ala | Arg | Ala | Ala | Leu | Met | Glu |
| 370 | | | | | 375 | | | | | 380 | | | | | |

```
Leu Gly Leu Pro Gly Ala Ala Tyr Ile Tyr Gln Gly Glu Glu Leu Gly
385                 390                 395                 400

Leu Phe Glu Val Ala Asp Ile Pro Trp Asp His Leu Glu Asp Pro Thr
            405                 410                 415

Ala Phe His Thr Thr Arg Asn Thr Met Asp Lys Gly Arg Asp Gly Cys
        420                 425                 430

Arg Val Pro Leu Pro Trp Thr Ala Ala Asp Glu Pro Ala Leu Ala Asp
            435                 440                 445

Phe Ser Arg Pro Ala Pro Ala Asp Asp Gly Thr Gly Glu Asn His Val
    450                 455                 460

Pro Leu Cys Ala Ala Gly Gln Phe Gly Thr Gly Ala Ser Phe Gly Phe
465                 470                 475                 480

Ser Pro Ala Val Arg Ala Asp Gly Val Thr Pro Ala Ala Asp Pro His
                485                 490                 495

Leu Pro Gln Pro Leu Trp Phe Lys Asp Tyr Ala Val Asp Val Glu Gln
            500                 505                 510

Ala Asp Pro Asp Ser Met Leu Ala Leu Tyr Arg Ala Ala Leu Ala Ile
    515                 520                 525

Arg Gln Glu Ser Leu Thr Ala Thr Arg Asp Thr Thr Ala Glu Gln Val
530                 535                 540

Asp Met Gly Asp Val Val Ala Tyr Thr Arg Ala Ala Val Gly Gly
545                 550                 555                 560

Arg Val Phe Thr Ser Ile Thr Asn Phe Gly Asn Ala Pro Val Ala Leu
                565                 570                 575

Pro Asp Gly Ser Val Val Leu Ala Ser Gly Pro Leu Thr Pro Glu Gly
            580                 585                 590

Gln Leu Pro Thr Asp Thr Ser Ala Trp Val Ile Lys
            595                 600

<210> SEQ ID NO 78
<211> LENGTH: 585
<212> TYPE: PRT
<213> ORGANISM: Bifidobacterium pseudolongum

<400> SEQUENCE: 78

Met Thr Leu Asn Asn Thr His Asp Asp Trp Trp Lys Gln Ala Val Val
1               5                   10                  15

Tyr Gln Val Tyr Pro Arg Ser Phe Arg Asp Ala Asn Gly Asp Gly Leu
                20                  25                  30

Gly Asp Ile Ala Gly Ile Thr Ser Arg Ile Pro Tyr Leu Arg Gln Leu
            35                  40                  45

Gly Val Asp Ala Leu Trp Leu Ser Pro Phe Tyr Pro Ser Glu Leu Ala
        50                  55                  60

Asp Gly Gly Tyr Asp Val Ile Asp Tyr Arg Asn Val Asp Pro Arg Leu
65                  70                  75                  80

Gly Thr Leu Asp Asp Phe Asp Ala Met Val Ala Ala His Ser Ala
                85                  90                  95

Gly Leu Lys Val Val Val Asp Ile Val Pro Asn His Thr Ser Asn Met
            100                 105                 110

His Pro Trp Phe Gln Glu Ala Leu Ala Ser Ala Pro Gly Ser Pro Ala
        115                 120                 125

Arg Asp Arg Tyr Ile Phe Arg Asp Gly Glu Gly Ala His Gly Glu Leu
    130                 135                 140

Pro Pro Asn Asn Trp Gln Ser Leu Phe Gly Gly Pro Ala Trp Glu Ala
```

-continued

```
            145                 150                 155                 160
Ala Gly Asp Gly Gln Trp Tyr Leu His Leu Phe Thr Lys Glu Gln Pro
                165                 170                 175
Asp Leu Asn Trp Lys Asn Pro Asp Val His Glu Asp Phe Arg Thr Thr
                180                 185                 190
Leu Arg Phe Trp Ser Asp Arg Gly Val Asp Gly Phe Arg Ile Asp Val
                195                 200                 205
Ala His Gly Leu Ala Lys Asp Leu Asp Ser Glu Pro Leu Lys Asp Leu
                210                 215                 220
Glu Arg Phe Pro Val Gly Gly Asn Pro Val Pro Gly His Pro Leu Trp
225                 230                 235                 240
Asp Arg Pro Glu Val His Glu Ile Tyr Arg Glu Trp Asn Lys Val Phe
                245                 250                 255
Asn Glu Tyr Asp Pro Pro Arg Phe Ala Val Gly Glu Ala Trp Val Pro
                260                 265                 270
Ala Glu His Gln His Leu Tyr Ala Ser Lys Asp Glu Leu Gly Gln Val
                275                 280                 285
Phe Asn Phe Glu Phe Ala Lys Ala Asn Trp Phe Ala Asp Asp Phe Arg
                290                 295                 300
Leu Ala Ile Glu Glu Gly Leu Ala Ser Ala Asp Glu Ser Lys Ser Thr
305                 310                 315                 320
Thr Thr Trp Val Met Ser Asn His Asp Val Pro Arg His Val Ser Arg
                325                 330                 335
Tyr Gly Leu Pro Gln Val His Thr Arg Gly Tyr His Glu Leu Pro Asn
                340                 345                 350
Asp Trp Leu Leu Arg Asn Gly Thr Thr Tyr Ile Glu Asp Arg Glu Leu
                355                 360                 365
Gly Thr Arg Arg Ala Arg Ala Ile Leu Met Glu Leu Gly Leu Pro
                370                 375                 380
Gly Ser Val Tyr Val Tyr Gln Gly Glu Glu Leu Gly Leu Pro Glu Val
385                 390                 395                 400
Ala Thr Ile Pro Trp Asp His Leu Glu Asp Pro Val Ala Phe Asn Thr
                405                 410                 415
Asp His Ser Asp Ala Ala Lys Gly Arg Asp Gly Cys Arg Val Pro Leu
                420                 425                 430
Pro Trp Ser Ala Gln Asp Met Pro Gln Pro Ala Pro Trp Asp Pro Glu
                435                 440                 445
Phe Gly Thr Gly Ala Ser Phe Gly Phe Ser Glu His Ala Gly Gly Arg
                450                 455                 460
Ala Ser Ala Asp Pro His Leu Pro Gln Pro Leu Trp Tyr Ala Gly Tyr
465                 470                 475                 480
Ala Ala Asp Met Glu Asp Thr Pro Ala Ser Met Leu Asn Leu Tyr
                485                 490                 495
Arg Arg Ala Met His Trp Arg Gln Glu His Leu Thr Pro Thr Gly Asp
                500                 505                 510
Thr Ser Leu Thr Trp Leu Ser Pro Gln Ser Phe Ala Asp Cys Gly Asp
                515                 520                 525
Asp Val Val Ala Tyr Ala Arg Pro Leu Ala Asp Ser Gly Asp Arg
                530                 535                 540
Phe Val Cys Ile Val Asn Phe Gly Ala Ala Ser Ile Glu Leu Pro His
545                 550                 555                 560
Gly Asp Val Met Met Arg Ser Ile Pro Phe Asp Gly Tyr Gln Leu Pro
                565                 570                 575
```

```
Ala Asp Ala Ala Val Trp Met Arg Ile
            580                 585

<210> SEQ ID NO 79
<211> LENGTH: 601
<212> TYPE: PRT
<213> ORGANISM: Bifidobacterium thermophilum

<400> SEQUENCE: 79

Met Ala Glu Arg Lys Ser Pro Gln Ser Ala Gln Glu Ser Thr Ala Ser
1               5                   10                  15

Asp Arg Ala Ala Ala Trp Trp His Gln Ala Val Val Tyr Gln Val
            20                  25                  30

Tyr Pro Arg Ser Phe Lys Asp Thr Thr Gly Ser Gly Leu Gly Asp Ile
            35                  40                  45

Ala Gly Val Thr Ser Arg Ile Gly Tyr Leu Lys Gln Leu Gly Val Asp
            50                  55                  60

Ala Ile Trp Leu Ser Pro Phe Tyr Pro Ser Gln Leu Ala Asp Gly Gly
65                  70                  75                  80

Tyr Asp Val Asp Asp Tyr Arg Asn Val Asp Pro Lys Leu Gly Thr Met
                85                  90                  95

Asp Asp Phe Asp Lys Leu Ala Lys Thr Ala His Glu Ala Gly Ile Lys
            100                 105                 110

Ile Val Val Asp Ile Val Pro Asn His Ser Ser Asn Leu His Pro Trp
            115                 120                 125

Phe Lys Ala Ala Leu Ala Ala Gly Pro Gly Ser Pro Glu Arg Asp Arg
130                 135                 140

Tyr Ile Phe Arg Asp Gly Arg Gly Glu His Gly Glu Leu Pro Pro Thr
145                 150                 155                 160

Asp Trp Val Ser His Phe Gly Gly Pro Ala Trp Thr Arg Val Pro Asp
                165                 170                 175

Gly Gln Trp Tyr Leu His Leu Phe Thr Val Glu Gln Pro Asp Trp Asn
            180                 185                 190

Trp Lys Asn Pro Asp Val Gln Ala Asp Phe Ile Lys Thr Leu Arg Phe
            195                 200                 205

Trp Leu Asp His Gly Ala Asp Gly Phe Arg Val Asp Val Ala His Gly
            210                 215                 220

Leu Cys Lys Asp Leu Asp Arg Asp Asn Leu Asp Gln Trp Ser Val Thr
225                 230                 235                 240

Pro Pro Ser Leu Pro Ala Asp Gly Ser His Pro Leu Tyr Asp Arg Asp
                245                 250                 255

Asp Val His Gln Ile Tyr Arg Glu Trp Arg Lys Val Phe Asn Glu Tyr
            260                 265                 270

Asp Pro Pro Ala Phe Ala Val Ala Glu Ala Trp Val Asn Pro Ala Arg
            275                 280                 285

Gln Tyr Leu Tyr Ala Ser Asp Asp Glu Leu Gly Gln Val Phe Asn Phe
            290                 295                 300

Glu Phe Ala Lys Lys Asn Trp Val Arg Asp Asp Met His Gln Ala Ile
305                 310                 315                 320

Glu Glu Gly Leu Glu Ala Ala Arg Arg Ser Gly Ser Thr Ala Thr Trp
                325                 330                 335

Val Met Ser Asn His Asp Val Pro Arg His Ala Ser Arg Tyr Ala Leu
            340                 345                 350

Pro Gln Val Pro Ser Thr Arg His His Gln Leu Ala His Asp Trp Leu
```

```
                355                 360                 365
Leu Arg Asp Gly Thr Ser Tyr His Glu Asp Arg Glu Ala Gly Thr Arg
    370                 375                 380

Arg Ala Arg Ala Ala Ile Leu Met Glu Leu Ala Leu Pro Gly Ser Ala
385                 390                 395                 400

Tyr Leu Tyr Gln Gly Glu Glu Leu Gly Leu Phe Glu Val Ala Asp Ile
                405                 410                 415

Pro Trp Asn Lys Leu Glu Asp Pro Thr Ala Arg Asn Ser Glu Arg Ala
            420                 425                 430

Ala Lys Asp Lys Gly Arg Asp Gly Cys Arg Val Pro Leu Pro Trp Val
        435                 440                 445

Ala Ala Asp Gly Val Glu Gly Ser Phe Gly Phe Ser Pro Arg Val Lys
    450                 455                 460

Ser Val Gly Ala Gly Val Ser Ala Asp Gln Ala Gly Gln Pro Ser Glu
465                 470                 475                 480

Pro Ala His Leu Pro Gln Pro Ala Trp Phe Ala Asp Phe Ala Ala Asp
                485                 490                 495

Arg Glu Ser Ala Gln Pro Glu Ser Met Leu Asn Leu Tyr Arg Arg Ala
            500                 505                 510

Leu Ala Leu Arg His Glu Leu Met Pro Ala Asp Thr Thr Leu Thr Trp
        515                 520                 525

Leu Asp Glu Asp Arg Pro Ser Asp Ala Pro Asp Gly Ala Asp Gly Gln
    530                 535                 540

His Gly Gly Val Ile Ala Tyr Arg Arg Ser Asn Gly Trp Ala Ser Val
545                 550                 555                 560

Thr Asn Phe Gly Ala Glu Pro Val Ala Leu Pro Ala Gly Glu Val Leu
                565                 570                 575

Leu Thr Ser Gly Glu Leu Cys Ser Asp Gly Arg Leu Pro Gln Asp Thr
            580                 585                 590

Thr Val Trp Leu Arg Leu Asn Gln Asp
        595                 600

<210> SEQ ID NO 80
<211> LENGTH: 662
<212> TYPE: PRT
<213> ORGANISM: Bifidobacterium breve

<400> SEQUENCE: 80

Met Tyr Phe His Ile Asn His Leu His Asp Thr Val Val Ile Asn Val
1               5                   10                  15

Ile Ser Lys His Gly Phe Thr Val Ala Val Arg Val Leu Leu Asn Pro
            20                  25                  30

Ile Thr Thr Asn Pro Gln Gln Ser Gly Ala Thr His His Val Ser His
        35                  40                  45

Thr Ile Thr His Ala Gln Lys Gly Ile Gly Met Thr Ala Asn Asn Leu
    50                  55                  60

Asn Asp Asp Trp Trp Lys Gln Ala Val Val Tyr Gln Ile Tyr Pro Arg
65                  70                  75                  80

Ser Phe Lys Asp Val Asn Gly Asp Gly Ile Gly Asp Ile Ala Gly Val
                85                  90                  95

Thr Glu Lys Met Asp Tyr Leu Lys Asn Leu Gly Val Asp Ala Ile Trp
            100                 105                 110

Leu Ser Pro Phe Tyr Pro Ser Asp Leu Ala Asp Gly Gly Tyr Asp Val
        115                 120                 125
```

```
Ile Asp Tyr Arg Asn Val Asp Pro Arg Leu Gly Thr Met Asp Asp Phe
130                 135                 140

Asp Ala Met Ala Lys Ala Ala His Glu Ala Gly Ile Lys Val Ile Val
145                 150                 155                 160

Asp Ile Val Pro Asn His Thr Ala Asp Lys His Val Phe Phe Lys Glu
                165                 170                 175

Ala Leu Ala Ala Glu Pro Gly Ser Pro Ala Arg Asp Arg Tyr Ile Phe
            180                 185                 190

Arg Asp Gly Arg Gly Glu His Gly Glu Leu Pro Pro Asn Asp Trp Gln
        195                 200                 205

Ser Phe Phe Gly Gly Pro Ala Trp Ala Arg Val Ala Asp Gly Gln Trp
210                 215                 220

Tyr Leu His Leu Phe Asp Lys Ala Gln Pro Asp Val Asn Trp Lys Asn
225                 230                 235                 240

Pro Asp Ile His Glu Glu Phe Lys Lys Thr Leu Arg Phe Trp Ser Asp
                245                 250                 255

His Gly Thr Asp Gly Phe Arg Ile Asp Val Ala His Gly Leu Ala Lys
            260                 265                 270

Asp Leu Glu Ser Lys Pro Leu Glu Glu Leu Gly Arg Glu Tyr Ser Val
        275                 280                 285

Val Gly Val Leu Asn His Asp Phe Ser His Pro Leu Phe Asp Arg Arg
290                 295                 300

Glu Val His Asp Ile Tyr Arg Glu Trp Arg Lys Val Phe Asn Glu Tyr
305                 310                 315                 320

Asp Pro Pro Arg Phe Ala Val Ala Glu Ala Trp Val Val Pro Glu His
                325                 330                 335

Gln His Leu Tyr Ala Ser Met Asp Glu Leu Gly Gln Ser Phe Asn Phe
            340                 345                 350

Asp Phe Ala Gln Ala Ser Trp Tyr Ala Asp Glu Phe Arg Ala Ala Ile
        355                 360                 365

Ala Ala Gly Leu Lys Ala Ala Glu Thr Gly Gly Ser Thr Thr Thr
370                 375                 380

Trp Val Met Asn Asn His Asp Val Pro Arg Ser Pro Ser Arg Tyr Gly
385                 390                 395                 400

Leu Pro Gln Val Lys Gly Ala Pro Tyr His Gln Leu Pro His Asp Trp
                405                 410                 415

Leu Leu Arg Asn Gly Thr Thr Tyr Pro Glu Asp Arg Glu Leu Gly Thr
            420                 425                 430

Arg Arg Ala Arg Ala Ala Leu Met Glu Leu Gly Leu Pro Gly Ala
        435                 440                 445

Ala Tyr Ile Tyr Gln Gly Glu Glu Leu Gly Leu Phe Glu Val Ala Asp
450                 455                 460

Ile Pro Trp Asp Arg Leu Glu Asp Pro Thr Ala Phe His Thr Ala Gln
465                 470                 475                 480

Ala Thr Met Asp Lys Gly Arg Asp Gly Cys Arg Val Pro Ile Pro Trp
                485                 490                 495

Thr Ala Ala Asn Glu Pro Thr Leu Ala Asp Phe Ser Arg Pro Ile Pro
            500                 505                 510

Ala Asp Asp Gly Thr Gly Glu Asn His Val Pro Leu Cys Ala Ala Gly
        515                 520                 525

Gln Phe Gly Thr Gly Ala Ser Phe Gly Phe Ser Pro Ala Thr Arg Ala
530                 535                 540

Glu Gly Val Thr Pro Ala Ala Asp Pro His Leu Pro Gln Pro Leu Trp
```

```
            545                 550                 555                 560
        Phe Lys Asp Tyr Ala Val Asp Val Glu Gln Ala Asp Pro Asp Ser Met
                        565                 570                 575
        Leu Ala Leu Tyr His Ala Ala Leu Ala Ile Arg Gln Glu Ser Leu Thr
                        580                 585                 590
        Ala Thr Arg Asp Thr Thr Ala Glu Gln Val Asp Met Gly Pro Asp Val
                        595                 600                 605
        Val Ala Tyr Thr Arg Ala Ala Val Gly Gly Arg Thr Phe Thr Ser Ile
                        610                 615                 620
        Thr Asn Phe Gly Thr Glu Pro Val Glu Leu Pro Gly Gly Ser Val Val
        625                 630                 635                 640
        Leu Thr Ser Gly Pro Leu Thr Pro Asp Gly Gln Leu Pro Thr Asp Thr
                        645                 650                 655
        Ser Ala Trp Val Ile Lys
                        660

<210> SEQ ID NO 81
<211> LENGTH: 606
<212> TYPE: PRT
<213> ORGANISM: Bifidobacterium breve

<400> SEQUENCE: 81

Met Thr Thr Phe Asn Arg Ala Ile Ile Pro Asp Ala Ile Arg Thr Asn
        1               5                   10                  15
        Gly Ala Thr Pro Asn Pro Trp Trp Ser Asn Ala Val Val Tyr Gln Ile
                        20                  25                  30
        Tyr Pro Arg Ser Phe Gln Asp Thr Asn Gly Asp Gly Leu Gly Asp Leu
                        35                  40                  45
        Lys Gly Ile Thr Ser Arg Leu Asp Tyr Leu Ala Asp Leu Gly Val Asp
                        50                  55                  60
        Val Leu Trp Leu Ser Pro Val Tyr Arg Ser Pro Gln Asp Asp Asn Gly
        65                  70                  75                  80
        Tyr Asp Ile Ser Asp Tyr Arg Asp Ile Asp Pro Leu Phe Gly Thr Leu
                        85                  90                  95
        Asp Asp Met Asp Glu Leu Leu Ala Glu Ala His Lys Arg Gly Leu Lys
                        100                 105                 110
        Ile Val Met Asp Leu Val Val Asn His Thr Ser Asp Glu His Ala Trp
                        115                 120                 125
        Phe Glu Ala Ser Lys Asp Lys Asp Pro His Ala Asp Trp Tyr Trp
                        130                 135                 140
        Trp Arg Pro Ala Arg Pro Gly His Glu Pro Thr Pro Gly Ala Glu
        145                 150                 155                 160
        Pro Asn Gln Trp Gly Ser Tyr Phe Gly Gly Ser Ala Trp Glu Tyr Ser
                        165                 170                 175
        Pro Glu Arg Gly Glu Tyr Tyr Leu His Gln Phe Ser Lys Lys Gln Pro
                        180                 185                 190
        Asp Leu Asn Trp Glu Asn Pro Ala Val Arg Arg Ala Val Tyr Asp Met
                        195                 200                 205
        Met Asn Trp Trp Leu Asp Arg Gly Ile Asp Gly Phe Arg Met Asp Val
                        210                 215                 220
        Ile Thr Leu Ile Ser Lys Arg Thr Asp Ala Asn Gly Arg Leu Pro Gly
        225                 230                 235                 240
        Glu Tyr Gly Ser Glu Leu His Asp Leu Pro Val Gly Glu Glu Gly Tyr
                        245                 250                 255
```

-continued

```
Ser Ser Pro Asn Pro Phe Cys Ala Asp Gly Pro Arg Gln Asp Glu Phe
            260                 265                 270

Leu Ala Glu Met Arg Arg Glu Val Phe Asp Gly Arg Asp Gly Phe Leu
        275                 280                 285

Thr Val Gly Glu Ala Pro Gly Ile Thr Ala Glu Arg Asn Glu His Ile
    290                 295                 300

Thr Asn Pro Ala Asn Gly Glu Leu Asp Met Leu Phe Leu Phe Glu His
305                 310                 315                 320

Val Asp Phe Asp Cys Asp Gly Val Lys Trp Lys Pro Leu Pro Leu Asp
                325                 330                 335

Leu Pro Gly Phe Lys Arg Ile Met Ala Gly Tyr Gln Thr Ala Val Glu
            340                 345                 350

Asn Val Gly Trp Ala Ser Leu Phe Thr Gly Asn His Asp Gln Pro Arg
            355                 360                 365

Val Val Ser Arg Trp Gly Asp Asp Ser Ser Glu Glu Ser Arg Val Arg
        370                 375                 380

Ser Ala Lys Ala Leu Gly Leu Met Leu His Met His Arg Gly Thr Pro
385                 390                 395                 400

Tyr Val Tyr Gln Gly Glu Glu Leu Gly Met Thr Asn Ala His Phe Thr
                405                 410                 415

Ser Leu Asp Gln Tyr Arg Asp Leu Glu Ser Leu Asn Ala Tyr Arg Gln
            420                 425                 430

Arg Val Glu Glu Ala Lys Val Gln Ser Pro Glu Ser Met Met Ala Gly
        435                 440                 445

Ile Ala Ala Arg Gly Arg Asp Asn Ser Arg Thr Pro Met Gln Trp Asp
    450                 455                 460

Gly Ser Ala Tyr Ala Gly Phe Thr Ala Pro Asp Ala Ala Thr Glu Pro
465                 470                 475                 480

Trp Ile Ser Val Asn Pro Asn His Ala Glu Ile Asn Ala Ala Gly Glu
                485                 490                 495

Phe Asp Asp Pro Asp Ser Val Tyr Ala Phe Tyr Lys Lys Leu Ile Ala
            500                 505                 510

Leu Arg His Asn Ser Ser Ile Val Ala Ala Gly Glu Trp Arg Leu Ile
        515                 520                 525

Asp Ala Asp Asp Ala His Val Tyr Ala Phe Thr Arg Thr Leu Gly Asn
    530                 535                 540

Glu Arg Leu Leu Val Val Val Asn Leu Ser Gly Arg Thr Val Asp Leu
545                 550                 555                 560

Pro Arg Glu Ser Thr Glu Leu Ile Ala Gly Gly Val Thr Glu Pro Asp
                565                 570                 575

Ile Ile Leu Ser Thr Tyr Asp Ala Pro His Thr Val Val Ser Leu Ala
            580                 585                 590

Asn Arg Glu Leu Asp Pro Trp Glu Ala Ala Ala Val Gln Leu
        595                 600                 605
```